US010040856B2

(12) United States Patent
Ruiz-Opazo et al.

(10) Patent No.: US 10,040,856 B2
(45) Date of Patent: Aug. 7, 2018

(54) ANTI-DESPR INHIBITORS AS THERAPEUTICS FOR INHIBITION OF PATHOLOGICAL ANGIOGENESIS AND TUMOR CELL INVASIVENESS AND FOR MOLECULAR IMAGING AND TARGETED DELIVERY

(71) Applicant: Trustees of Boston University, Boston, MA (US)

(72) Inventors: Nelson Ruiz-Opazo, Westwood, MA (US); Victoria L. M. Herrera, Westwood, MA (US)

(73) Assignee: TRUSTEES OF BOSTON UNIVERSITY, Boston, MA (US)

( * ) Notice: Subject to any disclaimer, the term of this patent is extended or adjusted under 35 U.S.C. 154(b) by 0 days.

(21) Appl. No.: 14/730,972

(22) Filed: Jun. 4, 2015

(65) Prior Publication Data

US 2016/0108124 A1     Apr. 21, 2016

Related U.S. Application Data

(63) Continuation of application No. 13/811,485, filed as application No. PCT/US2011/045056 on Jul. 22, 2011, now abandoned.

(60) Provisional application No. 61/367,206, filed on Jul. 23, 2010.

(51) Int. Cl.
| | |
|---|---|
| *A61K 39/00* | (2006.01) |
| *A61K 39/395* | (2006.01) |
| *A61K 38/18* | (2006.01) |
| *C07K 16/00* | (2006.01) |
| *C07K 16/28* | (2006.01) |
| *C07K 16/30* | (2006.01) |
| *A61K 49/22* | (2006.01) |
| *A61M 37/00* | (2006.01) |
| *A61K 47/48* | (2006.01) |
| *G01N 33/574* | (2006.01) |

(52) U.S. Cl.
CPC ......... *C07K 16/2863* (2013.01); *A61K 38/18* (2013.01); *A61K 47/481* (2013.01); *A61K 49/221* (2013.01); *A61M 37/0092* (2013.01); *C07K 16/28* (2013.01); *C07K 16/2869* (2013.01); *C07K 16/30* (2013.01); *G01N 33/57496* (2013.01); *A61K 2039/505* (2013.01); *A61K 2039/507* (2013.01); *C07K 2317/21* (2013.01); *C07K 2317/24* (2013.01); *C07K 2317/34* (2013.01); *C07K 2317/76* (2013.01); *G01N 2800/7028* (2013.01)

(58) Field of Classification Search
None
See application file for complete search history.

(56) References Cited

U.S. PATENT DOCUMENTS

| | | | |
|---|---|---|---|
| 4,867,973 | A | 9/1989 | Goers et al. |
| 7,504,490 | B1 | 3/2009 | Weinstock et al. |
| 2009/0028852 | A1 | 1/2009 | Herrera et al. |
| 2009/0317836 | A1 | 12/2009 | Kuhn et al. |
| 2011/0313229 | A1 | 12/2011 | Sugaya et al. |
| 2013/0022551 | A1 | 1/2013 | Ruiz-Opazo |
| 2013/0177500 | A1 | 7/2013 | Ruiz-Opaz et al. |
| 2014/0186344 | A1 | 7/2014 | Herrera et al. |

FOREIGN PATENT DOCUMENTS

| | | |
|---|---|---|
| WO | 03/002144 A1 | 1/2003 |
| WO | 2006055665 A2 | 5/2006 |
| WO | 2010114801 A1 | 10/2010 |
| WO | 2012012750 A1 | 1/2012 |
| WO | 2013/112467 A1 | 8/2013 |

OTHER PUBLICATIONS

Paul. Fundamental Immunology, 3rd Edition, Raven Press, New York, Chapter 8, pp. 292-295, 1993.*
MacCallum et al. Antibody-antigen Interactions: Contact Analysis and Binding Site Topography. Journal of Molecular Biology, 262:732-745, 1996.*
Casset et al. A peptide mimetic of an anti-CD4 monoclonal antibody by rational design. Biochemical and Biophysical Research Communications, 307:198-205, 2003.*
Vajdos et al. Comprehensive Functional Maps of the Antigen-binding Site of an Anti-ErbB2 Antibody Obtained with Shotgun Scanning Mutagenesis. Journal of Molecular Biology, Jul. 5, 2002;320(2):415-28.*
Brown et al. Tolerance to Single, but Not Multiple, Amino Acid Replacements in Antibody VH CDR2. Journal of Immunology. May 1996; 156(9):3285-91.*
Rudikoff et al. Single amino acid substitution altering antigen-binding specificity. Proc. Natl. Acad. Sci. USA, 79(6):1979-1983, Mar. 1982.*
Colman. Effects of amino acid sequence changes on antibody-antigen interactions. Research in Immunology, 145:33-36, 1994.*
Paul. Fundamental Immunology, 3rd Edition, Raven Press, New York, Chapter 8, pp. 292-295, 1993 (Year: 1993).*
MacCallum et al. Antibody-antigen Interactions: Contact Analysis and Binding Site Topography. Journal of Molecular Biology, 262: 732-745, 1996 (Year: 1996).*
Casset et al. A peptide mimetic of an anti-CD4 monoclonal antibody by rational design. Biochemical and Biophysical Research Communications, 307:198-205, 2003 (Year: 2003).*

(Continued)

*Primary Examiner* — Vanessa L. Ford
*Assistant Examiner* — Sandra E Dillahunt
(74) *Attorney, Agent, or Firm* — Nixon Peabody LLP; Ronald I. Eisenstein; Srividya Subramanian

(57) ABSTRACT

Provided herein are novel compositions comprising anti-DEspR antibodies and fragments thereof, including fully human, composite engineered human, humanized, monoclonal, and polyclonal anto-DEspR antibodies and fragments thereof, and methods of their use in a variety of therapeutic applications. The compositions comprising the anti-DEspR antibodies and fragments thereof described herein are useful in diagnostic and imaging methods, such as DEspR-targeted molecular imaging of angiogenesis, and for companion diagnostic and/or in vivo-non invasive imaging and/or assessments.

20 Claims, 42 Drawing Sheets

(56) References Cited

OTHER PUBLICATIONS

Vajdos et al. Comprehensive Functional Maps of the Antigen-binding Site of an Anti-ErbB2 Antibody Obtained with Shotgun Scanning Mutagenesis. Journal of Molecular Biology, Jul. 5, 2002;320(2):415-28 (Year: 2002).*
Brown et al. Tolerance to Single, but Not Multiple, Amino Acid Replacements in Antibody VH CDR2. Journal of Immunology. May 1996; 156(9):3285-91 (Year: 1996).*
Rudikoff et al. Single amino acid substitution altering antigen-binding specificity. Proc. Natl. Acad. Sci. USA, 79(6):1979-1983, Mar. 1982 (Year: 1982).*
Colman. Effects of amino acid sequence changes on antibody-antigen interactions. Research in Immunology, 145:33-36, 1994 (Year: 1994).*
Abdollahi et al., Drug Resistance Updates, 13:16-28 (2010). "Evading tumor evasion: Current concepts and perspectives of anti-angiogenic cancer therapy."
Bergers et al., Nature Reviews, 8:592-603 (2008). "Modes of resistance to anti-angiogenic therapy."
Carmeliet et al., Nature, 380:435-439 (1996). "Abnormal blood vessel development and lethality in embryos lacking a single VEGF allele."
Carmeliet, Nature Review, 438:932-936 (2005). "Angiogenesis in life, disease and medicine."
Clouthier et al., Development, 125:813-824 (1998). "Cranial and cardiac neural crest defects in endothelin-A receptor-deficient mice."
Crawford et al., Methods in Enzymology, 445:125-139 (2008). "Chapter Six: Mouse Models to Investigate Anti-Cancer Effects of VEGF Inhibitors."
Decano et al., Circulation, 119:1501-1509 (2009). "Early-Life Sodium Exposure Unmasks Susceptibility to Stroke in Hyperlipidemic, Hypertensive Heterozygous Tg25 Rats Transgenic for Human Cholesteryl Ester Transfer Protein."
Ebos et al., Cancer Cell, 15:232-239 (2009). "Accelerated Metastasis after Short-Term Treatment with a Potent Inhibitor of Tumor Angiogenesis."
Ferrara et al., Nature, 380:439-442 (1996). "Heterozygous embryonic lethality induced by targeted inactivation of the VEGF gene."
Ferrara, Cytokine & Growth Factor Reviews, 21:21-26 (2010). "Pathways mediating VEGF-independent tumor angiogenesis."
Hanahan et al., Cell, 144:646-674 (2011). "Hallmarks of Cancer: The Next Generation."
Herrera et al., Atherosclerosis, 177:9-18 (2004). "Analysis of gender-specific atherosclerosis susceptibility in transgenic[hCETP]25DS rat model."
Herrera et al., Physiol Genomics, 35:316-329 (2008). "Sex-specific hippocampus-dependent cognitive deficits and increased neuronal autophagy in DEspR haploinsufficiency in mice."
Lin et al., J. Clin. Invest., 105:71-77 (2000). "Origins of circulating endothelial cells and endothelial outgrowth from blood."
Loges et al., Genes & Cancer, 1(1):12-25 (2010). "Mechanisms of Resistance to Anti-Angiogenic Therapy and Development of Third-Generation Anti-Angiogenic Drug Candidates."
Paez-Ribes et al., Cancer Cell, 15:220-231 (2009). "Antiangiogenic Therapy Elicits Malignant Progression of Tumors to Increased Local Invasion and Distant Metastasis."
Ruiz-Opazo et al., Molecular Medicine, 4:96-108 (1998). "Molecular Characterization of a Dual Endothelin-1/Angiotensin II Receptor."
Swami, Nature Reviews Cancer, 8 (2008). "Multipotent tumour endothelial cells."
Julius et al, "Molecular Imaging of Vasa Vasorum Neovascularization via DEspR-targeted Contrast-enhanced Ultrasound Micro-imaging in Transgenic Atherosclerosis Rat Model", Molecular Imaging and Biology, vol. 13, No. 6, pp. 1096-1106, 2010.
Glorioso et al, "Association of ATP1A1 and Dear single-nucleotide polymorphism haplotypes with essential hypertension—Sex-specific and haplotype-specific effects", Circulation Research, vol. 100, No. 10, pp. 1522-1529, 2007.
Herrera et al, "Embryonic lethality in Dear gene-deficient mice: new player in angiogenesis", Physiological Genomics, vol. 23, No. 3, pp. 257-268, 2005.
Brown et al., "Tolerance of single, but not multiple, amino acid replacements in antibody VH CDR 2: a means of minimizing B cell wastage from somatic hypermutation?", J Immunol, 156(9):3285-91 (1996).
Casset et al., "A peptide mimetic of an anti-CD4 monoclonal antibody by rational design", Biochem Biophys Res : Commun, 307(1):198-205 (2003).
MacCallum et al., "Antibody-antigen interactions: contact analysis and binding site topography", J Mol Biol, 262 (5):732-45 (1996).
Paul, Fundamental Immunology, Chapter 8, 3rd Edition, Raven Press, New York, pp. 292-295 (1993).
Rudikoff et al., "Single amino acid substitution altering antigen-binding specificity", Proc Natl Arad Sci U S A, 79(6):1979-83 (1982).
Vajdos et al., "Comprehensive functional maps of the antigen-binding site of an anti-ErbB2 antibody obtained with shotgun scanning mutagenesis", J Mol Biol, 320(2):415-28 (2002).
Yang et al., "Identification of Local and Circulating Cancer Stem Cells in Human Liver Cancer", Hepatology, 47(3):919-928(2008).
UniProt Submission B0L3A2_Human [Retreived from the Internet Feb. 7, 2017; <http://www.uniprot.org/uniprot/B0L3A2.txt?version=11>] (2008).
Decano et al., "Dual enothelin-1/VEGFsp receptor (DEspR) roles in adult angiogenesis in despr+/-31 knockout mice and carotid artery disease rat model", Manuscript submitted to Circulation. (2010).
GenBank, dual endothelial-1 (VEGRsp)/angiotension II receptor [*Homo sapiens*], NCBI LOCUS ABP04239, AC ABP04236 GI:144954326 (2008).

* cited by examiner

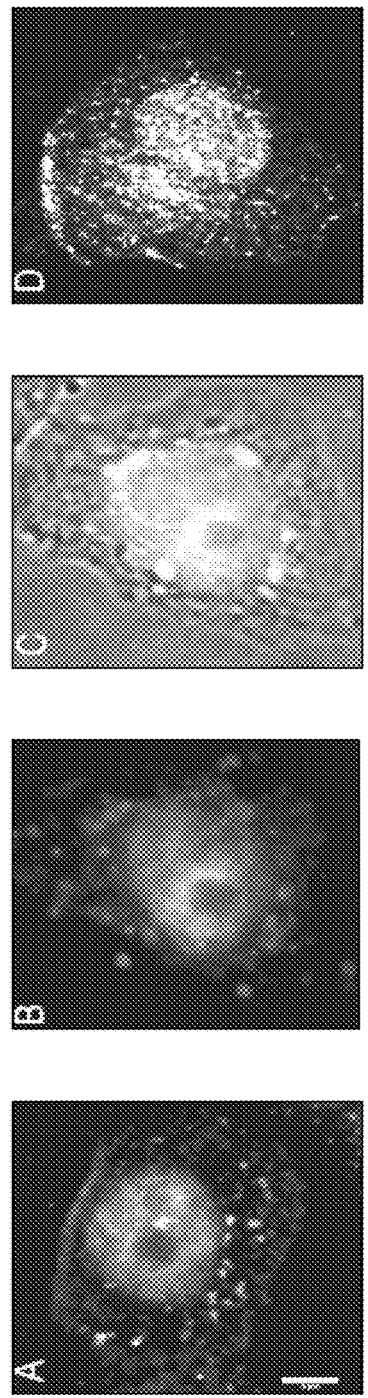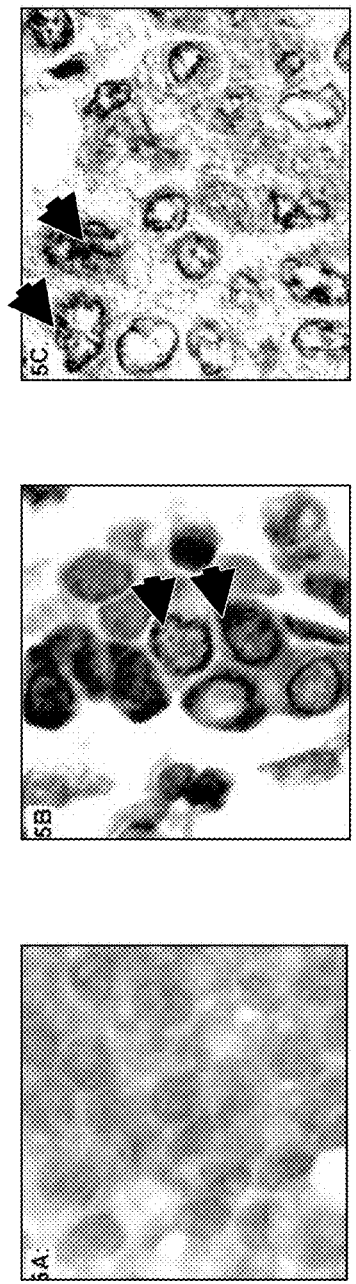

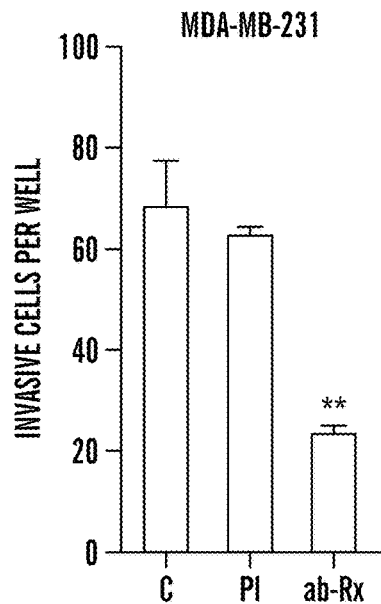
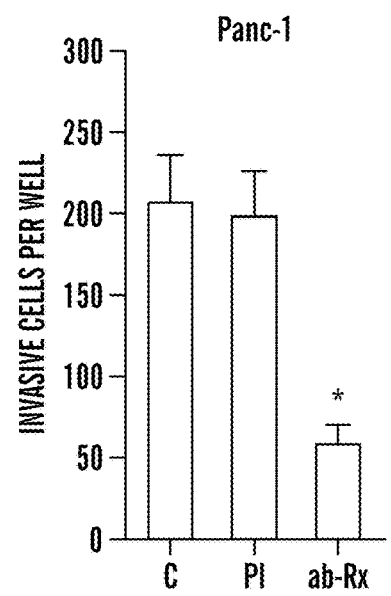
FIG. 6A  FIG. 6B
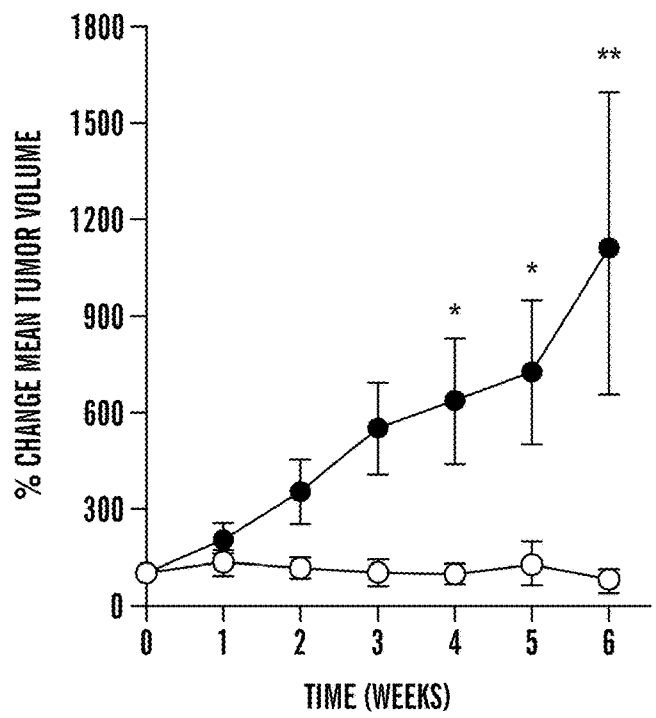
FIG. 7

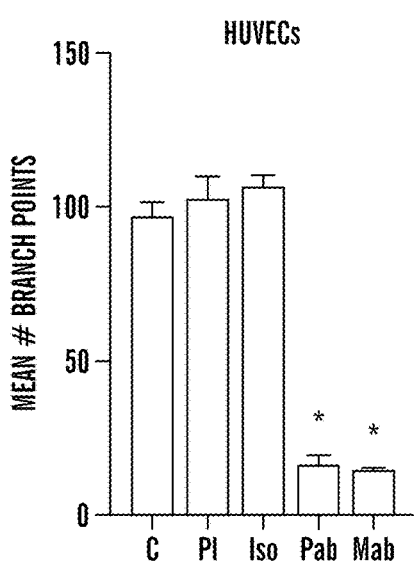
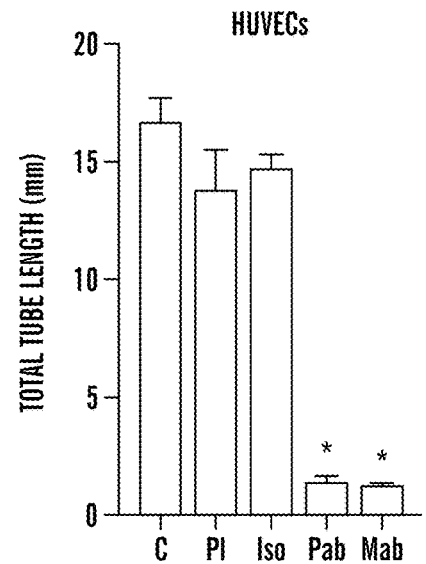
*FIG. 11A*  *FIG. 11B*
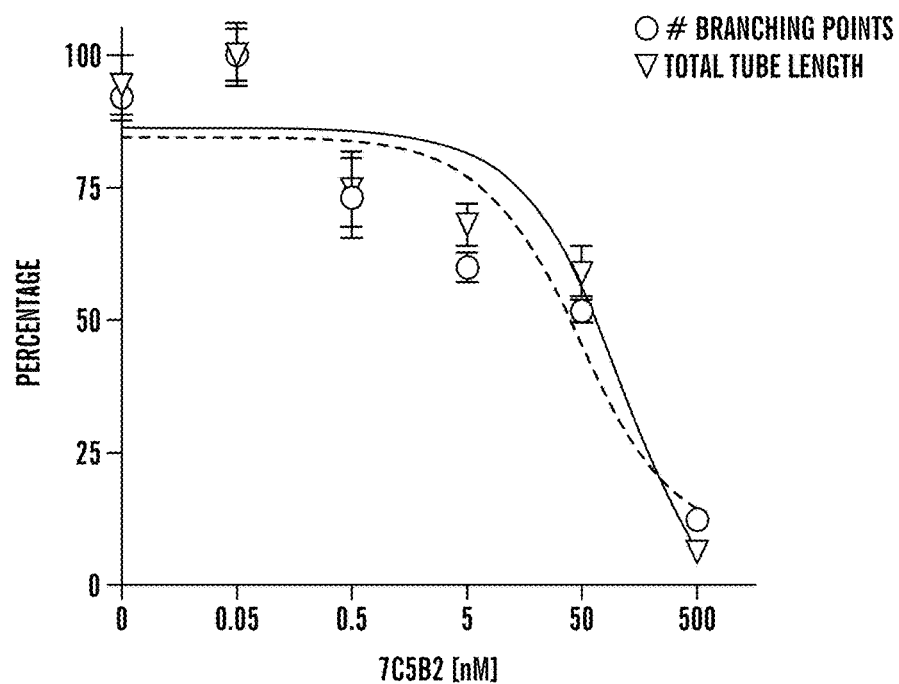
*FIG. 11C*

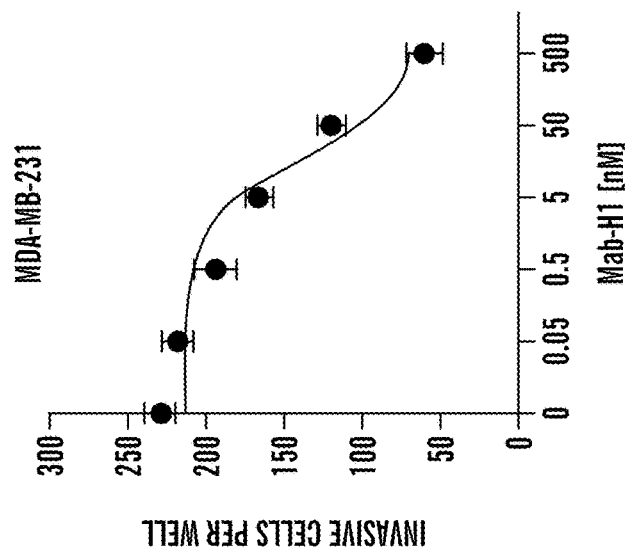
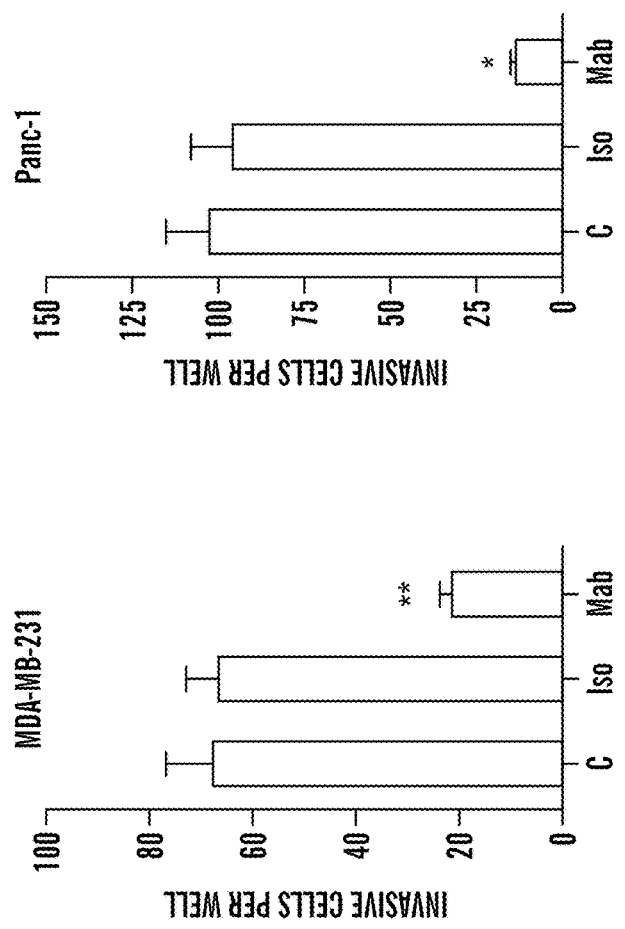
FIG. 12A
FIG. 12B
FIG. 12C

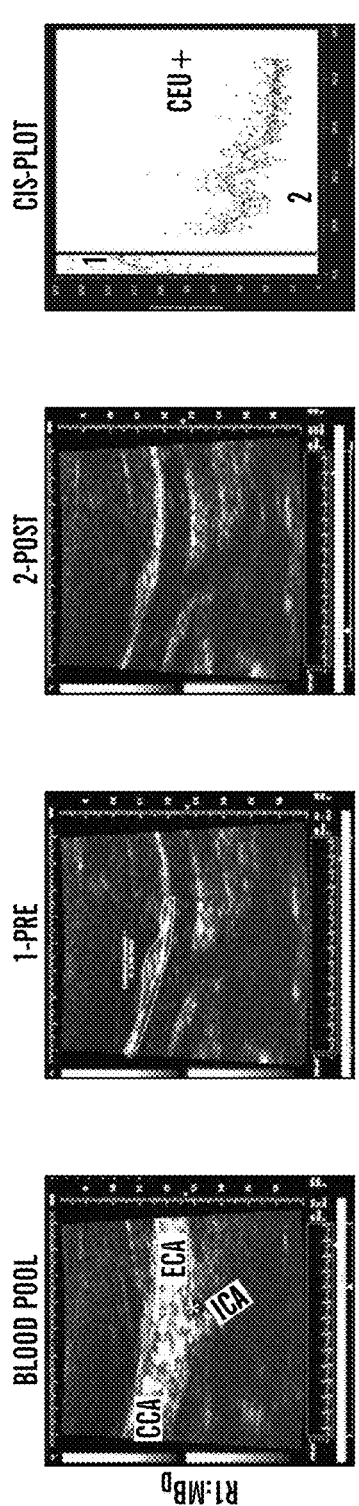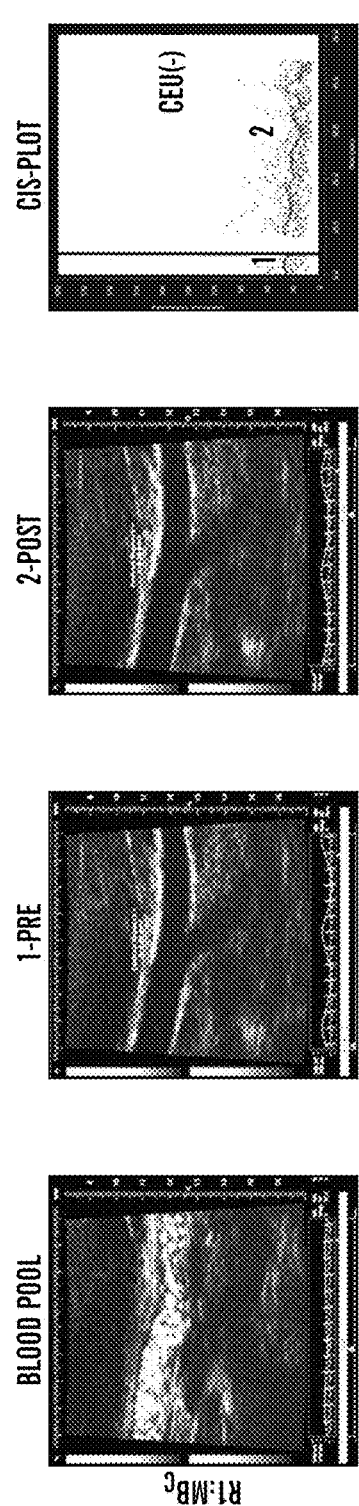
FIG. 19A
FIG. 19B

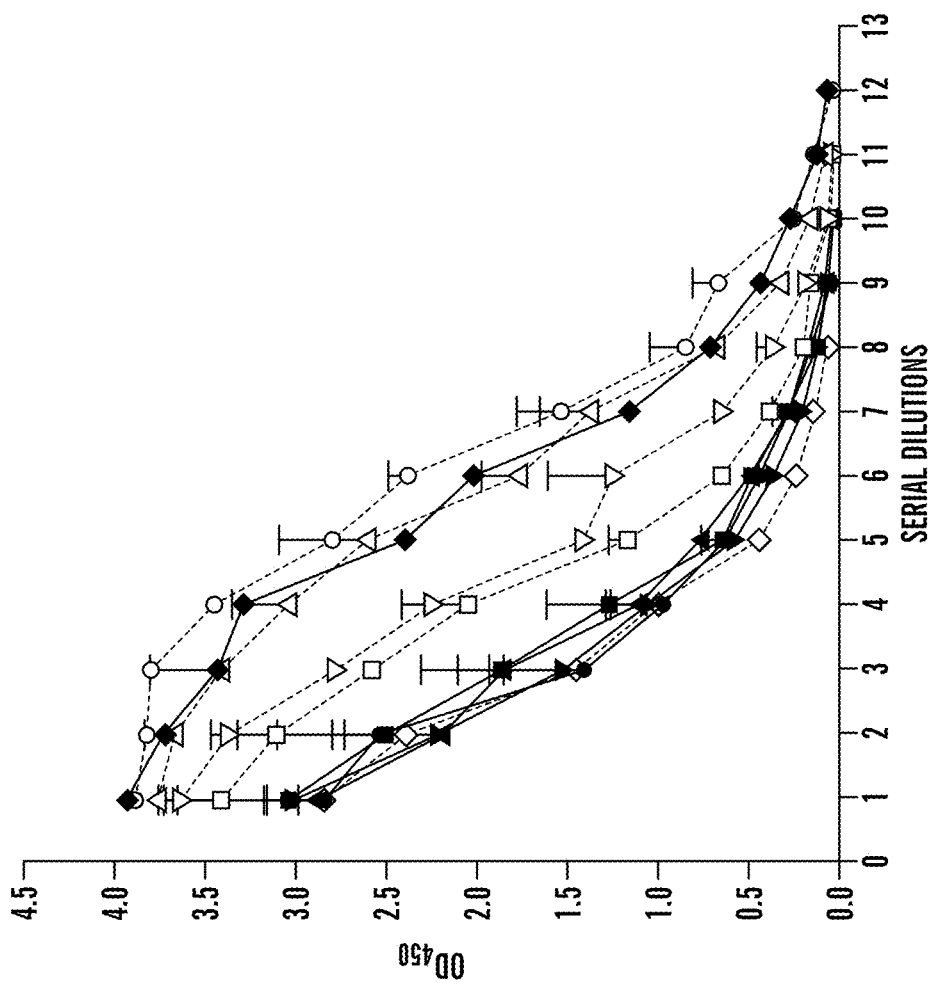
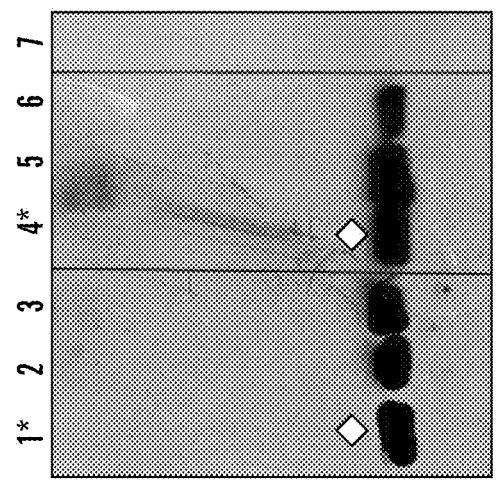
FIG. 28A
FIG. 28B

7C5B2 Hybridoma Heavy Chain Sequences

```
         10        20        30        40        50        60        70        80        90       100
CAGGTGCAACTGAAGGAGTCAGGACCTGGCCTGGTGGCGCCCTCACAGAGCCTGTCCATTACCTGCACTGTGTCTCTGGGTTTCTCATTAACCAGGTATGATA
 Q  V  Q  L  K  E  S  G  P  G  L  V  A  P  S  Q  S  L  S  I  T  C  T  V  S  G  F  S  L  T  S  Y  D
                        10                      20                      30

110       120       130       140       150       160       170       180       190       200
TAAGCTGGATTCGCCAGCCACCAGGAAAGGGTCTGGAGTGGCTTGGAGTAATAATGGACTGGTGGAAGGACAAAATTATAATTCAGCTTCATGTCCAGACT
    S  W  I  R  Q  P  P  G  K  G  L  E  W  L  G  V  I  M  W  G  G  T  N  Y  N  S  A  F  M  S  R  L
                40                      50                      60

210       220       230       240       250       260       270       280       290       300
GAGCATCAGCAAGGACAACTCCAAGAGCCAAGTTTTCTTAAAAATGAACAGTCTGCAAACTGATGACACAGCCATATATTACTGTGTAAGAGATGTCCGAGAT
 S  I  S  K  D  N  S  K  S  Q  V  F  L  K  M  N  S  L  Q  T  D  D  T  A  I  Y  Y  C  V  R  D  V  R  D
                70              80  82 a b c                      90

310       320       330       340       350
TAGGAGGGGTACTTCGACGTCTGGGGCGCAGGGACCACGGTCACCGTCTCCTCA
  Y  D  G  W  Y  F  D  V  W  G  A  G  T  T  V  T  V  S  S
100 a b c                      110
```

FIG. 34

7C5B2 Hybridoma Light Chain Sequences

```
        10         20         30         40         50         60         70         80         90        100
GATGTTTTGATGACCCAAACTCCACTCTCCCTGCCTGTCAGTCTTGGAGATCAAGCCTCCATCTCTTGCAGATCTAGTAAGAGTCTAGAAGCAATTGTACATAGTAATG
 D  V  L  M  T  Q  T  P  L  S  L  P  V  S  L  G  D  Q  A  S  I  S  C  R  S  S  K  S  L  E  N  S  N  G  N  N
                    10                  20                            27 a  b  c  d  e 110        120        130        140        150        160        170        180        190        200
GAAAACACCTATTTAGAATGGTACCTGCAGAAACCAGGCCAGTCTCCAAAGCTCCTGATCTACAAAGTTTCCAACCGATTTTCTGGGGTCCCAGACAGGTT
 C  N  T  Y  L  E  W  Y  L  Q  K  P  G  Q  S  P  K  L  L  I  Y  K  V  S  N  R  F  S  G  V  P  D  R  F
    30                        40                             50                            60

210        220        230        240        250        260        270        280        290        300
CAGTGGCAGTGGATCAGGGACAGATTTCACACTCAAGATCAGCAGAGTGGAGGCTGAGGATCTGGGAGTTTATTACTGCTTTCAAGGTTCACAATGTCCG
 S  G  S  G  S  G  T  D  F  T  L  K  I  S  R  V  E  A  E  D  L  G  V  Y  Y  C  F  Q  G  S  Q  C  P
                70                            80                            90

310        320        330
TACACGTTCGGAGGGGGGACCAAGCTGGAAATAAAAA
 Y  T  F  G  G  G  T  K  L  E  I  K
       100
```

FIG. 35

Composite Human Anti-hDEspR VH1 Heavy Chain Sequences

```
        10         20         30         40         50         60         70         80         90        100
CAGGTGCAGCTGCAGGAGAGCGGGCCCTGGCCTGGTGAAGCCTAGCCAGACCCTGAGCCTGACCTGCACCGTGAGCGGCTTCAGCCTGACCAGCTACGGAGACA
 Q  V  Q  L  Q  E  S  G  P  G  L  V  K  P  S  Q  T  L  S  L  T  C  T  V  S  G  F  S  L  T  S  Y  G  D
                  10                  20                                                30

110        120        130        140        150        160        170        180        190        200
TGAGCTGGATCAGACAGCCTCCTGGCAAGGGCCTGGAGTGGCTGGGCGTGATCTGGACCGGCGGCACCAACTACAACAGCGCCTTCATGAGCAGACT
  M  S  W  I  R  Q  P  P  G  K  G  L  E  W  L  G  V  I  W  T  G  G  T  N  Y  N  S  A  F  M  S  R  L
             40                              50                              60

210        220        230        240        250        260        270        280        290        300
ACCATCAGCAAGGACAACAGCAAGAGCACCGTGTACCTGCAGATGAACAGCCTGAGAGCCGAGGACACCGCCATCTACTACTGCGTGAGAGACAGAGAC
  T  I  S  K  D  N  S  K  S  T  V  Y  L  Q  M  N  S  L  R  A  E  D  T  A  I  Y  Y  C  V  R  D  R  D
     70                          80    82 a  b  c                                       90

310        320        330        340        350
TAGGAGACCGGCTACTTCGACGTGTGGGGCCAGGGCACCACCGTGACCGTGAGCAGC
  Y  D  W  F  D  V  W  G  Q  G  T  T  V  T  V  S  S
100 a  b  c                            110
```

```
        10          20          30          40          50          60          70          80          90         100
CAGGTGCAGCTGCAGGAGAGCGGGCCCTGGGTGAAGCCTAGCCAGACCCTGAGCCTGACCTGCACCGTGAGCGGCTTCAGCCTGAGCACCAGCTACGACA
 Q  V  Q  L  Q  E  S  G  P  W  V  K  P  S  Q  T  L  S  L  T  C  T  V  S  G  F  S  L  S  T  S  Y  D
                            10                      20                      30

110         120         130         140         150         160         170         180         190         200
TCAGCTGGATCAGACAGCCTCCTGGCAAGGGCCTGGAGTGGCTGGGCGTGATCTGGACCGGGGGCACCAACTACAACAGCGCCTTCATGAGCAGACT
 I  S  W  I  R  Q  P  P  G  K  G  L  E  W  L  G  V  I  W  T  G  G  T  N  Y  N  S  A  F  M  S  R  L
            40                      50                      60

210         220         230         240         250         260         270         280         290         300
GACCATCAGCAAGGACAACAGCAAGAACACCGTGTACCTGCAGATGAACAGCCTGAGAGCCGAGGACACCGCCATCTACTACTGCGTGAGAGACAGAGACT
 T  I  S  K  D  N  S  K  N  T  V  Y  L  Q  M  N  S  L  R  A  E  D  T  A  I  Y  Y  C  V  R  D  R  D
            70                      80  82 a b c                90

310         320         330         340         350
TACGACAGCGGTGTACTTCGAGGTGTGGGGCCAGGGCACCACCGTGACCGTGAGCAGC
 Y  D  S  G  V  Y  F  E  V  W  G  Q  G  T  T  V  T  V  S  S
            100 a b c                    110
```

```
         10         20         30         40         50         60         70         80         90        100
CAGGTGCAGCTGCAGGAGAGCGGGCCCTGGCCTGGTGAAGCCTAGCCAGACCCTGAGCCTGACCTGCACCGTGAGCGGCTTCAGCCTGAGCAGCTACGACACA
 Q   V   Q   L   Q   E   S   G   P   G   L   V   K   P   S   Q   T   L   S   L   T   C   T   V   S   G   F   S   L   S   S   Y   D   T
                             10                          20                          30

110        120        130        140        150        160        170        180        190        200
TCAGTGTGGATCAGACAGCCTCCTGGCCAAGGGCCTGGAGTGGCTGGGCGTGATCTGGACCGGGGGCACCAACTACAACAGCGCCTTCATGAGCAGACTG
 S   V   W   I   R   Q   P   P   G   K   G   L   E   W   L   G   V   I   W   T   G   G   T   N   Y   N   S   A   F   M   S   R   L
                 40                          50                          60

210        220        230        240        250        260        270        280        290        300
ACCATCAGCAAGGACAACAGCAAGAACACCGTGTACCTGCAGATGAACAGCCTGAGAGCCGAGGACACCGCCGTGTACTACTGCGTGAGAGACAGAGAC
 T   I   S   K   D   N   S   K   N   T   V   Y   L   Q   M   N   S   L   R   A   E   D   T   A   V   Y   Y   C   V   R   D   R   D
         70                  80  82a  b  c                     90

310        320        330        340        350
TACGACGGCTGGTACTTCGACGTGTGGGGCCAGGGCACCACCGTGACCGTGAGCAGC
 Y   D   G   W   Y   F   D   V   W   G   Q   G   T   T   V   T   V   S   S
        100 a  b  c                  110
```

FIG. 39

```
        10         20         30         40         50         60         70         80         90        100
CAGGTGCAGCTGCAGGAGAGCGGGCCCCTGGCCTGGTGAAGCCTAGCCAGACCCTGAGCCTGACCTGCACCGTGAGCGGCTTCAGCCTGACCAGCTACGACA
 Q  V  Q  L  Q  E  S  G  P  G  L  V  K  P  S  Q  T  L  S  L  T  C  T  V  S  G  F  S  L  T  S  Y  D
                        10                            20                            30

110        120        130        140        150        160        170        180        190        200
TCAGCTGGATCAGACAGCCTCCTGGCAAGGGCCTGGAGTGGCTGGGCGTGATCTGGACCGGCGGCACAACAGACTACAACAGCGCCTTCATGAGCAGACT
    S  W  I  R  Q  P  P  G  K  G  L  E  W  L  G  V  I  W  T  G  G  T  T  D  Y  N  S  A  F  M  S  R  L
                        40                            50                            60

210        220        230        240        250        260        270        280        290        300
GACCATCAGCAAGGACAACAGCAAGAACACCGTGTACCTGCAGATGAACAGCCTGAGAGCCGAGGACACCGCCGTGTACTACTGTGTGAGAGACAGAGAC
 T  I  S  K  D  N  S  K  N  T  V  Y  L  Q  M  N  S  L  R  A  E  D  T  A  V  Y  Y  C  V  R  D  R  D
                        70                  80   82  a  b  c                        90

310        320        330        340        350
TACGACGGCTGGTACTTCGACGTGTGGGGCCAGGGCACCACCGTGACCGTGAGCAGC
 Y  D  G  W  Y  F  D  V  W  G  Q  G  T  T  V  T  V  S  S
100  a  b  c                      110
```

*FIG. 40*

GACGTGCTGATGACCCAGAGCCCTCTGAGCCTGCCTGTGACCCTGGGCCAGCCTGCCAGCATCAGCTGCAGAAGCAGCCAGAGCATCGTGCACAGCAACG
D  V  L  M  T  Q  S  P  L  S  L  P  V  T  L  G  Q  P  A  S  I  S  C  R  S  S  Q  S  I  V  H  S  N
                                                                                    27 a  b  c  d  e

GCAACACCTACCTGGAGTGGTACCTGCAGAAGCCTGGCCAGAGCCCTCAGCTGCTGATCTACAAGGTGAGCAACAGATTCAGCGGCGTGCCTGACAGATT
G  N  T  Y  L  E  W  Y  L  Q  K  P  G  Q  S  P  Q  L  L  I  Y  K  V  S  N  R  F  S  G  V  P  D  R  F

CAGCGGCAGCGGCAGCGGCACCGACTTCACCCTGAAGATCAGCAGAGTGGAGGCCGAGGACGTGGGCGTGTACTACTGCTTCCAGGGCAGCCACGTGCCT
S  G  S  G  S  G  T  D  F  T  L  K  I  S  R  V  E  A  E  D  V  G  V  Y  Y  C  F  Q  G  S  H  V  P

TACACCTTCGGCCAGGGCACCAAGCTGGAGATCAAG
Y  T  F  G  Q  G  T  K  L  E  I  K

FIG. 41

```
         10         20         30         40         50         60         70         80         90        100
GACGTGGTGATGACCCAGAGCCCTCTGAGCCTGCCTGTGACCCTGGGCCAGCCAGCCAGCATCAGCTGCCAGAGCCAGAGCATCGTGCACAGCAACGGCAAG
 D  V  V  M  T  Q  S  P  L  S  L  P  V  T  L  G  Q  P  A  S  I  S  C  R  S  Q  S  I  V  H  S  N
                                                   10                    20                 27 a b c d e 110        120        130        140        150        160        170        180        190        200
GCAAGAACCTACCTGGAGTGGTACCTGCAGAAGCCTGGCCAGAGCCCTCAGCTGCTGATCTACAAGGTGAGCAACAGATTCAGCGGGGTGCCTGACAGATT
  G  T  Y  L  E  W  Y  L  Q  K  P  G  Q  S  P  Q  L  L  I  Y  K  V  S  N  R  F  S  G  V  P  D  R  F
        30                    40                      50                       60

210        220        230        240        250        260        270        280        290        300
CAGCGGCAGCGGCAGCGGCACCGACTTCACCCTGAAGATCAGCAGAGTGGAGGCCGAGGACGTGGGCGTGTACTACTGCTTCCAGGGCAGCCACGTGCCT
  S  G  S  G  S  G  T  D  F  T  L  K  I  S  R  V  E  A  E  D  V  G  V  Y  Y  C  F  Q  G  S  H  V  P
             70                      80                      90

310        320        330
TACACCTTCGGCCAGGGCACCAAGCTGGAGATCAAG
  Y  T  F  G  Q  G  T  K  L  E  I  K
                100
```

FIG. 42

SEQUENCE LISTING

<160> NUMBER OF SEQ ID NOS: 27

<210> SEQ ID NO 1
<211> LENGTH: 85
<212> TYPE: PRT
<213> ORGANISM: Homo sapiens

<400> SEQUENCE: 1

Met Thr Met Phe Lys Gly Ser Asn Glu Met Lys Ser Arg Trp Asn Trp
1               5                   10                  15

Gly Ser Ile Thr Cys Ile Ile Cys Phe Thr Cys Val Gly Ser Gln Leu
            20                  25                  30

Ser Met Ser Ser Lys Ala Ser Asn Phe Ser Gly Pro Leu Gln Leu
        35                  40                  45

Tyr Gln Arg Glu Leu Glu Ile Phe Ile Val Leu Thr Asp Val Pro Asn
    50                  55                  60

Tyr Arg Leu Ile Lys Glu Asn Ser His Leu His Thr Ile Val Asp
65                  70                  75                  80

Gln Gly Arg Thr Val
                85

<210> SEQ ID NO 2
<211> LENGTH: 26
<212> TYPE: PRT
<213> ORGANISM: Homo sapiens

<400> SEQUENCE: 2

Met Asn Phe Leu Leu Ser Trp Val His Trp Ser Leu Ala Leu Leu Leu
1               5                   10                  15

Tyr Leu His His Ala Lys Trp Ser Gln Ala
            20                  25

<210> SEQ ID NO 3
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(357)

<400> SEQUENCE: 3 cag gtg caa ctg aag gag tca gga cct ggc ctg gtg gcg ccc tca cag      48
Gln Val Gln Leu Lys Glu Ser Gly Pro Gly Leu Val Ala Pro Ser Gln
1               5                   10                  15 agc ctg tcc att acc tgc act gtc tct ggg ttc tca tta acc agc tat      96
Ser Leu Ser Ile Thr Cys Thr Val Ser Gly Phe Ser Leu Thr Ser Tyr
            20                  25                  30 gat ata agc tgg att cgc cag cca cca gga aag ggt ctg gag tgg ctt     144
Asp Ile Ser Trp Ile Arg Gln Pro Pro Gly Lys Gly Leu Glu Trp Leu
        35                  40                  45 gga gta ata tgg act ggt gga ggc aca aat tat aat tca gct ttc atg     192
Gly Val Ile Trp Thr Gly Gly Gly Thr Asn Tyr Asn Ser Ala Phe Met
    50                  55                  60 tcc aga ctg agc atc agc aag gac aac tcc aag agc caa gtt ttc tta     240
Ser Arg Leu Ser Ile Ser Lys Asp Asn Ser Lys Ser Gln Val Phe Leu
65                  70                  75                  80 aaa atg aac agt ctg caa act gat gac aca gcc ata tat tac tgt gta     288
Lys Met Asn Ser Leu Gln Thr Asp Asp Thr Ala Ile Tyr Tyr Cys Val
                85                  90                  95

```
aga gat cgg gat tac gac ggg tgg tac ttc gat gtc tgg ggc gca ggg     336
Arg Asp Arg Asp Tyr Asp Gly Trp Tyr Phe Asp Val Trp Gly Ala Gly
            100                 105                 110 acc acg gtc acc gtc tcc tca                                         357
Thr Thr Val Thr Val Ser Ser
        115

<210> SEQ ID NO 4
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ser Tyr
            20                  25                  30

Asp Ile Ser Trp Ile Arg Gln Pro Pro Gly Lys Gly Leu Glu Trp Leu
        35                  40                  45

Gly Val Ile Trp Thr Gly Gly Gly Thr Asn Tyr Asn Ser Ala Phe Met
    50                  55                  60

Ser Arg Leu Ser Ile Ser Lys Asp Asn Ser Lys Ser Gln Val Phe Leu
65                  70                  75                  80

Lys Met Asn Ser Leu Gln Thr Asp Asp Thr Ala Ile Tyr Tyr Cys Val
                85                  90                  95

Arg Asp Arg Asp Tyr Asp Gly Trp Tyr Phe Asp Val Trp Gly Ala Gly
            100                 105                 110

Thr Thr Val Thr Val Ser Ser
        115

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Phe Ser Leu Thr Ser Tyr Asp Ile Ser
1               5                   10

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Val Ile Trp Thr Gly Gly Gly Thr Asn Tyr Asn Ser Ala Phe Met Ser
1               5                   10                  15

<210> SEQ ID NO 7
<211> LENGTH: 11
<212> TYPE: PRT
<213> ORGANISM: Artificial Sequence
<220> FEATURE:
<223> OTHER INFORMATION: Description of Artificial Sequence: Synthetic
```

```
                              peptide

<400> SEQUENCE: 7

Asp Arg Asp Tyr Asp Gly Trp Tyr Phe Asp Val
1               5                   10

<210> SEQ ID NO 8
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 8 gat gtt ttg atg acc caa act cca ctc tcc ctg cct gtc agt ctt gga      48
Asp Val Leu Met Thr Gln Thr Pro Leu Ser Leu Pro Val Ser Leu Gly
1               5                   10                  15 gat caa gcc tcc atc tct tgc aga tct agt cag agc att gta cat agt      96
Asp Gln Ala Ser Ile Ser Cys Arg Ser Ser Gln Ser Ile Val His Ser
            20                  25                  30 aat gga aac acc tat tta gaa tgg tac ctg cag aaa cca ggc cag tct     144
Asn Gly Asn Thr Tyr Leu Glu Trp Tyr Leu Gln Lys Pro Gly Gln Ser
        35                  40                  45 cca aag ctc ctg atc tac aaa gtt tcc aac cga ttt tct ggg gtc cca     192
Pro Lys Leu Leu Ile Tyr Lys Val Ser Asn Arg Phe Ser Gly Val Pro
    50                  55                  60 gac agg ttc agt ggc agt gga tca ggg aca gat ttc aca ctc aag atc     240
Asp Arg Phe Ser Gly Ser Gly Ser Gly Thr Asp Phe Thr Leu Lys Ile
65                  70                  75                  80 agc aga gtg gag gct gag gat ctg gga gtt tat tac tgc ttt caa ggt     288
Ser Arg Val Glu Ala Glu Asp Leu Gly Val Tyr Tyr Cys Phe Gln Gly
                85                  90                  95 tca cat gtt ccg tac acg ttc gga ggg ggg acc aag ctg gaa ata aaa     336
Ser His Val Pro Tyr Thr Phe Gly Gly Gly Thr Lys Leu Glu Ile Lys
            100                 105                 110

<210> SEQ ID NO 9
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
```

<210> SEQ ID NO 10
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Arg Ser Ser Gln Ser Ile Val His Ser Asn Gly Asn Thr Tyr Leu Glu
1               5                   10                  15

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Lys Val Ser Asn Arg Phe Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Phe Gln Gly Ser His Val Pro Tyr Thr
1               5

<210> SEQ ID NO 13
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Ser Tyr
            20                  25                  30

Asp Ile Ser Trp Ile Arg Gln Pro Pro Gly Lys Gly Leu Glu Trp Leu
        35                  40                  45

Gly Val Ile Trp Thr Gly Gly Gly Thr Asn Tyr Asn Ser Ala Phe Met
    50                  55                  60

Ser Arg Leu Thr Ile Ser Lys Asp Asn Ser Lys Ser Thr Val Tyr Leu
65                  70                  75                  80

Gln Met Asn Ser Leu Arg Ala Glu Asp Thr Ala Ile Tyr Tyr Cys Val
                85                  90                  95

Arg Asp Arg Asp Tyr Asp Gly Trp Tyr Phe Asp Val Trp Gly Gln Gly
                100                 105                 110

Thr Thr Val Thr Val Ser Ser
            115

```
<210> SEQ ID NO 14
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Ser Tyr
            20                  25                  30

Asp Ile Ser Trp Ile Arg Gln Pro Pro Gly Lys Gly Leu Glu Trp Leu
        35                  40                  45

Gly Val Ile Trp Thr Gly Gly Gly Thr Asn Tyr Asn Ser Ala Phe Met
    50                  55                  60

Ser Arg Leu Thr Ile Ser Lys Asp Asn Ser Lys Asn Thr Val Tyr Leu
65                  70                  75                  80

Gln Met Asn Ser Leu Arg Ala Glu Asp Thr Ala Ile Tyr Tyr Cys Val
                85                  90                  95

Arg Asp Arg Asp Tyr Asp Gly Trp Tyr Phe Asp Val Trp Gly Gln Gly
            100                 105                 110

Thr Thr Val Thr Val Ser Ser
        115

<210> SEQ ID NO 15
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Ser Tyr
            20                  25                  30

Asp Ile Ser Trp Ile Arg Gln Pro Pro Gly Lys Gly Leu Glu Trp Leu
        35                  40                  45

Gly Val Ile Trp Thr Gly Gly Gly Thr Asn Tyr Asn Ser Ala Phe Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Ile Tyr Tyr Cys Val
                85                  90                  95

Arg Asp Arg Asp Tyr Asp Gly Trp Tyr Phe Asp Val Trp Gly Gln Gly
            100                 105                 110

Thr Thr Val Thr Val Ser Ser
        115

<210> SEQ ID NO 16
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 16

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Ser Tyr
            20                  25                  30

Asp Ile Ser Trp Ile Arg Gln Pro Pro Gly Lys Gly Leu Glu Trp Leu
        35                  40                  45

Gly Val Ile Trp Thr Gly Gly Gly Thr Asn Tyr Asn Ser Ala Phe Met
    50                  55                  60

Ser Arg Leu Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Val
                85                  90                  95

Arg Asp Arg Asp Tyr Asp Gly Trp Tyr Phe Asp Val Trp Gly Gln Gly
            100                 105                 110

Thr Thr Val Thr Val Ser Ser
        115

<210> SEQ ID NO 17
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 17

Gln Val Gln Leu Gln Glu Ser Gly Pro Gly Leu Val Lys Pro Ser Gln
1               5                   10                  15

Thr Leu Ser Leu Thr Cys Thr Val Ser Gly Phe Ser Leu Thr Ser Tyr
            20                  25                  30

Asp Ile Ser Trp Ile Arg Gln Pro Pro Gly Lys Gly Leu Glu Trp Leu
        35                  40                  45

Gly Val Ile Trp Thr Gly Gly Gly Thr Asn Tyr Asn Ser Ala Phe Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Val
                85                  90                  95

Arg Asp Arg Asp Tyr Asp Gly Trp Tyr Phe Asp Val Trp Gly Gln Gly
            100                 105                 110

Thr Thr Val Thr Val Ser Ser
        115

<210> SEQ ID NO 18
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Asp Val Leu Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser

```
                    35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gln Gly Thr Lys Leu Glu Ile Lys
                100                 105                 110
```

<210> SEQ ID NO 19
<211> LENGTH: 112
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 19

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Ile Val His Ser
                20                  25                  30

Asn Gly Asn Thr Tyr Leu Glu Trp Tyr Leu Gln Lys Pro Gly Gln Ser
            35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Gly
                85                  90                  95

Ser His Val Pro Tyr Thr Phe Gly Gln Gly Thr Lys Leu Glu Ile Lys
                100                 105                 110
```

<210> SEQ ID NO 20
<211> LENGTH: 9
<212> TYPE: PRT
<213> ORGANISM: Homo sapiens

<400> SEQUENCE: 20

```
Met Thr Met Phe Lys Gly Ser Asn Glu
1               5
```

<210> SEQ ID NO 21
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(357)

<400> SEQUENCE: 21

```
cag gtg cag ctg cag gag agc ggc cct ggc ctg gtg aag cct agc cag        48
Gln Val Gln Leu Gln Glu Ser Gly Pro Gly Leu Val Lys Pro Ser Gln
1               5                   10                  15 acc ctg agc ctg acc tgc acc gtg agc ggc ttc agc ctg acc agc tac        96
Thr Leu Ser Leu Thr Cys Thr Val Ser Gly Phe Ser Leu Thr Ser Tyr
                20                  25                  30
```

```
gac atc agc tgg atc aga cag cct cct ggc aag ggc ctg gag tgg ctg      144
Asp Ile Ser Trp Ile Arg Gln Pro Pro Gly Lys Gly Leu Glu Trp Leu
        35                  40                  45 ggc gtg atc tgg acc ggc ggc ggc acc aac tac aac agc gcc ttc atg      192
Gly Val Ile Trp Thr Gly Gly Gly Thr Asn Tyr Asn Ser Ala Phe Met
 50                  55                  60 agc aga ctg acc atc agc aag gac aac agc aag agc acc gtg tac ctg      240
Ser Arg Leu Thr Ile Ser Lys Asp Asn Ser Lys Ser Thr Val Tyr Leu
 65                  70                  75                  80 cag atg aac agc ctg aga gcc gag gac acc gcc atc tac tac tgc gtg      288
Gln Met Asn Ser Leu Arg Ala Glu Asp Thr Ala Ile Tyr Tyr Cys Val
                 85                  90                  95 aga gac aga gac tac gac ggc tgg tac ttc gac gtg tgg ggc cag ggc      336
Arg Asp Arg Asp Tyr Asp Gly Trp Tyr Phe Asp Val Trp Gly Gln Gly
                100                 105                 110 acc acc gtg acc gtg agc agc                                          357
Thr Thr Val Thr Val Ser Ser
        115

<210> SEQ ID NO 22
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(357)

<400> SEQUENCE: 22 cag gtg cag ctg cag gag agc ggc cct ggc ctg gtg aag cct agc cag       48
Gln Val Gln Leu Gln Glu Ser Gly Pro Gly Leu Val Lys Pro Ser Gln
 1               5                  10                  15 acc ctg agc ctg acc tgc acc gtg agc ggc ttc agc ctg acc agc tac       96
Thr Leu Ser Leu Thr Cys Thr Val Ser Gly Phe Ser Leu Thr Ser Tyr
                 20                  25                  30 gac atc agc tgg atc aga cag cct cct ggc aag ggc ctg gag tgg ctg      144
Asp Ile Ser Trp Ile Arg Gln Pro Pro Gly Lys Gly Leu Glu Trp Leu
        35                  40                  45 ggc gtg atc tgg acc ggc ggc ggc acc aac tac aac agc gcc ttc atg      192
Gly Val Ile Trp Thr Gly Gly Gly Thr Asn Tyr Asn Ser Ala Phe Met
 50                  55                  60 agc aga ctg acc atc agc aag gac aac agc aag aac acc gtg tac ctg      240
Ser Arg Leu Thr Ile Ser Lys Asp Asn Ser Lys Asn Thr Val Tyr Leu
 65                  70                  75                  80 cag atg aac agc ctg aga gcc gag gac acc gcc atc tac tac tgc gtg      288
Gln Met Asn Ser Leu Arg Ala Glu Asp Thr Ala Ile Tyr Tyr Cys Val
                 85                  90                  95 aga gac aga gac tac gac ggc tgg tac ttc gac gtg tgg ggc cag ggc      336
Arg Asp Arg Asp Tyr Asp Gly Trp Tyr Phe Asp Val Trp Gly Gln Gly
                100                 105                 110 acc acc gtg acc gtg agc agc                                          357
Thr Thr Val Thr Val Ser Ser
        115

<210> SEQ ID NO 23
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
```

```
<221> NAME/KEY: CDS
<222> LOCATION: (1)..(357)

<400> SEQUENCE: 23 cag gtg cag ctg cag gag agc ggc cct ggc ctg gtg aag cct agc cag      48
Gln Val Gln Leu Gln Glu Ser Gly Pro Gly Leu Val Lys Pro Ser Gln
1               5                   10                  15 acc ctg agc ctg acc tgc acc gtg agc ggc ttc agc ctg acc agc tac      96
Thr Leu Ser Leu Thr Cys Thr Val Ser Gly Phe Ser Leu Thr Ser Tyr
            20                  25                  30 gac atc agc tgg atc aga cag cct cct ggc aag ggc ctg gag tgg ctg     144
Asp Ile Ser Trp Ile Arg Gln Pro Pro Gly Lys Gly Leu Glu Trp Leu
        35                  40                  45 ggc gtg atc tgg acc ggc ggc acc aac tac aac agc gcc ttc atg         192
Gly Val Ile Trp Thr Gly Gly Thr Asn Tyr Asn Ser Ala Phe Met
    50                  55                  60 agc aga ttc acc atc agc aag gac aac agc aag aac acc gtg tac ctg     240
Ser Arg Phe Thr Ile Ser Lys Asp Asn Ser Lys Asn Thr Val Tyr Leu
65                  70                  75                  80 cag atg aac agc ctg aga gcc gag gac acc gcc atc tac tac tgc gtg     288
Gln Met Asn Ser Leu Arg Ala Glu Asp Thr Ala Ile Tyr Tyr Cys Val
                85                  90                  95 aga gac aga gac tac gac ggc tgg tac ttc gac gtg tgg ggc cag ggc     336
Arg Asp Arg Asp Tyr Asp Gly Trp Tyr Phe Asp Val Trp Gly Gln Gly
            100                 105                 110 acc acc gtg acc gtg agc agc                                         357
Thr Thr Val Thr Val Ser Ser
        115

<210> SEQ ID NO 24
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(357)

<400> SEQUENCE: 24 cag gtg cag ctg cag gag agc ggc cct ggc ctg gtg aag cct agc cag      48
Gln Val Gln Leu Gln Glu Ser Gly Pro Gly Leu Val Lys Pro Ser Gln
1               5                   10                  15 acc ctg agc ctg acc tgc acc gtg agc ggc ttc agc ctg acc agc tac      96
Thr Leu Ser Leu Thr Cys Thr Val Ser Gly Phe Ser Leu Thr Ser Tyr
            20                  25                  30 gac atc agc tgg atc aga cag cct cct ggc aag ggc ctg gag tgg ctg     144
Asp Ile Ser Trp Ile Arg Gln Pro Pro Gly Lys Gly Leu Glu Trp Leu
        35                  40                  45 ggc gtg atc tgg acc ggc ggc acc aac tac aac agc gcc ttc atg         192
Gly Val Ile Trp Thr Gly Gly Thr Asn Tyr Asn Ser Ala Phe Met
    50                  55                  60 agc aga ctg acc atc agc aag gac aac agc aag aac acc gtg tac ctg     240
Ser Arg Leu Thr Ile Ser Lys Asp Asn Ser Lys Asn Thr Val Tyr Leu
65                  70                  75                  80 cag atg aac agc ctg aga gcc gag gac acc gcc gtg tac tac tgc gtg     288
Gln Met Asn Ser Leu Arg Ala Glu Asp Thr Ala Val Tyr Tyr Cys Val
                85                  90                  95 aga gac aga gac tac gac ggc tgg tac ttc gac gtg tgg ggc cag ggc     336
Arg Asp Arg Asp Tyr Asp Gly Trp Tyr Phe Asp Val Trp Gly Gln Gly
            100                 105                 110
```

```
acc acc gtg acc gtg agc agc                                              357
Thr Thr Val Thr Val Ser Ser
        115

<210> SEQ ID NO 25
<211> LENGTH: 357
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(357)

<400> SEQUENCE: 25 cag gtg cag ctg cag gag agc ggc cct ggc ctg gtg aag cct agc cag     48
Gln Val Gln Leu Gln Glu Ser Gly Pro Gly Leu Val Lys Pro Ser Gln
1               5                   10                  15 acc ctg agc ctg acc tgc acc gtg agc ggc ttc agc ctg acc agc tac     96
Thr Leu Ser Leu Thr Cys Thr Val Ser Gly Phe Ser Leu Thr Ser Tyr
            20                  25                  30 gac atc agc tgg atc aga cag cct cct ggc aag ggc ctg gag tgg ctg    144
Asp Ile Ser Trp Ile Arg Gln Pro Pro Gly Lys Gly Leu Glu Trp Leu
        35                  40                  45 ggc gtg atc tgg acc ggc ggc acc aac tac aac agc gcc ttc atg        192
Gly Val Ile Trp Thr Gly Gly Thr Asn Tyr Asn Ser Ala Phe Met
    50                  55                  60 agc aga ttc acc atc agc aag gac aac agc aag aac acc gtg tac ctg    240
Ser Arg Phe Thr Ile Ser Lys Asp Asn Ser Lys Asn Thr Val Tyr Leu
65                  70                  75                  80 cag atg aac agc ctg aga gcc gag gac acc gcc gtg tac tac tgc gtg    288
Gln Met Asn Ser Leu Arg Ala Glu Asp Thr Ala Val Tyr Tyr Cys Val
                85                  90                  95 aga gac aga gac tac gac ggc tgg tac ttc gac gtg tgg ggc cag ggc    336
Arg Asp Arg Asp Tyr Asp Gly Trp Tyr Phe Asp Val Trp Gly Gln Gly
            100                 105                 110 acc acc gtg acc gtg agc agc                                        357
Thr Thr Val Thr Val Ser Ser
        115

<210> SEQ ID NO 26
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 26 gac gtg ctg atg acc cag agc cct ctg agc ctg cct gtg acc ctg ggc     48
Asp Val Leu Met Thr Gln Ser Pro Leu Ser Leu Pro Val Thr Leu Gly
1               5                   10                  15 cag cct gcc agc atc agc tgc aga agc agc cag agc atc gtg cac agc     96
Gln Pro Ala Ser Ile Ser Cys Arg Ser Ser Gln Ser Ile Val His Ser
            20                  25                  30 aac ggc aac acc tac ctg gag tgg tac ctg cag aag cct ggc cag agc    144
Asn Gly Asn Thr Tyr Leu Glu Trp Tyr Leu Gln Lys Pro Gly Gln Ser
        35                  40                  45 cct cag ctg ctg atc tac aag gtg agc aac aga ttc agc ggc gtg cct    192
Pro Gln Leu Leu Ile Tyr Lys Val Ser Asn Arg Phe Ser Gly Val Pro
    50                  55                  60
```

```
gac aga ttc agc ggc agc ggc agc ggc acc gac ttc acc ctg aag atc        240
Asp Arg Phe Ser Gly Ser Gly Ser Gly Thr Asp Phe Thr Leu Lys Ile
 65                  70                  75                  80 agc aga gtg gag gcc gag gac gtg ggc gtg tac tac tgc ttc cag ggc        288
Ser Arg Val Glu Ala Glu Asp Val Gly Val Tyr Tyr Cys Phe Gln Gly
                 85                  90                  95 agc cac gtg cct tac acc ttc ggc cag ggc acc aag ctg gag atc aag        336
Ser His Val Pro Tyr Thr Phe Gly Gln Gly Thr Lys Leu Glu Ile Lys
            100                 105                 110

<210> SEQ ID NO 27
<211> LENGTH: 336
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (1)..(336)

<400> SEQUENCE: 27 gac gtg gtg atg acc cag agc cct ctg agc ctg cct gtg acc ctg ggc         48
Asp Val Val Met Thr Gln Ser Pro Leu Ser Leu Pro Val Thr Leu Gly
  1               5                  10                  15 cag cct gcc agc atc agc tgc aga agc agc cag agc atc gtg cac agc         96
Gln Pro Ala Ser Ile Ser Cys Arg Ser Ser Gln Ser Ile Val His Ser
                 20                  25                  30 aac ggc aac acc tac ctg gag tgg tac ctg cag aag cct ggc cag agc        144
Asn Gly Asn Thr Tyr Leu Glu Trp Tyr Leu Gln Lys Pro Gly Gln Ser
             35                  40                  45 cct cag ctg ctg atc tac aag gtg agc aac aga ttc agc ggc gtg cct        192
Pro Gln Leu Leu Ile Tyr Lys Val Ser Asn Arg Phe Ser Gly Val Pro
 50                  55                  60 gac aga ttc agc ggc agc ggc agc ggc acc gac ttc acc ctg aag atc        240
Asp Arg Phe Ser Gly Ser Gly Ser Gly Thr Asp Phe Thr Leu Lys Ile
 65                  70                  75                  80 agc aga gtg gag gcc gag gac gtg ggc gtg tac tac tgc ttc cag ggc        288
Ser Arg Val Glu Ala Glu Asp Val Gly Val Tyr Tyr Cys Phe Gln Gly
                 85                  90                  95 agc cac gtg cct tac acc ttc ggc cag ggc acc aag ctg gag atc aag        336
Ser His Val Pro Tyr Thr Phe Gly Gln Gly Thr Lys Leu Glu Ile Lys
            100                 105                 110
```

ANTI-DESPR INHIBITORS AS THERAPEUTICS FOR INHIBITION OF PATHOLOGICAL ANGIOGENESIS AND TUMOR CELL INVASIVENESS AND FOR MOLECULAR IMAGING AND TARGETED DELIVERY

CROSS REFERENCE TO RELATED APPLICATIONS

This application is a continuation application under 35 U.S.C. § 120 of U.S. Ser. No. 13/811,485 filed Mar. 21, 2013, which is a 35 U.S.C. § 371 National Phase Entry Application of International Application No. PCT/US2011/045056 filed 22 Jul. 2011, which designates the U.S., and which claims benefit under 35 U.S.C. § 119(e) of U.S. Provisional Application Ser. No. 61/367,206 filed on 23 Jul. 2010, the contents of which are incorporated herein by reference in their entireties.

GOVERNMENT SUPPORT

This invention was made with Government Support Contract No. RR025771 awarded by the National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Aug. 3, 2017, is named 701586-073092 SL.txt and is 31,150 bytes in size.

FIELD OF THE INVENTION

This invention relates to monoclonal antibodies against DEspR, and their use as therapeutics in the inhibition of pathological angiogenesis and tumor cell invasiveness, as well as diagnostic agents and targeting agents for molecular imaging and targeted delivery of other therapeutic agents.

BACKGROUND

The establishment of a critical role of the angiogenic switch in tumorigenesis has made the rationale behind the development of anti-angiogenesis therapy clear (Hanahan & Weinberg 2007). Unfortunately, the ability to attain long-term efficacy of anti-angiogenesis therapy for all cancer-types, in order to reduce cancer to a dormant, chronic manageable disease without increasing morbidity from side effects, has not yet been achieved (Loges et al. 2010, Ferrara 2009, Abdollahi & Folkman 2009, Bergers & Hanahan 2008).

Cumulative observations indicate that all three FDA-approved VEGF pathway inhibitors (anti-VEGFbevacizumab or Avastin, AntiVEGFR2 sunitinib, and sorafanib) result in only transitory improvements in the form of tumor stasis or shrinkage, and only for certain cancers despite most, if not all cancer types exhibiting pathological angiogenesis (Carmeliet 2005; Bergers and Hanahan 2008). Moreover, while anti-VEGF pathway therapies have reduced primary tumor growth and metastasis in preclinical studies (Crawford & Ferrara 2008), recent mouse tumor model studies have reported that sunitinib and an anti-VEGFR2 antibody, DC101, increased metastasis of tumor cells despite inhibition of primary tumor growth and increased overall survival in some cases (Ebos et al. 2009, Paez-Ribes et al. 2009). Addressing this "antiangiogenesis therapy conundrum," cumulative observations have suggested several mechanisms of evasive and intrinsic resistances (Loges et al. 2010, Ferrara 2009, Abdollahi & Folkman 2009, Bergers & Hanahan 2008) such as: a) activation and/or upregulation of alternative pro angiogenic pathways, b) recruitment of bone marrow-derived pro-angiogenic cells, c) increased pericyte coverage for the tumor vasculature, attenuating the need for VEGF signaling; d) activation and enhancement of invasion and metastasis to provide access to normal tissue vasculature without obligate neovascularization; [for intrinsic resistance]: e) pre-existing multiplicity of redundant pro-angiogenic signals; f) pre-existing inflammatory cell-mediated vascular protection; g) tumor hypovascularity; and h) invasive and metastatic co-option of normal vessels without requisite angiogenesis (Bergers and Hanahan 2008).

SUMMARY OF THE INVENTION

Described herein are novel compositions comprising anti-DEspR antibodies and fragments thereof, including fully human, composite engineered human, humanized, monoclonal, and polyclonal anto-DEspR antibodies and fragments thereof, and methods of their use in a variety of applications, including, but not limited to: 1) anti-angiogenesis therapies and anti-tumor cell invasiveness relevant for treatment of cancer, 2) anti-angiogenesis approaches relevant to treatment of those vascular diseases where pathological angiogenesis plays a role in pathogenesis or progression such as in carotid artery disease, vasa vasorum neovascularization (thus impacting stroke), and vulnerable plaque neovascularization (thus impacting, for example, heart disease), and 3) pro-autophagy approaches pertinent to neurodegenerative diseases wherein increased autophagy can prevent the accumulation of toxic products or misfolded proteins or abnormal proteins as in Alzheimer's disease, Huntington's disease etc.

In addition, the compositions comprising the anti-DEspR antibodies and fragments thereof described herein are useful in diagnostic and imaging methods, such as DEspR-targeted molecular imaging of angiogenesis, which can be used, for example, in monitoring response to therapy, in vivo detection of tumor "angiogenic switch" or vascular mimicry. The compositions comprising the anti-DEspR antibodies and fragments thereof are useful for novel companion diagnostic and/or in vivo-non invasive imaging and/or assessments. Additionally, the value-added benefit of targeted delivery of therapeutic agents using the compositions comprising the anti-DEspR antibodies and fragments thereof is especially important in cancer wherein maximal efficacy is needed with minimal systemic toxicity. Notably, such diagnostics provide novel approaches for anti-angiogenic therapies for use in personalized medicine. Accordingly, the compositions comprising the anti-DEspR antibodies and fragments thereof described herein comprise targeting tools and/or modules for target-specific delivery of therapeutics, in forms such as toxins, drugs, small molecules, peptides, fusion proteins, chimeric proteins, nanoparticles, DNA, siRNA, etc., as well as for combinatorial target-specific diagnostics and therapeutics, termed herein as "theranostics."

Accordingly, provided herein, in some aspects are isolated anti-DEspR antibodies or antibody fragments thereof that specifically bind to DEspR (dual endothelin/VEGF signal peptide receptor) and reduce or inhibit DEspR biological activity.

In some embodiments of these aspects and all such aspects described herein, the anti-DEspR antibody or antibody fragment thereof specifically binds to DEspR comprising the amino acid sequence of SEQ ID NO:1. In some embodiments of these aspects, the antibody or antibody fragment thereof specifically binds to an epitope of DEspR comprising residues 1-9 of SEQ ID NO:1. In some embodiments of these aspects, the antibody or antibody fragment thereof specifically binds to an epitope of DEspR consisting essentially of residues 1-9 of SEQ ID NO: 1. In some embodiments of these aspects, the antibody or antibody fragment thereof specifically binds to an epitope of DEspR consisting of residues 1-9 of SEQ ID NO: 1.

In some embodiments of these aspects and all such aspects described herein, the anti-DEspR antibody or antibody fragment thereof specifically binds to DEspR at a VEGF signal peptide (VEGFsp) binding site. In some such embodiments, the VEGF signal peptide comprises the amino acid sequence of SEQ ID NO:2. In some such embodiments, the VEGF signal peptide consists essentially of the amino acid sequence of SEQ ID NO:2. In some such embodiments, the VEGF signal peptide consists of the amino acid sequence of SEQ ID NO:2.

In some embodiments of these aspects and all such aspects described herein, the anti-DEspR antibody is a monoclonal antibody or antibody fragment thereof.

In some embodiments of these aspects and all such aspects described herein, the anti-DEspR antibody or antibody fragment comprises a variable heavy (VH) chain amino acid sequence comprising a sequence of SEQ ID NO: 4.

In some embodiments of these aspects and all such aspects described herein, the anti-DEspR antibody or antibody fragment comprises a variable light (VL) chain amino acid sequence comprising a sequence of SEQ ID NO: 9.

In some embodiments of these aspects and all such aspects described herein, the anti-DEspR antibody or antibody fragment comprises a variable heavy (VH) chain amino acid sequence comprising a sequence of SEQ ID NO: 4 and a variable light (VL) chain amino acid sequence comprising a sequence of SEQ ID NO: 9.

In some embodiments of these aspects and all such aspects described herein, the anti-DEspR antibody is a humanized antibody or antibody fragment thereof.

In some embodiments of these aspects and all such aspects described herein, the anti-DEspR antibody or antibody fragment comprises one or more heavy chain CDR regions comprising a sequence selected from the group consisting of SEQ ID NO: 5, SEQ ID NO: 6, and SEQ ID NO: 7. In some such embodiments, one or more heavy chain CDR regions consist essentially of a sequence selected from the group consisting of SEQ ID NO: 5, SEQ ID NO: 6, and SEQ ID NO: 7. In some such embodiments, one or more heavy chain CDR regions consist of a sequence selected from the group consisting of SEQ ID NO: 5, SEQ ID NO: 6, and SEQ ID NO: 7.

In some embodiments of these aspects and all such aspects described herein, the anti-DEspR antibody or antibody fragment comprises one or more light chain CDR regions comprising a sequence selected from the group consisting of SEQ ID NO: 10, SEQ ID NO: 11, and SEQ ID NO: 12. In some such embodiments, one or more light chain CDR regions consist essentially of a sequence selected from the group consisting of SEQ ID NO: 10, SEQ ID NO: 11, and SEQ ID NO: 12. In some such embodiments, one or more light chain CDR regions consist of a sequence selected from the group consisting of SEQ ID NO: 10-SEQ ID NO: 11, and SEQ ID NO: 12.

In some embodiments of these aspects and all such aspects described herein, the anti-DEspR antibody or antibody fragment comprises one or more heavy chain CDR regions comprising a sequence selected from the group consisting of SEQ ID NO: 5, SEQ ID NO: 6, and SEQ ID NO: 7, and one or more light chain CDR regions comprising a sequence selected from the group consisting of SEQ ID NO: 10, SEQ ID NO: 11, and SEQ ID NO: 12. In some such embodiments, the one or more heavy chain CDR regions consist essentially of a sequence selected from the group consisting of SEQ ID NO: 5, SEQ ID NO: 6, and SEQ ID NO: 7. In some such embodiments, the one or more heavy chain CDR regions consist of a sequence selected from the group consisting of SEQ ID NO: 5, SEQ ID NO: 6, and SEQ ID NO: 7. In some such embodiments, the one or more light chain CDR regions consist essentially of a sequence selected from the group consisting of SEQ ID NO: 10, SEQ ID NO: 11, and SEQ ID NO: 12. In some such embodiments, the one or more light chain CDR regions consist of a sequence selected from the group consisting of SEQ ID NO: 10-SEQ ID NO: 11, and SEQ ID NO: 12.

In some embodiments of these aspects and all such aspects described herein, the anti-DEspR antibody is a composite antibody or antibody fragment thereof. In some such embodiments, the the anti-DEspR composite antibody or antibody fragment comprises one or more heavy chain CDR regions comprising a sequence selected from the group consisting of SEQ ID NO: 5, SEQ ID NO: 6, and SEQ ID NO: 7. In some such embodiments, the the anti-DEspR composite antibody or antibody fragment comprises one or more heavy chain CDR regions consisting essentially of a sequence selected from the group consisting of SEQ ID NO: 5, SEQ ID NO: 6, and SEQ ID NO: 7. In some such embodiments, the anti-DEspR composite antibody or antibody fragment comprises one or more heavy chain CDR regions consisting of a sequence selected from the group consisting of SEQ ID NO: 5, SEQ ID NO: 6, and SEQ ID NO: 7. In some such embodiments, the the anti-DEspR composite antibody or antibody fragment comprises one or more light chain CDR regions comprising a sequence selected from the group consisting of SEQ ID NO: 10, SEQ ID NO: 11, and SEQ ID NO: 12. In some such embodiments, the the anti-DEspR composite antibody or antibody fragment comprises one or more light chain CDR regions consisting essentially of a sequence selected from the group consisting of SEQ ID NO: 10, SEQ ID NO: 11, and SEQ ID NO: 12. In some such embodiments, the the anti-DEspR composite antibody or antibody fragment comprises one or more light chain CDR regions consists of a sequence selected from the group consisting of SEQ ID NO: 10, SEQ ID NO: 11, and SEQ ID NO: 12.

In some embodiments of these aspects and all such aspects described herein, the anti-DEspR antibody is a composite antibody or antibody fragment thereof comprising a variable heavy (VH) chain amino acid sequence selected from the group consisting of SEQ ID NO: 13-SEQ ID NO: 17. In some embodiments of these aspects and all such aspects described herein, the anti-DEspR antibody is a composite antibody or antibody fragment thereof consisting essentially of a variable heavy (VH) chain amino acid sequence selected from the group consisting of SEQ ID NO: 13-SEQ ID NO: 17. In some embodiments of these aspects and all such aspects described herein, the anti-DEspR antibody is a composite antibody or antibody fragment thereof consisting of a variable heavy (VH) chain amino acid sequence selected from the group consisting of SEQ ID NO: 13-SEQ ID NO: 17.

In some embodiments of these aspects and all such aspects described herein, the anti-DEspR antibody is a composite antibody or antibody fragment thereof comprising a variable light (VL) chain amino acid sequence selected from the group consisting of SEQ ID NO: 18 and SEQ ID NO: 19. In some embodiments of these aspects and all such aspects described herein, the anti-DEspR antibody is a composite antibody or antibody fragment thereof consisting essentially of a variable light (VL) chain amino acid sequence selected from the group consisting of SEQ ID NO: 18 and SEQ ID NO: 19. In some embodiments of these aspects and all such aspects described herein, the anti-DEspR antibody is a composite antibody or antibody fragment thereof consisting of a variable light (VL) chain amino acid sequence selected from the group consisting of SEQ ID NO: 18 and SEQ ID NO: 19.

In other embodiments of these aspects, the anti-DEspR antibody or antibody fragment thereof is an antibody expressed or produced by hybridomas 7C5C55 or G12E8.

In some embodiments of these aspects, the anti-DEspR antibody or antibody fragment thereof displays a similar binding pattern to the binding pattern displayed by an antibody expressed or produced by hybridomas 7C5B2, 7C5C55, or G12E8. In some embodiments of these aspects, the anti-DEspR antibody or antibody fragment thereof displays a similar avidity to the avidity displayed by an antibody expressed or produced by hybridomas 7C5B2, 7C5C55, or G12E8. In some embodiments of these aspects, the anti-DEspR antibody or antibody fragment thereof binds to the same epitope(s) as those epitope(s) bound by an antibody expressed or produced by hybridomas 7C5B2, 7C5C55, or G12E8.

In some embodiments of these aspects, the anti-DEspR antibody or antibody fragment thereof comprises an amino acid sequence of one or more CDRs of an antibody expressed or produced by hybridomas 7C5C55 or G12E8. In some embodiments of these aspects, the anti-DEspR antibody or antibody fragment thereof has one or more biological characteristics of a monoclonal antibody expressed or produced by hybridoma 7C5B2, 7C5C55, or G12E8. In some embodiments of these aspects, the anti-DEspR antibody or antibody fragment thereof specifically binds to an epitope of DEspR that is bound by an antibody expressed or produced by hybridoma 7C5B2, 7C5C55, or G12E8.

In some embodiments of these aspects and all such aspects described herein, the antibody fragment is a Fab fragment, a Fab' fragment, a Fd fragment, a Fd' fragment, a Fv fragment, a dAb fragment, a F(ab')2 fragment, a single chain fragment, a diabody, or a linear antibody.

In some embodiments of these aspects and all such aspects described herein, the anti-DEspR antibody or antibody fragment thereof further comprises an agent conjugated to the anti-DEspR antibody or antibody fragment thereof to form an immunoconjugate specific for DEspR. In some such embodiments, the agent conjugated to the antibody or antibody fragment thereof is a chemotherapeutic agent, a toxin, a radioactive isotope, a small molecule, an siRNA, a nanoparticle, or a microbubble.

In some aspects, provided herein are pharmaceutical compositions comprising any of the anti-DEspR antibodies or antibody fragments thereof described herein that specifically binds to DEspR, and a pharmaceutically acceptable carrier.

In some aspects, provided herein are methods of inhibiting angiogenesis in a subject having a disease or disorder dependent or modulated by angiogenesis, comprising administering to a subject in need thereof a therapeutically effective amount of a pharmaceutical composition comprising any of the anti-DEspR antibodies or antibody fragments thereof described herein that specifically binds to DEspR. In some embodiments of these aspects and all such aspects described herein, the disease or disorder dependent or modulated by angiogenesis is a cancer or a tumor. In some embodiments of these aspects and all such aspects described herein, the disease or disorder dependent or modulated by angiogenesis is selected from the group consisting of age-related macular degeneration, carotid artery disease, diabetic retinopathy, rheumatoid arthritis, neurodegenerative disorder, Alzheimer's disease, obesity, endometriosis, psoriasis, atherosclerosis, ocular neovascularization, neovascular glaucoma, osteoporsosis, and restenosis.

In some aspects, provided herein are methods of inhibiting tumor cell invasiveness in a subject having a cancer or a tumor, comprising administering to a subject in need thereof a therapeutically effective amount of a pharmaceutical composition comprising any of the anti-DEspR antibodies or antibody fragments thereof described herein that specifically binds to DEspR. In some embodiments of these aspects and all such aspects described herein, the method further comprises the administration of one or more chemotherapeutic agents, angiogenesis inhibitors, cytotoxic agents, or anti-proliferative agents.

In some aspects, provided herein are methods of inhibiting tumor growth and reducing tumor size or tumor metastasis in a subject having a tumor or metastasis by inhibiting DEspR expression and/or function in a cell, comprising administering to a subject in need thereof a therapeutically effective amount of a pharmaceutical composition comprising any of the anti-DEspR antibodies or antibody fragments thereof described herein that specifically binds to DEspR. In some embodiments of these aspects and all such aspects described herein, the DEspR expression and/or function is inhibited in a tumor cell, a tumor initiating cell, a cancer stem-like cell, a cancer stem cell, a metastatic tumor cell, an endothelial progenitor cell, an inflammatory cell, a tumor stromal cell, a tumor vasculature cell, or any combination thereof. In some such embodiments, the tumor vasculature cell is an endothelial cell, a pericyte, a smooth muscle cell, an adventitial cell, or any combination thereof.

In some aspects, provided herein are methods of inhibiting tumor resistance and tumor recurrence in a subject by inhibiting DEspR expression and/or function in a cell, the methods comprising administering to a subject in need thereof a therapeutically effective amount of a pharmaceutical composition comprising any of the anti-DEspR antibodies or antibody fragments thereof described herein that specifically binds to DEspR. In some embodiments of these aspects and all such aspects described herein, the DEspR expression and/or function is inhibited in a tumor cell, a tumor initiating cell, a cancer stem-like cell, a cancer stem cell, a metastatic tumor cell, or any combination thereof.

In some aspects, provided herein are methods of inhibiting cancer progression through promotion of autophagy of a cancer cell by inhibiting DEspR expression and/or function in a tumor cell, the methods comprising administering to a subject in need thereof a therapeutically effective amount of a pharmaceutical composition comprising any of the anti-DEspR antibodies or antibody fragments thereof described herein that specifically binds to DEspR. In some embodiments of these aspects and all such aspects described herein, the DEspR expression and/or function is inhibited in a tumor cell, a tumor initiating cell, a cancer stem-like cell, a cancer stem cell, a metastatic tumor cell, or any combination thereof.

In some aspects, provided herein are methods of promoting autophagy or a reduction in accumulation of intracellular noxious substances or pathogens by inhibiting DEspR expression and/or function in a cell, the methods comprising administering to a subject in need thereof a therapeutically effective amount of a pharmaceutical composition comprising any of the anti-DEspR antibodies or antibody fragments thereof described herein that specifically binds to DEspR. In some embodiments of these aspects and all such aspects described herein, the subject has Alzheimer's disease or Huntington's disease.

In some aspects, provided herein are methods of molecular imaging via targeting DEspR, the methods comprising administering an effective amount of a pharmaceutical composition comprising any of the anti-DEspR antibodies or antibody fragments thereof described herein that specifically binds to DEspR conjugated to a targeting moiety, and determining the presence or absence of the anti-DEspR antibodies or antibody fragments thereof conjugated to the targeting moiety using molecular imaging. In some embodiments of these aspects and all such aspects described herein, the molecular imaging is contrast-enhanced ultrasound imaging, MRI (magnetic resonance imaging), near infrared imaging, or photoacoustics imaging. In some embodiments of these aspects and all such aspects described herein, the targeting moiety is an antibody, a DEspR-binding peptide ligand, a small molecule, a nanoparticle, a polymer, an aptamer, or any combination thereof.

In some aspects, provided herein are methods of stratifying or classifying a tumor via determination of DEspR expression, the methods comprising contacting a cell with any of the anti-DEspR antibodies or antibody fragments thereof described herein that specifically binds to DEspR, and determining whether the anti-DEspR antibody or antibody fragment thereof binds to the cell after said contacting, such that binding of the DEspR antibody or antibody fragment thereof to the cell indicates that the cell expresses DEspR. In some embodiments of these aspects and all such aspects described herein, the cell is a tumor cell, an endothelial cell, a pericyte, a smooth muscle cell, an adventitial cell, a tumor stromal cell, or any combination thereof. In some such embodiments, the tumor stromal cell is a fibroblast, a myofibroblast, an inflammatory cell, a stellate cell, or any combination thereof. In some embodiments of these aspects and all such aspects described herein, the cell being contacted is in a tissue biopsy, a paraffin-embedded section, or a frozen section.

In some aspects, provided herein are methods for enhancing delivery of a therapeutic agent via DEspR-targeted sonoporation, the methods comprising delivering an effective amount of a pharmaceutical composition comprising any of the anti-DEspR antibodies or antibody fragments thereof described herein that specifically binds to DEspR and a therapeutic agent using targeted ultrasound delivery, to a subject in need thereof, such that delivery of the therapeutic agent is enhanced or increased relative to delivering the therapeutic agent in the absence of the pharmaceutical composition comprising any of the anti-DEspR antibodies or antibody fragments thereof described herein. In some embodiments of these aspects and all such aspects described herein, the therapeutic agent is a chemotherapeutic agent, a small molecule, a peptide, or an aptamer.

Also provided herein, in some aspects, are method for reducing toxicity of a therapeutic agent via DEspR-targeted sonoporation, the methods comprising delivering an effective amount of a pharmaceutical composition comprising any of the anti-DEspR antibodies or antibody fragments thereof described herein that specifically binds to DEspR and a therapeutic agent using targeted ultrasound delivery to a subject in need thereof, such that toxicity of the therapeutic agent is reduced relative to delivering the therapeutic agent in the absence of the pharmaceutical composition comprising any of the anti-DEspR antibodies or antibody fragments thereof described herein. In some embodiments of these aspects and all such aspects described herein, the therapeutic agent is a chemotherapeutic agent, a small molecule, a peptide, or an aptamer.

In some aspects, provided herein are methods for combining DEspR-targeted molecular imaging and DEspR-targeted delivery of a therapeutic agent. These methods comprise administering to a subject an effective amount of a therapeutic agent and a pharmaceutical composition comprising any of the anti-DEspR antibodies or antibody fragments thereof described herein conjugated to a targeting moiety, and determining the presence or absence of the anti-DEspR antibodies or antibody fragments thereof described herein conjugated to the targeting moiety using molecular imaging. In some embodiments of these aspects and all such aspects described herein, the molecular imaging is contrast-enhanced ultrasound imaging, MRI (magnetic resonance imaging), near infrared imaging, or photoacoustics imaging. In some embodiments of these aspects and all such aspects described herein, the therapeutic agent is a chemotherapeutic agent, a small molecule, a peptide, or an aptamer.

In other aspects, provided herein are pharmaceutical compositions comprising any of the anti-DEspR antibodies or antibody fragments thereof described herein that specifically binds to DEspR for use in inhibiting angiogenesis in a subject having a disease or disorder dependent or modulated by angiogenesis. In some embodiments of these aspects and all such aspects described herein, the disease or disorder dependent or modulated by angiogenesis is a cancer or a tumor. In some embodiments of these aspects and all such aspects described herein, the disease or disorder dependent or modulated by angiogenesis is selected from the group consisting of age-related macular degeneration, carotid artery disease, diabetic retinopathy, rheumatoid arthritis, neurodegenerative disorder, Alzheimer's disease, obesity, endometriosis, psoriasis, atherosclerosis, ocular neovascularization, neovascular glaucoma, osteoporsosis, and restenosis.

In some aspects, provided herein are pharmaceutical compositions comprising any of the anti-DEspR antibodies or antibody fragments thereof described herein that specifically binds to DEspR for use in inhibiting tumor cell invasiveness in a subject having a cancer or a tumor. In some embodiments of these aspects and all such aspects described herein, the pharmaceutical compositions further comprise one or more chemotherapeutic agents, angiogenesis inhibitors, cytotoxic agents, or anti-proliferative agents.

In some aspects, provided herein are pharmaceutical compositions comprising any of the anti-DEspR antibodies or antibody fragments thereof described herein that specifically binds to DEspR for use in inhibiting tumor growth and reducing tumor size or tumor metastasis by inhibiting DEspR expression and/or function in a cell in a subject in need thereof. In some embodiments of these aspects and all such aspects described herein, the DEspR expression and/or function is inhibited in a tumor cell, a tumor initiating cell, a cancer stem-like cell, a cancer stem cell, a metastatic tumor cell, an endothelial progenitor cell, an inflammatory cell, a tumor stromal cell, a tumor vasculature cell, or any combination thereof. In some such embodiments, the tumor vasculature cell is an endothelial cell, a pericyte, a smooth muscle cell, an adventitial cell, or any combination thereof.

In some aspects, provided herein are pharmaceutical compositions comprising any of the anti-DEspR antibodies or antibody fragments thereof described herein that specifically binds to DEspR for use in inhibiting tumor resistance and tumor recurrence by inhibiting DEspR expression and/or function in a cell in a subject in need thereof. In some embodiments of these aspects and all such aspects described herein, the DEspR expression and/or function is inhibited in a tumor cell, a tumor initiating cell, a cancer stem-like cell, a cancer stem cell, a metastatic tumor cell, or any combination thereof.

In some aspects, provided herein are pharmaceutical compositions comprising any of the anti-DEspR antibodies or antibody fragments thereof described herein that specifically binds to DEspR for use in inhibiting cancer progression through promotion of autophagy of a cancer cell by inhibiting DEspR expression and/or function in a tumor cell in a subject in need thereof. In some embodiments of these aspects and all such aspects described herein, the DEspR expression and/or function is inhibited in a tumor cell, a tumor initiating cell, a cancer stem-like cell, a cancer stem cell, a metastatic tumor cell, or any combination thereof.

In some aspects, provided herein are pharmaceutical compositions comprising any of the anti-DEspR antibodies or antibody fragments thereof described herein that specifically binds to DEspR for use in promoting autophagy or a reduction in accumulation of intracellular noxious substances or pathogens by inhibiting DEspR expression and/or function in a subject in need thereof. In some embodiments of these aspects and all such aspects described herein, the subject has Alzheimer's disease or Huntington's disease.

In some aspects, provided herein are pharmaceutical compositions comprising any of the anti-DEspR antibodies or antibody fragments thereof described herein that specifically binds to DEspR for use in enhancing delivery of a therapeutic agent via DEspR-targeted sonoporation using targeted ultrasound delivery to a subject in need thereof. In some embodiments of these aspects and all such aspects described herein, the therapeutic agent is a chemotherapeutic agent, a small molecule, a peptide, or an aptamer.

In some aspects, provided herein are pharmaceutical compositions comprising any of the anti-DEspR antibodies or antibody fragments thereof described herein that specifically binds to DEspR for use in reducing toxicity of a therapeutic agent via DEspR-targeted sonoporation using targeted ultrasound delivery to a subject in need thereof. In some embodiments of these aspects and all such aspects described herein, the therapeutic agent is a chemotherapeutic agent, a small molecule, a peptide, or an aptamer.

Definitions

A "DEspR antagonist" refers to a molecule capable of neutralizing, blocking, inhibiting, abrogating, reducing or interfering with DEspR activities including its binding to endothelin-1 or VEGFsp. DEspR antagonists include anti-DEspR antibodies and antigen-binding fragments thereof, receptor molecules and derivatives that bind specifically to DEspR thereby inhibiting, preventing, or sequestering its binding to its ligands, such as VEGFsp and endothelin-1.

The term "antibody" is used in the broadest sense and includes monoclonal antibodies (including full length or intact monoclonal antibodies), polyclonal antibodies, multivalent antibodies, multispecific antibodies (e.g., bispecific antibodies), and antibody fragments (see below) so long as they exhibit the desired biological activity and specificity.

As used herein, the term "target" refers to a biological molecule (e.g., peptide, polypeptide, protein, lipid, carbohydrate) to which a polypeptide domain which has a binding site can selectively bind. The target can be, for example, an intracellular target (e.g., an intracellular protein target) or a cell surface target (e.g., a membrane protein, a receptor protein). Preferably, a target is a cell surface target, such as a cell surface protein.

The term "specificity" refers to the number of different types of antigens or antigenic determinants to which an antibody or antibody fragment thereof as described herein can bind. The specificity of an antibody or antibody fragment thereof can be determined based on affinity and/or avidity. The affinity, represented by the equilibrium constant for the dissociation ($K_D$) of an antigen with an antigen-binding protein, is a measure of the binding strength between an antigenic determinant and an antigen-binding site on the antigen-binding protein, such as an antibody or antibody fragment thereof: the lesser the value of the $K_D$, the stronger the binding strength between an antigenic determinant and the antigen-binding molecule. Alternatively, the affinity can also be expressed as the affinity constant ($K_A$), which is $1/K_D$. As will be clear to the skilled person, affinity can be determined in a manner known per se, depending on the specific antigen of interest. Accordingly, an antibody or antibody fragment thereof as defined herein is said to be "specific for" a first target or antigen compared to a second target or antigen when it binds to the first antigen with an affinity (as described above, and suitably expressed, for example as a $K_D$ value) that is at least 10 times, such as at least 100 times, and preferably at least 1000 times, and up to 10000 times or more better than the affinity with which said amino acid sequence or polypeptide binds to another target or polypeptide.

Avidity is the measure of the strength of binding between an antigen-binding molecule (such as an antibody or antibody fragment thereof described herein) and the pertinent antigen. Avidity is related to both the affinity between an antigenic determinant and its antigen binding site on the antigen-binding molecule, and the number of pertinent binding sites present on the antigen-binding molecule. Typically, antigen-binding proteins (such as an antibody or antibody fragment thereof described herein) will bind to their cognate or specific antigen with a dissociation constant ($K_D$ of $10^{-5}$ to $10^{-12}$ moles/liter or less, and preferably $10^{-7}$ to $10^{-12}$ moles/liter or less and more preferably $10^{-8}$ to $10^{-12}$ moles/liter (i.e., with an association constant ($K_A$) of $10^5$ to $10^{12}$ liter/moles or more, and preferably $10^7$ to $10^{12}$ liter/moles or more and more preferably $10^8$ to $10^{12}$ liter/moles). Any $K_D$ value greater than $10^{-4}$ mol/liter (or any $K_A$ value lower than $10^4$ $M^{-1}$) is generally considered to indicate non-specific binding. The $K_D$ for biological interactions which are considered meaningful (e.g., specific) are typically in the range of $10^{-10}$ M (0.1 nM) to $10^{-5}$ M (10000 nM). The stronger an interaction is, the lower is its $K_D$. Preferably, a binding site on an antibody or antibody fragment thereof described herein will bind to the desired antigen with an affinity less than 500 nM, preferably less than 200 nM, more preferably less than 10 nM, such as less than 500 pM. Specific binding of an antigen-binding protein to an antigen or antigenic determinant can be determined in any suitable manner known per se, including, for example, Scatchard analysis and/or competitive binding assays, such as radioimmunoassays (RIA), enzyme immunoassays (EIA) and sandwich competition assays, and the different variants thereof known per se in the art; as well as other techniques as mentioned herein.

Accordingly, as used herein, "selectively binds" or "specifically binds" refers to the ability of an antibody or antibody fragment thereof described herein to bind to a target, such as a molecule present on the cell-surface, with a $K_D$ $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less. Specific binding can be influenced by, for example, the affinity and avidity of the polypeptide agent and the concentration of polypeptide agent. The person of ordinary skill in the art can determine appropriate conditions under which the polypeptide agents described herein selectively bind the targets using any suitable methods, such as titration of a polypeptide agent in a suitable cell binding assay.

As described herein, an "antigen" is a molecule that is bound by a binding site on a polypeptide agent, such as an antibody or antibody fragment thereof. Typically, antigens are bound by antibody ligands and are capable of raising an antibody response in vivo. An antigen can be a polypeptide, protein, nucleic acid or other molecule. In the case of conventional antibodies and fragments thereof, the antibody binding site as defined by the variable loops (L1, L2, L3 and H1, H2, H3) is capable of binding to the antigen. The term "antigenic determinant" refers to an epitope on the antigen recognized by an antigen-binding molecule, and more particularly, by the antigen-binding site of said molecule.

As used herein, an "epitope" can be formed both from contiguous amino acids, or noncontiguous amino acids juxtaposed by tertiary folding of a protein. Epitopes formed from contiguous amino acids are typically retained on exposure to denaturing solvents, whereas epitopes formed by tertiary folding are typically lost on treatment with denaturing solvents. An epitope typically includes at least 3, and more usually, at least 5, about 9, or about 8-10 amino acids in a unique spatial conformation. An "epitope" includes the unit of structure conventionally bound by an immunoglobulin $V_H/V_L$ pair. Epitopes define the minimum binding site for an antibody, and thus represent the target of specificity of an antibody. In the case of a single domain antibody, an epitope represents the unit of structure bound by a variable domain in isolation. The terms "antigenic determinant" and "epitope" can also be used interchangeably herein.

The term "monoclonal antibody" as used herein refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. The modifier "monoclonal" is not to be construed as requiring production of the antibody by any particular method. For example, the monoclonal antibodies to be used in accordance with the invention can be made by the hybridoma method first described by Kohler et al., Nature 256:495 (1975), or can be made by recombinant DNA methods (see, e.g., U.S. Pat. No. 4,816,567). The "monoclonal antibodies" can also be isolated from phage antibody libraries using the techniques described in Clackson et al., Nature 352:624-628 (1991) or Marks et al., J. Mol. Biol. 222:581-597 (1991), for example. A monoclonal antibody can be of any species, including, but not limited to, mouse, rat, goat, rabbit, and human monoclonal antibodies.

The term "antibody fragment," as used herein, refer to a protein fragment that comprises only a portion of an intact antibody, generally including an antigen binding site of the intact antibody and thus retaining the ability to bind antigen. Examples of antibody fragments encompassed by the present definition include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CH1 domain; (v) the Fv fragment having the $V_L$ and $V_H$ domains of a single arm of an antibody; (vi) the dAb fragment (Ward et al., Nature 341, 544-546 (1989)) which consists of a $V_H$ domain; (vii) isolated CDR regions; (viii) F(ab')$_2$ fragments, a bivalent fragment including two Fab' fragments linked by a disulphide bridge at the hinge region; (ix) single chain antibody molecules (e.g., single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments ($V_H$-$C_H1$-$V_H$-$C_H1$) which, together with complementary light chain polypeptides, form a pair of antigen binding regions (Zapata et al. Protein Eng. 8(10):1057-1062 (1995); and U.S. Pat. No. 5,641,870).

An "Fv" fragment is an antibody fragment which contains a complete antigen recognition and binding site. This region consists of a dimer of one heavy and one light chain variable domain in tight association, which can be covalent in nature, for example in scFv. It is in this configuration that the three CDRs of each variable domain interact to define an antigen binding site on the surface of the $V_H$-$V_L$ dimer Collectively, the six CDRs or a subset thereof confer antigen binding specificity to the antibody. However, even a single variable domain (or half of an Fv comprising only three CDRs specific for an antigen) has the ability to recognize and bind antigen, although usually at a lower affinity than the entire binding site.

Throughout the present specification and claims, the numbering of the residues in an immunoglobulin heavy chain is that of the EU index as in Kabat et al., Sequences of Proteins of Immunological Interest, 5th Ed. Public Health Service, National Institutes of Health, Bethesda, Md. (1991), which is also available on the world wide web, and is expressly incorporated herein in its entirety by reference. The "EU index as in Kabat" refers to the residue numbering of the human IgG1 EU antibody.

As used herein, "antibody variable domain" refers to the portions of the light and heavy chains of antibody molecules that include amino acid sequences of Complementarity Determining Regions (CDRs; i.e., CDR1, CDR2, and CDR3), and Framework Regions (FRs). $V_H$ refers to the variable domain of the heavy chain. $V_L$ refers to the variable domain of the light chain. According to the methods used in this invention, the amino acid positions assigned to CDRs and FRs can be defined according to Kabat (Sequences of Proteins of Immunological Interest (National Institutes of Health, Bethesda, Md., 1987 and 1991)) Amino acid numbering of antibodies or antigen binding fragments is also according to that of Kabat.

As used herein, the term "Complementarity Determining Regions" (CDRs), i.e., CDR1, CDR2, and CDR3) refers to the amino acid residues of an antibody variable domain the presence of which are necessary for antigen binding. Each variable domain typically has three CDR regions identified as CDR1, CDR2 and CDR3. Each complementarity determining region can comprise amino acid residues from a "complementarity determining region" as defined by Kabat (i.e., about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e., about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-917 (1987)). In some instances, a complementarity determining region can include amino acids from both a CDR region defined according to Kabat and a hypervariable loop. For example, the CDRH1 of the heavy chain of antibody 4D5 includes amino acids 26 to 35.

Framework regions" (hereinafter FR) are those variable domain residues other than the CDR residues. Each variable domain typically has four FRs identified as FR1, FR2, FR3 and FR4. If the CDRs are defined according to Kabat, the light chain FR residues are positioned at about residues 1-23 (LCFR1), 35-49 (LCFR2), 57-88 (LCFR3), and 98-107 (LCFR4) and the heavy chain FR residues are positioned about at residues 1-30 (HCFR1), 36-49 (HCFR2), 66-94 (HCFR3), and 103-113 (HCFR4) in the heavy chain residues. If the CDRs comprise amino acid residues from hypervariable loops, the light chain FR residues are positioned about at residues 1-25 (LCFR1), 33-49 (LCFR2), 53-90 (LCFR3), and 97-107 (LCFR4) in the light chain and the heavy chain FR residues are positioned about at residues 1-25 (HCFR1), 33-52 (HCFR2), 56-95 (HCFR3), and 102-113 (HCFR4) in the heavy chain residues. In some instances, when the CDR comprises amino acids from both a CDR as defined by Kabat and those of a hypervariable loop, the FR residues will be adjusted accordingly. For example, when CDRH1 includes amino acids H26-H35, the heavy chain FR1 residues are at positions 1-25 and the FR2 residues are at positions 36-49.

The "Fab" fragment contains a variable and constant domain of the light chain and a variable domain and the first constant domain ($C_H1$) of the heavy chain. F(ab')$_2$ antibody fragments comprise a pair of Fab fragments which are generally covalently linked near their carboxy termini by hinge cysteines between them. Other chemical couplings of antibody fragments are also known in the art.

"Single-chain Fv" or "scFv" antibody fragments comprise the $V_H$ and $V_L$ domains of antibody, wherein these domains are present in a single polypeptide chain. Generally the Fv polypeptide further comprises a polypeptide linker between the $V_H$ and $V_L$ domains, which enables the scFv to form the desired structure for antigen binding. For a review of scFv, see Pluckthun in The Pharmacology of Monoclonal Antibodies, Vol 113, Rosenburg and Moore eds. Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

The expression "linear antibodies" refers to the antibodies described in Zapata et al., Protein Eng., 8(10):1057-1062 (1995). Briefly, these antibodies comprise a pair of tandem Fd segments ($V_H$-$C_H1$-$V_H$-$C_H1$) which, together with complementary light chain polypeptides, form a pair of antigen binding regions. Linear antibodies can be bispecific or monospecific.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851-6855 (1984)).

"Humanized" forms of non-human (e.g., murine) antibodies are chimeric antibodies that are engineered or designed to comprise minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies can comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992). As used herein, a "composite human antibody" is a specific type of engineered or humanized antibody.

A "human antibody," "non-engineered human antibody," or "fully human antibody" is one which possesses an amino acid sequence which corresponds to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art. In one embodiment, the human antibody is selected from a phage library, where that phage library expresses human antibodies (Vaughan et al.

Nature Biotechnology 14:309-314 (1996): Sheets et al. Proc. Natl. Acad. Sci. 95:6157-6162 (1998)); Hoogenboom and Winter, J. Mol. Biol., 227:381 (1991); Marks et al., J. Mol. Biol., 222:581 (1991)). Human antibodies can also be made by introducing human immunoglobulin loci into transgenic animals, e.g., mice in which the endogenous mouse immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in the following scientific publications: Marks et al., Bio/Technology 10: 779-783 (1992); Lonberg et al., Nature 368: 856-859 (1994); Morrison, Nature 368:812-13 (1994); Fishwild et al., Nature Biotechnology 14: 845-51 (1996); Neuberger, Nature Biotechnology 14: 826 (1996); Lonberg and Huszar, Intern. Rev. Immunol. 13:65-93 (1995). Alternatively, the human antibody can be prepared via immortalization of human B lymphocytes producing an antibody directed against a target antigen (such B lymphocytes can be recovered from an individual or can have been immunized in vitro). See, e.g., Cole et al., Monoclonal Antibodies and Cancer Therapy, Alan R. Liss, p. 77 (1985); Boerner et al., J. Immunol, 147 (1):86-95 (1991); and U.S. Pat. No. 5,750,373.

An "affinity matured" antibody is one with one or more alterations in one or more CDRs thereof which result an improvement in the affinity of the antibody for antigen, compared to a parent antibody which does not possess those alteration(s). Preferred affinity matured antibodies will have nanomolar or even picomolar affinities for the target antigen. Affinity matured antibodies are produced by procedures known in the art. Marks et al. Bio/Technology 10:779-783 (1992) describes affinity maturation by $V_H$ and $V_L$ domain shuffling. Random mutagenesis of CDR and/or framework residues is described by: Barbas et al. Proc Nat. Acad. Sci, USA 91:3809-3813 (1994); Schier et al. Gene 169:147-155 (1995); Yelton et al. J. Immunol. 155:1994-2004 (1995); Jackson et al., J. Immunol 154(7):3310-9 (1995); and Hawkins et al., J. Mol. Biol. 226:889-896 (1992).

A "functional antigen binding site" of an antibody is one which is capable of binding a target antigen. The antigen binding affinity of the antigen binding site is not necessarily as strong as the parent antibody from which the antigen binding site is derived, but the ability to bind antigen must be measurable using any one of a variety of methods known for evaluating antibody binding to an antigen. Moreover, the antigen binding affinity of each of the antigen binding sites of a multivalent antibody herein need not be quantitatively the same. For multimeric antibodies, the number of functional antigen binding sites can be evaluated using ultracentrifugation analysis as described in Example 2 of U.S. Patent Application Publication No. 20050186208. According to this method of analysis, different ratios of target antigen to multimeric antibody are combined and the average molecular weight of the complexes is calculated assuming differing numbers of functional binding sites. These theoretical values are compared to the actual experimental values obtained in order to evaluate the number of functional binding sites.

As used herein, a "blocking" antibody or an antibody "antagonist" is one which inhibits or reduces biological activity of the antigen it binds. For example, a DEspR-specific antagonist antibody binds DEspR and inhibits the ability of DEspR to, for example, bind VEGFsp and induce angiogenesis, to induce vascular endothelial cell proliferation or to induce vascular permeability. In certain embodiments, blocking antibodies or antagonist antibodies completely inhibit the biological activity of the antigen.

Unless indicated otherwise, the expression "multivalent antibody" is used throughout this specification to denote an antibody comprising three or more antigen binding sites. For example, the multivalent antibody is engineered to have the three or more antigen binding sites and is generally not a native sequence IgM or IgA antibody.

An antibody having a "biological characteristic" of a designated antibody is one which possesses one or more of the biological characteristics of that antibody which distinguish it from other antibodies that bind to the same antigen.

In order to screen for antibodies which bind to an epitope on an antigen bound by an antibody of interest, a routine cross-blocking assay such as that described in Antibodies, A Laboratory Manual, Cold Spring Harbor Laboratory, Ed Harlow and David Lane (1988), can be performed.

A "species-dependent antibody" is one which has a stronger binding affinity for an antigen from a first mammalian species than it has for a homologue of that antigen from a second mammalian species. Normally, the species-dependent antibody "binds specifically" to a human antigen (i.e., has a binding affinity ($K_D$) value of no more than about $1\times10^{-7}$M, preferably no more than about $1X10^{-8}$ M and most preferably no more than about $1\times10^{-9}$ M) but has a binding affinity for a homologue of the antigen from a second nonhuman mammalian species which is at least about 50 fold, or at least about 500 fold, or at least about 1000 fold, weaker than its binding affinity for the human antigen. The species-dependent antibody can be any of the various types of antibodies as defined above, but typically is a humanized or human antibody.

As used herein, "antibody mutant" or "antibody variant" refers to an amino acid sequence variant of the species-dependent antibody wherein one or more of the amino acid residues of the species-dependent antibody have been modified. Such mutants necessarily have less than 100% sequence identity or similarity with the species-dependent antibody. In one embodiment, the antibody mutant will have an amino acid sequence having at least 75% amino acid sequence identity or similarity with the amino acid sequence of either the heavy or light chain variable domain of the species-dependent antibody, more preferably at least 80%, more preferably at least 85%, more preferably at least 90%, and most preferably at least 95%. Identity or similarity with respect to this sequence is defined herein as the percentage of amino acid residues in the candidate sequence that are identical (i.e., same residue) or similar (i e , amino acid residue from the same group based on common side-chain properties, see below) with the species-dependent antibody residues, after aligning the sequences and introducing gaps, if necessary, to achieve the maximum percent sequence identity. None of N-terminal, C-terminal, or internal extensions, deletions, or insertions into the antibody sequence outside of the variable domain shall be construed as affecting sequence identity or similarity.

To increase the half-life of the antibodies or polypeptide containing the amino acid sequences described herein, one can attach a salvage receptor binding epitope to the antibody (especially an antibody fragment), as described, e.g., in U.S. Pat. No. 5,739,277. For example, a nucleic acid molecule encoding the salvage receptor binding epitope can be linked in frame to a nucleic acid encoding a polypeptide sequence described herein so that the fusion protein expressed by the engineered nucleic acid molecule comprises the salvage receptor binding epitope and a polypeptide sequence described herein. As used herein, the term "salvage receptor binding epitope" refers to an epitope of the Fc region of an IgG molecule (e.g., $IgG_1$, $IgG_2$, $IgG_3$, or $IgG_4$) that is responsible for increasing the in vivo serum half-life of the IgG molecule (e.g., Ghetie et al., Ann. Rev. Immunol 18:739-766 (2000), Table 1). Antibodies with substitutions in an Fc region thereof and increased serum half-lives are also described in WO00/42072, WO 02/060919; Shields et al., J. Biol. Chem. 276:6591-6604 (2001); Hinton, J. Biol. Chem. 279:6213-6216 (2004)). In another embodiment, the serum half-life can also be increased, for example, by attaching other polypeptide sequences. For example, antibodies or other polypeptides useful in the methods of the invention can be attached to serum albumin or a portion of serum albumin that binds to the FcRn receptor or a serum albumin binding peptide so that serum albumin binds to the antibody or polypeptide, e.g., such polypeptide sequences are disclosed in WO01/45746. In one embodiment, the serum albumin peptide to be attached comprises an amino acid sequence of DICLPRWGCLW (SEQ ID NO:3). In another embodiment, the half-life of a Fab is increased by these methods. See also, Dennis et al. J. Biol. Chem. 277:35035-35043 (2002) for additional serum albumin binding peptide sequences.

A "chimeric DEspR receptor protein" is a DEspR molecule having amino acid sequences derived from at least two different proteins, at least one of which is a DEspR protein. In certain embodiments, the chimeric DEspR protein is capable of binding to and inhibiting the biological activity of DEspR.

An "isolated" antibody is one that has been identified and separated and/or recovered from a component of its natural environment. Contaminant components of its natural environment are materials that would interfere with diagnostic or therapeutic uses for the antibody, and can include enzymes, hormones, and other proteinaceous or nonproteinaceous solutes. In certain embodiments, the antibody will be purified (1) to greater than 95% by weight of antibody as determined by, for example, the Lowry method, and most preferably more than 99% by weight, (2) to a degree sufficient to obtain at least 15 residues of N-terminal or internal amino acid sequence by use of a spinning cup sequenator, or (3) to homogeneity by SDS-PAGE under reducing or nonreducing conditions using Coomassie blue or, silver stain. Isolated antibody includes the antibody in situ within recombinant cells since at least one component of the antibody's natural environment will not be present. Ordinarily, however, isolated antibody will be prepared by at least one purification step.

By "fragment" is meant a portion of a polypeptide, such as an antibody or antibody fragment thereof, or nucleic acid molecule that contains, preferably, at least 10%, 20%, 30%, 40%, 50%, 60%, 70%, 80%, 90%, 95%, or more of the entire length of the reference nucleic acid molecule or polypeptide. A fragment can contain 10, 20, 30, 40, 50, 60, 70, 80, 90, or 100, 200, 300, 400, 500, 600, or more nucleotides or 10, 20, 30, 40, 50, 60, 70, 80, 90, 100, 120, 140, 160, 180, 190, 200 amino acids or more.

An "anti-angiogenesis agent" or "angiogenesis inhibitor" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent as defined throughout the specification or known in the art, e.g., but are not limited to, antibodies to VEGF-A or to the VEGF-A receptor (e.g., KDR receptor or Flt-1 receptor), VEGF-trap, anti-PDGFR inhibitors such as Gleevec™ (Imatinib Mesylate). Anti-angiogensis agents also include native angiogenesis inhibitors, e.g., angiostatin, endostatin, etc. See, e.g., Klagsbrun and D'Amore, Annu. Rev. Physiol., 53:217-39 (1991); Streit and Detmar, Oncogene, 22:3172-3179 (2003) (e.g., Table 3 listing anti-angiogenic therapy in malignant melanoma); Ferrara & Alitalo, Nature Medicine 5:1359-1364 (1999); Tonini et al., Oncogene, 22:6549-6556 (2003) (e.g., Table 2 listing known antiangiogenic factors); and Sato. Int. J. Clin. Oncol., 8:200-206 (2003) (e.g., Table 1 lists anti-angiogenic agents used in clinical trials).

The term "anti-cancer therapy" refers to a therapy useful in treating cancer. Examples of anti-cancer therapeutic agents include, but are not limited to, e.g., surgery, chemotherapeutic agents, growth inhibitory agents, cytotoxic agents, agents used in radiation therapy, anti-angiogenesis agents, apoptotic agents, anti-tubulin agents, and other agents to treat cancer, such as anti-HER-2 antibodies (e.g., Herceptin®), anti-CD20 antibodies, an epidermal growth factor receptor (EGFR) antagonist (e.g., a tyrosine kinase inhibitor), HER1/EGFR inhibitor (e.g., erlotinib (Tarceva®)), platelet derived growth factor inhibitors (e.g., Gleevec™ (Imatinib Mesylate)), a COX-2 inhibitor (e.g., celecoxib), interferons, cytokines, antagonists (e.g., neutralizing antibodies) that bind to one or more of the following targets ErbB2, ErbB3, ErbB4, PDGFR-beta, BlyS, APRIL, BCMA or VEGF receptor(s), TRAIL/Apo2, and other bioactive and organic chemical agents, etc. Combinations thereof are also included in the invention.

The term "cytotoxic agent" as used herein refers to a substance that inhibits or prevents the function of cells and/or causes destruction of cells. The term is intended to include radioactive isotopes (e.g. $Ar^{211}$, $I^{131}$, $I^{125}$, $Y^{90}$, $Re^{186}$, $Re^{188}$, $Sm^{153}$, $Bi^{212}$, $P^{32}$ and radioactive isotopes of Lu), chemotherapeutic agents, and toxins such as small molecule toxins or enzymatically active toxins of bacterial, fungal, plant or animal origin, including fragments and/or variants thereof.

A "chemotherapeutic agent" is a chemical compound useful in the treatment of cancer. Examples of chemotherapeutic agents include, but are not limited to, alkylating agents such as thiotepa and CYTOXAN® cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omegaI1 (see, e.g., Agnew, Chem. Intl. Ed. Engl., 33: 183-186 (1994)); dynemicin, including dynemicin A; bisphosphonates, such as clodronate; an esperamicin; as well as neocarzinostatin chromophore and related chromoprotein enediyne antiobiotic chromophores), aclacinomysins, actinomycin, authramycin, azaserine, bleomycins, cactinomycin, carabicin, caminomycin, carzinophilin, chromomycinis, dactinomycin, daunorubicin, detorubicin, 6-diazo-5-oxo-L-norleucine, ADRIAMYCIN® doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK® polysaccharide complex (JHS Natural Products, Eugene, Oreg.); razoxane; rhizoxin; sizofuran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., TAXOL® paclitaxel (Bristol-Myers Squibb Oncology, Princeton, N.J.), ABRAXANE® Cremophor-free, albumin-engineered nanoparticle formulation of paclitaxel (American Pharmaceutical Partners, Schaumberg, Ill.), and TAXOTERE® doxetaxel (Rhone-Poulenc Rorer, Antony, France); chloranbucil; GEMZAR® gemcitabine; 6-thioguanine; mercaptopurine; methotrexate; platinum analogs such as cisplatin, oxaliplatin and carboplatin; vinblastine; platinum; etoposide (VP-16); ifosfamide; mitoxantrone; vincristine; NAVELBINE® vinorelbine; novantrone; teniposide; edatrexate; daunomycin; aminopterin; xeloda; ibandronate; irinotecan (Camptosar, CPT-11) (including the treatment regimen of irinotecan with 5-FU and leucovorin); topoisomerase inhibitor RFS 2000; difluoromethylornithine (DMFO); retinoids such as retinoic acid; capecitabine; combretastatin; leucovorin (LV); oxaliplatin, including the oxaliplatin treatment regimen (FOLFOX); lapatinib (Tykerb.®); inhibitors of PKC-alpha, Raf, H-Ras, EGFR (e.g., erlotinib (Tarceva®)) and VEGF-A that reduce cell proliferation and pharmaceutically acceptable salts, acids or derivatives of any of the above.

Also included in this definition are anti-hormonal agents that act to regulate or inhibit hormone action on tumors such as anti-estrogens and selective estrogen receptor modulators (SERMs), including, for example, tamoxifen (including NOLVADEX® tamoxifen), raloxifene, droloxifene, 4-hydroxytamoxifen, trioxifene, keoxifene, LY117018, onapristone, and FARESTON toremifene; aromatase inhibitors that inhibit the enzyme aromatase, which regulates estrogen production in the adrenal glands, such as, for example, 4(5)-imidazoles, aminoglutethimide, MEGASE® megestrol acetate, AROMASIN® exemestane, formestanie, fadrozole, RIVISOR® vorozole, FEMARA® letrozole, and ARIMIDEX® anastrozole; and anti-androgens such as flutamide, nilutamide, bicalutamide, leuprolide, and goserelin; as well as troxacitabine (a 1,3-dioxolane nucleoside cytosine analog); antisense oligonucleotides, particularly those which inhibit expression of genes in signaling pathways implicated in abherant cell proliferation, such as, for example, PKC-alpha, Ralf and H-Ras; ribozymes such as a VEGF expression inhibitor (e.g., ANGIOZYME® ribozyme) and a HER2 expression inhibitor; vaccines such as gene therapy vaccines, for example, ALLOVECTIN® vaccine, LEUVECTIN® vaccine, and VAXID® vaccine; PROLEUKIN® rIL-2; LURTOTECAN® topoisomerase 1 inhibitor; ABARELIX® rmRH; and pharmaceutically acceptable salts, acids or derivatives of any of the above.

A "growth inhibitory agent" as used herein refers to a compound or composition which inhibits growth of a cell in vitro and/or in vivo. Thus, the growth inhibitory agent can be one which significantly reduces the percentage of cells in S phase. Examples of growth inhibitory agents include agents that block cell cycle progression (at a place other than S phase), such as agents that induce G1 arrest and M-phase arrest. Classical M-phase blockers include the vincas (vincristine and vinblastine), TAXOL®, and topo II inhibitors such as doxorubicin, epirubicin, daunorubicin, etoposide, and bleomycin. Those agents that arrest G1 also spill over into S-phase arrest, for example, DNA alkylating agents such as tamoxifen, prednisone, dacarbazine, mechlorethamine, cisplatin, methotrexate, 5-fluorouracil, and ara-C. Further information can be found in The Molecular Basis of Cancer, Mendelsohn and Israel, eds., Chapter 1, entitled "Cell cycle regulation, oncogenes, and antineoplastic drugs" by Murakami et al. (WB Saunders: Philadelphia, 1995), especially p. 13.

The term "prodrug" as used in this application refers to a precursor or derivative form of a pharmaceutically active substance that is less cytotoxic to tumor cells compared to the parent drug and is capable of being enzymatically activated or converted into the more active parent form. See, e.g., Wilman, "Prodrugs in Cancer Chemotherapy" Biochemical Society Transactions, 14, pp. 375-382, 615th Meeting Belfast (1986) and Stella et al., "Prodrugs: A Chemical Approach to Targeted Drug Delivery," Directed Drug Delivery, Borchardt et al., (ed.), pp. 247-267, Humana Press (1985). The prodrugs described herein include, but are not limited to, phosphate-containing prodrugs, thiophosphate-containing prodrugs, sulfate-containing prodrugs, peptide-containing prodrugs, D-amino acid-modified prodrugs, glycosylated prodrugs, .beta.-lactam-containing prodrugs, optionally substituted phenoxyacetamide-containing prodrugs or optionally substituted phenylacetamide-containing prodrugs, 5-fluorocytosine and other 5-fluorouridine prodrugs which can be converted into the more active cytotoxic free drug. Examples of cytotoxic drugs that can be derivatized into a prodrug form for use in this invention include, but are not limited to, those chemotherapeutic agents described above.

By "radiation therapy" is meant the use of directed gamma rays or beta rays to induce sufficient damage to a cell so as to limit its ability to function normally or to destroy the cell altogether. It will be appreciated that there will be many ways known in the art to determine the dosage and duration of treatment. Typical treatments are given as a one time administration and typical dosages range from 10 to 200 units (Grays) per day.

By "reduce or inhibit" is meant the ability to cause an overall decrease preferably of 20% or greater, 30% or greater, 40% or greater, 45% or greater, more preferably of 50% or greater, of 55% or greater, of 60% or greater, of 65% or greater, of 70% or greater, and most preferably of 75%, 80%, 85%, 90%, 95%, or greater. Reduce or inhibit can refer to, for example, the symptoms of the disorder being treated, the presence or size of metastases or micrometastases, the size of the primary tumor, the presence or the size of the dormant tumor, or the size or number of the blood vessels in angiogenic disorders.

The term "intravenous infusion" refers to introduction of a drug into the vein of an animal or human subject over a period of time greater than approximately 5 minutes, preferably between approximately 30 to 90 minutes, although, according to the invention, intravenous infusion is alternatively administered for 10 hours or less. The term "intravenous bolus" or "intravenous push" refers to drug administration into a vein of an animal or human such that the body receives the drug in approximately 15 minutes or less, preferably 5 minutes or less.

The term "subcutaneous administration" refers to introduction of a drug under the skin of an animal or human subject, preferable within a pocket between the skin and underlying tissue, by relatively slow, sustained delivery from a drug receptacle. The pocket can be created by pinching or drawing the skin up and away from underlying tissue.

The term "subcutaneous infusion" refers to introduction of a drug under the skin of an animal or human subject, preferably within a pocket between the skin and underlying tissue, by relatively slow, sustained delivery from a drug receptacle for a period of time including, but not limited to, 30 minutes or less, or 90 minutes or less. Optionally, the infusion can be made by subcutaneous implantation of a drug delivery pump implanted under the skin of the animal or human subject, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human subject, where bolus drug delivery is preferably less than approximately 15 minutes, more preferably less than 5 minutes, and most preferably less than 60 seconds. Administration is preferably within a pocket between the skin and underlying tissue, where the pocket is created, for example, by pinching or drawing the skin up and away from underlying tissue.

A "disorder" is any condition that would benefit from treatment with, for example, an antibody described herein. This includes chronic and acute disorders or diseases including those pathological conditions which predispose the mammal to the disorder in question. Non-limiting examples of disorders to be treated herein include cancer; benign and malignant tumors; leukemias and lymphoid malignancies; neuronal, glial, astrocytal, hypothalamic and other glandular, macrophagal, epithelial, stromal and blastocoelic disorders; and inflammatory, angiogenic and immunologic disorders.

The word "label" when used herein refers to a detectable compound or composition which is conjugated directly or indirectly to the polypeptide. The label can be itself be detectable (e.g., radioisotope labels or fluorescent labels) or, in the case of an enzymatic label, can catalyze chemical alteration of a substrate compound or composition which is detectable.

By "subject" is meant a mammal, including, but not limited to, a human or non-human mammal, such as a bovine, equine, canine, ovine, or feline. Preferably, the subject is a human. Patients are also subjects herein.

BRIEF DESCRIPTION OF THE FIGURES

FIGS. 4A-4D demonstrate that DEspR and VEGFsp are also detected in tumor cells, with colocalization of VEGFsp and DEspR in the cell membrane and nuclear membrane using immunostaining DEspR cell-membrane and nuclear-membrane expression are detected in multiple tumor cell types, indicating that anti-DEspR therapy is effective for different cancer types. DEspR expression is detected in human lung non-small cell ca NCI-H727, lung giant cell tumor TIB-223/GCT; breast adenoca MDA-MB-231 (FIGS. 4A-4C) and MDA-MB-468, bladder ca 253J BV, colon adenoca SW480, hepatocellular ca, HEP3B, melanoma SK-MEL-2, osteosarcoma MG-63, ovarian adenoca HTB-161/NIH:OVCA R3, prostate adeno ca PC-3mm2, and pancreatic ca CRL-1469/PANC-1 (FIG. 4D).

FIGS. 5A-5C show that DEspR expression was not detected in in HCI-H292 lung mucoepidermoid ca, and HEPG2 hepatocellular ca (FIG. 5A), and CCL-86/Raji Burkitt's lymphoma, thus showing specificity of positive observations. Findings in NCI-727 lung ca cells (FIG. 5B) are corroborated on tumor-section immunostaining of Gr.III lung adenoca (FIG. 5C).

FIGS. 6A-6B show that in contrast to control (C) and pre-immune ab treatment (PI), DEspR-inhibition via anti-human DEspR antibody treatment inhibits tumor cell invasiveness in two cell lines tested, metastatic breast tumor MDA-MB-231 and pancreatic adenocarcinoma PANC-1 cell lines.

FIG. 7 shows that anti-DEspR treated rats ( ) exhibited minimal tumor growth compared with mock-treated controls (■), two-tailed t-test *P<0.05; **P<0.001.

FIGS. 11A-11C show inhibition of different parameters of angiogenesis by monoclonal antibody 7C5B2 and a polyclonal antibody preparation to DEspR. 7C5B2 monoclonal antibody was shown to immunostain HUVECs undergoing tube formation, pancreatic adenoca PANC-1, and breast cancer MDA-MB-231 cells. FIG. 11A shows mean number of branchpoints as a measure of neovessel complexity, and total length of tubes as a measure of neovessel density is shown in FIG. 11B. FIG. 11C shows concentration-dependent inhibition of in vitro serum-induced HUVEC tubulogenesis by monoclonal antibody 7C5B2. HUVEC (human umbilical vein endothelial cells) were grown onto Matrigel-coated wells in basal medium supplemented with 2% FBS (control), or 2% FBS+monoclonal antibody 7C5B2 (0.05-500 nM). The percentage of serum-induced tubulogenesis was determined as the difference between HUVECs grown in control conditions and the indicated monoclonal antibody 7C5B2-supplemented media. The % of the total tube length per well and the total number of branching points per well in the in vitro tube formation assay is presented. Data are shown as mean±standard error. Each experimental condition was performed in five replica wells. $EC_{50}$ for total tube length=4.34±0.45 nM; $EC_{50}$ for # branching points=3.97±0.51 nM.

FIGS. 12A-12C demonstrate that a monoclonal antibody 7C5B2 inhibits tumor cell invasiveness in MDA-MB-231 human breast cancer (FIG. 12A) and PANC-1 pancreatic cancer (FIG. 12B) cell lines (P<0.001*, <0.01*). FIG. 12C shows dose response curve of inhibition of MDA-MB-231 cell invasion by monoclonal antibody 7C5B2 ($EC_{50}$=3.55±0.32 nM). Data, mean±standard error of 5 replicates. *P<0.001, **P<0.01 (one way ANOVA, all pairwise multiple comparison Tukey's Test).

As shown in FIG. 14B, in contrast, a normal lung specimen does not exhibit any immunostaining for human DEspR or CD133.

FIG. 17A shows normal breast tissue: 3×-overlay of DEspR, aSMA and DAPI nuclear stain detects aSMA expression in mammary myoepithelial cells but no expression of DEspR in epithelial cells and microvessels. FIG. 17B shows 2×-immunofluorescence overlay of DEspR and DAPI nuclear stain and confirms absence of DEspR expression in normal breast tissue. FIG. 17C is a 4×-overlay of DEspR, aSMA, DAPI immunofluorescence and diffusion contrast imaging (DIC) that delineates tissue morphology, expression of aSMA. and non/minimal-expression of DEspR in normal mammary epithelium and endothelium. FIG. 17D is a 3×-Overlay of DAPI, aSMA and DEspR immunofluorescence in Gr.I-T1 invasive ductal carcinoma that detects DEspR expression in vascular endothelium, and co-localization with aSMA in mammary tissue. FIG. 17E is a 2×-overlay of DAPI and DEspR of breast cancer shown in panel 17D that highlights DEspR expression. FIG. 17F is a 4×-overlay of DAPI, aSMA, DEspR, DIC to elucidate DEspR spatial expression with tissue morphology of epithelial cells and microvessels. bar=20 microns.

FIG. 18A shows that normal pancreatic tissue, with a 3×-overlay of DEspR, aSMA and DAPI nuclear stain, detects minimal DEspR expression in microvessels. FIG. 18B shows a 4×-immunofluorescence overlay of DEspR, aSMA, DAPI, with DIC imaging of tissue morphology. FIG. 18C (left) shows a 3×-overlay of DEspR, aSMA, DAPI immunofluorescence; (right) shows a 4×-overlay of DEspR, aSMA, DAPI and diffusion contrast imaging (DIC) for tissue morphology that shows aSMA expression and non/minimal-expression of DEspR in normal endothelium. FIG. 18D shows that 3×-overlay of DAPI, aSMA and DEspR immunofluorescence in Gr.3-T3 pancreatic ductal carcinoma detects DEspR expression in vascular endothelium, and co-localization with aSMA. FIG. 18E shows a 2×-overlay of DAPI and DEspR of the image shown in FIG. 19D and highlights DEspR expression. FIG. 18F shows a 3×-overlay of DAPI, aSMA, DEspR, that shows increased DEspR expression in pancreatic ductal carcinoma cells. bar=20 microns.

FIGS. 19A-19E show representative contrast enhanced ultrasound (CEU)-images with contrast intensity signals (CIS) depicted. FIG. 19A shows $MB_D$ DEspR-targeted molecular imaging in transgenic rat-R1 demonstrating CEU-positive imaging and the characteristic drop in CIS-peak after acoustic disruption (|). FIG. 19B shows subsequent isotype-microbubble ($MB_C$) imaging in transgenic rat-R1 showing low peak CIS-levels and 'flat-line pattern of CIS pre- and post-destruction indicating CIU-negative imaging. FIG. 19C shows $MB_D$ DEspR-targeted molecular imaging in non-transgenic rat-R2 demonstrating CEU-negative imaging similar to $MB_C$ CEU-negative imaging. FIG. 19D shows a graph of CIS-differences ($\Delta$) among different study groups as notated distinguishing CEU-positive imaging in Tg $MB_D$ CEU+ group from the other CEU-negative groups.

FIGS. 20A-20H depict representative $MB_D$-specific contrast enhanced ultrasound (CEU)-positive images depicting complex pattern of acoustic destruction of adherent $MB_D$-microbubbles in a transgenic rat, R3. FIG. 20A shows representative CEU-image documenting blood pool of circulating $MB_D$s filling carotid artery lumen one-minute after bolus infusion. CCA, common carotid artery; ECA, external carotid artery; ICA, internal carotid artery; *, CCA bifurcation. FIGS. 20B-20D show scatter plots of contrast-intensity signals marked with same-dashed blocks to refer to corresponding regions of interest (ROI) in panel-20E. (20B) white solid line; (20C), white hatched line; (20D) white dotted line ROIs. FIG. 20E shows representative CEU-image that corresponds to #1 on scatter plots b,c,d documenting adherent DEspR-targeted microbubbles ($MB_D$) just prior to pre-acoustic destruction (black line). Adherent $MB_D$s are seen in the three ROIs encircled white solid line, white hatched line, and white dotted line. FIG. 20F shows representative CEU-image corresponding to #2 on scatter plots b-d showing a post-acoustic destruction dip in signal intensity compared to levels in #1 in the different ROIs respectively. FIG. 20G shows representative CEU-image corresponding to #3 on scatter plots b-d showing a post-acoustic destruction secondary peak in contrast intensity signals in the different ROIs. FIG. 20H shows representative CEU-image corresponding to #4 on scatter plots documenting the decline in contrast-intensity signals approaching baseline levels observed in isotype control or $MB_D$-infused CEU-negative images and demonstrating low background CIS levels.

FIG. 21A shows Masson trichrome stained section of carotid artery endothelium. FIGS. 21B-212C show differential interference contrast (DIC) image overlaid with fluorescence immunostaining for DEspR expression and DAPI nuclear stain. FIG. 21D shows control isotype-ab immunostaining and DAPI nuclear stain overlaid with DIC image of endothelium. FIG. 21E shows carotid artery Masson trichrome-stained section showing increased adventitial vasa vasorum neovessels. Boxed area is shown in higher magnification in FIG. 21F documenting rbc-filled vasa vasorum. FIG. 21G shows fluorescence immunostaining detects DEspR-positive expression in vasa vasorum and surrounding cells. FIG. 21H shows double immunostaining with α-SMA and DEspR detects αSMA co-expression in DEspR-positive neovessels. →, adherent DEspR-targeted microbubble $MB_D$; white arrowheads point to vasa vasorum neovessel in panels 21G and 21H; m, media; bar=10-microns panels 21A-21D, 21F; 20 microns panels 21E, 21G, 21H.

FIG. 22A shows scatter dot plot of pre-destruction CIS-peak levels highlighting a threshold (hatched bar) between $MB_D$-specific CEU-positive (CEU+) and CEU-negative (CEU−) imaging. FIG. 22B shows DEspR-positive immunostaining of carotid artery endothelium and expanded vasa vasorum; αSMA-positive immunostaining in smooth muscle cells (SMCs) in the media. Some vasa vasorum neovessels are double-immunostained for DEspR and αSMA. FIG. 22C shows corresponding DIC-image shows structural layers of carotid artery and vasa vasorum. FIG. 22D shows representative minimal to no DEspR-expression in rat carotid artery exhibiting CEU-negative imaging (shown here, nonTg rat-R2). Similar images obtained for CEU-negative transgenic rat carotid arteries. αSMA-immunostaining detects expression in SMCs in the media. Low levels of αSMA-immunostaining in the medial indicates synthetic SMC phenotype in both carotid arteries, consistent with hypertensive remodeling. FIG. 22D shows corresponding DIC-image shows structural layers of carotid artery and adventitia with no vasa vasorum expansion. Bar=20 microns (22B, 22C), 10 microns (22D, 22E). m, media; adv, adventitia; white small arrow, endothelium; white large arrow, vasa vasorum.

FIG. 23G shows number of MBs (mean +/−sem) per bound cell with increasing MB to cell ratio: $MB_D$ compared with isotype control $MB_C$ and control non-targeted $MB_O$. ***, ANOVA P<0.0001.

FIGS. 28A-28B show characterization of a human-specific anti-DEspR monoclonal antibody. (28A) Analysis by indirect ELISA of 10 candidate monoclonal antibody clones is shown. Serial dilutions from supernatants containing mAbs at 1 µg/ml were tested as follows: 1=1/2; 2 =1/4; 3=1/8; 4=1/16; 5=1/32; 6=1/64; 7=1/128; 8=1/256; 9=1/512; 10=1/1024; 11=1/2048 and 12=1/4096. white diamond, selected Mab 7c5b2 clone, open symbols, all others. (28B) Western blot analysis of purified Mabs (lanes 1-3), and "super clone" supernatants (lanes 4-6), with PBS serving as control (lane 7) are depicted. Selected 7C5B2 Mab in lanes 1 and 4 (diamond). Double immunostaining of HUVECs with anti-DEspR Mab-immunostaining and anti-VEGFsp immunostaining was performed and colocalization of DEspR and VEGFsp determined.

FIG. 34 shows the variable heavy chain amino acid (SEQ ID NO: 4) and nucleotide (SEQ ID NO: 3) sequence of the 7C5B2 antibody. CDR definitions and protein sequence numbering according to Kabat.

FIG. 35 shows the variable light chain amino acid (SEQ ID NO: 9) and nucleotide (SEQ ID NO: 8) sequence of a composite 7C5B2 antibody. CDR definitions and protein sequence numbering according to Kabat.

FIG. 36 shows an exemplary variable heavy chain amino acid (SEQ ID NO: 13) and nucleotide (SEQ ID NO: 21) sequence of a composite anti-DEspR humanized 7C5B2 antibody generated using the methods described herein. CDR definitions and protein sequence numbering according to Kabat.

Figure 37:
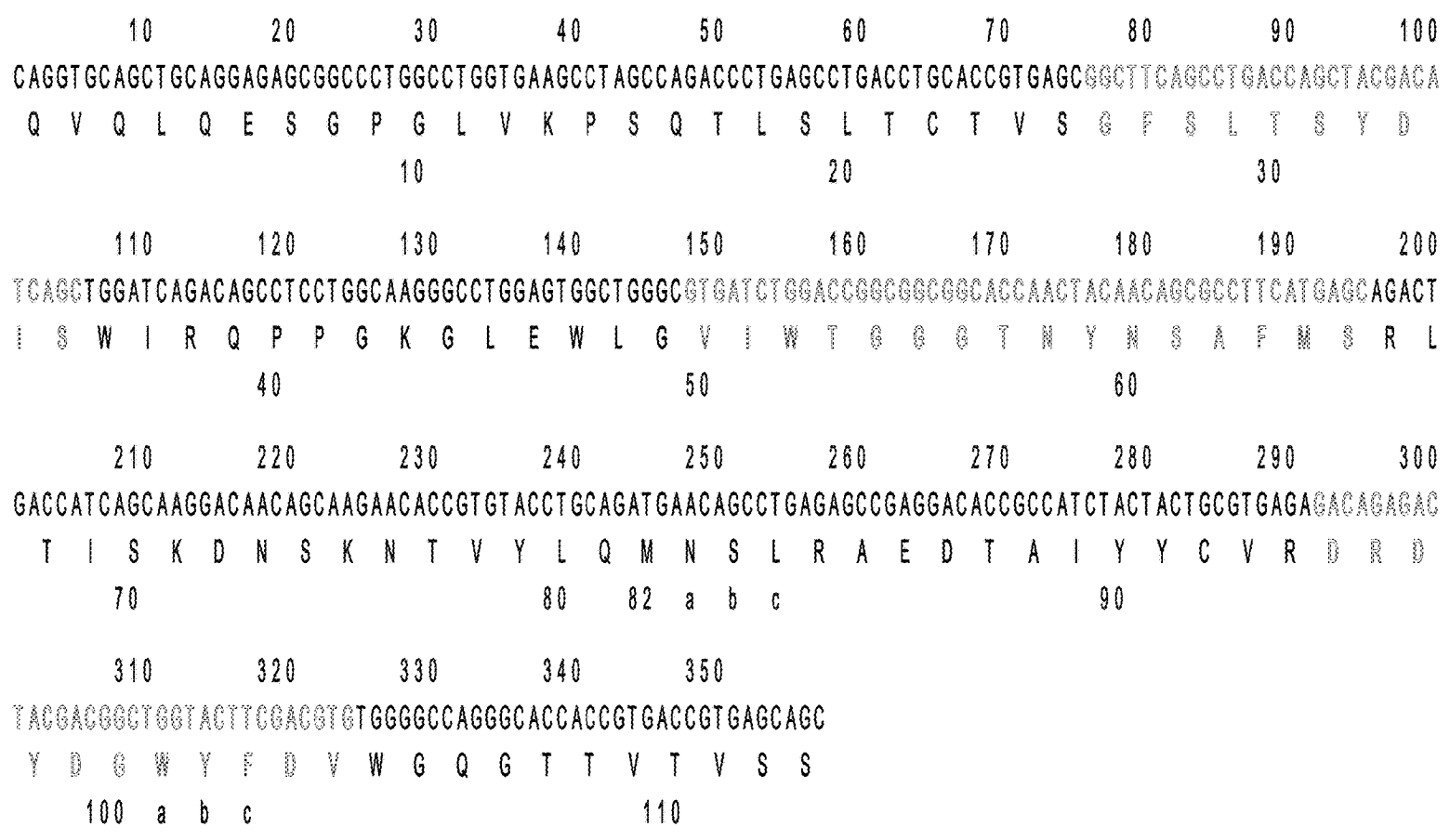

FIG. 37 shows an exemplary variable heavy chain amino acid (SEQ ID NO: 14) and nucleotide (SEQ ID NO: 22) sequence of a composite anti-DEspR humanized 7C5B2 antibody generated using the methods described herein. CDR definitions and protein sequence numbering according to Kabat.

FIG. 38 shows an exemplary variable heavy chain amino acid (SEQ ID NO: 15) and nucleotide (SEQ ID NO: 23) sequence of a composite anti-DEspR humanized 7C5B2 antibody generated using the methods described herein. CDR definitions and protein sequence numbering according to Kabat.

FIG. 39 shows an exemplary variable heavy chain amino acid (SEQ ID NO: 16) and nucleotide (SEQ ID NO: 24) sequence of a composite anti-DEspR humanized 7C5B2 antibody generated using the methods described herein. CDR definitions and protein sequence numbering according to Kabat.

FIG. 40 shows an exemplary variable heavy chain amino acid (SEQ ID NO: 17) and nucleotide (SEQ ID NO: 25) sequence of a composite anti-DEspR humanized 7C5B2 antibody generated using the methods described herein. CDR definitions and protein sequence numbering according to Kabat.

FIG. 41 shows an exemplary variable light chain amino acid (SEQ ID NO: 18) and nucleotide (SEQ ID NO: 26) sequence of a composite anti-DEspR humanized 7C5B2 antibody generated using the methods described herein. CDR definitions and protein sequence numbering according to Kabat.

FIG. 42 shows an exemplary variable light chain amino acid (SEQ ID NO: 19) and nucleotide (SEQ ID NO: 27) sequence of a composite anti-DEspR humanized 7C5B2 antibody generated using the methods described herein. CDR definitions and protein sequence numbering according to Kabat.

DETAILED DESCRIPTION

Figure 2:
FIG. 2 shows that DEspR contributes to adult tissue vascularity as seen in adult haplo-deficient (+/−) mice exhibiting decreased tissue vascularity using power Doppler analysis.

Provided herein are novel compositions comprising anti-DEspR antibodies and DEspR-binding fragments thereof, and methods of their use in anti-angiogenesis and anti-tumor proliferation and invasiveness therapies, such as the treatment of cancer, as well as the treatment of those vascular diseases where pathological angiogenesis plays a role, such as in carotid artery disease, vasa vasorum neovascularization (thus impacting, for example, stroke), and vulnerable plaque neovascularization (thus impacting, for example, heart disease). In addition, the compositions comprising the anti-DEspR antibodies and DEspR-binding fragments thereof described herein are useful in assessment and imaging methods, such as companion diagnostics for determining DEspR expression in tumor biopsies to identify likely reponders for personalized medicine approaches, DEspR-targeted molecular imaging of angiogenesis, which can be used, for example, in serial monitoring of response(s) to therapy, in vivo detection of tumor "angiogenic switch," or vascular mimicry. Further, such diagnostics provide novel approaches for anti-angiogenic therapies for use in personalized medicine applications. Furthermore, the compositions comprising the anti-DEspR antibodies and DEspR-binding fragments thereof described herein are useful as targeting moieties for other diagnostic and therapeutic compositions, in combination with delivery agents such as nanoparticles, polyplexes, microparticles, etc.

Therapies targeting the VEGF and VEGFR2 receptor pathways, such as bevacizumab, sunitinib, and sorafanib treatments, have recently been shown to have only transitory benefits, and appear to promote or induce a feedback angiogenic response, such that 10-fold increases in VEGF levels have been detected following anti-VEGF treatment (Willett et al., 2005 and Carmelie et al. 2005), and exacerbations of metastasis have been seen after VEGFR2 inhibitor (sunitinib) treatments.

In contrast, the inventors have discovered another angiogenesis arm of the VEGF system, based on their discovery that key, non-redundant, and distinct roles are played by interaction of the VEGF signal peptide (VEGFsp) with its receptor "DEspR" or "dual endothelin-1/VEGFsp receptor". The inventors have found that: a) a DEspR null mutation leads to E10.5-E12.5 embryonic lethality due to abnormal embryonic vasculogenesis and angiogenesis (Herrera et al. 2005); b) VEGFsp binds DEspR with high affinity, equal to what is observed for ET1 binding (Herrera et al. 2005); c) DEspR antibody-mediated inhibition in a rat mammary tumor model and DEspR haplo-deficiency in DEspR+/− mice reduces tumor growth in vivo (Herrera et al. 2005); d) VEGFsp stimulates adult rat aortic ring angiogenesis (Decano et al., 2010); and e) DEspR mediates adult angiogenesis and its expression is increased during carotid atherosclerotic vasa vasorum neovascularization, as described herein.

As described herein, the inventors further demonstrate that: a) DEspR expression is increased in several human cancer tumor vessels in both males and females (e.g., breast, lung, liver, bladder, pancrease, stomach, esophagus, colon, etc.), and surprisingly, also in a variety of tumor cells, including breast, lung, glioblastoma, bladder, melanoma, and pancreatic tumor cells, using tumor tissue arrays and tumor cell-line arrays respectively; as well as in cancer stem cells or cancer stem-like cells or tumor initiating cells; b) DEspR and VEGFsp are colocalized in both nuclear and cell membranes in cultured tumor cells; c) VEGFsp stimulates both tumor cell proliferation and invasiveness; and that d) DEspR inhibition via polyclonal and monoclonal anti-human DEspR antibodies potently suppress angiogenesis and tumor cell invasiveness, and reduce tumor growth rate and decrease tumor size significantly.

DEspR

The dual endothelin-1NEGF signal peptide activated receptor (DEspR), formerly DEAR was originally cloned from a Dahl salt-sensitive hypertensive rat brain cDNA library and was shown to be a single transmembrane receptor coupled to a Ca2+-mobilizing transduction pathway binding endothelin-1 (ET-1) and angiotensin-II (Ang II) with equivalent affinities (Ruiz-Opazo N. et al. (1998), Molecular characterization of a dual Endothelin-1/Angiotensin II Receptor. Mol Med. 4: 96-108). Subsequent molecular studies elucidated that the mouse ortholog does not interact with AngII but binds ET-1 and the vascular endothelial growth factor signal peptide (VEGFsp) with equal affinities instead. DEspR$^{-/-}$ double mutant deficiency in mice resulted in embryonic lethality due to impaired vasculogenesis, abnormal angiogenesis and vascular network formation. DEspR$^{-/-}$ embryos also showed abnormal neurogenesis marked by a hyperconvoluted neuroepithelium and dysregulated neural tube differentiation from the telencephalon to myelencephalon (Herrera VLM, et al., (2005), Embryonic lethality in Dear gene deficient mice: new player in angiogenesis. Physiol. Genomics 23: 257-268.). This phenotype is strikingly opposite to the proapoptotic effects observed in the developing neural tube in VEGF$^{+/-}$ deficient mice, although abnormalities in vasculogenesis and angiogenesis are similar (Herrera VLM, et al., (2005)).

Accordingly, the term " DEspR," as used herein, refers to the 85-amino acid dual endothelin/VEGF signal peptide receptor (DEspR) having the human amino acid native sequence of: MTMFKGSNEMKSRWNWGSITCI-ICFTCVGSQLSMSSSKASNFSGPLQLYQRELEIFIVLT-DVP NYRLIKENSHLHTTIVDQGRTV (SEQ ID NO:1), as described by, e.g., Glorioso et al. 2007, together with naturally occurring allelic, splice variants, and processed forms thereof.

As used herein a DEspR "native sequence" or DEspR "wild-type sequence" polypeptide comprises a polypeptide having the same amino acid sequence as a DEspR polypeptide derived from nature. Thus, a native sequence polypeptide can have the amino acid sequence of naturally-occurring polypeptide from any mammal. Such native sequence polypeptide can be isolated from nature or can be produced by recombinant or synthetic means. The term "native sequence" polypeptide specifically encompasses naturally-occurring truncated or secreted forms of the polypeptide (e.g., an extracellular domain sequence), naturally-occurring variant forms (e.g., alternatively spliced forms) and naturally-occurring allelic variants of the polypeptide.

A DEspR polypeptide "variant" means a biologically active DEspR polypeptide having at least about 80% amino acid sequence identity with a native sequence of a DEspR polypeptide. Such variants include, for instance, polypeptides wherein one or more amino acid residues are added, or deleted, at the N- or C-terminus of the polypeptide. Ordinarily, a variant has at least about 80% amino acid sequence identity, more preferably at least about 90% amino acid sequence identity, and even more preferably at least about 95% amino acid sequence identity with the native sequence polypeptide.

DEspR is part of the G protein coupled receptor family, and binds to endothelin-1 and to VEGF signal peptide (VEGFsp). VEGFsp has the human sequence MNFLLSWVHWSLALLLYLHHAKWSQA (SEQ ID NO:2). Typically, as used herein, DEspR refers to human DEspR. The term "DEspR" is also used to refer to truncated forms or fragments of the polypeptide comprising specific amino acids sequences of the 85-amino acid human dual endothelin/VEGF signal peptide receptor. Reference to any such forms of DEspR can be identified in the application, e.g., by "DEspR (1-9)."

DEspR Antagonists & Anti DEspR Antibodies

Provided herein are compositions and methods comprising DEspR antagonists that are capable of neutralizing, blocking, inhibiting, abrogating, reducing, or interfering with DEspR activities including its binding to endothelin-1 or VEGFsp. DEspR antagonists include, but are not limited to, anti-DEspR antibodies and antigen-binding fragments thereof, receptor molecules, small molecules, nanoparticles, polyplex combinations and derivatives thereof that bind specifically to DEspR thereby inhibiting, preventing, or sequestering its binding to its ligands, such as VEGFsp and endothelin-1.

Anti-DEspR Antibodies and Antibody Production

Accordingly, in some aspects, provided herein is an anti-DEspR antibody or antibody fragment thereof that is specific for a DEspR target, where the anti-DEspR antibody or antibody fragment thereof specifically binds to the DEspR target and reduces or inhibits DEspR biological activity. In some embodiments, the DEspR is human DEspR. In some embodiments, the DEspR target comprises an amino acid sequence of SEQ ID NO:1 or an allelic or splice variant thereof.

As used herein, an "anti-DEspR antibody" refers to an antibody that binds to DEspR with sufficient affinity and specificity. The antibody selected will normally have a binding affinity for DEspR, for example, the antibody can bind human DEspR with a $K_D$ value between $10^{-5}$ M to $10^{-10}$ M. As used herein, "selectively binds" or "specifically binds" refers to the ability of an anti-DEspR antibody or antibody fragment thereof described herein to bind to DEspR, with a $K_D$ $10^{-5}$ M (10000 nM) or less, e.g., $10^{-6}$ M, $10^{-7}$ M, $10^{-8}$ M, $10^{-9}$ M, $10^{-10}$ M, $10^{-11}$ M, $10^{-12}$ M, or less.

Antibody affinities can be determined, for example, by a surface plasmon resonance based assay (such as the BIAcore assay described in PCT Application Publication No. WO2005/012359); enzyme-linked immunoabsorbent assay (ELISA); and competition assays (e.g. RIA's), for example. In certain aspects described herein, an anti-DEspR antibody can be used as a therapeutic agent in targeting and interfering with diseases or conditions where DEspR activity is involved. Also, the anti-DEspR antibody can be subjected to other biological activity assays, e.g., in order to evaluate its effectiveness as a therapeutic, or its effectiveness as a diagnostic aid, etc. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). Other biological activity assays that can be used to assess an anti-DEspR antibody are described herein in the Examples section.

Thus, anti-DEspR antibodies or antibody fragments thereof that are useful in the compositions and methods described herein include any antibodies or antibody fragments thereof that bind with sufficient affinity and specificity to DEspR, i.e., are specific for DEspR, and can reduce or inhibit the biological activity of DEspR.

Accordingly, in some aspects, provided herein is an anti-DEspR antibody or antibody fragment thereof that binds to DEspR and inhibits DEspR biological activity or blocks interaction of DEspR with VEGFsp. In some embodiments of these aspects and all such aspects described herein, the VEGFsp has a sequence comprising the sequence of SEQ ID NO: 2. In some embodiments of these aspects and all such aspects described herein, the anto-DEspR antibody or antibody fragment thereof is specific for an epitope of DEspR comprising an extracellular portion of DEspR. In some embodiments of these aspects and all such aspects described herein, the anti-DEspR antibody or antibody fragment thereof is specific for an epitope of DEspR comprising amino acids 1-9 of SEQ ID NO: 1.

Further description and examples of anti-DEspR antibodies and antibody fragments thereof useful with the compositions and methods described herein, as well as methods of making and characterizing the same, are provided below:

Polyclonal Antibodies

Polyclonal antibodies are preferably raised in animals by multiple subcutaneous (sc) or intraperitoneal (ip) injections of the relevant antigen, e.g., DEspR(1-9) and an adjuvant. It can be useful, in some embodiments, to conjugate the relevant antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOC1_2$, or $R^1N{=}C{=}NR$, where R and $R^1$ are different alkyl groups.

Animals can be immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to 1/10 the original amount of peptide or conjugate in Freund's complete adjuvant by subcutaneous injection at multiple sites. Seven to 14 days later the animals are bled and the serum is assayed for antibody titer Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

Monoclonal Antibodies

Preferably, anti-DEspR antibodies or antibody fragments thereof for use with the compositions and methods described herein are anti-DEspR monoclonal antibodies or fragments thereof. The term "monoclonal antibody" refers to an antibody obtained from a population of substantially homogeneous antibodies, i.e., the individual antibodies comprising the population are identical except for possible naturally occurring mutations that can be present in minor amounts. Monoclonal antibodies are highly specific, being directed against a single antigen. Furthermore, in contrast to polyclonal antibody preparations that typically include different antibodies directed against different determinants (epitopes), each monoclonal antibody is directed against a single determinant on the antigen. Various methods for making monoclonal antibodies specific for DEspR as described herein are available in the art. For example, the monoclonal antibodies can be made using the hybridoma method first described by Kohler et al., Nature, 256:495 (1975), or by recombinant DNA methods (U.S. Pat. No. 4,816,567). "Monoclonal antibodies" can also be isolated from phage antibody libraries using the techniques described in Clackson et al., Nature 352:624-628 (1991) or Marks et al., J. Mol. Biol. 222:581-597 (1991), for example.

The term anti-DEspR "antibody fragment" refers to a protein fragment that comprises at least an antigen binding site of the intact antibody and thus retaining the ability to bind antigen. Examples of antibody fragments encompassed by the term antibody fragment include: (i) the Fab fragment, having $V_L$, $C_L$, $V_H$ and $C_H1$ domains; (ii) the Fab' fragment, which is a Fab fragment having one or more cysteine residues at the C-terminus of the $C_H1$ domain; (iii) the Fd fragment having $V_H$ and $C_H1$ domains; (iv) the Fd' fragment having $V_H$ and $C_H1$ domains and one or more cysteine residues at the C-terminus of the CH1 domain; (v) the Fv fragment having the $V_L$ and $V_H$ domains of a single arm of an antibody; (vi) the dAb fragment (Ward et al., Nature 341, 544-546 (1989)) which consists of a $V_H$ domain; (vii) isolated CDR regions; (viii) $F(ab')_2$ fragments, a bivalent fragment including two Fab' fragments linked by a disulphide bridge at the hinge region; (ix) single chain antibody molecules (e.g., single chain Fv; scFv) (Bird et al., Science 242:423-426 (1988); and Huston et al., PNAS (USA) 85:5879-5883 (1988)); (x) "diabodies" with two antigen binding sites, comprising a heavy chain variable domain ($V_H$) connected to a light chain variable domain ($V_L$) in the same polypeptide chain (see, e.g., EP 404,097; WO 93/11161; and Hollinger et al., Proc. Natl. Acad. Sci. USA, 90:6444-6448 (1993)); (xi) "linear antibodies" comprising a pair of tandem Fd segments ($V_H$-$C_H1$-$V_H$-$C_H1$) which, together with complementary light chain polypeptides, form a pair of antigen binding regions (Zapata et al. Protein Eng. 8(10):1057-1062 (1995); and U.S. Pat. No. 5,641,870).

In the hybridoma method of making an anti-DEspR monoclonal antibody, a mouse or other appropriate host animal, such as a hamster or macaque monkey, is immunized as described herein to elicit lymphocytes that produce or are capable of producing antibodies that will specifically bind to the DEspR protein or fragment thereof used for immunization. Alternatively, lymphocytes can be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol , 133:3001 (1984); Brodeur et al., Monoclonal Antibody Production Techniques and Applications, pp. 51-63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones can be subcloned by limiting dilution procedures and grown by standard methods (Goding, Monoclonal Antibodies: Principles and Practice, pp. 59-103 (Academic Press, 1986)). Suitable culture media for this purpose include, for example, D-MEM or RPMI-1640 medium. In addition, the hybridoma cells can be grown in vivo as ascites tumors in an animal.

The monoclonal antibodies secreted by the subclones are suitably separated from the culture medium, ascites fluid, or serum by conventional immunoglobulin purification procedures such as, for example, protein A-Sepharose, hydroxylapatite chromatography, gel electrophoresis, dialysis, or affinity chromatography.

DNA encoding the monoclonal antibodies can be readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA can be placed into expression vectors, which are then transfected into host cells such as E. coli cells, simian COS cells, Chinese hamster ovary (CHO) cells, or myeloma cells that do not otherwise produce immunoglobulin protein, to obtain the synthesis of monoclonal antibodies in the recombinant host cells. Recombinant production of antibodies is described in more detail below.

Anti-DEspR Hybridomas and Monoclonal Antibodies Thereof

In certain aspects described herein, anti-DEspR monoclonal antibodies include, but are not limited to, the monoclonal anti-DEspR antibody 7C5B2 produced or expressed by the hybridoma 7C5B2 described herein, and referred to as the "7C5B2 antibody," and derivatives or antigen-binding fragments thereof, including, for example, a "7C5B2 variable heavy chain," or a "7C5B2" variable light chain.

As described herein, the 7C5B2 hybridoma produces a monoclonal antibody, termed herein as the "7C5B2 anti-DEspR antibody" or "7C5B2 antibody," that is highly specific for DEspR and can potently inhibit DEspR biological activity. The biological characteristics of the 7C5B2 anti-DEspR antibody render it particularly useful for the compositions and methods described herein, including therapeutic and diagnostic applications. Accordingly, sequence analysis of the 7C5B2 antibody was performed, as described herein, to identify the heavy and light chain variable domain sequences, and complementarity determining region (CDR) sequences, of the 7C5B2 antibody for use in the compositions and methods described herein.

Throughout the present specification and claims, the numbering of the residues in an immunoglobulin heavy chain is that of the EU index as in Kabat et al., Sequences of Proteins of Immunological Interest, 5th Ed. Public Health Service, National Institutes of Health, Bethesda, Md. (1991), which is also available on the world wide web, and is expressly incorporated herein in its entirety by reference. The "EU index as in Kabat" refers to the residue numbering of the human IgG 1 EU antibody.

As used herein, "antibody variable domain" refers to the portions of the light and heavy chains of antibody molecules that include amino acid sequences of Complementarity Determining Regions (CDRs; i.e., CDR1, CDR2, and CDR3), and Framework Regions (FRs). $V_H$ refers to the variable domain of the heavy chain. $V_L$ refers to the variable domain of the light chain. According to the methods used herein, the amino acid positions assigned to CDRs and FRs can be defined according to Kabat (Sequences of Proteins of Immunological Interest (National Institutes of Health, Bethesda, Md., 1987 and 1991)). Amino acid numbering of antibodies or antigen binding fragments is also according to that of Kabat.

As used herein, the term "Complementarity Determining Regions" (CDRs), i.e., CDR1, CDR2, and CDR3) refers to the amino acid residues of an antibody variable domain the presence of which are necessary for antigen binding Each variable domain typically has three CDR regions identified as CDR1, CDR2 and CDR3. Each complementarity determining region can comprise amino acid residues from a "complementarity determining region" as defined by Kabat (i.e., about residues 24-34 (L1), 50-56 (L2) and 89-97 (L3) in the light chain variable domain and 31-35 (H1), 50-65 (H2) and 95-102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e., about residues 26-32 (L1), 50-52 (L2) and 91-96 (L3) in the light chain variable domain and 26-32 (H1), 53-55 (H2) and 96-101 (H3) in the heavy chain variable domain; Chothia and Lesk J. Mol. Biol. 196:901-

917 (1987)). In some embodiments, a complementarity determining region can include amino acids from both a CDR region defined according to Kabat and a hypervariable loop.

The nucleotide sequence encoding the $V_H$ or variable domain of the heavy chain of the 7C5B2 antibody, as obtained by sequence analysis of sequences obtained from the 7C5B2 hybridoma, is: CAGGTGCAACT-GAAGGAGTCAGGACCTGGCCTGGTGG CGCCCT-CACAGAGCCTGTCCATTACCTGCACT-GTCTCTGGGTTC TCATTAACCAGCTATGATATAAGCTGGATTCGCCA-GCCACCAGG AAAGGGTCTGGAGTGGCTTGGAG-TAATATGGACTGGTGGAGGC ACAAATTATAATTCA-GCTTTCATGTCCAGACTGAGCATCAGCAA GGACAACTCCAAGAGCCAAGTTTTCTTAAAAAT-GAACAGTCTGC AAACTGATGACACAGCCATATAT-TACTGTGTAAGAGATCGGGAT TACGACGGGTGG-TACTTCGATGTCTGGGGCGCAGGGACCACGGT CACCGTCTCCTCA (SEQ ID NO: 3).

The corresponding amino acid of the $V_H$ domain of the 7C5B2 antibody is: QVQL KESGPGLVAPSQSLSITCTVS-GFSLTSYDISWIRQPPGKGLEWLGVI WTGGGTNYN-SAFMSRLSISKDNSKSQVFLKMNSLQTDDTAIYYCV RDRDYDGWYFDVWGAGTTVTVSS (SEQ ID NO: 4).

The 10 amino acid complementarity determining region 1 or CDR1 of the $V_H$ domain of the 7C5B2 antibody is: GFSLTSYDIS (SEQ ID NO: 5). The 16 amino acid CDR2 of the $V_H$ domain of the 7C5B2 antibody is: VIWTGGGT-NYNSAFMS (SEQ ID NO: 6). The 11 amino acid CDR2 of the $V_H$ domain of the 7C5B2 antibody is: DRDYDG-WYFDV (SEQ ID NO: 7).

The nucleotide sequence encoding the $V_L$ or variable domain of the light chain of the 7C5B2 antibody, as obtained by sequence analysis of sequences obtained from the 7C5B2 hybridoma, is: GATGTTTTGATGACCCAAACTC-CACTCTCCCTGCCTGTCAGTC TTGGAGATCAAGC-CTCCATCTCTTGCAGATCTAGTCAGAGCATT GTA-CATAGTAATGGAAACACCTATTTAGAATGGTACCT GCAGAA ACCAGGCCAGTCTCCAAAGCTCCTGATC-TACAAAGTTTCCAACC GATTTTCTGGGGTCCCA-GACAGGTTCAGTGGCAGTGGATCAGGG ACA-GATTTCACACTCAAGATCAGCAGAGTGGAGGCTG AGGATCT GGGAGTTTATTACTGCTTTCAAGGTTCA-CATGTTCCGTACACGT TCGGAGGGGGGAC-CAAGCTGGAAATAAAA (SEQ ID NO: 8).

The corresponding amino acid of the $V_L$ domain of the 7C5B2 antibody is: DVLM TQTPLSLPVSLGDQASIS-CRSSQSIVHSNGNTYLEWYLQKPGQSPK LLIYKVSN-RFSGVPDRFSGSGSGTDFTLKISRVEAEDLGVYY-CFQG SHVPYTFGGGTKLEIK (SEQ ID NO: 9).

The 16 amino acid complementarity determining region 1 or CDR1 of the $V_L$ domain of the 7C5B2 antibody is: RSSQSIVHSNGNTYLE (SEQ ID NO: 10). The 7 amino acid CDR2 of the $V_L$ domain of the 7C5B2 antibody is: KVSNRFS (SEQ ID NO: 11). The 9 amino acid CDR2 of the $V_L$ domain of the 7C5B2 antibody is: FQGSHVPYT (SEQ ID NO: 12).

As shown in Table 1, sequence analysis of the heavy and light chain variable regions of the 7C5B2 antibody indicates strong homology to human germline sequences:

TABLE 1

Antibody Sequence Analysis[a]

|  | H Chain | L Chain |
|---|---|---|
| CDR 1 Length | 10aa | 16aa |
| CDR 2 Length | 16aa | 7aa |
| CDR 3 Length | 11aa | 9aa |
| Closest Human Germline[b] | IGHV4-59*01 (64%) | IGKV2-30*01 (82%) |
| Closest Human FW1[b] | IGHV4-31*01 (84%) | IGKV2-30*01 (78%) |
| Closest Human FW2[b] | IGHV4-61*01 (93%) | IGKV2-40*01 (93%) |
| Closest Human FW3[b] | IGHV3-66*01 (60%) | IGKV2-30*01 (97%) |
| Closest Human J[b] | IGHJ6 (91%) | IGKJ2 (90%) |

[a]CDR definitions and sequence numbering according to Kabat
[b]Germline ID(s) indicated followed by % homology Accordingly, in some embodiments of the aspects provided herein, the heavy and/or light chain variable domain(s) sequence(s) of the 7C5B2 antibody, i.e., SEQ ID NO: 3, SEQ ID NO: 4, SEQ ID NO: 8, and/or SEQ ID NO: 9 can be used to generate, for example, humanized antibodies, as described elsewhere herein.

In some aspects, monoclonal antibodies that specifically bind to DEspR are provided having one or more biological characteristics of the 7C5B2 monoclonal antibody. As used herein, an antibody having a "biological characteristic" of a designated antibody, such as the 7C5B2 antibody, is one that possesses one or more of the biological characteristics of that antibody which distinguish it from other antibodies that bind to the same antigen.

Accordingly, in some such embodiments of these aspects, having a biological characteristic of the 7C5B2 monoclonal antibody can include having an $ED_{50}$ value (i.e., the dose therapeutically effective in 50% of the population) at or around the $ED_{50}$ value of the 7C5B2 antibody for the given population; having an $EC_{50}$ value (i.e., the dose that achieves a half-maximal inhibition of a given parameter or phenotype) at or around the $EC_{50}$ value of the 7C5B2 antibody for a given parameter or phenotye. The effects of any particular dosage can be monitored by a suitable bioassay. For example, in some embodiments of these aspects, the given parameter or phenotype to be inhibited by the antibody that specifically binds to DEspR and has one or more biological characteristics of the 7C5B2 antibody can include, but is not limited to, the mean total tube number in an in vitro tubulogenesis assay, the mean total tube length in an in vitro tubulogenesis assay, the mean number of branching points in an in vitro tubulogenesis assay, the mean number of vessel connections in an in vitro tubulogenesis assay, and/or tumor cell invasiveness.

Accordingly, in those embodiments where the phenotype to be inhibited is mean total tube length, as measured using an in vitro tubulogenesis assay, the $EC_{50}$ value of the monoclonal antibody having a biological characteristic of the 7C5B2 monoclonal antibody is 10 nM or less, 9 nM or less, 8 nM or less, 7 nM or less, 6 nM or less, 5 nM or less, 4 nM or less, 3 nM or less, 2 nM or less, or 1 nM or less. In some such embodiments, the $EC_{50}$ value of the monoclonal antibody is in the range of 3.0-5.0 nM, in the range of 3.1-4.9 nM, in the range of 3.2-4.8 nM, in the range of 3.3-4.7 nM, in the range of 3.4-4.6 nM, in the range of 3.5-4.5 nM, in the range of 3.6-4.4 nM, in the range of 3.7-4.3 nM, in the range of 3.8-4.2 nM, or in the range of 3.9-4.1 nM. In some embodiments, the $EC_{50}$ value for inhibiting mean total tube length of the monoclonal antibody having a biological characteristic of the 7C5B2 monoclonal antibody is in the range of 3.8 nM-4.8 nM.

For example, in those embodiments where the phenotype to be inhibited is number of branch points, as measured using an in vitro tubulogenesis assay, the $EC_{50}$ value of the monoclonal antibody having a biological characteristic of the 7C5B2 monoclonal antibody is 10 nM or less, 9 nM or less, 8 nM or less, 7 nM or less, 6 nM or less, 5 nM or less, 4 nM or less, 3 nM or less, 2 nM or less, or 1 nM or less. In some such embodiments, the $EC_{50}$ value of the monoclonal antibody is in the range of 3.0-5.0 nM, in the range of 3.1-4.9 nM, in the range of 3.2-4.8 nM, in the range of 3.3-4.7 nM, in the range of 3.4-4.6 nM, in the range of 3.5-4.5 nM, in the range of 3.6-4.4 nM, in the range of 3.7-4.3 nM, in the range of 3.8-4.2 nM, or in the range of 3.9-4.1 nM. In some embodiments, the $EC_{50}$ value for inhibiting total number of branch points of the monoclonal antibody having a biological characteristic of the 7C5B2 monoclonal antibody is in the range of 3.4 nM-4.5 nM, in the range of 3.5 nM-4.4 nM, in the range of 3.6 nM-4.3 nM, in the range of 3.7 nM-4.2 nM, in the range of 3.8 nM-4.1 nM, in the range of 3.9 nM-4.0 nM.

For example, in those embodiments where the phenotype to be inhibited is tumor cell invasiveness, as measured in vitro, the $EC_{50}$ value of the monoclonal antibody having a biological characteristic of the 7C5B2 monoclonal antibody is 10 nM or less, 9 nM or less, 8 nM or less, 7 nM or less, 6 nM or less, 5 nM or less, 4 nM or less, 3 nM or less, 2 nM or less, or 1 nM or less. In some such embodiments, the $EC_{50}$ value of the monoclonal antibody is in the range of 3.0-5.0 nM, in the range of 3.1-4.9 nM, in the range of 3.2-4.8 nM, in the range of 3.3-4.7 nM, in the range of 3.4-4.6 nM, in the range of 3.5-4.5 nM, in the range of 3.6-4.4 nM, in the range of 3.7-4.3 nM, in the range of 3.8-4.2 nM, or in the range of 3.9-4.1 nM. In some embodiments, the $EC_{50}$ value for inhibiting tumor cell invasiveness of the monoclonal antibody having a biological characteristic of the 7C5B2 monoclonal antibody is in the range of 3.2 nM-3.9 nM, in the range of 3.3 nM-3.8 nM, 3.4 nM-3.7 nM, or in the range of 3.5 nM-3.6 nM.

In some embodiments of the aspects described herein, anti-DEspR antibodies for use in the compositions and methods described herein include monoclonal antibodies that bind to the same epitope or epitopes of DEspR as the monoclonal anti-DEspR 7C5B2 antibody.

In other aspects described herein, anti-DEspR antibodies for use in the compositions and methods described herein include: the monoclonal anti-DEspR antibody 7C5C5 produced or expressed by the hybridoma 7C5C5 described herein, referred to as the "7C5C5 antibody," and derivatives or fragments thereof; monoclonal antibodies that bind to the same epitope or epitopes of DEspR as the monoclonal anti-DEspR 7C5C5 antibody; the monoclonal anti-DEspR antibody 5G12E8 produced or expressed by the hybridoma5G12E8described herein, referred to as the "5G12E8 antibody," and derivatives or fragments thereof; monoclonal antibodies that bind to the same epitope or epitopes of DEspR as the monoclonal anti-DEspR 5G12E8 antibody; and monoclonal antibodies produced by hybridomas 2E4A8, 2E4B11, 2E4H10, 8E7D11, 8E2F6, E2G4 and 8E7F8.

In addition to generation and production via hybridomas, antibodies or antibody fragments that specifically bind DEspR can be isolated from antibody phage libraries generated using the techniques described in McCafferty et al., Nature, 348:552-554 (1990). Clackson et al., Nature, 352: 624-628 (1991) and Marks et al., J. Mol. Biol., 222:581-597 (1991) describe the isolation of murine and human antibodies, respectively, using phage libraries. Subsequent publications describe the production of high affinity (nM range) human antibodies by chain shuffling (Marks et al., Bio/Technology, 10:779-783 (1992)), as well as combinatorial infection and in vivo recombination as a strategy for constructing very large phage libraries (Waterhouse et al., Nuc. Acids. Res., 21:2265-2266 (1993)). Thus, these techniques are viable alternatives to traditional monoclonal antibody hybridoma techniques for isolation of monoclonal antibodies.

The DNA sequences encoding the antibodies or antibody fragment that specifically bind DEspR also can be modified, for example, by substituting the coding sequence for human heavy- and light-chain constant domains in place of the homologous murine sequences (U.S. Pat. No. 4,816,567; Morrison, et al., Proc. Natl. Acad. Sci. USA, 81:6851 (1984)), or by covalently joining to the immunoglobulin coding sequence all or part of the coding sequence for a non-immunoglobulin polypeptide, as also described elsewhere herein.

Such non-immunoglobulin polypeptides can be substituted for the constant domains of an antibody, or they can be substituted for the variable domains of one antigen-combining site of an antibody to create a chimeric bivalent antibody comprising one antigen-combining site having specificity for an antigen and another antigen-combining site having specificity for a different antigen.

Humanized and Human Antibodies

Provided herein, in some aspects, are humanized anti-DEspR antibodies for use in the compositions and methods described herein. Humanized forms of non-human (e g., murine) antibodies refer to chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies can comprise residues that are not found in the recipient antibody or in the donor antibody. These modifications are made to further refine antibody performance. In general, a humanized antibody can comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also can comprise at least a portion of an immunoglobulin constant region (Fc), typically that of a human immunoglobulin. For further details, see Jones et al., Nature 321:522-525 (1986); Riechmann et al., Nature 332:323-329 (1988); and Presta, Curr. Op. Struct. Biol. 2:593-596 (1992).

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., Nature, 321:522-525 (1986); Riechmann et al., Nature, 332:323-327 (1988); Verhoeyen et al., Science, 239:1534-1536 (1988)), by substituting rodent CDRs or CDR sequences for the corresponding sequences of a human antibody. Accordingly, such humanized antibodies are chimeric antibodies (U.S. Pat. No. 4,816,567) where substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies. In some embodiments, humanized antibodies comprising one or more variable domains comprising the amino acid sequence of the variable heavy (SEQ ID NO: 4) and/or variable light (SEQ ID NO: 9) chain domains of the murine anti-DEspR antibody 7C5B2, are provided.

Accordingly, in some embodiments of the aspects described herein, one or more heavy and/or one or more light chain CDR regions of a humanized anti-DEspR antibody or antibody fragment thereof comprises a sequence of the 7C5B2 antibody described herein. In some such embodiments, the one or more variable heavy chain CDR regions comprises a sequence selected from the group consisting of SEQ ID NO: 5, SEQ ID NO: 6, or SEQ ID NO: 7. In some such embodiments, the one or more variable light chain CDR regions comprises a sequence selected from the group consisting of SEQ ID NO: 10, SEQ ID NO: 11, or SEQ ID NO: 12. In some such embodiments, the one or more variable heavy chain CDR regions comprises a sequence selected from the group consisting of SEQ ID NO: 5, SEQ ID NO: 6, or SEQ ID NO: 7, and the one or more variable light chain CDR regions comprises a sequence selected from the group consisting of SEQ ID NO: 10, SEQ ID NO: 11, or SEQ ID NO: 12.

In some embodiments of the aspects described herein, a humanized anti-DEspR monoclonal antibody comprises mutated human IgG 1 framework regions and one or more heavy and/or one or more light chain CDR regions from the murine anti-human DEspR monoclonal antibody 7C5B2, described herein, that blocks binding of human DEspR to its ligands. In some such embodiments, the one or more variable heavy chain CDR regions comprises a sequence selected from the group consisting of SEQ ID NO: 5, SEQ ID NO: 6, or SEQ ID NO: 7. In some such embodiments, the one or more variable light chain CDR regions comprises a sequence selected from the group consisting of SEQ ID NO: 10, SEQ ID NO: 11, or SEQ ID NO: 12. In some such embodiments, the one or more variable heavy chain CDR regions comprises a sequence selected from the group consisting of SEQ ID NO: 5, SEQ ID NO: 6, or SEQ ID NO: 7, and the one or more variable light chain CDR regions comprises a sequence selected from the group consisting of SEQ ID NO: 10, SEQ ID NO: 11, or SEQ ID NO: 12.

In some embodiments, a humanized anti-DEspR monoclonal antibody comprises mutated human IgG4 framework regions and one or more heavy and/or one or more light chain CDR regions from the murine anti-human DEspR monoclonal antibody 7C5B2, described herein, that blocks binding of human DEspR to its ligands. In some such embodiments, the one or more variable heavy chain CDR regions comprises a sequence selected from the group consisting of SEQ ID NO: 5, SEQ ID NO: 6, or SEQ ID NO: 7. In some such embodiments, the one or more variable light chain CDR regions comprises a sequence selected from the group consisting of SEQ ID NO: 10, SEQ ID NO: 11, or SEQ ID NO: 12. In some such embodiments, the one or more variable heavy chain CDR regions comprises a sequence selected from the group consisting of SEQ ID NO: 5, SEQ ID NO: 6, or SEQ ID NO: 7, and the one or more variable light chain CDR regions comprises a sequence selected from the group consisting of SEQ ID NO: 10, SEQ ID NO: 11, or SEQ ID NO: 12.

The choice of human variable domains, both light and heavy, to be used in making the humanized antibodies is very important to reduce antigenicity. According to the so-called "best-fit" method, the amino acid sequences of the variable heavy and light chain domains of a rodent antibody, such as that of the 7C5B2 antibody (SEQ ID NO: 4 and SEQ ID NO: 9, respectively), are screened against the entire library of known human variable-domain sequences. The human sequence which is closest to that of the rodent is then accepted as the human framework (FR) for the humanized antibody (Sims et al., J. Immunol , 151:2296 (1993); Chothia et al., J. Mol. Biol., 196:901 (1987)). Another method uses a particular framework derived from the consensus sequence of all human antibodies of a particular subgroup of light or heavy chains. The same framework can be used for several different humanized antibodies (Carter et al., Proc. Natl. Acad. Sci. USA, 89:4285 (1992); Presta et al., J. Immunol , 151:2623 (1993)).

It is further important that antibodies be humanized with retention of high affinity for the antigen and other favorable biological properties, for example, the anti-angiogenic properties of the anti-DEspR antibody 7C5B2 described herein. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Exemplary humanized antibodies and affinity matured variants thereof directed against the VEGF antigen are described in, for example, U.S. Pat. No. 6,884,879 issued Feb. 26, 2005.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90:2551 (1993); Jakobovits et al., Nature, 362:255-258 (1993); Bruggermann et al., Year in Immuno , 7:33 (1993); and Duchosal et al. Nature 355:258 (1992).

Alternatively, phage display technology (McCafferty et al., Nature 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat protein gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B-cell. Phage display can be performed in a variety of formats; for their review see, e.g., Johnson, Kevin S, and Chiswell, David J., Current Opinion in Structural Biology 3:564-571 (1993). Several sources of V-gene segments can be used for phage display. Clackson et al., Nature, 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., J. Mol. Biol. 222:581-597 (1991), or Griffith et al., EMBO J. 12:725-734 (1993). See, also, U.S. Pat. Nos. 5,565,332 and 5,573,905.

Human antibodies can also be generated by in vitro activated B cells (see U.S. Pat. Nos. 5,567,610 and 5,229,275).

Design & Generation of Composite Human Antibodies

In some embodiments of the aspects described herein, composite human antibody technology that generates de-immunized 100% engineered human antibodies at the outset can be used to prepare humanized composite anti-DEspR antibodies for use in the compositions and methods described herein, using, for example, a technology as described by Antitope.

Briefly, as used herein, "composite human antibodies" comprise multiple sequence segments ("composites") derived from V-regions of unrelated human antibodies that are selected to maintain monoclonal antibody sequences critical for antigen binding of the starting murine precursor anti-human DEspR monoclonal antibody, such as 7C5B2 antibody, and which have all been filtered for the presence of potential T-cell epitopes using "in silico tools" (Holgate & Baker, 2009). The close fit of human sequence segments with all sections of the starting antibody V regions and the elimination of CD4+ T cell epitopes from the outset allow this technology to circumvent immunogenicity in the development of '100% engineered human' therapeutic antibodies while maintaining optimal affinity and specificity through the prior analysis of sequences necessary for antigen-specificity (Holgate & Baker 2009).

As described herein, structural models of mouse anti-hDEspR antibody V regions were produced using Swiss PDB and analysed in order to identify important "constraining" amino acids in the V regions that were likely to be essential for the binding properties of the antibody. Residues contained within the CDRs (using Kabat definition) together with a number of framework residues were considered to be important. Both the $V_H$ and $V_L$ ($V_K$) sequences of anti-hDEspR, as described herein as SEQ ID NO: 4 and SEQ ID NO: 9, comprise typical framework residues and the CDR1, CDR2, and CDR3 motifs are comparable to many murine antibodies, as described elsewhere herein.

From the above analysis, it was determined that composite human sequences of anti-hDEspR can be created with a wide latitude of alternatives outside of CDRs but with only a narrow menu of possible alternative residues within the CDR sequences. Analysis indicated that corresponding sequence segments from several human antibodies could be combined to create CDRs similar or identical to those in the murine sequences. For regions outside of and flanking the CDRs, a wide selection of human sequence segments were identified as possible components of novel anti-DEspR composite human antibody V regions for use with the compositions and methods described herein (see, for example, Table 1).

Based upon these analyses, a large preliminary set of sequence segments that could be used to create novel anti-DEspR composite human antibody variants were selected and analysed using iTope™ technology for in silico analysis of peptide binding to human MHC class II alleles (Perry et al 2008), and using the TCED™ (T Cell Epitope Database) of known antibody sequence-related T cell epitopes (Bryson et al 2010). Sequence segments that were identified as significant non-human germline binders to human MHC class II or that scored significant hits against the TCED™ were discarded. This resulted in a reduced set of segments, and combinations of these were again analysed, as above, to ensure that the junctions between segments did not contain potential T cell epitopes. Selected segments were then combined to produce heavy and light chain V region sequences for synthesis.

Accordingly, provided herein are variable heavy and light chain sequences for use in anti-DEspR composite human antibody or engineered human antibody production. In some embodiments, an anti-DEspR composite human antibody can comprise a variable heavy ($V_H$) chain amino acid sequence selected from the group consisting of: QVQLQESGPGLVKPSQTLSLTCTVSGFSLT SYDISWIRQPPGKGLEWLGVIWTGGGTNYNSAFMSRLTISKDNSKST VYLQMNSLRAEDTAIYYCVRDRDYDGWYFDVWGQGTTVTVSS (SEQ ID NO: 13);

QVQLQESGPGLVKPSQTLSLTCTVSGFSLTSYDISWIRQPPGKGLEWL GVIWTGGGTNYNSAFMSRLTISKDNSKNTVYLQMNSLRAEDTAIYY CVRDRDYDGWYFDVWGQGTTVTVSS (SEQ ID NO: 14);

QVQLQESGPGLVKPSQTLSLTCTVSGFSLTSYDISWIRQPPGKGLEW LGVIWTGGGTNYNSAFMSRFTISKDNSKNTVYLQMNSLRAEDTAIY YCVRDRDYDGWYFDVWGQGTTVTVSS (SEQ ID NO: 15);

QVQLQESGPGLVKPSQTLSLTCTVSGFSLTSYDISWIRQPPGKGLEWL GVIWTGGGTNYNSAFMSRLTISKDNSKNTVYLQMNSLRAEDTAVYY CVRDRDYDGWYFDVWGQGTTVTVSS (SEQ ID NO:16); and QVQLQESGPGLVKPSQTLSLTCTVSGFSLTSYDISWIRQPPGKGLEWL GVIWTGGGTNYNSAFMSRFTISKDNSKNTVYLQMNSLRAEDTAVYY CVRDRDDYDGWYFDVWGQGTTVTVSS (SEQ ID NO: 17).

In some embodiments, an anti-DEspR composite human antibody can comprise a variable light ($V_L$) chain amino acid sequence selected from the group consisting of: DVLMTQS PLSLPVTLGQPASISCRSSQSIVHSNGNTYLEWYLQKPGQSPQLLI YKVSNRFSGVPDRFSGSGSGTDFTLKISRVEAEDVGVYYCFQGSH VPYTFGQGTKLEIK (SEQ ID NO: 18) and DVVMTQSPLSLPVTLGQPASISCRSSQSIVHSNGNTYLEWYLQKPG QSPQLLIYKVSNRFSGVPDRFSGSGSGTDFTLKISRVEAEDVGVYY CFQGSHVPYTFGQGTKLEIK (SEQ ID NO: 19).

In some embodiments, an anti-DEspR composite human antibody can comprise a heavy chain CDR1 region comprising an amino acid sequence of SEQ ID NO: 5. In some embodiments, an anti-DEspR composite human antibody can comprise a heavy chain CDR2 region comprising an amino acid sequence of SEQ ID NO: 6. In some embodiments, an anti-DEspR composite human antibody can comprise a heavy chain CDR3 region comprising an amino acid sequence of SEQ ID NO: 7.

In some embodiments, an anti-DEspR composite human antibody can comprise a light chain CDR1 region comprising a sequence of SEQ ID NO: 10. In some embodiments, an anti-DEspR composite human antibody can comprise a light chain CDR2 region comprising an amino acid sequence of SEQ ID NO: 11. In some embodiments, an anti-DEspR composite human antibody can comprise a light chain CDR3 region comprising an amino acid sequence of SEQ ID NO: 12.

Antibody Fragments

In some embodiments of the aspects described herein, an antibody specific for DEspR, such as, for example the anti-DEspR 7C5B2 antibody; an anti-DEspR antibody comprising one or more heavy chain CDR regions comprising a sequence selected from the group consisting of SEQ ID NO: 5, SEQ ID NO: 6, or SEQ ID NO: 7; an anti-DEspR antibody comprising one or more light chain CDR regions comprises a sequence selected from the group consisting of SEQ ID NO: 10, SEQ ID NO: 11, or SEQ ID NO: 12; an anti-DEspR composite human antibody comprising a variable heavy ($V_H$) chain amino acid sequence selected from the group consisting of SEQ ID NO: 4 and SEQ ID NO: 13-SEQ ID NO: 17; or an anti-DEspR composite human antibody comprising a variable light ($V_L$) chain amino acid sequence selected from the group consisting of SEQ ID NO: 9, SEQ ID NO: 18, and SEQ ID NO: 19 can be treated or processed into an antibody fragment thereof.

Various techniques have been developed and are available for the production of antibody fragments. Traditionally, these fragments were derived via proteolytic digestion of intact antibodies (see, e.g., Morimoto et al., Journal of Biochemical and Biophysical Methods 24:107-117 (1992) and Brennan et al., Science, 229:81 (1985)). However, these fragments can now be produced directly by recombinant host cells. For example, antibody fragments can be isolated from the antibody phage libraries discussed above. Alternatively, Fab'-SH fragments can be directly recovered from E. coli and chemically coupled to form F(ab')$_2$ fragments (Carter et al., Bio/Technology 10:163-167 (1992)). According to another approach, F(ab')$_2$ fragments can be isolated directly from recombinant host cell culture. Other techniques for the production of antibody fragments will be apparent to the skilled practitioner. In other embodiments, the antibody fragment of choice is a single chain Fv fragment (scFv). See WO 93/16185.

In some embodiments of the aspects described herein, a human DEspR-specific antibody fragment is a Fab fragment comprising $V_L$, $C_L$, $V_H$ and $C_H1$ domains. Fab fragments comprise a variable and constant domain of the light chain and a variable domain and the first constant domain ($C_H1$) of the heavy chain. In some such embodiments, the $V_H$ domain is selected from the group consisting of SEQ ID NO: 4 and SEQ ID NO: 13-SEQ ID NO: 17. In some such embodiments, the $V_H$ domain comprises one or more heavy chain CDR regions comprising a sequence selected from the group consisting of SEQ ID NO: 5, SEQ ID NO: 6, and SEQ ID NO: 7. In some such embodiments, the $V_L$ domain is selected from the group consisting of SEQ ID NO: 9, SEQ ID NO: 18, and SEQ ID NO: 19. In some such embodiments, the $V_L$ domain comprises one or more light chain CDR regions comprising a sequence selected from the group consisting of SEQ ID NO: 10, SEQ ID NO: 11, or SEQ ID NO: 12.

In some embodiments of the aspects described herein, a human DEspR-specific antibody fragment is a Fab' fragment, which is a Fab fragment having one or more cysteine residues at the C-terminus of the $C_H1$ domain.

In some embodiments of the aspects described herein, a human DEspR-specific antibody fragment is a Fd fragment comprising $V_H$ and $C_H1$ domains. In some such embodiments, the $V_H$ domain is selected from the group consisting of SEQ ID NO: 4 and SEQ ID NO: 13-SEQ ID NO: 17. In some such embodiments, the $V_H$ domain comprises one or more heavy chain CDR regions comprising a sequence selected from the group consisting of SEQ ID NO: 5, SEQ ID NO: 6, and SEQ ID NO: 7.

In some embodiments of the aspects described herein, a human DEspR-specific antibody fragment is a Fd' fragment comprising $V_H$ and $C_H1$ domains and one or more cysteine residues at the C-terminus of the $C_H1$ domain. In some such embodiments, the $V_H$ domain is selected from the group consisting of SEQ ID NO: 4 and SEQ ID NO: 13-SEQ ID NO: 17. In some such embodiments, the $V_H$ domain comprises one or more heavy chain CDR regions comprising a sequence selected from the group consisting of SEQ ID NO: 5, SEQ ID NO: 6, and SEQ ID NO: 7.

Single-chain Fv or scFv antibody fragments comprise the $V_H$ and $V_L$ domains of antibody, such that these domains are present in a single polypeptide chain. Generally, a Fv polypeptide further comprises a polypeptide linker between the $V_H$ and $V_L$ domains, which enables the scFv to form the desired structure for antigen binding. For a review of scFv, see Pluckthun in The Pharmacology of Monoclonal Antibodies, Vol 113, Rosenburg and Moore eds. Springer-Verlag, New York, pp. 269-315 (1994). Accordingly, in some embodiments of the aspects described herein, a human DEspR-specific antibody fragment is a Fv fragment comprising the $V_L$ and $V_H$ domains of a single arm of an antibody. In some such embodiments, the $V_H$ domain is selected from the group consisting of SEQ ID NO: 4 and SEQ ID NO: 13-SEQ ID NO: 17. In some such embodiments, the $V_H$ domain comprises one or more heavy chain CDR regions comprising a sequence selected from the group consisting of SEQ ID NO: 5, SEQ ID NO: 6, and SEQ ID NO: 7. In some such embodiments, the $V_L$ domain is selected from the group consisting of SEQ ID NO: 9, SEQ ID NO: 18, and SEQ ID NO: 19. In some such embodiments, the $V_L$ domain comprises one or more light chain CDR regions comprising a sequence selected from the group consisting of SEQ ID NO: 10, SEQ ID NO: 11, or SEQ ID NO: 12.

The term diabodies refers to small antibody fragments with two antigen-binding sites, which fragments comprise a heavy chain variable domain ($V_H$) connected to a light chain variable domain ($V_L$) in the same polypeptide chain ($V_H$ and $V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., Proc. Natl. Acad. Sci. USA, 90:6444-6448 (1993).

Accordingly, in some embodiments of the aspects described herein, a human DEspR-specific antibody fragment is a diabody comprising two antigen binding sites, comprising a heavy chain variable domain ($V_H$) connected to a light chain variable domain ($V_L$) in the same polypeptide chain. In some such embodiments, the $V_H$ domain is selected from the group consisting of SEQ ID NO: 4 and SEQ ID NO: 13-SEQ ID NO: 17. In some such embodiments, the $V_H$ domain comprises one or more heavy chain CDR regions comprising a sequence selected from the group consisting of SEQ ID NO: 5, SEQ ID NO: 6, and SEQ ID NO: 7. In some such embodiments, the $V_L$ domain is selected from the group consisting of SEQ ID NO: 9, SEQ ID NO: 18, and SEQ ID NO: 19. In some such embodiments, the $V_L$ domain comprises one or more light chain CDR regions comprising a sequence selected from the group consisting of SEQ ID NO: 10, SEQ ID NO: 11, or SEQ ID NO: 12.

In some embodiments of the aspects described herein, a human DEspR-specific antibody fragment is a dAb fragment comprising a $V_H$ domain. In some such embodiments, the $V_H$ domain is selected from the group consisting of SEQ ID NO: 4 and SEQ ID NO: 13-SEQ ID NO: 17. In some such embodiments, the $V_H$ domain comprises one or more heavy chain CDR regions comprising a sequence selected from the group consisting of SEQ ID NO: 5, SEQ ID NO: 6, and SEQ ID NO: 7.

In some embodiments of the aspects described herein, a human DEspR-specific antibody fragment comprises isolated CDR regions. In some such embodiments, the isolated CDR region comprises one or more heavy chain CDR regions comprising a sequence selected from the group consisting of SEQ ID NO: 5, SEQ ID NO: 6, and SEQ ID NO: 7. In some such embodiments, the isolated CDR region comprises one or more light chain CDR regions comprising a sequence selected from the group consisting of SEQ ID NO: 10, SEQ ID NO: 11, or SEQ ID NO: 12.

In some embodiments of the aspects described herein, the human DEspR-specific antibody fragment is a F(ab')$_2$ fragment, which comprises a bivalent fragment comprising two Fab' fragments linked by a disulphide bridge at the hinge region.

Linear antibodies refers to the antibodies as described in Zapata et al., Protein Eng., 8(10):1057-1062 (1995). Briefly, these antibodies comprise a pair of tandem Fd segments ($V_H$-$C_H$1-$V_H$-$C_H$1) which, together with complementary light chain polypeptides, form a pair of antigen binding regions. Linear antibodies can be bispecific or monospecific.

In some embodiments of the aspects described herein, a human DEspR-specific antibody fragment is a linear antibody comprising a pair of tandem Fd segments ($V_H$-$C_H$1-$V_H$-$C_H$1) which, together with complementary light chain polypeptides, form a pair of antigen binding regions. In some such embodiments, the $V_H$ domain is selected from the group consisting of SEQ ID NO: 4 and SEQ ID NO: 13-SEQ ID NO: 17. In some such embodiments, the $V_H$ domain comprises one or more heavy chain CDR regions comprising a sequence selected from the group consisting of SEQ ID NO: 5, SEQ ID NO: 6, and SEQ ID NO: 7. In some such embodiments, the $V_L$ domain is selected from the group consisting of SEQ ID NO: 9, SEQ ID NO: 18, and SEQ ID NO: 19. In some such embodiments, the $V_L$ domain comprises one or more light chain CDR regions comprising a sequence selected from the group consisting of SEQ ID NO: 10, SEQ ID NO: 11, or SEQ ID NO: 12.

In other embodiments of these aspects, a human DEspR-specific antibody fragment has specificity for the same epitope as the monoclonal anti-DEspR antibody 7C5B2, described herein, and produced by hybridoma 7C5B2.

Some further examples of DEspR-inhibiting antibodies are described in PCT/US2005/041594, the contents of which are incorporated herein by reference in their entirety.

Other Amino Acid Sequence Modifications

In some embodiments of the aspects described herein, amino acid sequence modification(s) of the antibodies or antibody fragments thereof specific for DEspR described herein are contemplated. For example, it can be desirable to improve the binding affinity and/or other biological properties of the antibody Amino acid sequence variants of the antibody are prepared by introducing appropriate nucleotide changes into the antibody nucleic acid, or by peptide synthesis. Such modifications include, for example, deletions from, and/or insertions into and/or substitutions of, residues within the amino acid sequences of the antibody. Any combination of deletion, insertion, and substitution is made to arrive at the final construct, provided that the final construct possesses the desired characteristics, e.g., binding specificity, inhibition of biological activity. The amino acid changes also can alter post-translational processes of the antibody, such as changing the number or position of glycosylation sites.

A useful method for identification of certain residues or regions of the antibody that are preferred locations for mutagenesis is called "alanine scanning mutagenesis" as described by Cunningham and Wells Science, 244:1081-1085 (1989). Here, a residue or group of target residues are identified (e.g., charged residues such as arg, asp, his, lys, and glu) and replaced by a neutral or negatively charged amino acid (most preferably alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include antibody with an N-terminal methionyl residue or the antibody fused to a cytotoxic polypeptide. Other insertional variants of the antibody molecule include the fusion to the N- or C-terminus of the antibody to an enzyme (e.g. for ADEPT) or a polypeptide which increases the serum half-life of the antibody.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated for use in the antibodies or antibody fragments thereof specific for DEspR described herein.

Substantial modifications in the biological properties of the antibodies or antibody fragments thereof specific for DEspR are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids can be grouped according to similarities in the properties of their side chains (in A. L. Lehninger, in Biochemistry, second ed., pp. 73-75, Worth Publishers, New York (1975)): (1) non-polar: Ala (A), Val (V), Leu (L), Ile (I), Pro (P), Phe (F), Trp (W), Met (M); (2) uncharged polar: Gly (G), Ser (S), Thr (T), Cys (C), Tyr (Y), Asn (N), Gln (Q); (3) acidic: Asp (D), Glu (E); (4) basic: Lys (K), Arg (R), His (H).

Alternatively, naturally occurring residues can be divided into groups based on common side-chain properties: (1) hydrophobic: Norleucine, Met, Ala, Val, Leu, Ile; (2) neutral hydrophilic: Cys, Ser, Thr, Asn, Gln; (3) acidic: Asp, Glu; (4) basic: His, Lys, Arg; (5) residues that influence chain orientation: Gly, Pro; (6) aromatic: Trp, Tyr, Phe. Non-conservative substitutions will entail exchanging a member of one of these classes for another class.

Any cysteine residue not involved in maintaining the proper conformation of the antibodies or antibody fragments thereof specific for DEspR also can be substituted, generally with serine, to improve the oxidative stability of the molecule and prevent aberrant crosslinking Conversely, cysteine bond(s) can be added to the antibody to improve its stability (particularly where the antibody is an antibody fragment such as an Fv fragment).

A particularly preferred type of substitutional variant involves substituting one or more hypervariable region residues of a parent antibody (e.g., the monoclonal anti-DEspR antibody 7C5B2, or a humanized or human antibody or antibody fragment thereof specific for DEspR, as provided herein). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g. binding affinity) as herein disclosed. In order to identify candidate hypervariable region sites for modification, alanine scanning mutagenesis can be performed to identify hypervariable region residues contributing significantly to antigen binding.

Alternatively, or additionally, it can be beneficial to analyze a crystal structure of the antigen-antibody complex to identify contact points between the antibody or antibody fragments thereof specific for DEspR and human DEspR. Such contact residues and neighboring residues are candidates for substitution according to the techniques elaborated herein. Once such variants are generated, the panel of variants is subjected to screening as described herein and antibodies or antibody fragments thereof with superior properties in one or more relevant assays can be selected for further development.

Another type of amino acid variant of the antibody alters the original glycosylation pattern of the antibody. By altering is meant deleting one or more carbohydrate moieties found in the antibody, and/or adding one or more glycosylation sites that are not present in the antibody.

Glycosylation of antibodies is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine can also be used.

Addition of glycosylation sites to the antibodies or antibody fragments thereof specific for DEspR is accomplished by altering the amino acid sequence such that it contains one or more of the above-described tripeptide sequences (for N-linked glycosylation sites). The alteration can also be made by the addition of, or substitution by, one or more serine or threonine residues to the sequence of the original antibody (for O-linked glycosylation sites).

Where the antibody comprises an Fc region, the carbohydrate attached thereto can be altered. For example, antibodies with a mature carbohydrate structure that lacks fucose attached to an Fc region of the antibody are described in US Pat Appl No US 2003/0157108 Al, Presta, L. See also US 2004/0093621 Al (Kyowa Hakko Kogyo Co., Ltd). Antibodies with a bisecting N-acetylglucosamine (G1cNAc) in the carbohydrate attached to an Fc region of the antibody are referenced in WO03/011878, Jean-Mairet et al. and U.S. Pat. No. 6,602,684, Umana et al. Antibodies with at least one galactose residue in the oligosaccharide attached to an Fc region of the antibody are reported in WO97/30087, Patel et al. See, also, WO98/58964 (Raju, S.) and WO99/22764 (Raju, S.) concerning antibodies with altered carbohydrate attached to the Fc region thereof.

In some embodiments, it can be desirable to modify the antibodies or antibody fragments thereof specific for DEspR described herein with respect to effector function, e.g., so as to enhance antigen-dependent cell-mediated cyotoxicity (ADCC) and/or complement dependent cytotoxicity (CDC) of the antibody. This can be achieved by introducing one or more amino acid substitutions in an Fc region of the antibody or antibody fragment thereof . Alternatively or additionally, cysteine residue(s) can be introduced in the Fc region, thereby allowing interchain disulfide bond formation in this region. The homodimeric antibody thus generated can have improved internalization capability and/or increased complement-mediated cell killing and antibody-dependent cellular cytotoxicity (ADCC). See Caron et al., J. Exp Med. 176:1191-1195 (1992) and Shopes, B. J. Immunol 148: 2918-2922 (1992). Homodimeric antibodies with enhanced anti-tumor activity can also be prepared using heterobifunctional cross-linkers as described in Wolff et al. Cancer Research 53:2560-2565 (1993). Alternatively, an antibody can be engineered which has dual Fc regions and can thereby have enhanced complement lysis and ADCC capabilities. See Stevenson et al. Anti-Cancer Drug Design 3:219-230 (1989).

For example, WO00/42072 (Presta, L.) describes antibodies with improved ADCC function in the presence of human effector cells, where the antibodies comprise amino acid substitutions in the Fc region thereof. Preferably, the antibody with improved ADCC comprises substitutions at positions 298, 333, and/or 334 of the Fc region (Eu numbering of residues). Preferably the altered Fc region is a human IgG1 Fc region comprising or consisting of substitutions at one, two or three of these positions. Such substitutions are optionally combined with substitution(s) which increase Clq binding and/or CDC.

Antibodies with altered C1q binding and/or complement dependent cytotoxicity (CDC) are described in WO99/51642, U.S. Pat. Nos. 6,194,551B1, 6,242,195B1, 6,528,624B1 and 6,538,124 (Idusogie et al.). The antibodies comprise an amino acid substitution at one or more of amino acid positions 270, 322, 326, 327, 329, 313, 333 and/or 334 of the Fc region thereof (Eu numbering of residues).

To increase the serum half life of the antibody specific for DEspR described herein, one can incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG.sub.1, IgG.sub.2, IgG.sub.3, or IgG.sub.4) that is responsible for increasing the in vivo serum half-life of the IgG molecule.

Antibodies with improved binding to the neonatal Fc receptor (FcRn), and increased half-lives, are described in WO00/42072 (Presta, L.) and US2005/0014934A1 (Hinton et al.). These antibodies comprise an Fc region with one or more substitutions therein which improve binding of the Fc region to FcRn. For example, the Fc region can have substitutions at one or more of positions 238, 250, 256, 265, 272, 286, 303, 305, 307, 311, 312, 314, 317, 340, 356, 360, 362, 376, 378, 380, 382, 413, 424, 428 or 434 (Eu numbering of residues). The preferred Fc region-comprising antibody variant with improved FcRn binding comprises amino acid substitutions at one, two or three of positions 307, 380 and 434 of the Fc region thereof (Eu numbering of residues). In one embodiment, the antibody has 307/434 mutations.

Engineered antibodies specific for DEspR with three or more (preferably four) functional antigen binding sites are also contemplated (US Appln No. US2002/0004587 A1, Miller et al.).

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

Immunoconjugates

In some embodiments of these aspects, immunoconjugates comprising the antibody and antibody fragments specific for DEspR described herein are conjugated to an agent such as a chemotherapeutic agent, toxin (e.g. an enzymatically active toxin of bacterial, fungal, plant or animal origin, or fragments thereof), a small molecule, an siRNA, a nanoparticle, a targeting agent (e.g., a microbubble), or a radioactive isotope (i.e., a radioconjugate) can be used. Such immunoconjugates can be used, for example, in diagnostic, theranostic, or targeting methods.

Chemotherapeutic agents useful in the generation of such immunoconjugates are described herein. Enzymatically active toxins and fragments thereof which can be used include diphtheria A chain, nonbinding active fragments of diphtheria toxin, exotoxin A chain (from *Pseudomonas aeruginosa*), ricin A chain, abrin A chain, modeccin A chain, alpha-sarcin, Aleurites fordii proteins, dianthin proteins, *Phytolaca americana* proteins (PAPI, PAPII, and PAP-S), momordica charantia inhibitor, curcin, crotin, sapaonaria officinalis inhibitor, gelonin, mitogellin, restrictocin, phenomycin, enomycin and the tricothecenes. A variety of radionuclides are available for the production of radioconjugate antibodies. Examples include $^{212}$Bi, $^{131}$I, $^{131}$In, $^{90}$Y and $^{186}$Re.

Conjugates of the antibodies specific for DEspR described herein and a cytotoxic agent can be made using any of a variety of bifunctional protein coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al. Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In other embodiments, the DEspR-specific antibody or antibody fragment thereof can be conjugated to a "receptor" (such as, for example, streptavidin) for utilization in tumor pretargeting wherein the antibody-receptor conjugate is administered to the subject, followed by removal of unbound conjugate from the circulation using a clearing agent and then administration of a "ligand" (e.g. avidin) which is conjugated to a cytotoxic agent (e.g. a radionucleotide). In some embodiments, the DEspR-specific antibody or antibody fragment thereof can be conjugated to biotin, and the biotin conjugated antibody or antibody fragment thereof can be further conjugated or linked to a streptavidin-bound or -coated agent, such as a streptavidin-coated microbubble, for use in, for example, molecular imaging of angiogenesis.

Immunoliposomes

The antibodies and antibody fragments thereof specific for DEspR described herein can also be formulated as immunoliposomes. Liposomes containing the antibody are prepared by methods known in the art, such as described in Epstein et al., Proc. Natl. Acad. Sci. USA, 82:3688 (1985); Hwang et al., Proc. Natl. Acad. Sci. USA, 77:4030 (1980); and U.S. Pat. Nos. 4,485,045 and 4,544,545. Liposomes with enhanced circulation time are disclosed in U.S. Pat. No. 5,013,556.

Particularly useful liposomes can be generated, for example, by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody of the invention can be conjugated to the liposomes as described in Martin et al. J. Biol. Chem. 257: 286-288 (1982) via a disulfide interchange reaction. A chemotherapeutic agent is optionally contained within the liposome. See Gabizon et a/. J. National Cancer Inst. 81(19) 1484 (1989)

The hybridoma cell lines 7C5B2, 7C5C5, and 5G12E8 are being maintained and stored.

Compositions and Therapeutic & Diganotic Uses of Anti-DEspR Antibodies and Fragments Thereof Certain aspects described herein are based, in part, on the discovery by the inventors that DEspR plays contributes to adult tissue vascularity, as well as playing a critical role in angiogenesis during embryonic development, and further that DEspR is surpisingly expressed in certain tumor cells, cancer stem cells or stem-like cells, or tumor initiating cells, as well as in tumor-surrounding blood vessels' endothelial cells, pericytes, and smooth muscle cells. The inventors further discovered that inhibition of DEspR, using DEspR-specific inhibitors, such as the anti-DEspR antibodies and antibody fragments thereof described herein, can inhibit a variety of parameters that characterize tumor metastasis, including cell invasiveness, tumor growth, such as tumor volume or tumor mass, as well as parameters that characterize angiogenesis, including neovessel tube length, neovessel branching, and formation of vessel interconnections. The anti-DEspR antibodies and antibody fragments thereof described herein are further highly suitable for antibody-target sonoporation and demonstrate enhanced penetration and efficacy when administered using, for example, ultrasound methods. In addition, the inventors have determined that DEspR serves as a diagnostic marker for a variety of disease conditions.

Anti-Angiogenic Therapeutics and Treatments

Angiogenesis is a process of tissue vascularization that involves both the growth of new developing blood vessels into a tissue (neo-vascularization) and co-opting of existing blood vessels to a target site. Blood vessels are the means by which oxygen and nutrients are supplied to living tissues and waste products are removed from living tissue. Angiogenesis can be a critical biological process. For example, angiogenesis is essential in reproduction, development and wound repair. Conversely, inappropriate angiogenesis can have severe negative consequences. For example, it is only after solid tumors are vascularized as a result of angiogenesis that the tumors have a sufficient supply of oxygen and nutrients that permit it to grow rapidly and metastasize.

Where the growth of new blood vessels is the cause of, or contributes to, the pathology associated with a disease, inhibition of angiogenesis, using the compositions and methods described herein, can reduce the deleterious effects of the disease. Non-limiting examples include tumors, carotid artery disease, rheumatoid arthritis, diabetic retinopathy, inflammatory diseases, restenosis, and the like. Where the growth of new blood vessels is required to support growth of a deleterious tissue, inhibition of angiogenesis, using the compositions and methods described herein, can reduce the blood supply to the tissue and thereby contribute to reduction in tissue mass based on blood supply requirements. Non-limiting examples include growth of tumors where neovascularization is a continual requirement in order that the tumor growth beyond a few millimeters in thickness, and for the establishment of solid tumor metastases. Another example is coronary plaque enlargement.

There are a variety of diseases or disorders in which angiogenesis is believed to lead to negative consequences, referred to as pathological angiogenesis, or diseases or disorders dependent or modulated by angiogenesis, including but not limited to, inflammatory disorders such as immune and non-immune inflammation, chronic articular rheumatism and psoriasis, disorders associated with inappropriate or inopportune invasion of vessels such as diabetic retinopathy, neovascular glaucoma, restenosis, capillary proliferation in atherosclerotic plaques and osteoporosis, and cancer associated disorders, such as solid tumors, solid tumor metastases, angiofibromas, retrolental fibroplasia, hemangiomas, Kaposi sarcoma and the like cancers which require neovascularization to support tumor growth. In a preferred embodiment of the aspects described herein, the methods are directed to inhibiting angiogenesis in a subject with cancer.

The antibodies and antibody fragments specific for DEspR described herein, such as, for example the anti-DEspR 7C5B2 antibody; an anti-DEspR antibody comprising one or more heavy chain CDR regions comprising a sequence selected from the group consisting of SEQ ID NO: 5, SEQ ID NO: 6, or SEQ ID NO: 7; an anti-DEspR antibody comprising one or more light chain CDR regions comprising a sequence selected from the group consisting of SEQ ID NO: 10, SEQ ID NO: 11, or SEQ ID NO: 12; an anti-DEspR composite human antibody comprising a variable heavy ($V_H$) chain amino acid sequence selected from the group consisting of SEQ ID NO: 4 and SEQ ID NO: 13-SEQ ID NO: 17; or an anti-DEspR composite human antibody comprising a variable light ($V_L$) chain amino acid sequence selected from the group consisting of SEQ ID NO: 9, SEQ ID NO: 18, and SEQ ID NO: 19, and fragments thereof, can be used in compositions and methods of antiangiogenic therapy. These antiangiogenic therapies can be used as novel cancer treatment strategies aimed at inhibiting existing tumor blood vessels and development of tumor blood vessels required for providing nutrients to support tumor growth. Because angiogenesis is involved in both primary tumor growth and metastasis, the antiangiogenic treatments using the antibodies and antibody fragments specific for DEspR described herein are capable of inhibiting the neoplastic growth of tumor at the primary site, as well as preventing micro- and macro-metastasis of tumors at the secondary sites, therefore allowing attack of the tumors by other therapeutics.

Addtionally, the antibodies and antibody-fragments specific for DEspR described herein, such as, for example the anti-DEspR 7C5B2 antibody; an anti-DEspR antibody comprising one or more heavy chain CDR regions comprising a sequence selected from the group consisting of SEQ ID NO: 5, SEQ ID NO: 6, or SEQ ID NO: 7; an anti-DEspR antibody comprising one or more light chain CDR regions comprising a sequence selected from the group consisting of SEQ ID NO: 10, SEQ ID NO: 11, or SEQ ID NO: 12; an anti-DEspR composite human antibody comprising a variable heavy ($V_H$) chain amino acid sequence selected from the group consisting of SEQ ID NO: 4 and SEQ ID NO: 13-SEQ ID NO: 17; or an anti-DEspR composite human antibody comprising a variable light ($V_L$) chain amino acid sequence selected from the group consisting of SEQ ID NO: 9, SEQ ID NO: 18, and SEQ ID NO: 19, and fragments thereof, can be used in methods of antimetastasis therapy. Such antimetastasis therapies provide novel cancer treatment strategies aimed at inhibiting concurrent inhibition of tumor vascularization and tumor cell invasiveness for treatment and/or inhibition of micrometastasis and macrometastasis, as further described herein. Furthermore, since DEspR is also expressed in tumor cells, including cancer stem cells, as demonstrated herein, immunoconjugates of DEspR specific antibodies or antibody fragments thereof, as described herein, can be generated by conjugation to any agent such as a toxin, cytotoxic or pro-apoptotic agent, and can further inhibit tumor growth by directly targeting/killing tumor cells and cancer stem cells.

Accordingly, angiogenesis-dependent diseases and disorders that can be treated using the methods and compositions comprising antibodies and antibody fragments specific for DEspR described herein, such as, for example, the anti-DEspR 7C5B2 antibody; an anti-DEspR antibody comprising one or more heavy chain CDR regions comprising a sequence selected from the group consisting of SEQ ID NO: 5, SEQ ID NO: 6, or SEQ ID NO: 7; an anti-DEspR antibody comprising one or more light chain CDR regions comprising a sequence selected from the group consisting of SEQ ID NO: 10, SEQ ID NO: 11, or SEQ ID NO: 12; an anti-DEspR composite human antibody comprising a variable heavy ($V_H$) chain amino acid sequence selected from the group consisting of SEQ ID NO: 4 and SEQ ID NO: 13-SEQ ID NO: 17; or an anti-DEspR composite human antibody comprising a variable light ($V_L$) chain amino acid sequence selected from the group consisting of SEQ ID NO: 9, SEQ ID NO: 18, and SEQ ID NO: 19, and fragments thereof, are those diseases and disorders affected by vascular growth. In other words, an "angiogenesis-dependent disease or disorder" refers to those diseases or disorders that are dependent on a rich blood supply and blood vessel proliferation for the diseases' pathological progression (e.g., metastatic tumors), or diseases or disorders that are the direct result of aberrant blood vessel proliferation (e.g., diabetic retinopathy and hemangiomas).

Non-limiting examples of angiogenesis-dependent diseases or disorder that can be treated using the compositions and methods described herein include abnormal vascular proliferation, ascites formation, psoriasis, age-related macular degeneration, thyroid hyperplasia, preeclampsia, rheumatoid arthritis and osteoarthritis, carotid artery disease, vaso vasorum neovascularization, vulnerable plaque neovascularization, neurodegenerative disorders, Alzheimer's disease, obesity, pleural effusion, atherosclerosis, endometriosis, diabetic/other retinopathies, ocular neovascularizations such as neovascular glaucoma and corneal neovascularization, disorders associated with inappropriate or inopportune invasion of vessels such as diabetic retinopathy, macular degeneration, neovascular glaucoma, restenosis, capillary proliferation in atherosclerotic plaques and osteoporosis, and cancer associated disorders, such as solid tumors, solid tumor metastases, angiofibromas, retrolental fibroplasia, hemangiomas, Kaposi sarcoma, cancers which require neovascularization to support tumor growth, etc.

Accordingly, described herein are methods of inhibiting angiogenesis in a tissue of a subject or individual having a disease or disorder dependent or modulated by angiogenesis, where the disease or disorder can be treated by the inhibition of angiogenesis. Generally, the methods comprise administering to the subject a therapeutically effective amount of a composition comprising an angiogenesis-inhibiting amount of a DEspR inhibitor. In some embodiments, the methods further comprises selecting or diagnosing a subject having or at risk for a disease or disorder modulated by angiogenesis.

In some embodiments of these methods and all such methods described herein, the DEspR inhibitor is an antibody or antibody fragment thereof. Accordingly, in some aspects, an anti-DEspR antibody or antibody-fragment thereof that is specific for a DEspR target is provided, where the anti-DEspR antibody or antibody-fragment thereof specifically binds to the DEspR target and reduces or inhibits DEspR biological activity, thus inhibiting angiogenesis in the subject having a disease or disorder dependent on angiogenesis.

In some such embodiments, the DEspR is human DEspR. In some such embodiments, the DEspR target has a sequence comprising SEQ ID NO:1 or an allelic variant thereof. In some such embodiments of these methods, an antibody or antibody fragment thereof that specifically binds to DEspR and inhibits DEspR biological activity blocks interaction of DEspR with VEGFsp. In some such embodiments, the VEGFsp has a sequence comprising the sequence of SEQ ID NO:2. In some such embodiments, the antibody or antibody fragment thereof is specific for an epitope of DEspR comprising an extracellular portion of DEspR. In some embodiments, the antibody or antibody fragment thereof is specific for an epitope of DEspR comprising amino acids 1-9 of SEQ ID NO:1.

In some such embodiments of these compositions and methods for inhibiting angiogenesis, the anti-DEspR antibody or antibody-fragment thereof is the anti-DEspR 7C5B2 antibody or fragment thereof. In some such embodiments, the anti-DEspR antibody or antibody-fragment thereof comprises one or more heavy chain CDR regions comprising a sequence selected from the group consisting of SEQ ID NO: 5, SEQ ID NO: 6, or SEQ ID NO: 7. In some such embodiments, the anti-DEspR antibody or antibody-fragment thereof comprises one or more light chain CDR regions comprising a sequence selected from the group consisting of SEQ ID NO: 10, SEQ ID NO: 11, or SEQ ID NO: 12. In some such embodiments, the anti-DEspR antibody or antibody-fragment thereof comprises one or more heavy chain CDR regions comprising a sequence selected from the group consisting of SEQ ID NO: 5, SEQ ID NO: 6, or SEQ ID NO: 7, and one or more light chain CDR regions comprising a sequence selected from the group consisting of SEQ ID NO: 10, SEQ ID NO: 11, or SEQ ID NO: 12. In some such embodiments, the anti-DEspR antibody or antibody-fragment thereof comprises a variable heavy ($V_H$) chain amino acid sequence selected from the group consisting of SEQ ID NO: 4 and SEQ ID NO: 13-SEQ ID NO: 17. In some such embodiments, the anti-DEspR antibody or antibody-fragment thereof comprises a variable light ($V_L$) chain amino acid sequence selected from the group consisting of SEQ ID NO: 9, SEQ ID NO: 18, and SEQ ID NO: 19, and fragments thereof.

In other embodiments of these compositions and methods for inhibiting angiogenesis, monoclonal anti-DEspR antibodies or antibody fragments thereof that specifically bind to DEspR are provided having one or more biological characteristics of the 7C5B2 monoclonal antibody. In some such embodiments, having a biological characteristic of the 7C5B2 monoclonal antibody can include having an $ED_{50}$ value (i.e., the dose therapeutically effective in 50% of the population) at or around the $ED_{50}$ value of the 7C5B2 antibody for the given population; or having an $EC_{50}$ value (i.e., the dose that achieves a half-maximal inhibition of a given parameter or phenotype) at or around the $EC_{50}$ value of the 7C5B2 antibody for a given parameter or phenotye. For example, in some embodiments of these aspects, the given parameter or phenotype to be inhibited by the antibody that specifically binds to DEspR can include, but is not limited to, the mean total tube number in an in vitro tubulogenesis assay, the mean total tube length in an in vitro tubulogenesis assay, the mean number of branching points in an in vitro tubulogenesis assay, the mean number of vessel connections in an in vitro tubulogenesis assay, and tumor cell invasiveness.

In some embodiments these compositions and methods for inhibiting angiogenesis, a humanized anti-DEspR monoclonal antibody or antibody fragment thereof is provided for use in the compositions and methods for inhibiting angiogenesis as described herein. In some embodiments, one or more variable heavy chain CDR regions of the humanized anti-DEspR antibody or antibody fragment thereof comprises a sequence selected from the group consisting of SEQ ID NO: 5-SEQ ID NO: 7. In some embodiments, one or more variable light chain CDR regions of the humanized anti-DEspR antibody or antibody fragment thereof comprises a sequence selected from the group consisting of SEQ ID NO: 10-SEQ ID NO: 12. In some such embodiments, the anti-DEspR antibody or antibody-fragment thereof comprises one or more heavy chain CDR regions comprising a sequence selected from the group consisting of SEQ ID NO: 5, SEQ ID NO: 6, or SEQ ID NO: 7, and one or more light chain CDR regions comprising a sequence selected from the group consisting of SEQ ID NO: 10, SEQ ID NO: 11, or SEQ ID NO: 12. In some embodiments, the humanized anti-DEspR monoclonal antibody comprises mutated human IgG1 framework regions and antigen-binding complementarity-determining regions (CDRs) selected from the group consisting of SEQ ID NO: 5-SEQ ID NO: 7 and the group consisting of SEQ ID NO: 10-SEQ ID NO: 12, that blocks binding of human DEspR to its ligands. In some embodiments, the humanized anti-DEspR antibody comprises mutated human IgG4 framework regions and antigen-binding complementarity-determining regions (CDRs) from the selected from the group consisting of SEQ ID NO: 5-SEQ ID NO: 7 and the group consisting of SEQ ID NO: 10-SEQ ID NO: 12, that blocks binding of human DEspR to its ligands.

In other embodiments of these aspects, the anti-DEspR antibody is an antibody fragment having specificity for the same epitope as the monoclonal anti-DEspR antibody 7C5B2, described herein, and produced by hybridoma 7C5B2. In some such embodiments, the anti-DEspR antibody is an antibody fragment comprising one or more variable heavy chain CDR sequences selected from the group consisting of SEQ ID NO: 5-SEQ ID NO: 7 and/or one or more variable light chain CDR sequences selected from the the group consisting of SEQ ID NO: 10-SEQ ID NO: 12 of the 7C5B2 monoclonal antibody. In some embodiments, the antibody fragment is a Fab fragment. In some embodiments, the anti-DEspR antibody fragment is a Fab' fragment. In some embodiments, the anti-DEspR antibody fragment is a Fd fragment. In some embodiments, the anti-DEspR antibody fragment is a Fd' fragment. In some embodiments, the antibody fragment is a Fv fragment. In some embodiments, the anti-DEspR antibody fragment is a dAb fragment. In some embodiments, the anti-DEspR antibody fragment comprises isolated CDR regions. In some embodiments, the anti-DEspR antibody fragment is a F(ab')$_2$ fragment. In some embodiments, the anti-DEspR antibody fragment is a single chain antibody molecule. In some embodiments, the anti-DEspR antibody fragment is a diabody comprising two antigen binding sites. In some embodiments, the anti-DEspR antibody fragment is a linear antibody comprising a pair of tandem Fd segments ($V_H$-$C_H1$-$V_H$-$C_H1$).

Accordingly, in some aspects, the disease or disorder dependent or modulated by angiogenesis is cancer, where the rapidly dividing neoplastic cancer cells require an efficient blood supply to sustain their continual growth of the tumor. Inhibition of angiogenesis or tumor cell invasiveness or a combination thereof using the compositions and therapeutic methods described herein at the primary tumor site and secondary tumor site serve to prevent and limit metastasis and progression of disease.

Accordingly, in some aspects, provided herein are methods to treat a subject having or at risk for a cancer or tumor comprising administering an effective amount of an anti-DEspR antibody or antibody fragment thereof. In some such embodiments of these methods for treating cancer, the anti-DEspR antibody or antibody fragment thereof is the anti-DEspR 7C5B2 antibody or fragment thereof. In some such embodiments, the anti-DEspR antibody or antibody-fragment thereof comprises one or more heavy chain CDR regions comprising a sequence selected from the group consisting of SEQ ID NO: 5, SEQ ID NO: 6, and SEQ ID NO: 7. In some such embodiments, the anti-DEspR antibody or antibody-fragment thereof comprises one or more light chain CDR regions comprising a sequence selected from the group consisting of SEQ ID NO: 10, SEQ ID NO: 11, and SEQ ID NO: 12. In some such embodiments, the anti-DEspR antibody or antibody-fragment thereof comprises one or more heavy chain CDR regions comprising a sequence selected from the group consisting of SEQ ID NO: 5, SEQ ID NO: 6, and SEQ ID NO: 7 and one or more light chain CDR regions comprising a sequence selected from the group consisting of SEQ ID NO: 10, SEQ ID NO: 11, and SEQ ID NO: 12. In some such embodiments, the anti-DEspR antibody or antibody-fragment thereof comprises a variable heavy ($V_H$) chain amino acid sequence selected from the group consisting of SEQ ID NO: 4 and SEQ ID NO: 13-SEQ ID NO: 17. In some such embodiments, the anti-DEspR antibody or antibody-fragment thereof comprises a variable light ($V_L$) chain amino acid sequence selected from the group consisting of SEQ ID NO: 9, SEQ ID NO: 18, and SEQ ID NO: 19, and fragments thereof.

In some embodiments, the methods can further comprise first selecting or diagnosing the subject having or at risk for a cancer or tumor. In some such embodiments, the diagnosis of the subject can comprise administering to the subject an anti-DEspR antibody or antibody fragment thereof coupled to a label, for example, a radioactive label, or a label used for molecular imaging, as described elsewhere herein. In such embodiments, detection of the labeled anti-DEspR antibody or antibody fragment is indicative of the subject having a cancer or tumor.

The terms "cancer" and "cancerous" refer to or describe the physiological condition in mammals that is typically characterized by unregulated cell growth. Included in this definition are benign and malignant cancers, as well as dormant tumors or micrometastases. Accordingly, the terms "cancer" or "tumor" as used herein refers to an uncontrolled growth of cells which interferes with the normal functioning of the bodily organs and systems, including cancer stem cells and tumor vascular niches. A subject that has a cancer or a tumor is a subject having objectively measurable cancer cells present in the subject's body. Included in this definition are benign and malignant cancers, as well as dormant tumors or micrometastases. Cancers which migrate from their original location and seed vital organs can eventually lead to the death of the subject through the functional deterioration of the affected organs. Hematopoietic cancers, such as leukemia, are able to out-compete the normal hematopoietic compartments in a subject, thereby leading to hematopoietic failure (in the form of anemia, thrombocytopenia and neutropenia) ultimately causing death.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

Metastases are most often detected through the sole or combined use of magnetic resonance imaging (MRI) scans, computed tomography (CT) scans, blood and platelet counts, liver function studies, chest X-rays and bone scans in addition to the monitoring of specific symptoms.

Examples of cancer include but are not limited to, carcinoma, lymphoma, blastoma, sarcoma, and leukemia. More particular examples of such cancers include, but are not limited to, basal cell carcinoma, biliary tract cancer; bladder cancer; bone cancer; brain and CNS cancer; breast cancer; cancer of the peritoneum; cervical cancer; choriocarcinoma; colon and rectum cancer; connective tissue cancer; cancer of the digestive system; endometrial cancer; esophageal cancer; eye cancer; cancer of the head and neck; gastric cancer (including gastrointestinal cancer); glioblastoma; hepatic carcinoma; hepatoma; intra-epithelial neoplasm; kidney or renal cancer; larynx cancer; leukemia; liver cancer; lung cancer (e.g., small-cell lung cancer, non-small cell lung cancer, adenocarcinoma of the lung, and squamous carcinoma of the lung); lymphoma including Hodgkin's and non-Hodgkin's lymphoma; melanoma; myeloma; neuroblastoma; glioblastoma; oral cavity cancer (e.g., lip, tongue, mouth, and pharynx); ovarian cancer; pancreatic cancer; prostate cancer; retinoblastoma; rhabdomyosarcoma; rectal cancer; cancer of the respiratory system; salivary gland carcinoma; sarcoma; skin cancer; squamous cell cancer; stomach cancer; testicular cancer; thyroid cancer; uterine or endometrial cancer; cancer of the urinary system; vulval cancer; as well as other carcinomas and sarcomas; as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

In other aspects, the compositions and methods described herein are used in the treatment or inhibition or imaging of artherosclerotic plaques and atherosclerosis. Atherosclerosis is the most common form of vascular disease and is a disorder of large arteries that underlies most coronary artery disease, aortic aneurysm, cerebrovascular disease and arterial disease of lower extremities (Libby, in "The Principles of Internal Medicine", 15th ed., Braunward et al. (editors), Saunders, Philadelphia, Pa., 2001, pp. 1377-1382.). The pathogenesis of atherosclerosis occurs as a reaction to injury (Libby, in "The Principles of Internal Medicine", 15th ed., Braunward et al. (editors), Saunders, Philadelphia, Pa., 2001, pp. 1377-1382.). The injury to the endothelium can be subtle, resulting in a loss of the ability of the cells to function normally. Examples of types of injury to the endothelium include hypercholesterolemia and mechanical stress (Ross, 1999, N. Engl. J. Med., 340:115).

The process of atherosclerosis involves inflammation, and white blood cells (e.g., lymphocytes, monocytes, and macrophages) are often present throughout the development of atherosclerosis. Atherosclerosis begins when monocytes are activated and move out of the bloodstream into the wall of an artery. There, they are transformed into foam cells, which collect cholesterol and other fatty materials. In time, these fat-laden foam cells accumulate and form atheromas in the lining of the artery's wall, causing a thickening and hardening of the wall. Atheromas can be scattered throughout medium-sized and large arteries, but usually form where the arteries branch. Treatment of and diagnosis of atherosclerosis is important because it often leads to heart disease and can also cause stroke or other vascular problems such as claudication.

Accordingly, in some embodiments of the aspects described herein, pathological angiogenesis in atherosclerotic plaques and in the vasa vasorum of atherosclerotic arteries (coronary and carotid artery disease) is considered a risk and/or causal factor for vulnerable plaque progression and disruption. Thus, in some such embodiments, a subject having an angiogenic disorder to be treated using the compositions and methods described herein can have or be at risk for atherosclerosis. As used herein, "atherosclerosis" refers to a disease of the arterial blood vessels resulting in the hardening of arteries caused by the formation of multiple atheromatous plaques within the arteries. Atherosclerosis can be associated with other disease conditions, including but not limited to, coronary heart disease events, cerebrovascular events, acute coronary syndrome, and intermittent claudication. For example, atherosclerosis of the coronary arteries commonly causes coronary artery disease, myocardial infarction, coronary thrombosis, and angina pectoris. Atherosclerosis of the arteries supplying the central nervous system frequently provokes strokes and transient cerebral ischemia. In the peripheral circulation, atherosclerosis causes intermittent claudication and gangrene and can jeopardize limb viability. Atherosclerosis of an artery of the splanchnic circulation can cause mesenteric ischemia. Atherosclerosis can also affect the kidneys directly (e.g., renal artery stenosis). Also, persons who have previously experienced one or more non-fatal atherosclerotic disease events are those for whom the potential for recurrence of such an event exists.

Sometimes these other diseases can be caused by or associated with other than atherosclerosis. Therefore, in some embodiments, one first diagnoses that atherosclerosis is present prior to administering the compositions described herein to the subject. A subject is "diagnosed with atherosclerosis" or "selected as having atherosclerosis" if at least one of the markers of symptoms of atherosclerosis is present. In one such embodiment, the subject is "selected" if the person has a family history of atherosclerosis or carries a known genetic mutation or polymorphism for high cholesterol. In one embodiment, a subject is diagnosed by measuring an increase level of C-reactive protein (CRP) in the absence of other inflammatory disorders. In other embodiments, atherosclerosis is diagnosed by measuring serum levels of homocysteine, fibrinogen, lipoprotein (a), or small LDL particles. Alternatively a computed tomography scan, which measures calcium levels in the coronary arteries, can be used to select a subject having atherosclerosis. In one embodiment, atherosclerosis is diagnosed by an increase in inflammatory cytokines. In one embodiment, increased interleukin-6 levels is used as an indicator to select an individual having atherosclerosis. In other embodiments, increased interleukin-8 and/or interleukin-17 level is used as an indicator to select an individual having atherosclerosis.

In other aspects, the compositions and methods described herein are used in blocking or inhibiting angiogenesis that occurs in age-related macular degeneration. It is known, for example, that VEGF contributes to abnormal blood vessel growth from the choroid layer of the eye into the retina, similar to what occurs during the wet or neovascular form of age-related macular degeneration. Macular degeneration, often called AMD or ARMD (age-related macular degeneration), is the leading cause of vision loss and blindness in Americans aged 65 and older. New blood vessels grow (neovascularization) beneath the retina and leak blood and fluid. This leakage causes permanent damage to light-sensitive retinal cells, which die off and create blind spots in central vision or the macula. Accordingly, encompassed in the methods disclosed herein are subjects treated for age-related macular degeneration with anti-angiogenic therapy.

In other aspects, the compositions and methods described herein are used in blocking or inhibiting angiogenesis that occurs in a subject having diabetic retinopathy, where abnormal blood vessel growth is associated with diabetic eye diseases and diabetic macular edema. When normal blood vessels in the retina are damaged by tiny blood clots due to diabetes, a chain reaction is ignited that culminates in new blood vessel growth. However, the backup blood vessels are faulty; they leak (causing edema), bleed and encourage scar tissue that detaches the retina, resulting in severe loss of vision. Such growth is the hallmark of diabetic retinopathy, the leading cause of blindness among young people in developed countries. Therefore, encompassed in the methods disclosed herein are subjects treated for diabetic retinopathy and/or diabetic macular edema.

In other aspects, the compositions and methods described herein are used in blocking or inhibiting angiogenesis that occurs in a subject having rheumatoid arthritis. Rheumatoid arthritis (RA) is characterized by synovial tissue swelling, leukocyte ingress and angiogenesis, or new blood vessel growth. The expansion of the synovial lining of joints in rheumatoid arthritis (RA) and the subsequent invasion by the pannus of underlying cartilage and bone necessitate an increase in the vascular supply to the synovium, to cope with the increased requirement for oxygen and nutrients. Angiogenesis is now recognized as a key event in the formation and maintenance of the pannus in RA (Paleolog, E. M., Arthritis Res. 2002;4 Suppl 3:S81-90; Afuwape A O, Histol Histopathol. 2002;17(3):961-72). Even in early RA, some of the earliest histological observations are blood vessels. A mononuclear infiltrate characterizes the synovial tissue along with a luxuriant vasculature. Angiogenesis is integral to formation of the inflammatory pannus and without angiogenesis, leukocyte ingress could not occur (Koch, A. E., Ann. Rheum. Dis. 2000, 59 Suppl 1:i65-71). Disruption of the formation of new blood vessels would not only prevent delivery of nutrients to the inflammatory site, it could also reduce joint swelling due to the additional activity of VEGF, a potent proangiogenic factor in RA, as a vascular permeability factor. Anti-VEGF hexapeptide RRKRRR (dRK6) can suppress and mitigate the arthritis severity (Seung-Ah Yoo, et. al., 2005, supra). Accordingly, encompassed in the methods disclosed herein are subjects having or being treated for rheumatoid arthritis.

In other aspects, the compositions and methods described herein are used in blocking or inhibiting angiogenesis that occurs in Alzheimer's disease Alzheimer's disease (AD) is the most common cause of dementia worldwide. AD is characterized by an excessive cerebral amyloid deposition leading to degeneration of neurons and eventually to dementia. The exact cause of AD is still unknown. It has been shown by epidemiological studies that long-term use of non-steroidal anti-inflammatory drugs, statins, histamine H2-receptor blockers, or calcium-channel blockers, all of which are cardiovascular drugs with an anti-angiogenic effects, seem to prevent Alzheimer's disease and/or influence the outcome of AD patients. Therefore, AD angiogenesis in the brain vasculature can play an important role in AD. In Alzheimer's disease, the brain endothelium secretes the precursor substrate for the beta-amyloid plaque and a neurotoxic peptide that selectively kills cortical neurons. Moreover, amyloid deposition in the vasculature leads to endothelial cell apoptosis and endothelial cell activation which leads to neovascularization. Vessel formation could be blocked by the VEGF antagonist SU 4312 as well as by statins, indicating that anti-angiogenesis strategies can interfere with endothelial cell activation in AD (Schultheiss C., el. al., 2006; Grammas P., et. al., 1999) and can be used for preventing and/or treating AD. Accordingly, encompassed in the methods disclosed herein are subjects being treated for Alzheimer's disease.

In other aspects, the compositions and methods described herein are used in blocking or inhibiting angiogenesis that occurs in ischemic regions in the brain, which can contribute to edema, leaky neovessels, and predispose a subject to hemorrhagic transformation after an ischemic stroke event, thus worsening the morbidity and mortality risk from the stroke event Inhibition of leaky angiogenic neovessels using the compositions and methods described herein can reduce neurologic deficits from an ischemic stroke event, as well as prevent the progression to hemorrhagic stroke. Currently, there is no therapy for ischemic hemorrhagic transformation nor effective therapies to reduce the neurologic deficits from stroke.

In other aspects, the compositions and methods described herein are used in blocking or inhibiting angiogenesis that occurs in obesity. Adipogenesis in obesity involves interplay between differentiating adipocytes, stromal cells, and blood vessels. Close spatial and temporal interrelationships between blood vessel formation and adipogenesis, and the sprouting of new blood vessels from preexisting vasculature was coupled to adipocyte differentiation. Adipogenic/angiogenic cell clusters can morphologically and immunohistochemically be distinguished from crown-like structures frequently seen in the late stages of adipose tissue obesity. Administration of anti-vascular endothelial growth factor (VEGF) antibodies inhibited not only angiogenesis but also the formation of adipogenic/angiogenic cell clusters, indicating that the coupling of adipogenesis and angiogenesis is essential for differentiation of adipocytes in obesity and that VEGF is a key mediator of that process. (Satoshi Nishimura et. al., 2007, Diabetes 56:1517-1526). It has been shown that the angiogenesis inhibitor, TNP-470 was able to prevent diet-induced and genetic obesity in mice (Ebba Bräkenhielm et. al., Circulation Research, 2004;94:1579). TNP-470 reduced vascularity in the adipose tissue, thereby inhibiting the rate of growth of the adipose tissue and obesity development. Accordingly, encompassed in the methods disclosed herein are subjects suffering from obesity.

In other aspects, the compositions and methods described herein are used in blocking or inhibiting angiogenesis that occurs in endometriosis. Excessive endometrial angiogenesis is proposed as an important mechanism in the pathogenesis of endometriosis (Healy, D L., et. al., Hum Reprod Update. 1998 September-October; 4(5):736-40). The endometrium of patients with endometriosis shows enhanced endothelial cell proliferation. Moreover there is an elevated expression of the cell adhesion molecule integrin vβ3 in more blood vessels in the endometrium of women with endometriosis when compared with normal women. The U.S. Pat. No. 6,121,230 described the use of anti-VEGF agents in the treatment of endometriosis and is Patent is incorporated hereby reference. Accordingly, encompassed in the methods disclosed herein are subjects having or being treated for endometriosis.

As described herein, any of a variety of tissues, or organs comprised of organized tissues, can support angiogenesis in disease conditions including skin, muscle, gut, connective tissue, joints, bones and the like tissue in which blood vessels can invade upon angiogenic stimuli.

The individual or subject to be treated as described herein in various embodiments is desirably a human patient, although it is to be understood that the methods are effective with respect to all mammals, which are intended to be included in the term "patient" or "subject". In this context, a mammal is understood to include any mammalian species in which treatment of diseases associated with angiogenesis is desirable. The terms "subject" and "individual" are used interchangeably herein, and refer to an animal, for example a human, recipient of the DEspR-specific antibodies and antibody fragments described herein. For treatment of disease states which are specific for a specific animal such as a human subject, the term "subject" refers to that specific animal. The terms "non-human animals" and "non-human mammals" are used interchangeably herein, and include mammals such as rats, mice, rabbits, sheep, cats, dogs, cows, pigs, and non-human primates. The term "subject" also encompasses any vertebrate including but not limited to mammals, reptiles, amphibians and fish. However, advantageously, the subject is a mammal such as a human, or other mammals such as a domesticated mammal, e.g. dog, cat, horse, and the like, or production mammal, e.g. cow, sheep, pig, and the like are also encompassed in the term subject.

Modes of Administration

The DEspR-specific antagonist agents, such as anti-DEspR antibodies or antibody fragments thereof, described herein can be administered to a subject in need thereof by any appropriate route which results in an effective treatment in the subject. As used herein, the terms "administering," and "introducing" are used interchangeably and refer to the placement of an anti-DEspR antibody or antibody fragment thereof into a subject by a method or route which results in at least partial localization of such agents at a desired site, such as a site of inflammation or cancer, such that a desired effect(s) is produced.

In some embodiments, the anti-DEspR antibody or antibody fragment thereof is administered to a subject having an angiogenic disorder to be inhibited by any mode of administration that delivers the agent systemically or to a desired surface or target, and can include, but is not limited to, injection, infusion, instillation, and inhalation administration. To the extent that anti-DEspR antibodies or antibody fragments thereof can be protected from inactivation in the gut, oral administration forms are also contemplated. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the anti-DEspR antibodies or antibody fragments thereof for use in the methods described herein are administered by intravenous infusion or injection.

The phrases "parenteral administration" and "administered parenterally" as used herein, refer to modes of administration other than enteral and topical administration, usually by injection. The phrases "systemic administration," "administered systemically", "peripheral administration" and "administered peripherally" as used herein refer to the administration of the bispecific or multispecific polypeptide agent other than directly into a target site, tissue, or organ, such as a tumor site, such that it enters the subject's circulatory system and, thus, is subject to metabolism and other like processes.

The DEspR-specific antagonists described herein are administered to a subject, e.g., a human subject, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes. Local administration, for example, to a tumor or cancer site where angiogenesis is occurring, is particularly desired if extensive side effects or toxicity is associated with the use of the DEspR antagonist. An ex vivo strategy can also be used for therapeutic applications in some embodiments. Ex vivo strategies involve transfecting or transducing cells obtained from a subject with a polynucleotide encoding a DEspR antagonist. The transfected or transduced cells are then returned to the subject. The cells can be any of a wide range of types including, without limitation, hematopoietic cells (e.g., bone marrow cells, macrophages, monocytes, dendritic cells, T cells, or B cells), fibroblasts, epithelial cells, endothelial cells, keratinocytes, or muscle cells.

In some embodiments, when the DEspR-specific antagonist is an anti-DEspR antibody or antibody fragment thereof, the antibody or antibody fragment thereof is administered by any suitable means, including parenteral, subcutaneous, intraperitoneal, intrapulmonary, and intranasal, and, if desired for local immunosuppressive treatment, intralesional administration. Parenteral infusions include intramuscular, intravenous, intraarterial, intraperitoneal, or subcutaneous administration. In some embodiments, the antibody or antibody fragment thereof is suitably administered by pulse infusion, particularly with declining doses of the antibody. Preferably the dosing is given by injections, most preferably intravenous or subcutaneous injections, depending in part on whether the administration is brief or chronic.

In some embodiments, the DEspR-specific antagonist compound is administered locally, e.g., by direct injections, when the disorder or location of the tumor permits, and the injections can be repeated periodically. The DEspR-specific antagonist can also be delivered systemically to the subject or directly to the tumor cells, e.g., to a tumor or a tumor bed following surgical excision of the tumor, in order to prevent or reduce local recurrence or metastasis, for example of a dormant tumor or micrometastases.

Administration by Sonoporation

Antibody-targeted sonoporation methods are contemplated for use in some embodiments of the methods for inhibiting angiogenesis described herein, in order to enhance the efficacy and potency of the therapeutic compositions comprising anti-DEspR antibodies and antibody fragments thereof provided herein.

The inventors have discovered that DEspR-targeted sonoporation of pharmaceutical compositions comprising anti-DEspR monoclonal antibodies and antibody fragments provides surprisingly enhanced reduction of tumor growth and metastases, indicating enhanced penetration and delivery of the compositions, and enhances delivery to sites of pathological angiogenesis, and to tumor cells, and tumor initiating cells or cancer stem cells or cancer stem-like cells. Further, the inventors have discovered that sonoporation of anti-DEspR antibodiets and antibody fragments thereof in combination with other therapeutic agents, such as small molecule compounds or other drug compounds, can be used to enhance delivery of the other therapeutic agents, thus providing a means of targeted and enhanced delivery.

Accordingly, in some embodiments of the methods of inhibiting angiogenesis described herein, anti-DEspR antibodies and antibody fragments thereof are administered to a subject in need thereof by sonoporation.

As used herein, "sonoporation" refers to the use of sound, preferably at ultrasonic frequencies, or the interaction of ultrasound with contrast agents (e.g., stabilized microbubbles) for temporarily modifying the permeability of cell plasma membranes, thus allowing uptake of large molecules, such as therapeutic agents. The membrane permeability caused by the sonoporation is transient, leaving the agents trapped inside the cell after the ultrasound exposure. Sonoporation employs acoustic cavitation of microbubbles to enhance delivery of large molecules.

Accordingly, in some embodiments of the methods, therapeutic anti-DEspR agents, such as the anti-DEspR antibodies and antibody fragments thereof described herein, mixed with ultrasound contrast agents, such as microbubbles, can be injected locally or systemically into a subject in need of treatment for an angiogenic disorder, and ultrasound can be coupled and even focused into the defined area, e.g., tumor site, to achieve targeted delivery of the anti-DEspR antibodies and antibody fragments thereof described herein. Additionally, the anti-DEspR antibody or antibody fragment thereof is known to target the tumor vessel endothelium, thus directing the sonoporation to areas of increased DEspR expression in tumor endothelial cells. In addition to the operator-determined focused ultrasound, anti-DEspR targeting of a microbubble can be used to target the sonoporation-mediated enhanced entry of any therapeutic agent, including antiDEspR monoclonal antibody per se, into said targeted cancerous areas.

In some embodiments, the methods use focused ultrasound methods to achieve targeted delivery of the anti-DEspR antibodies and antibody fragments thereof described herein. As used herein, HIFU or "High Intensity Focused Ultrasound" refers to a non-invasive therapeutic method using high-intensity ultrasound to heat and destroy malignant or pathogenic tissue without causing damage to overlying or surrounding health tissue. Typically, HIFU has been used in tissue ablation techniques, whereby the biological effects of HIFU treatment, including coagulative necrosis and structural disruption, can be induced in a tissue requiring ablation, such as a solid tumor site. However, as described in Khaibullina A. et al., J Nucl Med. 2008 February; 49(2):295-302, and WO2010127369, the contents of which are herein incorporated in their entireties by reference, HIFU can also be used as a means of delivery of therapeutic agents, such as antibodies or antibody fragments thereof.

Methods using contrast-enhanced ultrasound (CEUS) are also contemplated for use with anti-DEspR inhibiting agents described herein. Contrast-enhanced ultrasound (CEUS) refers to the application of ultrasound contrast medium and ultrasound contrast agents to traditional medical sonography. Ultrasound contrast agents refer to agents that rely on the different ways in which sound waves are reflected from interfaces between substances. This can be the surface of a small air bubble or a more complex structure. Commercially available contrast media include gas-filled microbubbles that are administered intravenously to the systemic circulation. Microbubbles have a high degree of echogenicity, i.e., the ability of an object to reflect the ultrasound waves. The echogenicity difference between the gas in the microbubbles and the soft tissue surroundings of the body is immense, and enhances the ultrasound backscatter, or reflection of the ultrasound waves, to produce a unique sonogram with increased contrast due to the high echogenicity difference. Contrast-enhanced ultrasound can be used with the compositions and methods described herein to image a variety of conditions and disorders, such as angiogenesis dependent disorders, as described herein A variety of microbubble contrast agents are available for use with the compositions and methods described herein. Microbubbles can differ in their shell makeup, gas core makeup, and whether or not they are targeted.

The microbubble shell material determines how easily the microbubble is taken up by the immune system. A more hydrophilic shell material tends to be taken up more easily, which reduces the microbubble residence time in the circulation. This reduces the time available for contrast imaging. The shell material also affects microbubble mechanical elasticity. The more elastic the material, the more acoustic energy it can withstand before bursting. Example of materials used in current microbubble shells include albumin, galactose, lipid, and polymers, as described in Lindner, J. R. 2004. Microbubbles in medical imaging: current applications and future directions. Nat Rev Drug Discov. 3: 527-32, the contents of which are herein incoporated by reference in their entireties.

The microbubble gas core is an important part of the ultrasound contrast microbubble because it determines the echogenicity. When gas bubbles are caught in an ultrasonic frequency field, they compress, oscillate, and reflect a characteristic echo—this generates the strong and unique sonogram in contrast-enhanced ultrasound. Gas cores can be composed of, for example, air, or heavy gases like perfluorocarbon, or nitrogen. Heavy gases are less water-soluble so they are less likely to leak out from the microbubble to impair echogenicity. Therefore, microbubbles with heavy gas cores are likely to last longer in circulation.

Regardless of the shell or gas core composition, microbubble size are typically fairly uniform. They can lie within in a range of 1-4 micrometres in diameter. That makes them smaller than red blood cells, which allows them to flow easily through the circulation as well as the microcirculation.

Targeting ligands that bind to receptors characteristic of angiogenic disorders, such as DEspR, can be conjugated to microbubbles, enabling the microbubble complex to accumulate selectively in areas of interest, such as diseased or abnormal tissues. This form of molecular imaging, known as targeted contrast-enhanced ultrasound, will only generate a strong ultrasound signal if targeted microbubbles bind in the area of interest. Targeted contrast-enhanced ultrasound has many applications in both medical diagnostics and medical therapeutics. Microbubbles targeted with an agent that binds to DEspR, such as an anti-DEspR antibody or antibody fragment thereof, are injected systemically in a small bolus. These DEspR-targeted microbubbles can travel through the circulatory system, eventually finding their respective targets and binding specifically. Ultrasound waves can then be directed on the area of interest. If a sufficient number of DEspR-targeted microbubbles have bound in the area, their compressible gas cores oscillate in response to the high frequency sonic energy field. The DEspR-targeted microbubbles also reflect a unique echo that is in stark contrast to the surrounding tissue due to the orders of magnitude mismatch between microbubble and tissue echogenicity. The ultrasound system converts the strong echogenicity into a contrast-enhanced image of the area of interest, revealing the location of the bound DEspR-targeted microbubbles. Detection of bound microbubbles can then show that the area of interest is expressing DEspR, which can be indicative of a certain disease state, or identify particular cells in the area of interest. In addition, targeted sonoporation can be done at the site where DEspR-targeted microbubbles are attached, thus achieving targeted delivery of any therapeutic agent (drug, siRNA, DNA, small molecule) encapsulated in or carried on the echogenic microbubble.

Accordingly, in some embodiments of the methods described herein, an anti-DEspR antibody or antibody fragment thereof, such as, for example, an anti-DEspR 7C5B2 antibody or fragment thereof, an anti-DEspR antibody or antibody-fragment thereof comprising one or more heavy chain CDR regions comprising a sequence selected from the group consisting of SEQ ID NO: 5, SEQ ID NO: 6, or SEQ ID NO: 7; an anti-DEspR antibody or antibody-fragment thereof comprising one or more light chain CDR regions comprising a sequence selected from the group consisting of SEQ ID NO: 10, SEQ ID NO: 11, or SEQ ID NO: 12; an anti-DEspR antibody or antibody-fragment comprising a variable heavy ($V_H$) chain amino acid sequence selected from the group consisting of SEQ ID NO: 4 and SEQ ID NO: 13-SEQ ID NO: 17; and/or an anti-DEspR antibody or antibody-fragment thereof comprising a variable light ($V_L$) chain amino acid sequence selected from the group consisting of SEQ ID NO: 9, SEQ ID NO: 18, and SEQ ID NO: 19, is administered to a subject in need of treatment for an angiogenic disorder, such as for example, cancer, using a targeted ultrasound delivery. In some such embodiments, the targeted ultrasound delivery comprises using microbubbles as contrast agents to which an anti-DEspR antibody or antibody fragment thereof,. In some such embodiments, the targeted ultrasound is HIFU.

Pharmaceutical Formulations

For the clinical use of the methods described herein, administration of the DEspR antagonists, such as the anti-DEspR antibodies or antibody fragments thereof described herein, can include formulation into pharmaceutical compositions or pharmaceutical formulations for parenteral administration, e.g., intravenous; mucosal, e.g., intranasal; ocular, or other mode of administration. In some embodiments, the anti DEspR antibodies or antibody fragments thereof described herein can be administered along with any pharmaceutically acceptable carrier compound, material, or composition which results in an effective treatment in the subject. Thus, a pharmaceutical formulation for use in the methods described herein can contain an anti-DEspR antibody or antibody fragment thereof as described herein in combination with one or more pharmaceutically acceptable ingredients.

The phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. The phrase "pharmaceutically acceptable carrier" as used herein means a pharmaceutically acceptable material, composition or vehicle, such as a liquid or solid filler, diluent, excipient, solvent, media, encapsulating material, manufacturing aid (e.g., lubricant, talc magnesium, calcium or zinc stearate, or steric acid), or solvent encapsulating material, involved in maintaining the stability, solubility, or activity of, an anti-DEspR antibody or antibody fragment thereof. Each carrier must be "acceptable" in the sense of being compatible with the other ingredients of the formulation and not injurious to the patient. The terms "excipient", "carrier", "pharmaceutically acceptable carrier" or the like are used interchangeably herein.

The anti-DEspR antibodies or antibody fragments thereof described herein can be specially formulated for administration of the compound to a subject in solid, liquid or gel form, including those adapted for the following: (1) parenteral administration, for example, by subcutaneous, intramuscular, intravenous or epidural injection as, for example, a sterile solution or suspension, or sustained-release formulation; (2) topical application, for example, as a cream, ointment, or a controlled-release patch or spray applied to the skin; (3) intravaginally or intrarectally, for example, as a pessary, cream or foam; (4) ocularly; (5) transdermally; (6) transmucosally; or (79) nasally. Additionally, an anti-DEspR antibody or antibody fragment thereof can be implanted into a patient or injected using a drug delivery system. See, for example, Urquhart, et al., Ann. Rev. Pharmacol. Toxicol. 24: 199-236 (1984); Lewis, ed. "Controlled Release of Pesticides and Pharmaceuticals" (Plenum Press, New York, 1981); U.S. Pat. Nos. 3,773,919; and 35 3,270,960.

Therapeutic formulations of the DEspR-specific antagonist agents, such as anti-DEspR antibodies or antibody fragments thereof, described herein can be prepared for storage by mixing a DEspR-specific antagonist having the desired degree of purity with optional pharmaceutically acceptable carriers, excipients or stabilizers (Remington's Pharmaceutical Sciences 16th edition, Osol, A. Ed. (1980)), in the form of lyophilized formulations or aqueous solutions. Acceptable carriers, excipients, or stabilizers are nontoxic to recipients at the dosages and concentrations employed, and include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG). Exemplary lyophilized anti-VEGF antibody formulations are described in WO 97/04801, expressly incorporated herein be reference.

Optionally, but preferably, the formulations comprising the compositions described herein contain a pharmaceutically acceptable salt, typically, e.g., sodium chloride, and preferably at about physiological concentrations. Optionally, the formulations of the invention can contain a pharmaceutically acceptable preservative. In some embodiments the preservative concentration ranges from 0.1 to 2.0%, typically v/v. Suitable preservatives include those known in the pharmaceutical arts. Benzyl alcohol, phenol, m-cresol, methylparaben, and propylparaben are examples of preservatives. Optionally, the formulations of the invention can include a pharmaceutically acceptable surfactant at a concentration of 0.005 to 0.02%.

The therapeutic formulations of the compositions comprising DEspR-specific antagonists, such as anti-DEspR antibodies and antibody fragments thereof, described herein can also contain more than one active compound as necessary for the particular indication being treated, preferably those with complementary activities that do not adversely affect each other. For example, in some embodiments, it can be desirable to further provide antibodies which bind to EGFR, VEGF (e.g. an antibody which binds a different epitope on VEGF), VEGFR, or ErbB2 (e.g., Herceptin™) Alternatively, or in addition, the composition can comprise a cytotoxic agent, cytokine, growth inhibitory agent and/or VEGFR antagonist. Such molecules are suitably present in combination in amounts that are effective for the purpose intended.

The active ingredients of the therapeutic formulations of the compositions comprising DEspR-specific antagonists described herein can also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

In some embodiments, sustained-release preparations can be used. Suitable examples of sustained-release preparations include semipermeable matrices of solid hydrophobic polymers containing the DEspR-specific antagonist, such as an anti-DEspR antibody, in which the matrices are in the form of shaped articles, e.g., films, or microcapsule. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and y ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods. When encapsulated antibodies remain in the body for a long time, they can denature or aggregate as a result of exposure to moisture at 37° C., resulting in a loss of biological activity and possible changes in immunogenicity. Rational strategies can be devised for stabilization depending on the mechanism involved. For example, if the aggregation mechanism is discovered to be intermolecular S—S bond formation through thio-disulfide interchange, stabilization can be achieved by modifying sulfhydryl residues, lyophilizing from acidic solutions, controlling moisture content, using appropriate additives, and developing specific polymer matrix compositions.

The therapeutic formulations to be used for in vivo administration, such as parenteral administration, in the methods described herein can be sterile, which is readily accomplished by filtration through sterile filtration membranes, or other methods known to those of skill in the art.

Dosages and Duration

The DEspR-specific antagonists described herein, such as anti-DEspR antibodies and antibody fragments thereof, are formulated, dosed, and administered in a fashion consistent with good medical practice. Factors for consideration in this context include the particular disorder being treated, the particular subject being treated, the clinical condition of the individual subject, the cause of the disorder, the site of delivery of the agent, the method of administration, the scheduling of administration, and other factors known to medical practitioners. The "therapeutically effective amount" of the DEspR-specific antagonist to be administered will be governed by such considerations, and refers to the minimum amount necessary to ameliorate, treat, or stabilize, the cancer; to increase the time until progression (duration of progression free survival) or to treat or prevent the occurrence or recurrence of a tumor, a dormant tumor, or a micrometastases. The DEspR -specific antagonist is optionally formulated with one or more additional therapeutic agents currently used to prevent or treat cancer or a risk of developing a cancer. The effective amount of such other agents depends on the amount of VEGF-specific antagonist present in the formulation, the type of disorder or treatment, and other factors discussed above. These are generally used in the same dosages and with administration routes as used herein before or about from 1 to 99% of the heretofore employed dosages.

Depending on the type and severity of the disease, about 1μg/kg to 100 mg/kg (e.g., 0.1-20 mg/kg) of a DEspR-specific antagonist is an initial candidate dosage for administration to a subject, whether, for example, by one or more separate administrations, or by continuous infusion. A typical daily dosage might range from about 1μg/kg to about 100 mg/kg or more, depending on the factors mentioned above. Particularly desirable dosages include, for example, 5 mg/kg, 7.5 mg/kg, 10 mg/kg, and 15 mg/kg. For repeated administrations over several days or longer, depending on the condition, the treatment is sustained until, for example, the cancer is treated, as measured by the methods described above or known in the art. However, other dosage regimens can be useful. In one non-limiting example, if the DEspR-specific antagonist is an anti-DEspR antibody or antibody fragment thereof, the anti-DEspR antibody or antibody fragment thereof is administered once every week, every two weeks, or every three weeks, at a dose range from about 5 mg/kg to about 15 mg/kg, including but not limited to 5 mg/kg, 7.5 mg/kg, 10 mg/kg or 15 mg/kg. The progress of using the methods described herein can be easily monitored by conventional techniques and assays.

The duration of a therapy using the methods described herein will continue for as long as medically indicated or until a desired therapeutic effect (e.g., those described herein) is achieved. In certain embodiments, the DEspR-specific antagonist therapy, such as a DEspR-specific antibody or antibody fragment described herein is continued for 1 month, 2 months, 4 months, 6 months, 8 months, 10 months, 1 year, 2 years, 3 years, 4 years, 5 years, 10 years, 20 years, or for a period of years up to the lifetime of the subject.

Efficacy of the Treatment

The efficacy of the treatment methods for cancer comprising therapeutic formulations of the compositions comprising the DEspR-specific antagonists described herein can be measured by various endpoints commonly used in evaluating cancer treatments, including but not limited to, tumor regression, tumor weight or size shrinkage, time to progression, duration of survival, progression free survival, overall response rate, duration of response, and quality of life. Because the DEspR-specific antagonists, e.g., anti-DEspR antibodies and antibody fragments thereof, described herein target the tumor vasculature, cancer cells, and some cancer stem cell subsets, they represent a unique class of multi-targeting anticancer drugs, and therefore can require unique measures and definitions of clinical responses to drugs. For example, tumor shrinkage of greater than 50% in a 2-dimensional analysis is the standard cut-off for declaring a response. However, the anti-DEspR-antibodies or antibody fragments thereof described herein can cause inhibition of metastatic spread without shrinkage of the primary tumor, or can simply exert a tumoristatic effect. Accordingly, novel approaches to determining efficacy of an anti-angiogenic therapy should be employed, including for example, measurement of plasma or urinary markers of angiogenesis, and measurement of response through molecular imaging, using, for example, an DEspR-antibody or antibody fragment conjugated to a label, such as a microbubble. In the case of cancers, the therapeutically effective amount of the DEspR-antibody or antibody fragment thereof can reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder. To the extent the DEspR-antibody or antibody fragment thereof can prevent growth and/or kill existing cancer cells, it can be cytostatic and/or cytotoxic. For cancer therapy, efficacy in vivo can, for example, be measured by assessing the duration of survival, duration of progression free survival (PFS), the response rates (RR), duration of response, and/or quality of life.

In other embodiments, described herein are methods for increasing progression free survival of a human subject susceptible to or diagnosed with a cancer. Time to disease progression is defined as the time from administration of the drug until disease progression or death. In a preferred embodiment, the combination treatment of the invention using a DEspR-specific antagonist, such as an anti-DEspR antibody or antibody fragment thereof, and one or more chemotherapeutic agents significantly increases progression free survival by at least about 1 month, 1.2 months, 2 months, 2.4 months, 2.9 months, 3.5 months, preferably by about 1 to about 5 months, when compared to a treatment with chemotherapy alone. In another embodiment, the methods decribed herein significantly increase response rates in a group of human subjects susceptible to or diagnosed with a cancer who are treated with various therapeutics. Response rate is defined as the percentage of treated subjects who responded to the treatment. In one embodiment, the combination treatment described herein using a DEspR-specific antagonist, such as an anti-DEspR antibody or antibody fragment thereof, and one or more chemotherapeutic agents significantly increases response rate in the treated subject group compared to the group treated with chemotherapy alone.

As used herein, the terms "treat" "treatment" "treating," or "amelioration" refer to therapeutic treatments, wherein the object is to reverse, alleviate, ameliorate, inhibit, slow down or stop the progression or severity of a condition associated with, a disease or disorder. The term "treating" includes reducing or alleviating at least one adverse effect or symptom of a condition, disease or disorder associated with a chronic immune condition, such as, but not limited to, a chronic infection or a cancer. Treatment is generally "effective" if one or more symptoms or clinical markers are reduced. Alternatively, treatment is "effective" if the progression of a disease is reduced or halted. That is, "treatment" includes not just the improvement of symptoms or markers, but also a cessation of at least slowing of progress or worsening of symptoms that would be expected in absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, and remission (whether partial or total), whether detectable or undetectable. The term "treatment" of a disease also includes providing relief from the symptoms or side-effects of the disease (including palliative treatment).

For example, in some embodiments, the methods described herein comprise administering an effective amount of the anti-DEspR antibodies or antibody fragments thereof described herein to a subject in order to alleviate a symptom of a cancer, or other such disorder characterized by excess or unwanted angiogenesis. As used herein, "alleviating a symptom of a cancer" is ameliorating or reducing any condition or symptom associated with the cancer. As compared with an equivalent untreated control, such reduction or degree of prevention is at least 5%, 10%, 20%, 40%, 50%, 60%, 80%, 90%, 95%, or 100% as measured by any standard technique. Ideally, the cancer is completely cleared as detected by any standard method known in the art, in which case the cancer is considered to have been treated. A patient who is being treated for a cancer is one who a medical practitioner has diagnosed as having such a condition. Diagnosis can be by any suitable means. Diagnosis and monitoring can involve, for example, detecting the level of cancer cells in a biological sample (for example, a tissue or lymph node biopsy, blood test, or urine test), detecting the level of a surrogate marker of the cancer in a biological sample, detecting symptoms associated with the specific cancer, or detecting immune cells involved in the immune response typical of such a cancer infections.

The term "effective amount" as used herein refers to the amount of an anti-DEspR antibody or antibody fragment thereof needed to alleviate at least one or more symptom of the disease or disorder, and relates to a sufficient amount of pharmacological composition to provide the desired effect, i.e., inhibit the formation of new blood vessels. The term "therapeutically effective amount" therefore refers to an amount of an anti-DEspR antibody or antibody fragment thereof using the methods as disclosed herein, that is sufficient to effect a particular effect when administered to a typical subject. An effective amount as used herein would also include an amount sufficient to delay the development of a symptom of the disease, alter the course of a symptom disease (for example but not limited to, slow the progression of a symptom of the disease), or reverse a symptom of the disease. Thus, it is not possible to specify the exact "effective amount". However, for any given case, an appropriate "effective amount" can be determined by one of ordinary skill in the art using only routine experimentation.

Effective amounts, toxicity, and therapeutic efficacy can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dosage can vary depending upon the dosage form employed and the route of administration utilized. The dose ratio between toxic and therapeutic effects is the therapeutic index and can be expressed as the ratio $LD_{50}/ED_{50}$. Compositions and methods that exhibit large therapeutic indices are preferred. A therapeutically effective dose can be estimated initially from cell culture assays. Also, a dose can be formulated in animal models to achieve a circulating plasma concentration range that includes the $IC_{50}$ (i.e., the concentration of the anti-DEspR antibody or antibody fragment thereof), which achieves a half-maximal inhibition of symptoms) as determined in cell culture, or in an appropriate animal model. Levels in plasma can be measured, for example, by high performance liquid chromatography. The effects of any particular dosage can be monitored by a suitable bioassay. The dosage can be determined by a physician and adjusted, as necessary, to suit observed effects of the treatment.

Combination Antiangiogenic Therapies

In other embodiments, the methods provided for inhibiting angiogenesis in a tissue of a subject or individual having a disease or disorder dependent or modulated by angiogenesis by administering to the subject a therapeutically effective amount of a composition comprising an angiogenesis-inhibiting amount of an anti-DEspR inhibitor, such as an anti-DEspR antibody or antibody fragment thereof, can further comprise administration one or more additional treatments such as angiogenic inhibitors, chemotherapy, radiation, surgery, or other treatments known to those of skill in the art to inhibit angiogenesis.

In some embodiments, the methods described herein further comprise administration of a combination of at least one DEspR-specific antagonist, such an anti-DEspR antibody or antibody fragment thereof, with one or more additional anti-cancer therapies. Examples of additional anti-cancer therapies include, without limitation, surgery, radiation therapy (radiotherapy), biotherapy, immunotherapy, chemotherapy, or a combination of these therapies. In addition, cytotoxic agents, anti-angiogenic and anti-proliferative agents can be used in combination with the DEspR-specific antagonist.

In certain aspects of any of the methods and uses, the invention provides treating cancer by administering effective amounts of an anti-DEspR antibody and one or more chemotherapeutic agents to a subject susceptible to, or diagnosed with, locally recurrent or previously untreated cancer. A variety of chemotherapeutic agents can be used in the combined treatment methods and uses of the invention. An exemplary and non-limiting list of chemotherapeutic agents contemplated for use in the methods described herein is provided under "Definition," or described herein.

In some embodiments, the methods described herein comprise administration of a DEspR-specific antagonist with one or more chemotherapeutic agents (e.g., a cocktail) or any combination thereof. In certain embodiments, the chemotherapeutic agent is for example, capecitabine, taxane, anthracycline, paclitaxel, docetaxel, paclitaxel protein-bound particles (e.g., Abraxane™) doxorubicin, epirubicin, 5-fluorouracil, cyclophosphamide or combinations thereof therapy. As used herein, combined administration includes simultaneous administration, using separate formulations or a single pharmaceutical formulation, and consecutive administration in either order, wherein preferably there is a time period while both (or all) active agents simultaneously exert their biological activities. Preparation and dosing schedules for such chemotherapeutic agents can be used according to manufacturers' instructions or as determined empirically by the skilled practitioner. Preparation and dosing schedules for chemotherapy are also described in Chemotherapy Service Ed., M. C. Perry, Williams & Wilkins, Baltimore, Md. (1992). Accordingly, in some embodiments, the chemotherapeutic agent can precede, or follow administration of the DEspR-specific antagonist or can be given simultaneously therewith.

In some other embodiments of the methods described herein, other therapeutic agents useful for combination tumor therapy with the DEspR antagonists, such as antibodies, of the invention include antagonists of other factors that are involved in tumor growth, such as EGFR, ErbB2 (also known as Her2), ErbB3, ErbB4, or TNF. In some embodiments, it can be beneficial to also administer one or more cytokines to the subject. In some embodiments, the DEspR antagonist is co-administered with a growth inhibitory agent. For example, the growth inhibitory agent can be administered first, followed by the DEspR antagonist. However, simultaneous administration or administration of the DEspR antagonist first is also contemplated. Suitable dosages for the growth inhibitory agent are those presently used and can be lowered due to the combined action (synergy) of the growth inhibitory agent and DEspR antagonist.

Examples of additional angiogenic inhibitors that can be used in combination with the DEspR inhibitors, such as anti-DEspR antibodies and antibody fragments thereof, described herein include, but are not limited to: direct angiogenesis inhibitors, Angiostatin, Bevacizumab (Avastin®), Arresten, Canstatin, Combretastatin, Endostatin, NM-3, Thrombospondin, Tumstatin, 2-methoxyestradiol, cetuximab (Erbitux®), panitumumab (Vectibix™), trastuzumab (Herceptin®) and Vitaxin; and indirect angiogenesis inhibitors: ZD1839 (Iressa), ZD6474, 0S1774 (Tarceva), CI1033, PKI1666, IMC225 (Erbitux), PTK787, SU6668, SU11248, Herceptin, and IFN-α, CELEBREX® (Celecoxib), THALOMID® (Thalidomide), and IFN-α.

In some embodiments, the additional angiogenesis inhibitors for use in the methods described herein include but are not limited to small molecule tyrosine kinase inhibitors (TKIs) of multiple pro-angiogenic growth factor receptors. The three TKIs that are currently approved as anti-cancer therapies are erlotinib (Tarceva®), sorafenib (Nexavar®), and sunitinib (Sutent®).

In some embodiments, the angiogenesis inhibitors for use in the methods described herein include but are not limited to inhibitors of mTOR (mammalian target of rapamycin) such as temsirolimus (Toricel™), bortezomib (Velcade®), thalidomide (Thalomid®), and Doxycyclin, In other embodiments, the angiogenesis inhibitors for use in the methods described herein include one or more drugs that target the VEGF pathway. Bevacizumab (Avastin®) was the first drug that targeted new blood vessels to be approved for use against cancer. It is a monoclonal antibody that binds to VEGF, thereby blocking VEGF from reaching the VEGF receptor (VEGFR). Other drugs, such as sunitinib (Sutent®) and sorafenib (Nexavar®), are small molecules that attach to the VEGF receptor itself, preventing it from being turned on. Such drugs are collectively termed VEGF inhibitors. As the VEGF/VPF protein interacts with the VEGFRs, inhibition of either the ligand VEGF, e.g. by reducing the amount that is available to interact with the receptor; or inhibition of the receptor's intrinsic tyrosine kinase activity, blocks the function of this pathway. This pathway controls endothelial cell growth, as well as permeability, and these functions are mediated through the VEGFRs.

Accordingly, as described herein, "VEGF inhibitors" for use as angiogenesis inhibitors include any compound or agent that produces a direct or indirect effect on the signaling pathways that promote growth, proliferation and survival of a cell by inhibiting the function of the VEGF protein, including inhibiting the function of VEGF receptor proteins. These include any organic or inorganic molecule, including, but not limited to modified and unmodified nucleic acids such as antisense nucleic acids, RNAi agents such as siRNA or shRNA, peptides, peptidomimetics, receptors, ligands, and antibodies that inhibit the VEGF signaling pathway. The siRNAs are targeted at components of the VEGF pathways and can inhibit the VEGF pathway. Preferred VEGF inhibitors, include for example, AVASTIN® (bevacizumab), an anti-VEGF monoclonal antibody of Genentech, Inc. of South San Francisco, Calif., VEGF Trap (Regeneron/Aventis). Additional VEGF inhibitors include CP-547,632 (3-(4-Bromo-2,6-difluoro-benzyloxy)-5-[3-(4-pyrrolidin 1-yl-butyl)-ureido]-isothiazole-4-carboxylic acid amide hydrochloride; Pfizer Inc. , NY), AG13736, AG28262 (Pfizer Inc.), SU5416, SU11248, & SU6668 (formerly Sugen Inc., now Pfizer, New York, N.Y.), ZD-6474 (AstraZeneca), ZD4190 which inhibits VEGF-R2 and -R1 (AstraZeneca), CEP-7055 (Cephalon Inc., Frazer, Pa.), PKC 412 (Novartis), AEE788 (Novartis), AZD-2171), NEXAVAR® (BAY 43-9006, sorafenib; Bayer Pharmaceuticals and Onyx Pharmaceuticals), vatalanib (also known as PTK-787, ZK-222584: Novartis & Schering: AG), MACUGEN® (pegaptanib octasodium, NX-1838, EYE-001, Pfizer Inc./ Gilead/Eyetech), IM862 (glufanide disodium, Cytran Inc. of Kirkland, Wash., USA), VEGFR2-selective monoclonal antibody DC101 (ImClone Systems, Inc.), angiozyme, a synthetic ribozyme from Ribozyme (Boulder, Colo.) and Chiron (Emeryville, Calif.), Sirna-027 (an siRNA-based VEGFR1 inhibitor, Sirna Therapeutics, San Francisco, Calif.) Caplostatin, soluble ectodomains of the VEGF receptors, Neovastat (Æterna Zentaris Inc; Quebec City, Calif.), ZM323881 CalBiochem. Calif., USA), pegaptanib (Macugen) (Eyetech Pharmaceuticals), an anti-VEGF aptamer and combinations thereof.

VEGF inhibitors are also disclosed in U.S. Pat. Nos. 6,534,524 and 6,235,764, both of which are incorporated in their entirety. Additional VEGF inhibitors are described in, for example in WO 99/24440 (published May 20, 1999), International Application PCT/IB99/00797 (filed May 3, 1999), in WO 95/21613 (published Aug. 17, 1995), WO 99/61422 (published Dec. 2, 1999), U.S. Pat. Publ. No. 20060094032 "siRNA agents targeting VEGF", U.S. Patent 6, 534,524 (discloses AG13736), U.S. Patent 5,834,504 (issued Nov. 10, 1998), WO 98/50356 (published Nov. 12, 1998), U.S. Pat. 5, 883,113 (issued Mar. 16, 1999), U.S. Pat. 5, 886,020 (issued Mar. 23, 1999), U.S. Patent 5,792,783 (issued Aug. 11, 1998), U.S. Pat. No. 6,653,308 (issued Nov. 25, 2003), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), WO 01/02369 (published Jan. 11, 2001); U.S. Provisional Application No. 60/491,771 piled Jul. 31, 2003); U.S. Provisional Application No. 60/460,695 (filed Apr. 3, 2003); and WO 03/106462A1 (published Dec. 24, 2003). Other examples of VEGF inhibitors are disclosed in International Patent Publications WO 99/62890 published Dec. 9, 1999, WO 01/95353 published Dec. 13, 2001 and WO 02/44158 published Jun. 6, 2002.

In other embodiments, the angiogenesis inhibitors for use in the methods described herein include anti-angiogenic factors such as alpha-2 antiplasmin (fragment), angiostatin (plasminogen fragment), antiangiogenic antithrombin III, cartilage-derived inhibitor (CDI), CD59 complement fragment, endostatin (collagen XVIII fragment), fibronectin fragment, gro-beta (a C-X-C chemokine), heparinases heparin hexasaccharide fragment, human chorionic gonadotropin (hCG), interferon alpha/beta/gamma, interferon inducible protein (IP-10), interleukin-12, kringle 5 (plasminogen fragment), beta-thromboglobulin, EGF (fragment), VEGF inhibitor, endostatin, fibronection (45 kD fragment), high molecular weight kininogen (domain 5), NK1, NK2, NK3 fragments of HGF, PF-4, serpin proteinase inhibitor 8, TGF-beta-1, thrombospondin-1, prosaposin, p53, angioarrestin, metalloproteinase inhibitors (TIMPs), 2-Methoxyestradiol, placental ribonuclease inhibitor, plasminogen activator inhibitor, prolactin 16 kD fragment, proliferin-related protein (PRP), retinoids, tetrahydrocortisol-S transforming growth factor-beta (TGF-b), vasculostatin, and vasostatin (calreticulin fragment). pamidronate thalidomide, TNP470, the bisphosphonate family such as amino-bisphosphonate zoledronic acid. bombesin/gastrin-releasing peptide (GRP) antagonists such as RC-3095 and RC-3940-II (Bajol A M, et. al., British Journal of Cancer (2004) 90, 245-252), anti-VEGF peptide RRKRRR (dRK6) (Seung-Ah Yoo, J. Immuno, 2005, 174: 5846-5855).

Thus, in connection with the administration of a DEspR inhibitor, such as anti-DEspR antibodies and antibody fragments thereof, a compound which inhibits angiogenesis indicates that administration in a clinically appropriate manner results in a beneficial effect for at least a statistically significant fraction of patients, such as improvement of symptoms, a cure, a reduction in disease load, reduction in tumor mass or cell numbers, extension of life, improvement in quality of life, or other effect generally recognized as positive by medical doctors familiar with treating the particular type of disease or condition.

Examples of additional DEspR inhibitors include, but are not limited to, molecules which block the binding of VEGFsp, ET-1 and/or other ET-1 orVEGFsp-like ligands to DEspR, compounds which interfere with downstream signaling events of DEspR, or other compounds or agents that inhibit activation of the receptor. Such compounds can bind to DEspR and prevent binding of VEGFsp, ET-1 or other mimetic ligands. Other inhibitors including small molecules that bind to the DEspR domain that binds to VEGFsp, soluble DEspR receptors, peptides containing the DEspR ET-1 and/or VEGFsp binding domains, etc. are also contemplated.

The compositions described herein can also contain more than one active compound as necessary for the particular indication being treated, and these active compounds are preferably those with complementary activities that do not adversely affect each other. For example, it can be desirable to further provide antibodies or antagonists that bind to EGFR, VEGF, VEGFR, or ErbB2 (e.g., Herceptin.™). Alternatively, or in addition, the composition can comprise a cytotoxic agent, cytokine, growth inhibitory agent and/or VEGFR antagonist. Such molecules are suitably present in combination in amounts that are effective for the purpose intended.

In certain aspects of any of the methods and uses described herein, other therapeutic agents useful for combination cancer therapy with the antibody of the invention include other anti-angiogenic agents. Many anti-angiogenic agents have been identified and are known in the arts, including those listed by Carmeliet and Jain (2000). In some embodiments, the DEspR antagonist, such as a humanized anti-DEspR antibody or antibody fragment thereof described herein is used in combination with a VEGF antagonist or a VEGF receptor antagonist such as VEGF variants, soluble VEGF receptor fragments, aptamers capable of blocking VEGF or VEGFR, neutralizing anti-VEGFR antibodies, low molecule weight inhibitors of VEGFR tyrosine kinases and any combinations thereof. Alternatively, or in addition, two or more anti-DEspR antagonists can be co-administered to the subject.

For the treatment of diseases, as described herein, the appropriate dosage of DEspR-specific antagonists will depend on the type of disease to be treated, as defined above, the severity and course of the disease, whether the DEspR-specific antagonist is administered for preventive or therapeutic purposes, previous therapeutic indications, the subject's clinical history and response to the DEspR-specific antagonist, and the discretion of the attending physician. The DEspR-specific antagonist is suitably administered to the subject at one time or over a series of treatments. In a combination therapy regimen, the DEspR-specific antagonist and the one or more anti-cancer therapeutic agents described herein are administered in a therapeutically effective or synergistic amount. As used herein, a therapeutically effective amount is such that co-administration of a DEspR-specific antagonist and one or more other therapeutic agents, or administration of a composition described herein, results in reduction or inhibition of the cancer as described herein.

A therapeutically synergistic amount is that amount of a DEspR-specific antagonist and one or more other therapeutic agents necessary to synergistically or significantly reduce or eliminate conditions or symptoms associated with a particular disease.

The DEspR-specific antagonist and the one or more other therapeutic agents can be administered simultaneously or sequentially in an amount and for a time sufficient to reduce or eliminate the occurrence or recurrence of a tumor, a dormant tumor, or a micrometastases. The DEspR-specific antagonist and the one or more other therapeutic agents can be administered as maintenance therapy to prevent or reduce the likelihood of recurrence of the tumor.

As will be understood by those of ordinary skill in the art, the appropriate doses of chemotherapeutic agents or other anti-cancer agents will be generally around those already employed in clinical therapies, e.g., where the chemotherapeutics are administered alone or in combination with other chemotherapeutics. Variation in dosage will likely occur depending on the condition being treated. The physician administering treatment will be able to determine the appropriate dose for the individual subject.

In addition to the above therapeutic regimes, the subject can be subjected to radiation therapy.

In certain embodiments of any of the methods, uses and compositions described herein, the administered DEspR antibody is an intact, naked antibody. However, in some embodiments, the DEspR antibody can be conjugated with a cytotoxic agent. In certain embodiments of any of the methods and uses, the conjugated DEspR antibody and/or DEspR antibody fragment thereof is/are internalized by the cell, resulting in increased therapeutic efficacy of the conjugate in killing the cancer cell to which it binds. In some embodiments, the cytotoxic agent conjugated to the DEspR antibody and/or DEspR antibody fragment thereof targets or interferes with nucleic acid in the cancer cell. Examples of such cytotoxic agents include maytansinoids, calicheamicins, ribonucleases and DNA endonucleases, and are further described elsewhere herein.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims. Definitions of common terms in immunology, and molecular biology can be found in The Merck Manual of Diagnosis and Therapy, 18th Edition, published by Merck Research Laboratories, 2006 (ISBN 0-911910-18-2); Robert S. Porter et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8); Immunology by Werner Luttmann, published by Elsevier, 2006. Definitions of common terms in molecular biology are found in Benjamin Lewin, Genes IX, published by Jones & Bartlett Publishing, 2007 (ISBN-13: 9780763740634); Kendrew et al. (eds.), The Encyclopedia of Molecular Biology, published by Blackwell Science Ltd., 1994 (ISBN 0-632-02182-9); and Robert A. Meyers (ed.), Maniatis et al., Molecular Cloning: A Laboratory Manual, Cold Spring Harbor Laboratory Press, Cold Spring Harbor, N.Y., USA (1982); Sambrook et al., Molecular Cloning: A Laboratory Manual (2 ed.), Cold Spring Harbor Laboratory Press, Cold Spring Harbor, N.Y., USA (1989); Davis et al., Basic Methods in Molecular Biology, Elsevier Science Publishing, Inc., New York, USA (1986); or Methods in Enzymology: Guide to Molecular Cloning Techniques Vol.152, S. L. Berger and A. R. Kimmerl Eds., Academic Press Inc., San Diego, USA (1987); Current Protocols in Molecular Biology (CPMB) (Fred M. Ausubel, et al. ed., John Wiley and Sons, Inc.), Current Protocols in Protein Science (CPPS) (John E. Coligan, et. al., ed., John Wiley and Sons, Inc.) and Current Protocols in Immunology (CPI) (John E. Coligan, et. al., ed. John Wiley and Sons, Inc.), which are all incorporated by reference herein in their entireties.

As used herein, the term "comprising" means that other elements can also be present in addition to the defined elements presented. The use of "comprising" indicates inclusion rather than limitation.

As used herein the term "consisting essentially of" refers to those elements required for a given embodiment. The term permits the presence of additional elements that do not materially affect the basic and novel or functional characteristic(s) of that embodiment of the invention.

The term "consisting of" refers to compositions, methods, and respective components thereof as described herein, which are exclusive of any element not recited in that description of the embodiment.

Further, unless otherwise required by context, singular terms shall include pluralities and plural terms shall include the singular. As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth.

Other than in the operating examples, or where otherwise indicated, all numbers expressing quantities of ingredients or reaction conditions used herein should be understood as modified in all instances by the term "about." The term "about" when used in connection with percentages can mean ±1%.

It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

All patents and other publications identified are expressly incorporated herein by reference for the purpose of describing and disclosing, for example, the methodologies described in such publications that could be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

This invention is further illustrated by the following examples which should not be construed as limiting.

EXAMPLES

Example 1

Development of Novel Anti-Human Dual Endothelin-1/VEGFsp Receptor (anti-hDEspR) Monoclonal Antibody Treatments as Inhibitors of Tumor Angiogenesis and Tumor Cell Invasiveness DEspR is a key angiogenesis player in embryonic development as seen in DEspR$^{-/-}$ knockout mice (Herrera et al. 2005), and contributes to adult tissue vascularity as seen in adult haplo-deficient (+/−) mice exhibiting decreased tissue vascularity shown by power Doppler analysis (FIG. 2).

Based on the association of tumor invasion and metastasis with intrinsic and evasive resistance to VEGF-targeted therapies, the combination of anti-invasive and anti-metastatic drugs with anti-angiogenesis therapies is important to analyze (Bergers and Hanahan 2008). This new therapeutic mandate for anti-cancer therapies can be addressed through a novel therapy comprising DEspR-inhibition, since DEspR and VEGFsp expression are detected in human endothelial cells, increased in tumor vessels, detected in cancer cells in tumor tissue arrays and in different established metastatic cancer cell lines, and since inhibition of DEspR decreases both angiogenesis and tumor cell invasiveness using corresponding established in vitro assays, as shown herein.

Figure 3C:
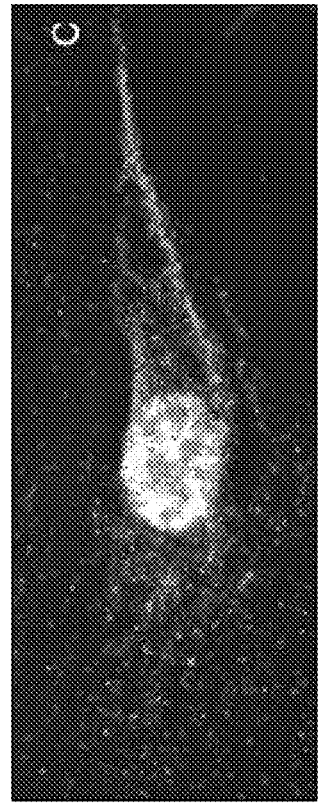
FIGS. 3A-3E show that DEspR and VEGFsp are detected by immunostaining in umbilical vein endothelial cells (HUVECs) (FIGS. 3A-3C) and microvascular endothelial cells (HMECS) under both basal and angiogenic tube-formation conditions. Importantly, inhibition of angiogenesis neovessel tube length is seen using both anti-DEspR (Ab1) and anti-VEGFsp (Ab2) antibodies in HUVECs (FIG. 3D) and HMECs (FIG. 3E) angiogenesis assays. (Tukey's all pairwise multiple comparison P<0.001 for both HUVECs and HMECs). Similar findings were observed for other angiogenesis parameters including neovessel branching and interconnections made.
Figure 1:
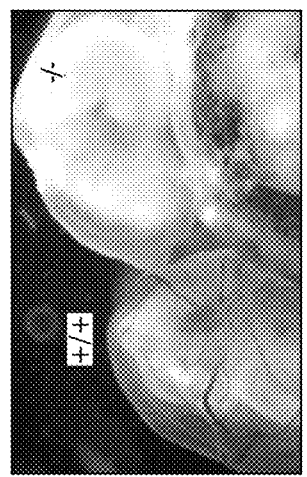
FIG. 1 shows that DEspR is a key angiogenesis player in embryoinic development using DEspR (formerly called Dear, deposited in Gen Bank as Dear) null or knockout ($Dear^{-/-}$) mice.
Figure 3A:
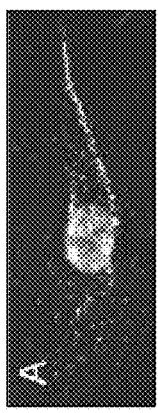
Figure 3B:
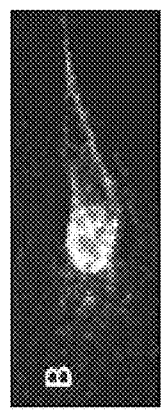
Figure 3E:
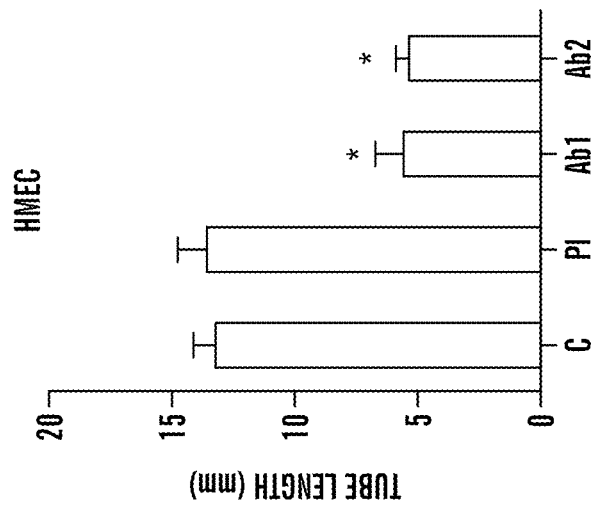
Figure 3D:
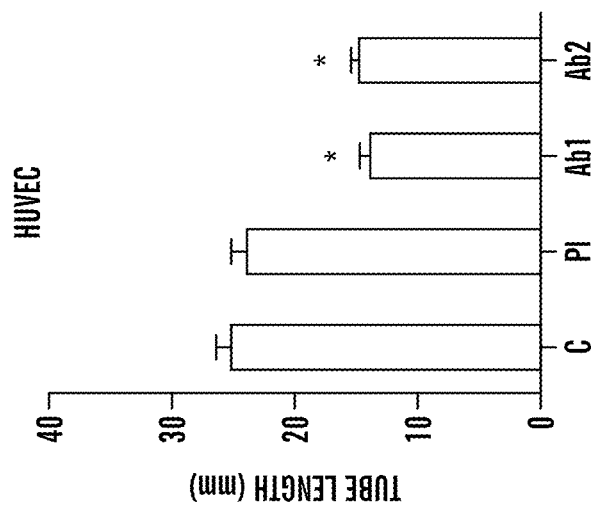

DEspR and VEGFsp were detected by immunostaining in umbilical vein endothelial cells (HUVECs) and microvascular endothelial cells (HMECS) in both basal and angiogenic tube-formation conditions (FIGS. 3A-3E). Importantly, inhibition of angiogenesis neovessel tube length was seen using both anti-DEspR (Ab1) and anti-VEGFsp (Ab2) antibodies in HUVECs (FIG. 3D) and HMECs (FIG. 3E) angiogenesis assays (Tukey's pairwise multiple comparison P<0.001 for both HUVECs and HMECs). Similar findings were observed using other angiogenesis parameters, such as neovessel branching and inter-connections made. Equally important, DEspR and VEGFsp were also detected in tumor cells, with colocalization of VEGFsp and DEspR in the cell membrane and nuclear membrane. Representative immunostaining is shown in FIGS. 3A-3C.

DEspR cell-membrane and nuclear-membrane expression were detected in multiple tumor cell types, indicating that anti-DEspR therapy is effective for different cancer types. Briefly, DEspR expression was detected in human lung non-small cell ca NCI-H727, lung giant cell tumor TIB-223/GCT; breast adenoca MDA-MB-231 (FIGS. 4A-4C) & MDA-MB-468, bladder ca 253J BV, colon adenoca SW480, hepatocellular ca HEP3B, melanoma SK-MEL-2, osteosarcoma MG-63, ovarian adenoca HTB-161/NIH:OVCA R3, prostate adeno ca PC-3mm2, and pancreatic ca CRL-1469/PANC-1 (FIGS. 4D). DEspR expression was not detected in HCI-H292 lung mucoepidermoid ca, and HEPG2 hepatocellular ca (FIG. 5A), and CCL-86/Raji Burkitt's lymphoma, thus showing specificity of positive observations. Findings in NCI-727 lung ca cells (FIGS. 5B) were corroborated on tumor-section immunostaining of Gr.III lung adenoca (FIGS. 5C).

As shown in FIGS. 6A-6B, in contrast to control (C) and pre-immune ab treatment (PI), DEspR-inhibition via anti-humanDEspR antibody treatment inhibits tumor cell invasiveness in two cell lines tested, metastatic breast tumor MDA-MB-231 and pancreatic adenocarcinoma PANC-1 cell lines. The ability to target both tumor angiogenesis and tumor cell invasiveness through DEspR inhibition can more effectively address combined angiogenesis-metastasis phenotypes seen in aggressive tumors and in evasive resistance to current anti-VEGF therapies.

In vivo proof has also been demonstrated in an irradiation-induced mammary tumor model in immunocompetent rats using anti-ratDEspR antibody (Herrera et al. 2005). As shown in FIG. 7, anti-DEspR treated rats exhibited minimal tumor growth compared with mock-treated controls.

Figure 8B:
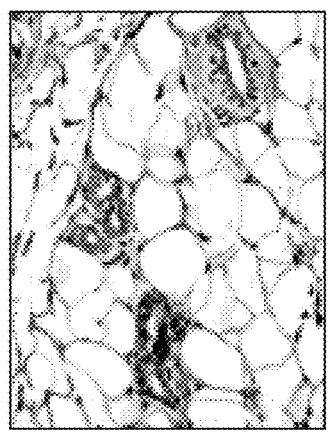
FIGS. 8A-8D show, using immunohistochemical analysis, that DEspR is expressed in mammary tumors cells (FIG. 8A) similar to MDA-MB-231 breast cancer cels, with no expression in normal breast tissue (FIG. 8B). In addition, residual tumors in treated rats exhibited normalization of blood vessels (FIG. 8C) in contrast to mock-treated tumors which showed disrupted endothelium in tumor vessels with encroachment of tumor cells into the lumen (FIG. 8D).
Figure 8D:
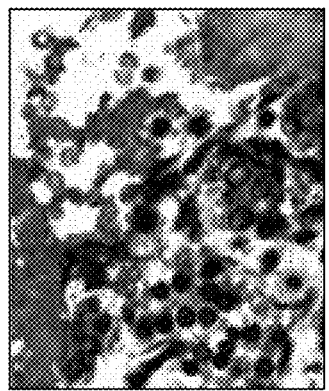
Figure 8A:
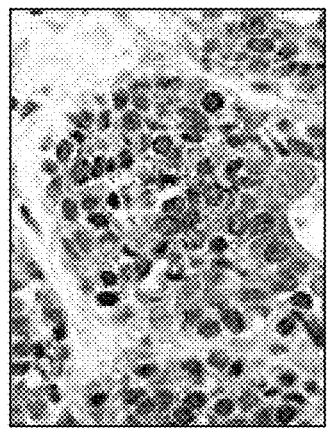
Figure 8C:
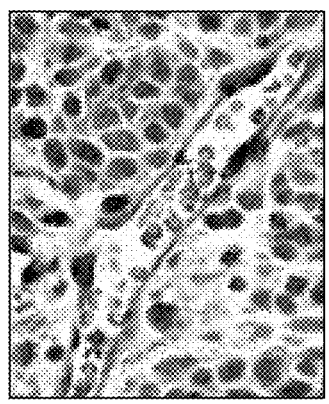

Concordantly, immunohistochemical analysis of mammary tumors showed DEspR expression in tumor cells (FIG. 8A) similar to human MDA-MB231 breast cancer cells, with no expression in normal breast tissue (FIG. 8B). Importantly, residual tumors in treated rats exhibited normalization of blood vessels (FIG. 8C) in contrast to mock-treated tumors which showed disrupted endothelium in tumor vessels with encroachment of tumor cells into the lumen (FIG. 8D).

Clinically, the addition of VEGFsp/DEspR-targeted anti-angiogenic therapies to current VEGF/VEGFR2-targeted therapies can additively or synergistically lead to the desired endpoint of increasing overall survival in cancer patients. Given that there are several VEGF/VEGFR2 therapies already in the clinics, the translational development of anti-DEspR therapy as described herein is done in order to provide this addition.

Logistically, the experiments described herein demonstrate successful development of precursor polyclonal anti-rat DEspR antibodies (FIGS. 7 and 8A-8D; Herrera et al. 2005) and polyclonal anti-human DEspR ab (FIGS. 5A-5C and 6A-6B; Glorioso et al. 2007) that exhibit robust affinity, specificity and functionality.

There are key advantages for selecting the human monoclonal antibody therapy approaches described herein for DEspR-targeted anti-angiogenesis therapy and target-specific molecular imaging. Humanized/all human monoclonal antibody therapies (Ab-Rx) are a rapidly growing class of human therapeutics (Carter 2006) and have a relatively high success rate at 18-24% compared to new chemical entities, including small-molecule agents at 5% (Imai & Takaoka 2006).

We have developed and validated a murine monoclonal antibody specific for human-DEspR, termed herein as the 7C5B2 antibody, using a 9-amino acid (aa)-long epitope located in the extracellular amino-terminal end of hDEspR (Glorioso et al., 2007).

Briefly, mice were immunized with a KLH-conjugated antigenic peptide comprising the NH$_2$-terminal 9 amino acids of hDEspR, i.e., DEspR(1-9). After four injections, sera were collected for screening of antibody titer using free antigenic peptide as antigen. The mouse exhibiting the best titer was used for fusion experiments. Supernatants of fused clones were screened by ELISA using free antigenic peptide as antigen. All positive clones were transferred onto 24-well plate and re-tested/confirmed by ELISA. The 10 best clones were selected for further testing, which comprised the candidate monoclonal antibodies, anti-hDEspR monoclonal antibody. Relative affinities of prospective monoclonal antibodies were determined by ELISA using the supernatant from 10 best clones identified.

Analysis of relative monoclonal antibody affinity for antigenic hDEspR 9-aa peptide identified clones 7C5C5 and 7C5B2 as the monoclonal antibodies with strongest affinity. These two were selected for expansion and subsequent large-scale production based upon their higher affinity for the antigenic peptide.

To ascertain specificity, low-(5G12E8), mid-(2E4H6), and high-affinity (7C5B2) monoclonal antibodies were tested for western blot analysis by testing the subclone supernatant, and the subsequent purified antibody. Candidate anti-hDEspR monoclonal antibodies were specific for the predicted 10 kD protein for hDEspR. Western blot analysis was done using total cellular protein isolated from Cos1 hDEspR-transfected cells as antigen, primary antibody comprised purified antibody and subclone supernatant of 3 selected clones, 10% gel concentration in order to detect the expected 10 kD molecular weight protein of hDEspR. Nitrocellulose (PIERCE) was used with a transfer buffer of 3.07 g Tris, 14.4 g Glycine, 200 ml methanol, 800 ml dH2O. HRP-anti mouse polyvalent immunoglubulins were used (Sigma #0412) 1:100,000; ECL reagent (SuperSignal West Femto Kit #34094), Stain reagent Kodak RP-X-Omat, and x-film (Kodak X-film #XBT-1).

The Western blot results demonstrated specificity of anti-hDEspR monoclonal antibody regardless of relative affinity, and identified more than one successful anti-hDEspR monoclonal antibody. Of the antibodies tested, the monoclonal antibody clone with highest relative affinity and specificity was clone 7C5B2.

The top candidate anti-hDEspR monoclonal antibodies were tested for inhibition of angiogenesis parameters in order to identify candidate anti-hDEspR mAb-Rxtic as anti-angiogenic using established in vitro assays.

To assess anti-angiogenic properties specific to human cells, commercially available, pre-validated established angiogenesis assays based on human umbilical vein cells (HUVECs) were used. Multiple in vitro-assay angiogenesis parameters were monitored, such as number of angiogenic tubes formed, ability of "neovessels" or tubes to branch (# branch points), ability of said neovessel branches to connect and form complex connections (# branch=connections), and robustness of angiogenesis represented by neovessel tube length (tube length in mm) Purified 7C5B2 anti-DESPR monoclonal antibody's ability to inhibit HUVECS angiogenic capacity in vitro was assessed accordingly.

An optimal effective concentration of anti-hDEspR 7C5B2 monoclonal antibody that can inhibit >80% of neovessel tube length and number of branch points was first assessed. This optimal inhibitor concentration for anti-angiogenesis efficacy was found to be 500 nM of the anti-hDEspR 7C5B2 monoclonal antibody. This concentration was then used in a series of experiments to evaluate other in vitro parameters of angiogenesis.

The anti-hDEspR 7C5B2 monoclonal antibody effectively inhibited different in vitro parameters of angiogenesis, such as number of neovessel tubes formed, branch points, branch connections and tube length. The anti-hDEspR 7C5B2 monoclonal antibody worked as well if not better than a previously validated polyclonal antibody, thus validating its potential as a monoclonal therapeutic.

The anti-hDEspR 7C5B2 monoclonal antibody was also tested for specific binding to tumor vessel endothelium and/or tumor cells in human cancer tissue arrays. The anti-hDEspR 7C5B2 monoclonal antibody was evaluated in immunohistochemical analyses of human tumor tissue-arrays comprised of core biopsy specimens representing tumors and normal tissue on the same slide. Conditions that optimized specificity and sensitivity of detection using formalin-fixed, paraffin embedded core biopsy sections were tested. Double-immunofluorescence experiments were performed in order to evaluate hDEspR expression and CD133 expression, with the latter serving as a marker for putative cancer stem cells. Antigen-retrieval was performed and used anti-hDEspR monoclonal antibody at 1:10, and commercially available anti-CD133 mAb at 1:20 dilution.

Figure 14A:
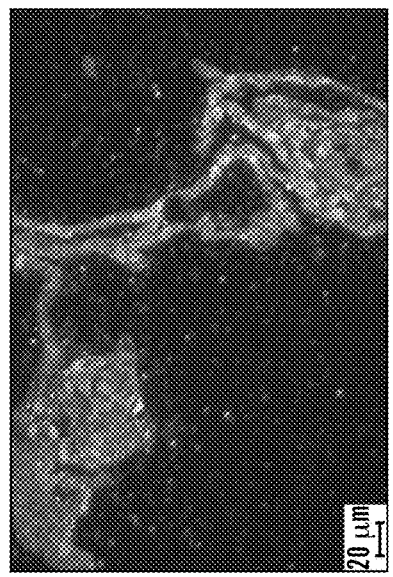
FIGS. 14A-14B show immunohistochemical analysis of human tumor tissue-arrays comprised of core biopsy specimens representing tumors and normal tissue on the same slide using an anti-human DEspR 7C5B2 monoclonal antibody. Conditions that optimized specificity and sensitivity of detection were first tested using formalin-fixed, paraffin embedded core biopsy sections. Double-immunofluorescence experiments were performed to evaluate human DEspR expression and CD133 expression, with the latter serving as a marker for cancer stem cells. Antigen-retrieval was performed using anti-human DEspR monoclonal antibody at 1:10, and commercially available anti-CD133 monoclonal antibody at 1:20 dilutions. Representative immunohistochemical analysis of human tumor tissue-arrays using anti-human DEspR 7C5B2 monoclonal antibody detected increased expression of hDEspR (Alexa-568red) in stage II-lung cancer tumor cells, as shown in FIG. 14A. Some tumor cells were immunostained double-positive for both human DEspR and CD133, while other tumor cells immunostained only for CD133. These observations demonstrate that human DEspR is also present in CD133-positive cancer stem cells, as well as CD133-negative tumor cells.
Figure 15A:
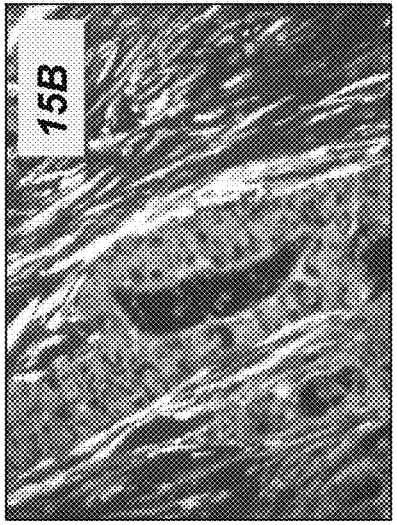
FIGS. 15A-15B show that there is minimal DEspR expression in normal human pancreas (FIG. 15B), with α-smooth muscle actin serving as positive control, while, in contrast, stage IV pancreatic cancer tumor cells and tumor blood vessels exhibits increased DEspR expression (FIG. 15A).
Figure 14B:
Figure 15B:
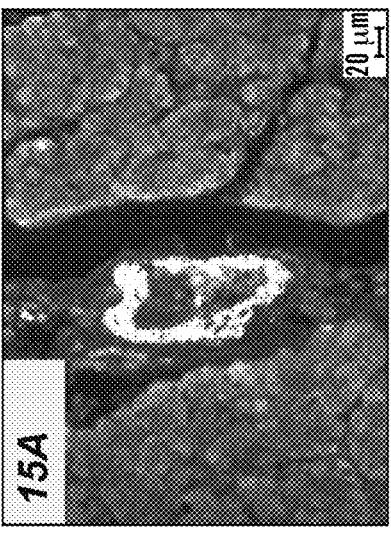
Figure 16C:
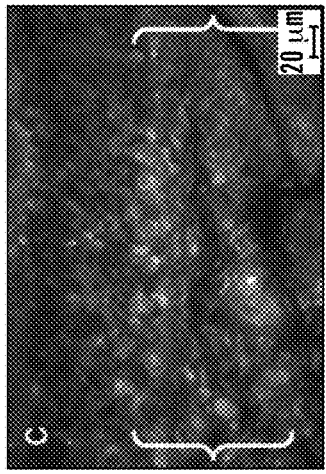
FIGS. 16A-16D demonstrate DEspR-targeted ultrasound molecular imaging and show that a DEspR-specific antibody (FIG. 16A) detects DEspR+endothelial lesions (FIG. 16B) and vasa vasorum angiogenesis (FIG. 16C). Quantitation of contrast intensity is done using integrated VisualSonics Micro-imaging System software (FIG. 16D) and demonstrates increased contrast intensity in DEspR+carotid artery endothelium and vasa vasorum, in contrast to both low contrast intensity in DEspR(−) endothelium and vasa vasorum, and isotype-microbubble controls. P<0.0001, ANOVA and pairwise multiple comparison. Anti-DEspR-antibody is biotinylated and coupled to streptavidin-PEG coated commercially available microbubbles for ultrasound analysis and imaging.
Figure 16B:
Figure 16A:
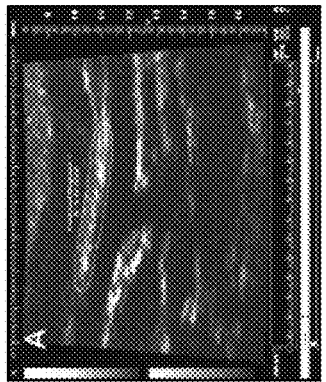
Figure 16D:
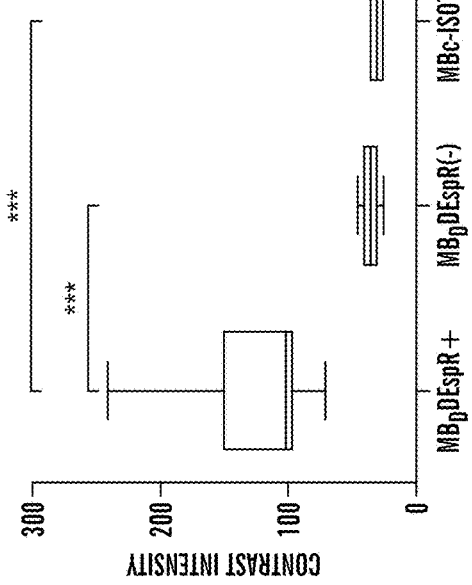
Figure 17A:
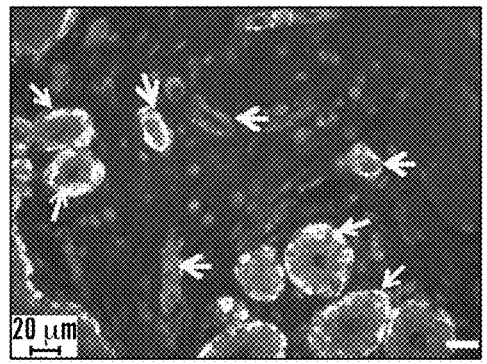
FIGS. 17A-17F show immunohistochemical analysis of DEspR expression in human breast tissue using an anti-DEspR monoclonal antibody (FIGS. 17A-17C) normal; Grade-1, T1 invasive ductal carcinoma (FIGS. 17D-17F).
Figure 17D:
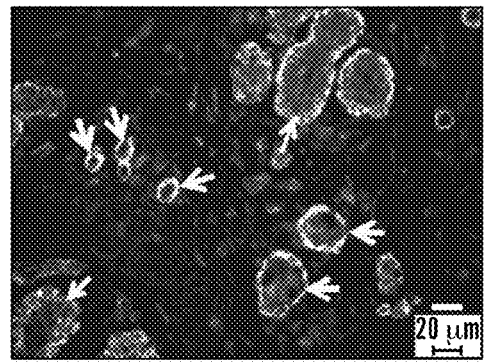
Figure 17B:
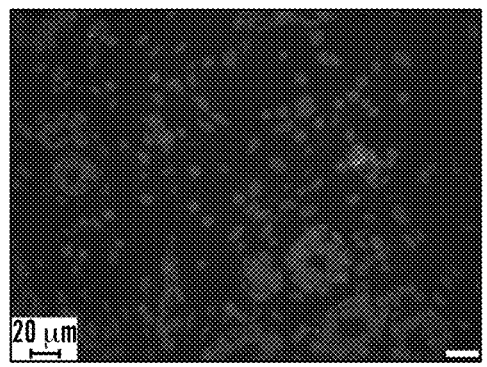
Figure 17E:
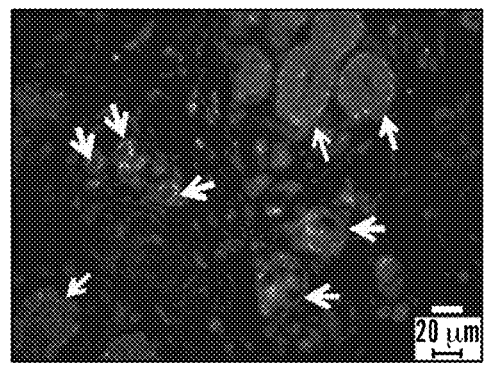
Figure 17C:
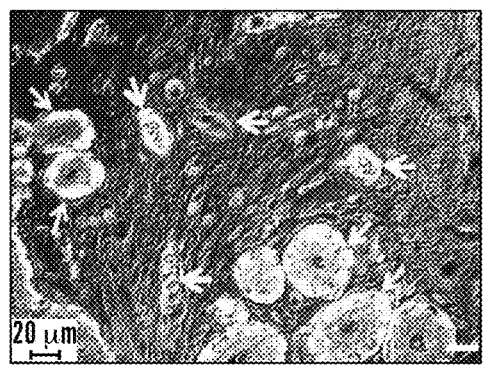
Figure 17F:
Figure 18A:
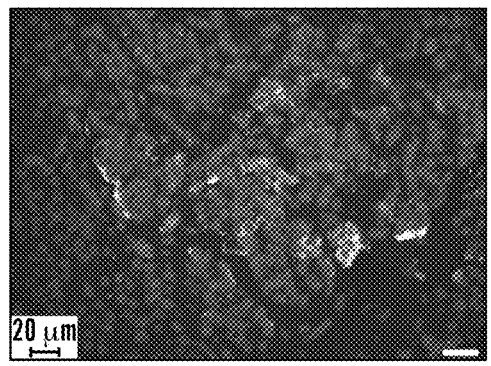
FIGS. 18A-18F show monoclonal antibody immunohistochemical analysis of DEspR expression in normal pancreatic tissue (FIGS. 18A-18C) normal; and Grade-3, T3 pancreatic ductal carcinoma (FIGS. 18D-18F).
Figure 18D:
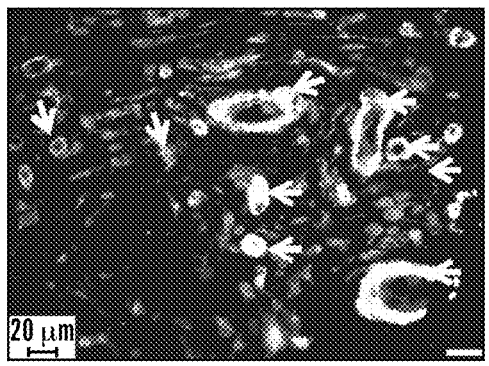
Figure 18B:
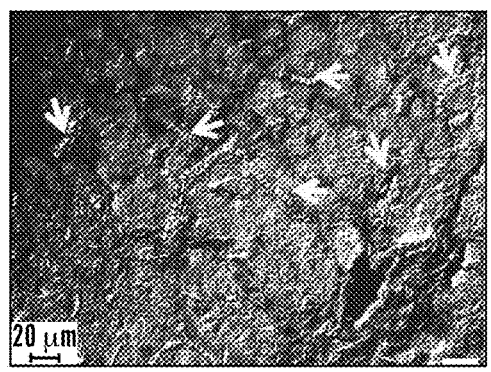
Figure 18E:
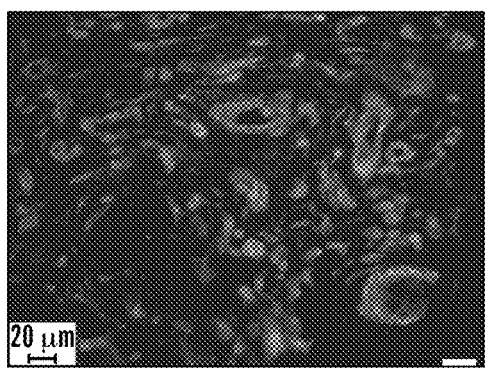
Figure 18C:
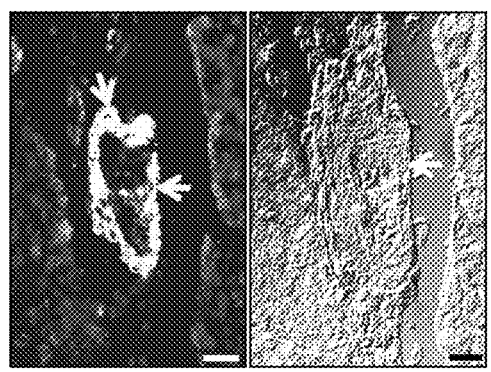
Figure 18F:
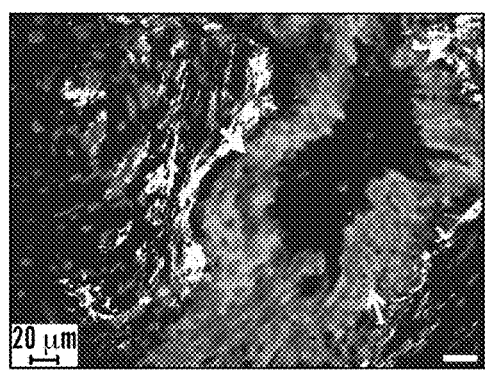

As shown in FIGS. 14A-14B, representative immunohistochemical analysis of human tumor tissue-arrays using anti-hDEspR 7C5B2 monoclonal antibody detected increased expression of hDEspR in stage II-lung cancer tumor cells (FIG. 14A). Some tumor cells are double immunostain-positive for both hDEspR and CD133, with other tumor cells immunostained for CD133. These observations demonstrate that hDEspR is also present in postulated CD133-positive cancer stem cells, as well as CD133-negative tumor cells. In contrast, normal lung specimen does not exhibit any immunostaining for hDEspR or CD133 (FIG. 14B). In addition, increased DEspR expression was observed in a variety of CD133+ cancer stem cell subsets, as detected by immunofluorescence with a combination of anti-DEspR, anti-CD133 and anti-CXCR4 monoclonal antibodies, including NBC mda-mb-231 cells, pancreatic ductal adenoca Pancl cells, glioblastoma cells, and breast cancer cells. Accordingly, in some embodiments, the compositions and methods described herein can be used in targeted treatments for tumor resistance and/or recurrence by targeting cancer stem cells or cancer initiating cells.

Figure 9:
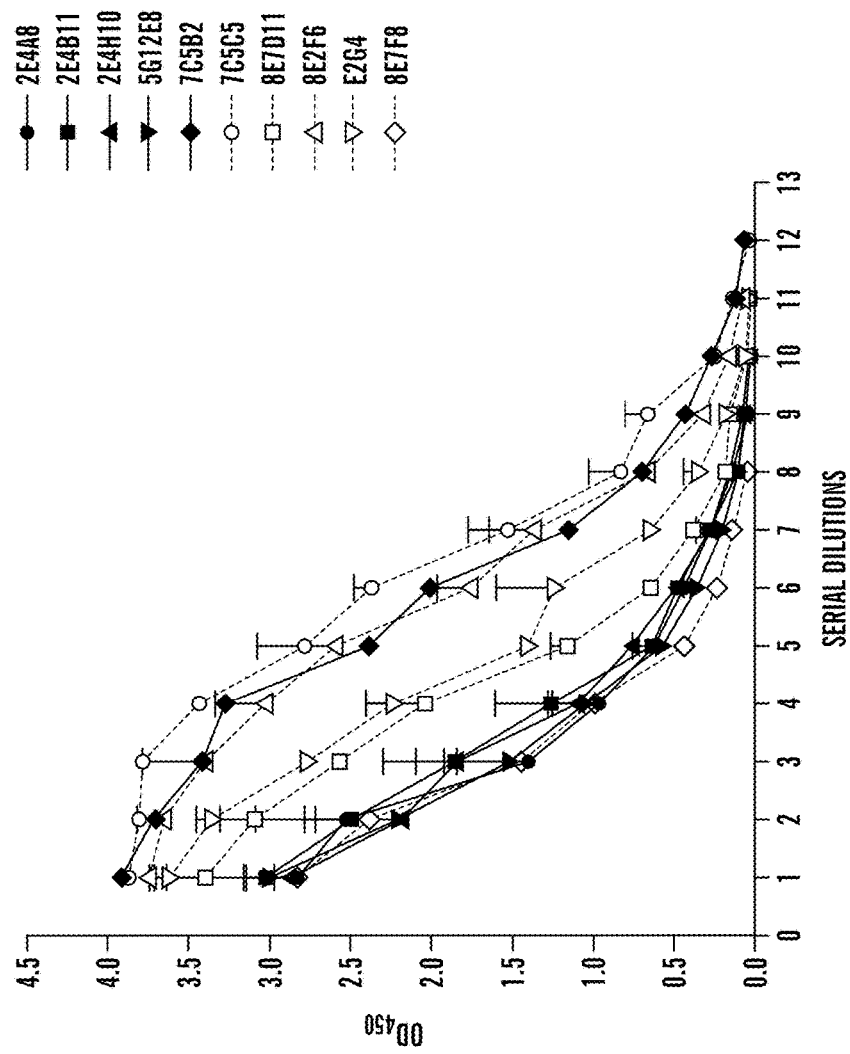
FIG. 9 shows characterization of selected monoclonal antibodies. Monoclonal antibodies 2E4A8, 2E4B11, 2E4H10, 5G12E8, 7C5B2, 7C5C5, 8E7D11, 8E2F6, E2G4 and 8E7F8 were tested by indirect ELISA using standard procedures. Serial dilutions from supernatants containing monoclonal antibodies at 1 µg/ml were tested as follows: 1=1/2; 2=1/4; 3=1/8; 4=1/16; 5=1/32; 6=1/64; 7=1/128; 8=1/256; 9=1/512; 10=1/1024; 11=1/2048 and 12=1/4096.
Figure 10:
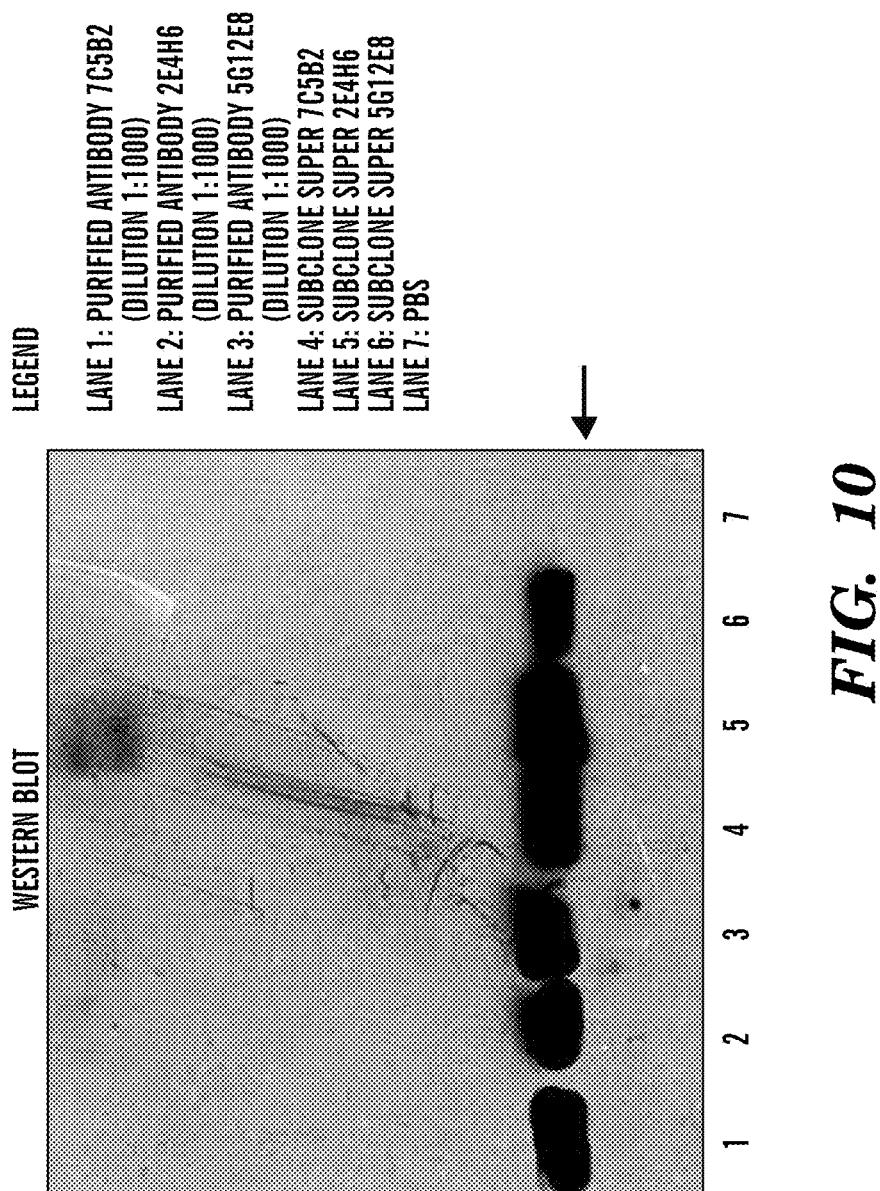
FIG. 10 shows Western blot analysis of monoclonal antibodies tested. To ascertain specificity, low-(5G12E8), mid-(2E4H6), and high-affinity (7C5B2) monoclonal antibodies were tested as well as the subclone supernatant, and the subsequent purified antibody. The anti-human DEspR monoclonal antibodies are specific for the predicted 10 kD protein for human DEspR. Western blot analysis was performed using total cellular protein isolated from Cos1 human DEspR-transfected cells as antigen, primary antibody comprised purified antibody and subclone supernatant of 3 selected clones, 10% gel concentration in order to detect the expected 10 kD molecular weight protein of human DEspR. Nitrocellulose (PIERCE) with a transfer buffer of 3.07 g Tris, 14.4 g Glycine, 200ml methanol, 800 ml $dH_2O$ were used. HRP-anti mouse polyvalent immunoglubulins (Sigma #0412) were used at 1:100,000; ECL reagent (SuperSignal West Femto Kit #34094), Stain reagent Kodak RP-X-Omat, and x-film (Kodak X-film #XBT-1). The Western blot results demonstrate specificity of anti-human DEspR monoclonal antibodies regardless of relative affinity, thus identifying more than one successful anti-human DEspR monoclonal antibody. The results indicate that the monoclonal antibody clone with highest relative affinity and specificity is clone 7C5B2.
Figure 13A:
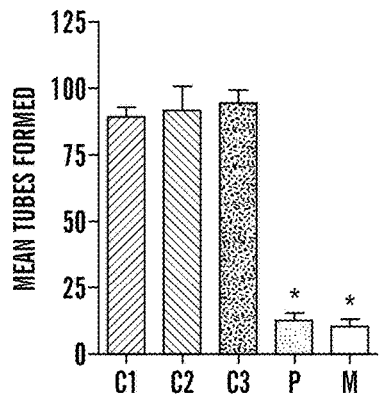
FIGS. 13A-13D show effects of an anti-human DEspR monoclonal antibody 7C5B2 (IgG2b isotype) on in vitro serum-induced HUVEC tubulogenesis (established in vitro angiogenesis assay). HUVECs (human umbilical vein endothelial cells) were grown onto Matrigel-coated wells in basal medium supplemented with 2% FBS (control C1), or 2% FBS+pre-immune IgG isotype control for polyclonal anti-hDESPR antibody (500 nM, control C2), or 2% FBS+ IgG2b isotype control for anti-hDESPR mAB (500 nM, C3 control) or 2% FBS+polyclonal anti-hDEspR (500 nM, P) or 2% FBS+monoclonal antibody 7C5B2 (500 nM, M). Quantitative analysis of the mean number of tubes formed per well is shown in FIG. 13A, the mean number of branching points per well is shown in FIG. 13B, the mean number of connections per well is shown in FIG. 13C and the mean total tube length in mm per well is shown in FIG. 13D, using the in vitro tube formation assay. Data are shown as mean±standard error. Each experimental condition was performed in five replica wells. Statistically significant differences (as compared with respective control conditions), are indicated as follows: *P<0.001 (one way ANOVA followed by all pairwise multiple comparison Tukey Test).
Figure 13B:
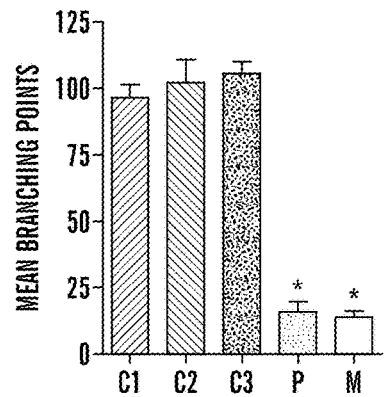
Figure 13C:
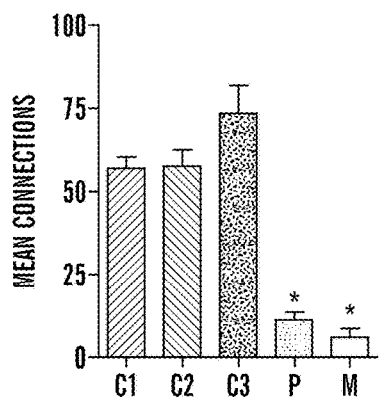
Figure 13D:
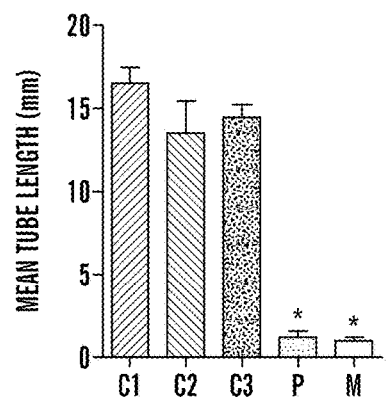

Accordingly, to summarize, this murine antibody "7C5B2" exhibited high affinity binding by ELISA to the 9 aa-long epitope (FIG. 9), demonstrates specificity by western blot (FIG. 10), immunostains HUVECs undergoing tubeformation (FIGS. 3A-3E), and pancreatic adenoca PANC-1, and breast cancer MDA-MB-231 cells.

We demonstrated functional efficacy in vitro by showing that both the polyclonal (Pab) and monoclonal anti-DEspR 7C5B2, specific for human DEspR, inhibit different parameters of angiogenesis in HUVECs (FIGS. 10A-10C): mean number of branchpoints as a measure of neovessel complexity (FIG. 10A), and total length of tubes as a measure of neovessel density (FIG. 10B). Dose response curve for inhibition (FIG. 10C) showed equivalent robustness to inhibit both angiogenesis parameters. Importantly, murine 7C5B2 also inhibits tumor cell invasiveness in MDA-MB-231 human breast cancer and PANC-1 pancreatic cancer cell lines.

This murine anti-human DEspR monoclonal antibody 7C5B2 is thus shown to have high affinity, specificity, and functionality serves as the starting antibody for the development of anti-DEspR composite de-immunized all human antibodies, as described herein.

Accordingly, described herein are the development, characterization, and in vitro efficacy testing of anti-hDEspR composite de-immunized all human monoclonal antibody (cdHMAb) for use as novel antibody therapies aimed at addressing evasive and intrinsic resistances to current anti-VEGF/VEGFR2 antiangiogenic therapies.

We have selected Antitope's Composite Human Antibody technology to generate anti-hDEspR deimmunized human monoclonal antibodies for antibody therapeutics (Antitope, 2010). This technology generates de-immunized 100% human antibodies at the outset, in contrast to non-deimmunized human antibodies derived from phage and transgenic mice technologies. Briefly, composite human antibodies comprise multiple sequence segments ("composites") derived from V-regions of unrelated human antibodies are selected to maintain monoclonal antibody sequences critical for antigen binding of the starting murine precursor anti-human DEspR monoclonal antibody, and are filtered for the presence of potential T-cell epitopes using proprietary "in silico tools" (Holgate & Baker 2009). The close fit of human sequence segments with all sections of the starting antibody V regions and the elimination of CD4+ T cell epitopes from the outset circumvent immunogenicity in the development of '100% human' therapeutic antibodies while maintaining optimal affinity and specificity through the prior analysis of sequences necessary for antigen-specificity (Holgate & Baker 2009) Immunogenicity can hinder clinical applications of 100% human monoclonal antibodies (Chester et al. 2009).

Briefly, "composite human antibodies" comprise multiple sequence segments ("composites") derived from V-regions of unrelated human antibodies that are selected to maintain monoclonal antibody sequences critical for antigen binding of the starting murine precursor anti-human DEspR monoclonal antibody, such as 7C5B2 antibody, and which have all been filtered for the presence of potential T-cell epitopes using "in silico tools" (Holgate & Baker, 2009). The close fit of human sequence segments with all sections of the starting antibody V regions and the elimination of CD4+ T cell epitopes from the outset allow this technology to circumvent immunogenicity in the development of '100% human' therapeutic antibodies while maintaining optimal affinity and specificity through the prior analysis of sequences necessary for antigen-specificity (Holgate & Baker 2009).

As described herein, structural models of mouse anti-hDEspR antibody V regions were produced using Swiss PDB and analysed in order to identify important "constraining" amino acids in the V regions that were likely to be essential for the binding properties of the antibody. Residues contained within the CDRs (using Kabat definition) together with a number of framework residues were considered to be important. Both the $V_H$ and $V_L$ ($V_K$) sequences of anti-hDEspR, as described herein as SEQ ID NO: 4 and SEQ ID NO: 9, comprise typical framework residues and the CDR1, CDR2, and CDR3 motifs are comparable to many murine antibodies.

From the above analysis, it was determined that composite human sequences of anti-hDEspR can be created with a wide latitude of alternatives outside of CDRs but with only a narrow menu of possible alternative residues within the CDR sequences. Analysis indicated that corresponding sequence segments from several human antibodies could be combined to create CDRs similar or identical to those in the murine sequences. For regions outside of and flanking the CDRs, a wide selection of human sequence segments were identified as possible components of novel anti-DEspR composite human antibody V regions for use with the compositions and methods described herein (see, for example, Table 1).

Based upon these analyses, a large preliminary set of sequence segments that could be used to create novel anti-DEspR composite human antibody variants were selected and analysed using iTope™ technology for in silico analysis of peptide binding to human MHC class II alleles (Perry et al 2008), and using the TCED™ (T Cell Epitope Database) of known antibody sequence-related T cell epitopes (Bryson et al 2010). Sequence segments that were identified as significant non-human germline binders to human MHC class II or that scored significant hits against the TCED™ were discarded. This resulted in a reduced set of segments, and combinations of these were again analysed, as above, to ensure that the junctions between segments did not contain potential T cell epitopes. Selected segments were then combined to produce heavy and light chain V region sequences for synthesis. Exemplary heavy chain V region sequences provided herein and generated using the above-described methods include SEQ ID NO: 13-SEQ ID NO: 17. Exemplary heavy chain V region sequences provided herein and generated using the above-described methods include SEQ ID NO: 18-SEQ ID NO: 19.

In vitro efficacy of the antibodies described herein are assessed by examining dose response-inhibition of angiogenesis of HUVECs (human umbilical vein cells) and HMECs (adult human microvascular endothelial cells) in angiogenesis assays (see FIGS. 3A-3E, 10A-10C), which in some embodiments are set-up with co-cultured cancer cells, such as PANC-1 and MDA-MB-231, and in some embodiments in normoxia and hypoxia (2% O2) conditions. Both HUVECs and HMECs are used for the following reasons: HUVECs is the standard in the field, but as these cells are umbilical vein derived, and adult microvascular endothelial cells (HMECs) are also used. In addition, angiogenesis is assessed with co-cultured cancer cells, in addition to the fetal bovine serum that is usually added in angiogenesis assays, in order to better simulate angiogenic factors that cancer cells produce which contribute to evasive and intrinsic resistance.

In some embodiments, since hypoxia is one of the triggers for angiogenesis, and one of the contributing factors suspected of underlying evasive resistance to current anti-VEGF therapies, in vitro efficacy assays are conducted in normoxia and in 2% O2 hypoxia. Composite deimmunized monoclonal antibody -mediated inhibition of tumor cell invasiveness in vitro is analyzed using MDA-MB-231 and PANC-1 cells and by using established quantitative assays. These are also done in normoxia and 2% O2-hypoxia conditions, to test a more aggressive tumor cell phenotype known to be associated with hypoxia.

The effects of anti-hDEspR inhibition are compared to controls, which can include untreated controls, isotype controls, murine precursor anti-hDEspR monoclonal antibody controls, and bevacizumab controls. Each point for angiogenesis and tumor cell invasiveness assays are done using at least 5 replicates. Furthermore, for the top 2 candidate-leads, dose response curve inhibition responses are also performed, where each dosage is studied using at least 5 replicates.

Assays can be analyzed by one way ANOVA and multiple pairwise comparison to assess significant changes. Mean levels of %-inhibition from control by each candidate lead (e.g., 5-10) are used to rank them according to different assays, and the highest ranked two identifies the top-2 leads corresponding to best inhibitor of angiogenesis and tumor cell invasiveness in both for example, normoxia and hypoxia conditions, and in both, for example, MDA-MB-231 and PANC-1 cancer cell lines respectively.

Tumor array analysis is done to corroborate specificity and sensitivity of each to detect tumor cells and tumor neovessels in tissue arrays of human biopsy core samples form different cancer tissue types. This is performed on a tissue array panel representing solid tumors from brain, pancreas, lung, breast, ovarian, prostate, bladder, colon, stomach. Results are analyzed for specificity given the same immunochemistry conditions used in validation of the murine precursor anti-hDEspR Mab-H1. As shown, there is minimal DEspR expression in normal human pancreas, whereas in stage IV pancreatic cancer exhibits increased DEspR expression in pancreatic tumor cells and tumor blood vessels. The composite deimmunized monoclonal antibody candidate leads are ranked and the top-2 that have the best detection of tumor cells and tumor neovessels with optimal signal to noise ratio in tumor tissue array immunohistochemistry are determined This can be compared to tumor-array immunostaining observations obtained with the murine precursor anti-hDEspR Mab.

In addition to de-immunizing the antibodies described herein using in silico screening of T-cell epitopes to minimize and reduce immunogenicity, the composite humanized anti-hDEspR composite deimmunized monoclonal antibodies are tested in vitro for immunogenicity in order to select for the least immunogenic composite all human Mab. Immunogenicity screening can be performed using a representative of 50 donors, which has proven to correlate with clinical observations (Baker & Jones 2007).

Immunogenicity testing, along with the other in vitro assays of specificity and efficacy allows for the selection of a top anti-hDEspR lead, based on a combination of factors, including best affinity (ELISA), specificity (western blot analysis), in vitro efficacy (inhibition of angiogenesis and tumor cell invasiveness) and lowest immunogenicity. A priori ascertainment of low immunogenicity by elimination of T cell epitopes in the composite antibody humanization process, and low immunogenicity ascertainment by using ex vivo T cell assay technology are important translational research steps, since high immunogenicity limits ab therapeutic efficacy (Iwai & Takaoka 2006) despite target-specificity and total humanization as has been discussed in clinical studies for Infliximab, Alemtuzumab (review by Baker & Jones 2007).

The top composite deimmunized monoclonal antibodies leads are tested for in vivo efficacy by testing anti-DEspR-mediated inhibition of tumor growth, angiogenesis and metastasis in established human cancer cell line xenograft and metastasis models in immuno-compromised mice. Cancer tissue types representative of evasive resistance (breast cancer) and intrinsic resistance (pancreatic cancer) as observed in published reports are also tested. For example, MDA-MB-231 breast cancer and PANC-1 pancreatic carcinoma cell lines are used, since both can be used to generate xenograft and metastasis spleen-infusion models. For MDA-MB-231 orthotopic and metastasis models nude mice are used (Oh et al. 2009, Roland et al. 2009). For PANC-1 xenograft subcutaneous models nude mice are used as described (Zheng et al. 2008) and NOG mice for PANC-1 metastasis model as described (Suemizu et al. 2007).

Through the strategic use of anti-humanDEspR-specific (e.g., composite deimmunized monoclonal antibody primary lead) and anti-human-VEGF-specific (bevacizumab) antibodies, and a murine-DEspR-specific Mab, 1) efficacy of anti-DEspR therapy compared with anti-VEGF therapy alone can be assessed, and 2) determination of synergistic efficacy using a combination of anti-DEspR and anti-VEGF antibodies.

Treatment in xenograft models begin when tumors are 200-300 mm in size to simulate clinical cancer therapy scenarios. To assess anti-DEspR therapy efficacy in metastasis models, a sustained treatment regimen begun 5 days after the intrasplenic infusion of cancer cells is assessed, as described (Oh et al. 2009). To assess whether anti-DEspR therapy induces increased risk for metastasis observed with sunitinib (Ebos et al. 2009), Ebos's experiment are performed, whereby anti-murineDEspR Mab is infused daily for 7 doses beginning 7 days prior to cancer cell infusion. 250 ug is used for each antibody-therapeutic given IP 2×/week as described for bevacizumab (Roland et al. 2009), and 3×per week for anti-DEspR (Herrera et al. 2005).

Treatment outcomes are assessed by multifaceted parameters: serial imaging of tumor volume and tumor angiogenesis for orthotopic mammary and subcutaneous pancreatic tumors by, for example, high-resolution Vevo770 ultrasound imaging and power Doppler analysis. Overall survival is determined, and at this endpoint, repeat ultrasound imaging and histological analysis of tumor size and angiogenesis is done, along with histological analysis of malignancy phenotype: nuclear grade, tumor cell invasion of stroma, tumor cell vascular mimicry, loss of integrity of tumor neovessels and macrophage infiltrates.

Heterozygous DEspR+/–mice live beyond 1 year and breed, which is in contrast to VEGF+/–haplodeficiency which is embryonic lethal at E11.5. However, since adverse effects have been observed in patients on anti-VEGF (bevacizumab) and anti-VEGFR2 (sunitinib, sorafanib) therapies, the anti-humanDEspR-specific antibodies described herein are also tested for these effects. Analysis of parameters of potential adverse effects are done in PANC-1 and MDA-MB-231 xenograft models treated with cdHMAb-H1 and mDEspR-Mab. For example, potential a) cardiotoxicity can be monitored by serial non-invasive ultrasound cardiac function analysis; b) hypertension can be monitored by tail cuff BP; c) bowel perforation can be monitored on post-mortem anatomical inspection at endpoint; d) bleeding, thrombosis can be monitored by examination and vascular ultrasound and Doppler flow analysis, and e) toxicity screen can be performed, such as liver function tests, renal function tests, complete blood count, blood chemistries at endpoint of study. These parameters are compared in mock-treated age-matched tumor model controls.

Analysis of Molecular Imaging of Tumor Angiogenesis and Tumor Cell Vascular Mimicry Changes in Response to Therapy by Contrast-enhanced Ultrasound Imaging of DespR-targeted Neovessels Compared with VEGFR2-Targeted Tumor Neovessels Molecular imaging of angiogenesis in tumors has been demonstrated by contrast-enhanced ultrasound imaging using anti-VEGFR2 antibody-directed microbubbles with imaging and contrastenhanced analysis done using the VisualSonics Vevo770 high-resolution ultrasound system (Willmann et al. 2007). We have used this same system to detect anti-DEspR antibody-directed microbubbles in carotid artery disease vasa vasorum angiogenesis in a transgenic rat atherosclerotic model associated with carotid artery disease progression and stroke risk (Decano et al. 2010). As shown in FIGS. 16A-16D, DEspR-targeted molecular imaging (16A) detects DEspR+ endothelial lesions (16B) and vasa asorum angiogenesis (16C). Quantitation of contrast intensity is done using integrated software (16D).

DEspR-targeted molecular imaging is used to test composite deimmunized monoclonal antibodies as the targeting module for molecular imaging applicable to xenograft tumor cell vascular mimicry, and microbubbles are confined to the vascular lumen. MouseDEspR-specific molecular imaging using composite deimmunized monoclonal antibodies as described herein is performed in order to monitor mouse-derived tumor angiogenesis, and is compared to VEGFR2-specific molecular imaging. The observations described herein provide proof that composite deimmunized monoclonal antibodies specific for DEspR can serve as the targeting module for molecular imaging of tumor cell vascular mimicry in a mouse model; that molecular imaging of DEspR expression provides a translatable diagnostic in vivo imaging modality to assess tumor angiogenesis, and that comparative analysis of DEspR-specific molecular imaging provides new insight into the differential contribution of tumor cell vascular mimicry and tumor angiogenesis.

Both MDA-MB-231 xenograft orthotopic and PANC-1 xenograft heterotopic tumor models, as well as a PANC-1 intrasplenic-infusion liver metastasis model are used for molecular imaging experiments. Isotype-antibody molecular imaging is used as a control to demonstrate specificity of DEspR-positive molecular imaging. Identical conditions are followed for anti-DEspR and anti-VEGFR2 molecular imaging in order to validate comparative analysis. For example, a composite deimmunized monoclonal antibody can be used to target tumor cell vascular mimicry; an anti-DEspR composite deimmunized monoclonal antibody can be used to target mouse neovessel formation monoclonal antibody in human xenograft tumors; anti-VEGFR2 can be used as a comparative benchmark, and an isotype antibody can be used as a negative control.

REFERENCES

Baker M P, Jones T D. 2007. Identification and removal of immunogenicity in therapeutic proteins. Curr Opin Drug Disc Dev 10:219-227.

Bergers G, Hanahan D. 2008. Modes of resistance to anti-angiogenic therapy. Nature Reviews—Cancer 8:592-603.

Bocci G, Man S, Green S K, Francia G, Ebos J M, du Manoir J M, Weinerman A, Emmenegger U, Ma L, Thorpe P, Davidoff A, Huber J, Hicklin D J, Kerbel R S., 2004. Increased plasma VEGF as a surrogate marker for optimal therapeutic dosing of VEGF receptor-2 monoclonal antibodies. Cancer Res 64:6616-6625.

Butler J M, Kobayashi H, Rafii S. 2010. Instructive role of the vascular niche in promoting tumor growth and tissue repair by angiogenic factors. Nature Reviews—Cancer 10:138-146.

Carmeliet P. 2005. Angiogenesis in life, disease and medicine. Nature 438:932-936.

Carter P J. 2006. Potent antibody therapeutics by design. Nature Reviews Immunology 6:343-357.

Chester K A, Baker M, Mayer A. 2005. Overcoming the immunologic response to foreign enzymes in cancer therapy. Expert Rev Clin Immunol 1:549-559.

Crawford Y, Ferrara N. 2008. Mouse models to investigate anti-cancer effects of VEGF inhibitors. Methods Enzymol 445:125-139.

Decano J L, Matsubara Y, Moran A M, Ruiz-Opazo N, Herrera V L M. 2010. Dual endothelin-1/VEGFsp receptor (DEspR) roles in adult angiogenesis in despr+/− knockout mice and carotid artery disease rat model. (Manuscript submitted to Circulation.)

Ebos J M, Lee C R, Cruz-Munoz W, Bjarnason G A, Christensen J G, Kerbel R S. 2009. Accelerated metastasis after short-term treatment with a potent inhibitor of tumor angiogenesis. Cancer Cell 15:232-239.

Ferrara N. 2009. Pathways mediating VEGF-independent tumor angiogenesis. Cytokine Growth Factor doi: 10.1016/j.cytogfr.2009.11.003.

Glorioso N, Herrera V L M, Bagamasbad P, Filigheddu F, Troffa C, Argiolas G, Bulla E, Decano J L, Ruiz-Opazo N. 2007. Association of ATP1A1 and Dear SNP-haplotypes with essential hypertension: sex-specific and haplotype-specific effects. Circ Res 100: 1522-1529.

Herrera V L M, Ponce L R, Bagamasbad P D, VanPelt B D, Didishvili T, Ruiz-Opazo N. 2005. Embryonic lethality in Dear gene-deficient mice: new player in angiogenesis. Physiol Genomics 2005; 23:257-268.

Holgate R G E, Baker M P. 2009. Circumventing immunogenicity in the development of therapeutic antibodies. IDrugs 12:233-237.

Imai K, Takaoka A. 2006. Comparing antibody and small-molecule therapies for cancer. Nature Reviews Cancer 6:714-727.

Jubb A M, Oates A J, Holden S, Koeppen H. 2006. Predicting benefit from anti-angiogenic agents in malignancy. Nature Reviews—Cancer 6:626-635.

Loges S, Schmidt T, Carmeliet P. 2010. Mechanisms of resistance to anti-angiogenic therapy and development of third-generation anti-angiogenic drug candidates. Genes & Cancer 1:12-25.

Oh S, Stish B, Sachdev D, Cehn H, Dudek A, Vallera D A. 2009. A novel reduced immunogenicity bispecific targeted toxin simultaneously recognizing human epidermal growth factor and interleukin-4 receptors in a mouse model of metastatic breast carcinoma. Clin Cancer Res 15:6137-6147 (PMCID: PMC2756320 [Available on 2010 Oct. 1).

Paez-Ribes M, Allen E, Hudock J, Takeda T, Okuyama H, Vinals F, Inoue M, Bergers G, Hanahan D, Casanovas O. 2009. Antiangiogenic therapy elicits malignant progression of tumors to increased local invasion and distant metastasis. Cancer Cell 15:220-231.

Roland C L, Dineen S P, Lynn K D, Sullivan L A, Dellinger M T, Sadegh L, Sullivan J P, Shames D S, Brekken R A. 2009 Inhibition of vascular endothelial growth factor reduces angiogenesis and modulates immune cell infiltration of orthotopic breast cancer xenografts. Mol Cancer Ther 8:1761-1771.

Stewart D J, Kutryk M J, Fitchett D, Freeman M, Camack N, Su Y, Della Siega A, Bilodeau L, Burton J R, Proulx G, Radhakrishnan S; NORTHERN Trial Investigators. 2009. VEGF gene therapy fails to improve perfusion of ischemic myocardium in patients with advanced coronary disease: results of the NORTHERN trial. Mol Ther. 17:1109-1115.

Suemizu H, Monnai M, Ohnishi Y, Ito M, Tamaoki N, Nakamura M. 2007. Identification of a key molecular regulator of liver metastasis in human pancreatic carcinoma using a novel quantitative model of metastasis in NOD/SCID/yc null (NOG) mice. Int J Oncology 31:741-751.

Willett C G, Boucher Y, Duda D G, diTomaso E, Munn L, Tong R T, Kozin S V, Petit L, Jain R K, Chung D C, Sahani D V, Kalva S P, Cohen K S, Scadden D T, Fischman A J, Clark J W, Ryan D P, Zhu A X, Blaszkowsky L S, Shellito P C, Mino-Kenudson M, Lauwers G Y. 2005. Surrogate markers for antiangiogenic therapy and doselimiting toxicities for Bevacizumab with radiation and chemotherapy: continued experience of a phase I trial in rectal cancer patients. J Clin Oncol. 23:8136-8139.

Willmann J K, Paulmurugan R, Chen K, Gheysens O, Rodriguez-Porcel M, Lutz A M, Chen I Y, Chen X, Gambhir S. 2008. US imaging of tumor angiogenesis with microbubbles targeted to vascular endothelial growth factor receptor type 2 in mice. Radiology 246:508-518.

Zheng X, Cui X, Huang M T, Liu Y, Shih W J, Lin Y, Lu Y P, Wagner G C, Conney A H. 2008. Inhibitory effect of voluntary running wheel exercise on the growth of human pancreatic PACN-1 and prostate PC-3 xenograft tumors in immuno-deficient mice. Oncology Rep 19:1583-1588 (PMCID: PMC2825748).

Example 2

Molecular Imaging of Vasa Vasorum Neovascularization via DEspR-targeted Contrast-Enhanced Ultrasound Micro-Imaging in Transgenic Atherosclerosis Rat Model Given that carotid vasa vasorum neovascularization is associated with increased risk for stroke and cardiac events, the in vivo study described herein was designed to investigate molecular imaging of carotid artery vasa vasorum neovascularization via target-specific contrast-enhanced ultrasound (CEU) micro-imaging. Accordingly, molecular imaging was performed in male transgenic rats with carotid artery disease (CAD) and non-transgenic controls using DEspR (dual endothelinl/VEGFsp receptor)-targeted microbubbles ($MB_D$) and the Vevo770 micro-imaging system and CEU-imaging software.

It was found that DEspR-targeted CEU-positive imaging exhibited significantly higher contrast intensity signal (CIS)-levels and pre-/post-destruction CIS-differences in 7/13 transgenic rats, in contrast to significantly lower CIS-levels and differences in control isotype-targeted microbubble ($MB_S$)-CEU imaging (n=8) and in $MB_D$ CEU-imaging of 5/5 non-transgenic control rats (P<0.0001). Ex vivo immunofluorescence analysis demonstrated binding of $MB_D$ to DEspR-positive endothelial cells, and association of DEspR-targeted increased contrast intensity signals with DEspR expression in vasa vasorum neovessel and intimal lesions. In vitro analysis demonstrated dose-dependent binding of $MB_D$ to DEspR-positive human endothelial cells with increasing %cells bound and number of $MB_D$ per cell, in contrast to $MB_S$ or non-labeled microbubbles (P<0.0001).

The dual endothelin-1 (ET1)/vascular endothelial growth factor-signal peptide (VEGFsp) receptor or DEspR (formerly dear gene as deposited in GenBank) [1] plays a key role in developmental angiogenesis deduced from the embryonic lethal phenotype exhibited by despr$^{-/-}$ knockout mice due to absent embryonic and extraembryonic angiogenesis, aborted dorsal aorta vasculogenesis, and abnormal cardiac development [2]. While exhibiting similar abnormal vasculogenesis and angiogenesis phenotypes with VEGF$^{+/-}$ haploinsufficient mice, despr$^{-/-}$ null mice exhibit distinct neural tube phenotypes [2-4]. Consistent with its role in developmental angiogenesis, DEspR inhibition results in decreased tumor angiogenesis and tumor growth in adult rat mammary tumors and mouse melanomas [2].

Development of target-specific contrast enhanced ultrasonography (CEU)-imaging, herein referred to as "molecular imaging" of vascular disease neovascularization is important since carotid artery vasa vasorum neovascularization is associated with increased risk for stroke [5,6]. However, successful molecular imaging of vasa vasorum neovessels has not been reported, although detection by non-targeted CEU-imaging has [7]. On the other hand, successful molecular imaging in different disease models detecting different targets [8,9] has shown the potential of molecular imaging in different disease contexts, such as αvβ3 in tumor and hind limb ischemia angiogenesis [10,11], VEGFR2 in tumor angiogenesis [12], ICAM-1 in transplant rejection [13], L-selectin in malignant lymphnodes [14], and ICAM-1 and VCAM-1 in atherosclerosis [15], P-selectin in myocardial ischemia [16,17], GIIb/IIIa and fibrinogen in thrombosis [18,19]. Molecular imaging of vascular disease neovascularization in studies targeting VEGFR2-, ICAM-1 and VCAM-1 did not detect vasa vasorum neovessels in a hyperlipidemic rabbit model of injury-induced vascular neovascularization[9,20].

Demonstrated herein is molecular imaging of DEspR in carotid artery lesions and expanded vasa vasorum neovessels in transgenic-hyperlipidemic, hypertensive carotid artery disease rat model.

Materials and Methods

Animals. In order to facilitate molecular imaging studies of pathological angiogenesis in vascular lesions or in expanded vasa vasorum neovessels, a carotid artery disease rat model with hypertension-atherosclerosis as risk factors, the Tg25[hCETP] Dahl-S rat model, Tg25, transgenic for human cholesteryl ester transfer protein which develops accelerated stroke [21] or later-onset coronary heart disease, was selected [22]. 4-month old transgenic male rats (n=13) projected to be around early-midpoint along the disease course of stroke [21] or coronary atherosclerosis phenotype [22], were studied for DEspR-targeted molecular imaging (n=13). $MB_D$-infused non-transgenic, non-atherosclerotic littermates were studied as negative biological controls (n=5). Isotype-specific $MB_C$-infused transgenic rats (n=8), with the following subgroups: 4 transgenic rats which exhibited $MB_D$-specific CEU-positive imaging, and 4 de novo transgenic rats, were studied concurrently as negative imaging controls.

Target-specific CEU-molecular imaging. The Vevo770 high resolution ultrasound system with contrast mode software, and streptavidin-coated "target ready" MicroMarker microbubbles (VisualSonics Inc, Canada) previously validated for molecular imaging of VEGFR2 on tumor angiogenesis in mice was used [12]. To target the microbubble to rat DEspR-positive endothelial cells, target ready-MicroMarker microbubbles were linked to biotinylated anti-DEspR antibody ($MB_D$) via streptavidin-biotin coupling. For control, target ready-MicroMarker microbubbles were linked to biotinylated, isotype-antibody ($MB_C$). Each bolus comprised of 3-4×10$^8$ microbubbles in 200-microliters saline, infused into the rat tail vein over 8-seconds.

CEU-imaging of rat carotid arteries comprised a sequence of steps aimed at optimizing MB-target binding, eliminating confounders, and ascertaining reproducible CEU-imaging. Baseline images of the carotid artery were first obtained and immobilized the scanhead to maintain the optimal B-mode view of the common, external, and internal carotid arteries in one 2D image. One minute after MB bolus infusion, the MB blood pool was documented by B-mode imaging for all rats to ascertain MB infusion and to demonstrate absence of contrast intensity in surrounding tissue. A wait of 4-5 minutes was taken to allow $MB_D$ adherence to DEspR-positive endothelial targets [12], and to allow clearance of unbound circulating microbubbles [23]. Clearance of most circulating MBs facilitates detection of increased contrast intensity signals due to adherent MBs validated for detection using the Vevo770 imaging system [23]. Adherent MBs were defined by the loss of contrast-intensity upon acoustic destruction performed using pre-set Contrast Enhanced software (VisualSonics, Inc, Canada) as described [12].

Four regions of interest (ROI) on the carotid artery were monitores: the common carotid artery, bifurcation, external and internal carotid arteries. Quantitation of contrast intensity signals (CIS) resulting from backscatter of adherent targeted-microbubbles was done using contrast-enhanced analysis program validated for the Vevo770 imaging platform (VisualSonics Inc, Canada) detecting pre- and post-acoustic disruption contrast intensity signals. The contralateral carotid artery was checked immediately, and the same CEU-imaging protocol followed. After a 20-minute interval to allow complete clearance of any residual MBs, a pre-set destruction sequence was performed for subsequent CEU-imaging with isotype-specific $MB_C$s following identical procedures. For quantitative comparative analyses, the difference in contrast intensity signals between pre- and post-acoustic destruction, CIS-difference, as well as their respective pre-destruction CIS-peak levels were studied for each carotid artery per rat.

Histology and Immunofluorescence Staining of Rat Carotid Arteries. After CEU-imaging, carotid arteries were collected en bloc preserving the surrounding tissue around the common (CCA), external (ECA) and internal (ICA) carotid arteries including the carotid artery bifurcation. The ECA was cut longer than the ICA to be able to distinguish the two. Longitudinal serial sections were obtained per carotid artery (50-100 sections) and staining every 10th slide with Masson-trichrome allowed proper orientation and site-specific analyses corresponding to ROIs in CEU-imaging. The flanking serial sections to MT-stained slides of interest were then immunostained. Double immunofluorescence staining was done on deparaffinized sections via sequential antigen retrieval, treatment to reduce background, blocking, incubation with primary antibody at 4° C. overnight, secondary antibody incubation overnight at 4° C. with AlexaFluor 568 goat anti-mouse IgG and AlexaFluor 488 goat anti-rabbit IgG, washing, and mounting using Prolong Gold with DAPI (Invitrogen, CA). Negative controls were run using rabbit-isotype antibody for anti-rat DEspR antibody. A Zeiss Axioskop2plus microscope was used for fluorescence imaging and differential interference contrast (DIC) photomicroscopy to provide morphological information overlay to immunostained sections. Low 2.5× magnification was used for proper orientation and site-specific identification along the carotid artery.

In vitro analysis of $MB_D$ and DEspR positiveendothelial cell interactions Human-specific DEspR-targeted $MB_D$s were made following identical procedures for rat-specific DEspR molecular imaging with the exception of the use of an anti-humanDEspR monoclonal antibody. Fixed numbers of human umbilical vein endothelial cells (HUVECs) were seeded onto IBIDI perfusion 6-lane μ-slide VI (ibidiGmbH, Germany). After 24 hours, $MB_D$-type microbubbles were infused at the following MB-cell ratios: 8×, 80×, and 800×. Negative controls comprised of 800× $MB_C$s and 800× non-targeted microbubbles, $MB_O$s. These were all infused at 20 dynes/cm² shear stress 1-way flow on the same 6-lane micro-flow chamber slide. After 45 minutes of incubation, DAPI nuclear staining was performed and excess MBs were washed with HUVECs media at same shear stress. Phase contrast and epifluorescence microscopy was performed in 6 random high power fields. Cells and microbubbles were documented by photomicroscopy and counted as to per cent cells with bound MB, and number of MBs per cell. We compared $MB_D$, $MB_C$ and non-targeted microbubbles $MB_O$.

Statistical analysis. Values are expressed as mean±S.E.M. Data were analyzed with Prism 5 statistics software (GraphPad Software Inc, CA). Where applicable, nonparametric ANOVA and Dunn's multiple comparison tests or ANOVA and Tukey's multiple pairwise comparison tests were used. For two group comparison, nonparametric Kruskal Wallis test was performed using Prism5 (GraphPad Software Inc, CA).

Results

DEspR-targeted Molecular Imaging of Carotid Artery. Given the need for detecting vascular disease-associated angiogenesis in carotid artery disease [5,6], DEspR was tested to determine whether it can serve as an endothelial target for contrast enhanced ultrasonographic (CEU)-imaging of pathological angiogenesis in carotid artery disease lesions or vasa vasorum neovascularization. The Tg25 rat model of carotid artery disease was used, comparing 4-month old male Tg25 rats projected to be at midpoint of atherosclerotic disease course [21, 22], with age-matched non-transgenic male littermates. Compared to coronary artery disease, investigation of carotid artery disease provides a tactical experimental system with less movement artifacts.

Figure 19C:
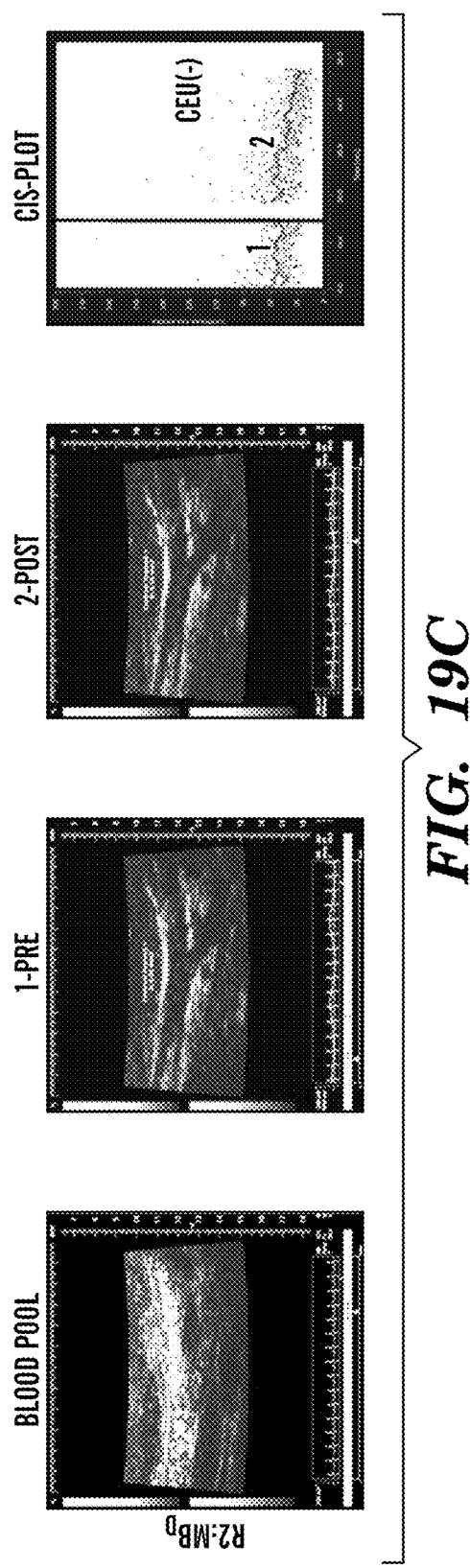

Using the Vevo770 ultrasound contrast-enhanced imaging system and DEspR-targeted microbubbles ($MB_D$) compared with control isotype-microbubbles ($MB_C$), $MB_D$-specific CEU-positive imaging was detected in different regions-of-interest (ROI) along the common carotid artery (CCA), carotid artery bifurcation, proximal internal and/or external carotid arteries in 7/13 transgenic rats. $MB_D$-specific CEU-positive imaging was defined as stably increased contrast intensity signals detected after circulating microbubbles have cleared, and which decreased upon acoustic destruction (FIG. 19A). The peak pre-destruction contrast intensity signals and the differences in pre-/post-destruction contrast intensity signals (CIS-differences) were significantly higher in $MB_D$-specific CEU-positive images (FIG. 19A, Table 2) compared with CEU-imaging observed in isotype $MB_C$-infused rats (FIG. 19B) and in $MB_D$-infused non-transgenic control rats (n=5), with the latter two empirically defining CEU-negative imaging. Notably, of the 7 transgenic rats exhibiting $MB_D$-specific CEU-positive imaging, four exhibited CEU-positive imaging in both carotid arteries, while three exhibited CEU-negative imaging on the contra-lateral carotid artery, suggesting selectivity of $MB_D$-specific CEU-positive imaging and concordant with specificity (Table 2). Moreover, six transgenic rats exhibited CEU-negative imaging with low peak contrast intensity signals, "flat-line" pre-/post-destruction CIS-plot pattern, and minimal CIS-differences (FIGS. 19D, 19E, Table 2) similar to CEU-negative imaging observed in $MB_C$-control rats (FIG. 19B) and in $MB_D$-infused non-transgenic controls (FIG. 19C).

Figure 19E:
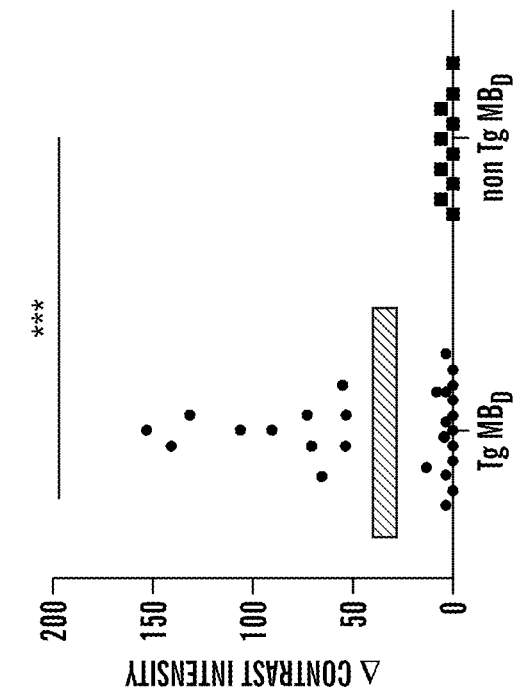
Figure 19D:
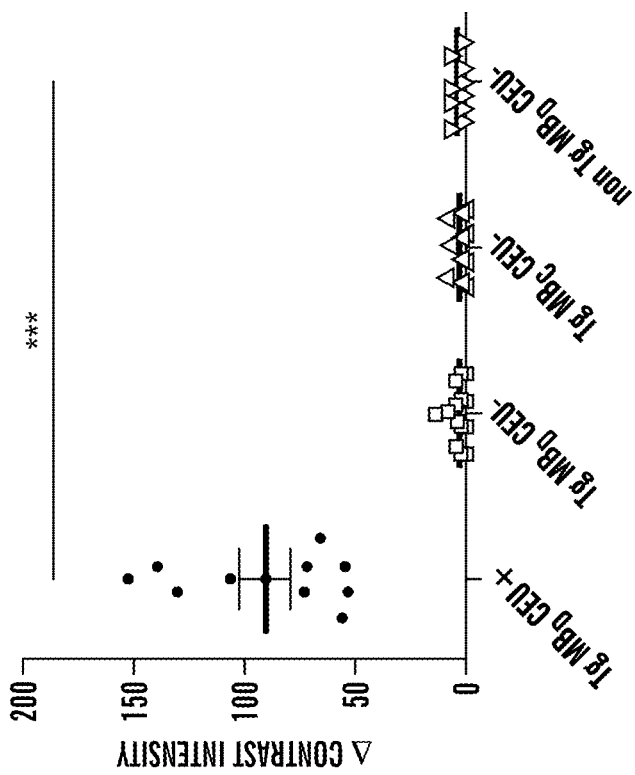

Altogether, these observations provide compelling evidence that $MB_D$-based CEU-positive images are specific and due to adherent $MB_D$s in said carotid arteries. Statistical analysis by one way analysis of variance (ANOVA) and post-hoc multiple comparison testing establish that the CIS-differences of $MB_D$-specific CEU-positive imaging are significantly higher, P<0.0001, compared to each CEU-negative imaging study group, respectively (Table 2, FIG. 19D). Interestingly, since CEU-positive imaging is detected only in transgenic rats, and with 54% of transgenic rats exhibiting $MB_D$-specific CEU-positive imaging at 4 months of age equivalent to an early-midpoint of the typical model disease course in males [21, 22], average CIS-differences are significantly different (P<0.0001) between transgenic rats and their non-transgenic controls (FIG. 19E). With 7/13 transgenic rats exhibiting CEU-positive imaging, and 6/13 exhibiting CEU-negative imaging upon $MB_D$ infusion, a sub-grouping of transgenic rats based on $MB_D$ CEU-imaging CIS-differences at the 4-month midpoint of the disease course is apparent (FIG. 19E).

Interestingly, the CIS-plots of three transgenic rats with the highest $MB_D$-specific CIS-differences exhibited the expected post-acoustic destruction drop in signal intensity but had secondary peaks of contrast intensity signals followed subsequently by decline to low/baseline levels (FIGS. 20A-20H). This post-acoustic destruction/disruption pattern is consistent with a particular sequence of microbubble events: microbubble fragmentation accounting for the drop, residual microbubble acoustic stimulation accounting for the secondary peak, followed by acoustically driven diffusion accounting for the subsequent steady decline to baseline levels.

Figure 21A:
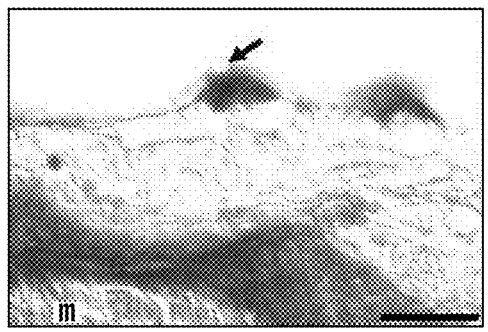
FIGS. 21A-21H depict representative histological and fluorescence immunostaining analysis of carotid arteries with DEspR-positive molecular imaging corresponding to rat-R1 (panels 21A-21D), and rat-R3 in (panels 21E-21H).
Figure 21B:
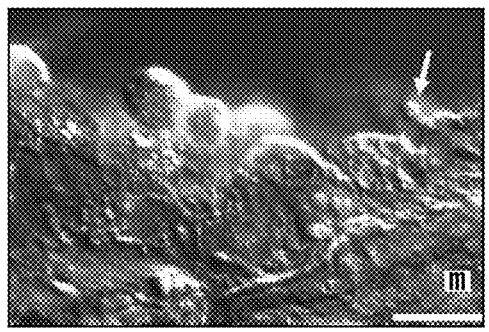
Figure 21C:
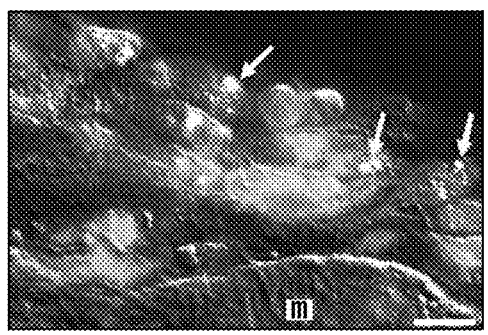
Figure 21D:
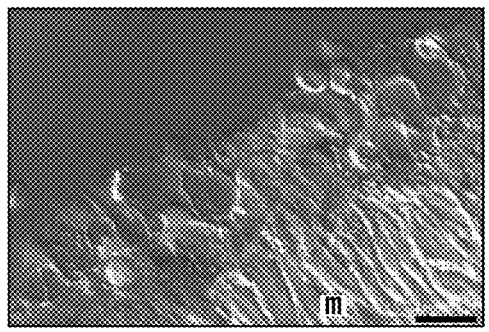

Histological analysis detects $MB_D$-microbubbles on DEspR-positive endothelial cells. Unexpectedly, Masson-trichrome stained histological analysis detected a few microbubbles still attached to endothelial cells or within intimal lesions (FIG. 21A) obtained from R1:$MB_D$ rat with CEU-positive imaging shown. Corresponding DEspR-immunostaining on the adjacent serial section confirmed adherence of $MB_D$-microbubbles to DEspR-positive endothelial cells (FIGS. 21B, 21C). Immunostaining with isotype antibody confirms specificity of DEspR-positive immunostaining (FIG. 21D). Altogether, these observations corroborate $MB_D$-binding and specificity of $MB_D$-binding to DEspR-positive endothelium. Survival of PEG-coated Target-ready MicroMarker microbubbles (VisualSonics, Inc., Canada) through PBS-buffered 4% paraformaldehyde fixation, paraffin embedding and deparaffinization parallels our observation that PEG-based biomaterials survive fixation, paraffin embedding, deparaffinization and Masson trichrome staining [24].

Figure 20A:
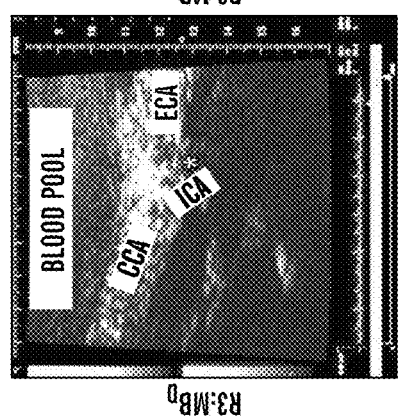
Figure 20B:
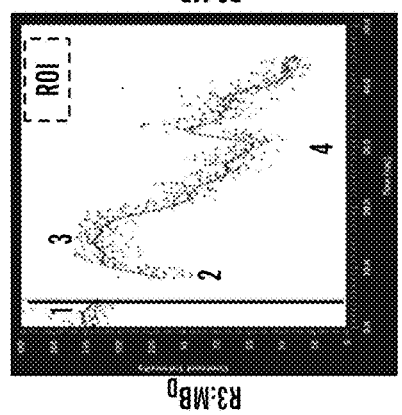
Figure 20C:
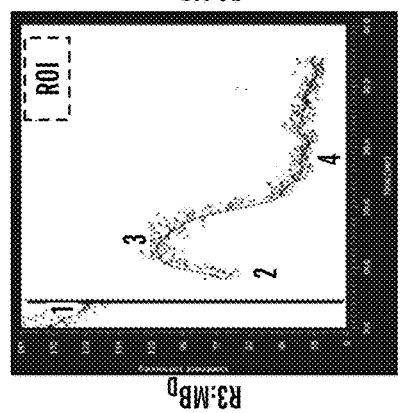
Figure 20D:
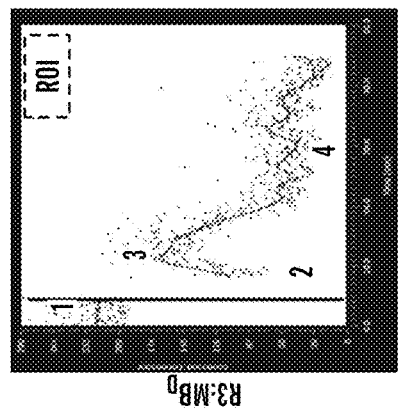
Figure 20E:
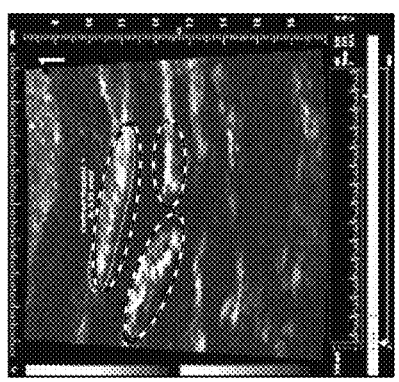
FIG. 20E shows a graph of CIS-difference between all transgenic rats (Tg+) and non-transgenic rats (nonTg). Hatched bar represents a threshold between $MB_D$-infused CEU+ and $MB_D$-infused CEU-transgenic rats. Blood pool, CEU-image 1 minute after bolus injection of MBs, demonstrating equivalent MB-infusion among different rats and minimal contrast-intensity signals from movement artifacts. 1-Pre, pre-acoustic destruction CEU-images obtained 4-minutes after bolus infusion, in order to allow MB-adherence to target, if any, and to document minimal, if any, circulating MBs in the lumen. Image corresponds to #1 on CIS-plot. 2-Post, CEU-image after acoustic destruction corresponding to #2 on scatter plot. CIS-plot, scatter plot of contrast-intensity signals (CIS) in representative regions of interest (encircled in aqua). #1, CIS detected pre-acoustic destruction; #2, CIS detected post-acoustic destruction (2). Black line and following gap mark period of acoustic destruction in CIS-scatter plots. $MB_D$, DEspR-targeted microbubble; $MB_C$, control isotype-targeted microbubble; Tg, transgenic rat; nonTg, nontransgenic control rat; CEU+, CEU positive imaging; CEU−, CEU negative imaging, $\Delta$ Contrast Intensity, pre-/post-destruction CIS-difference; ***, P<0.0001.
Figure 20F:
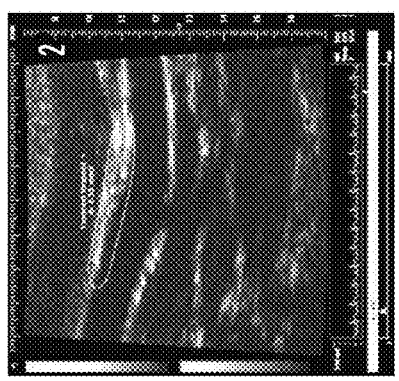
Figure 20G:
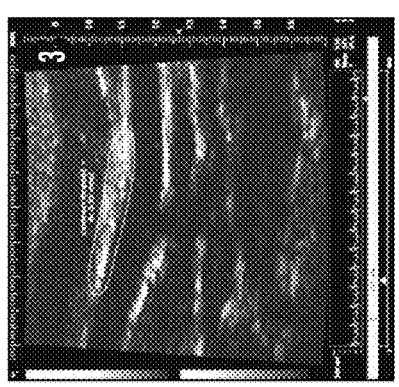
Figure 20H:
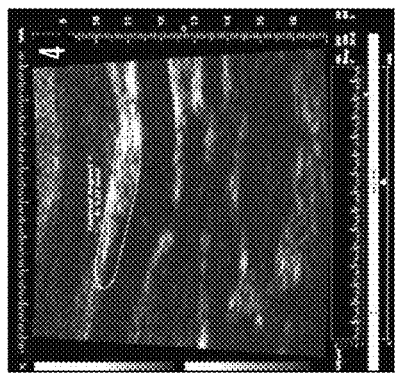
Figure 21E:
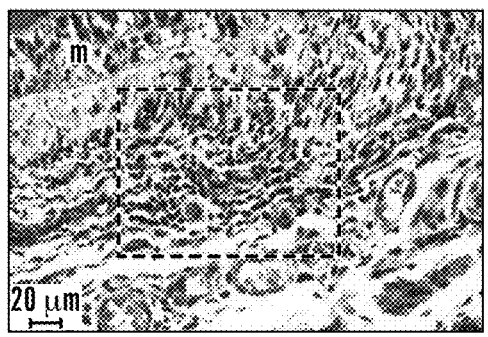
Figure 21F:
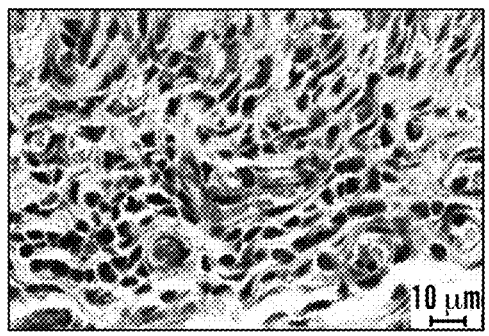
Figure 21G:
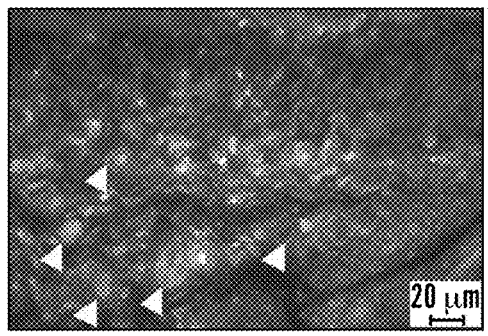
Figure 21H:
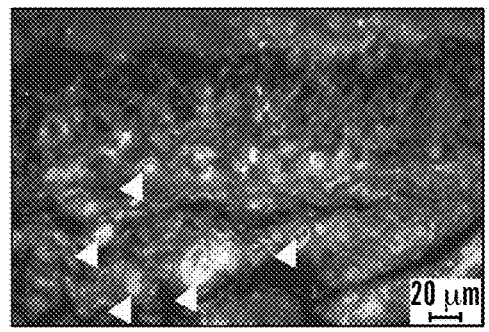

Histological analysis of R3:$MB_D$ rat shown in FIGS. 20A-20H also detected increased endothelial DEspR-positive expression and luminal endothelial pathology, as well as marked carotid vasa vasoral expansion by neovascularization (FIG. 21E, 21F) with DEspR-positive expression in vasa vasorum neovessel (FIG. 21G). Double-immunofluorescence immunostaining with DEspR and α-smooth muscle actin (αSMA) detected some co-localization of DEspR+ αSMA-positive immunostaining in carotid artery vasa vasorum (FIG. 21H).

Figure 22A:
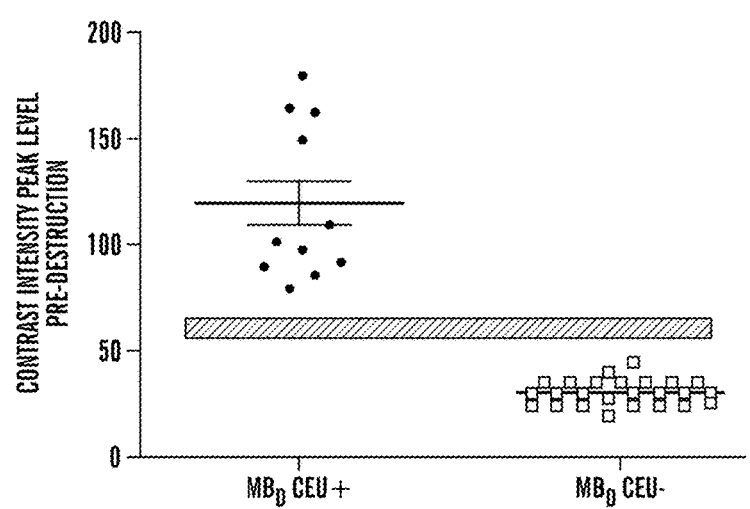
FIGS. 22A-22E depict representative fluorescence immunostaining analysis of carotid arteries from rats exhibiting $MB_D$-specific CEU-positive imaging (22B, 22C) and CEU-negative imaging (22D, 22E).
Figure 22B:
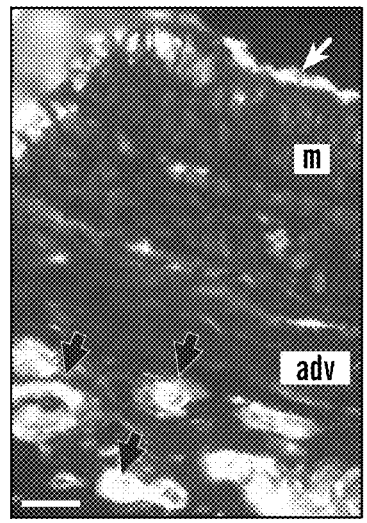
Figure 22D:
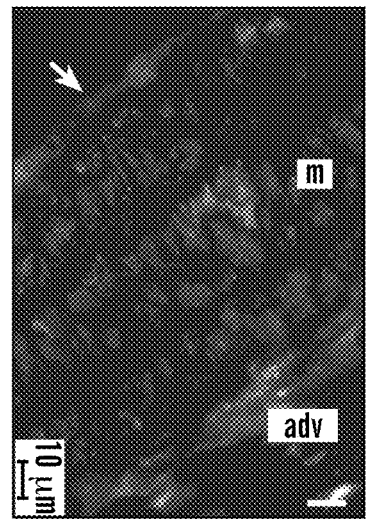
Figure 22C:
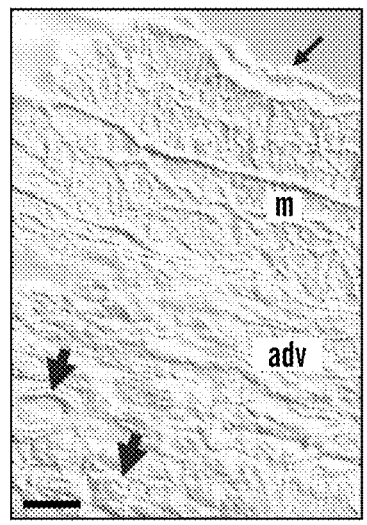
Figure 22E:
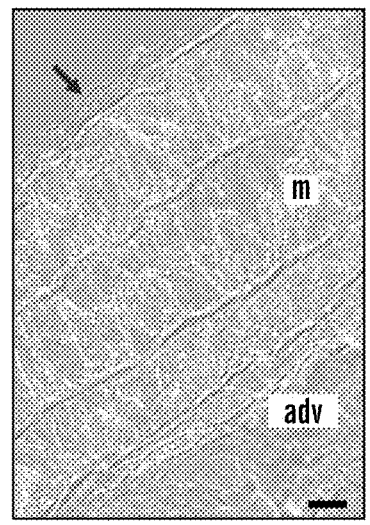

Increased DESPR-expression is associated with DEspR positivemolecular imaging. To determine whether increased level and/or area of DEspR-expression is associated with $MB_D$-specific CEU-positive imaging defined by higher CIS-differences (FIG. 19D) and higher pre-destruction CIS-peak levels (FIG. 22A), double immunofluorescence-staining was performed with anti-DEspR and anti-α-smooth muscle alpha actin (αSMA) antibodies, the latter serving as a positive control for immunostaining of vascular smooth muscle cells in the media. Serial sections from representative rats were analyzed (n=3/group) with $MB_D$-specific bilateral CEU-positive imaging, $MB_D$-infused bilateral CEU-negative imaging, and with one-sided CEU-positive/CEU-negative imaging. Analysis of immunofluorescence and differential-interference contrast (DIC)-microscopy showed that $MB_D$-specific CEU-positive imaging is associated with DEspR+ expression in carotid intimal lesions, vasa vasorum neovascularization and DEspR+ expression in vasa vasorum neovessels (FIGS. 21B, 21C, 22B, 22C, Table 2). In contrast, rat carotid arteries exhibiting $MB_D$-CEU-negative molecular imaging were associated with minimal, if any, DEspR+ endothelial expression (FIG. 22D, Table 2). Low levels of αSMA expression in carotid media smooth muscle cells (SMCs) compared with the expanded vasa vasorum were also noted (FIG. 22A), due, without wishing to be bound or limited by a theory, most likely to the synthetic state of SMCs in these hypertensive rats, since αSMA expression is deinduced in synthetic or proliferating SMCs [25]. These observations link $MB_D$-specific CEU-positive imaging in this rat model with increased DEspR expression intensity and area in both intimal lesions and vasa vasorum neovessel density.

Figure 23C:
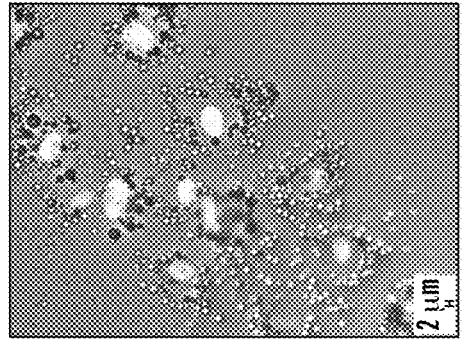
FIGS. 23A-23G depicts phase contrast-fluorescence microscopy analysis of anti-humanDEspR-targeted microbubbles ($MB_D$) binding to human endothelial cells, HUVECs, in vitro. Increasing DEspR-targeted microbubbles ($MB_D$) to cell ratio (23A) 8×, (23B) 80×, and (23C) 800×. (23D) Isotype control ($MB_C$) at 800×; (23E) non-targeted control $MB_O$ at 800×. (23F) % of HUVECs with bound MBs (■) and no MB binding (□).
Figure 23B:
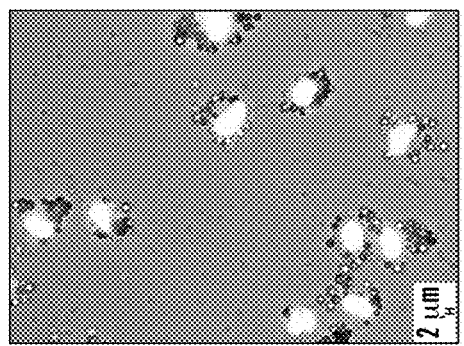
Figure 23A:
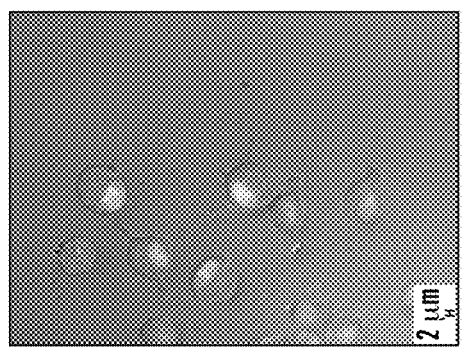
Figure 23E:
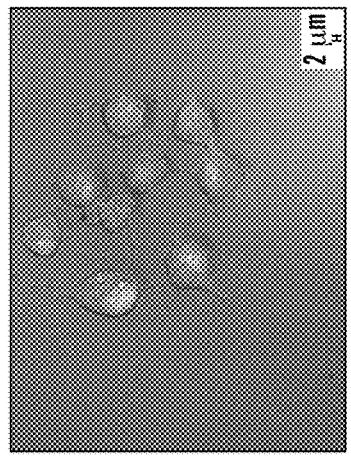
Figure 23D:
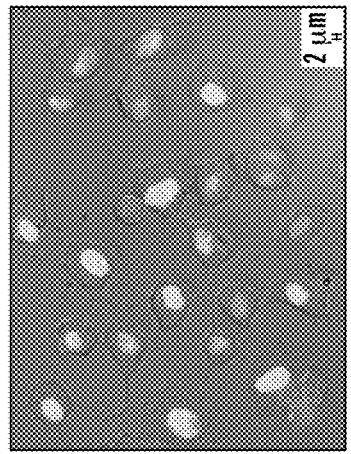
Figure 23G:
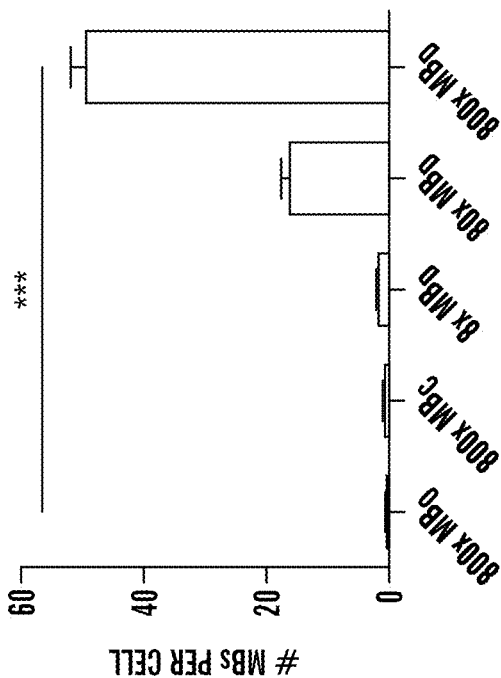
Figure 23F:
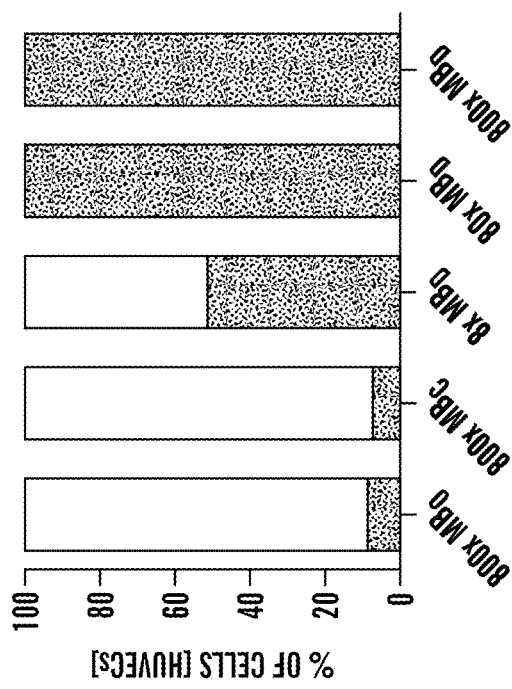

In vitro analysis of dose-response $MB_D$-adherence to DEspR positiveendothelial cells. In order to further dissect $MB_D$ interactions with DEspR-positive cells, the dose-response of $MB_D$ adherence in vitro was tested. In order to avail of standardized primary cultures of endothelial cells and to gain translational insight into molecular imaging in humans, human umbilical vein endothelial cells (HUVECs) which express DEspR in proliferating and pro-angiogenesis culture conditions as detected by a human-specific anti-DEspR monoclonal antibody were used. Using increasing number of $MB_D$s from 8x, 80x, and 800x$MB_D$ to cell ratio, it was observed that HUVECs are increasingly bound by $MB_D$s being 100% bound at 80x $MB_D$:cell ratio (FIGS. 23A-23C), in contrast to 800x $MB_C$s (FIG. 23D) and non-targeted $MB_O$s (FIG. 23E) which bound 6.8% and 8.2% of HUVECs respectively (FIG. 23F). Moreover, analysis of number of MBs bound per cell after a 45-minute incubation and wash at flow rates with aortic-like shear stress of >20dyne/cm$^2$ revealed significant differences in number of MBs bound per cell increasing from 8x, 80x to 800x as follows: 2.3, 17 and 49 MBs/cell, with only 0.6 and 1.1 MB/cell for non-targeted MBs and isotype $MB_C$s (ANOVA P<0.0001). These observations reflect the relative stability and specificity of the MB-cell interaction. Importantly, cell toxicity was not observed upon contact of MB with cells even at high-dose 800x $MB_D$.

Although VEGFR2-targeted molecular imaging of tumor angiogenesis has been reported [12], previous VEGFR2-targeted molecular imaging of vasa vasorum neovascularization was not successful, along with other vascular adhesion molecule targets, leading authors of these reports to suggest that vasa vasoral flow might be a technical hurdle for target-specific CEU-molecular imaging [9]. Accordingly, the molecular imaging of DEspR-positive endothelial cells in carotid artery disease demonstrated herein (FIGS. 19A-22E) provide novel research and diagnostic tools for in vivo molecular imaging of carotid artery disease endothelium and expanded vasa vasorum. Without wishing to be bound or limited by theory, given optimal ultrasound imaging parameters, the likely factors for differential success in target-specific CEU-molecular imaging could be differences in molecular thresholds defined by the level and/or area of expression of the target, and/or in technical thresholds defined by density and size of, as well as flow in target vessel(s). These thresholds must be surpassed concurrently for detectable targeted CEU-positive imaging or molecular imaging. More specifically, the level of DEspR expression, the degree of luminal endothelial pathology, and the density of vasa vasorum neovascularization, along with the larger size of the rat carotid artery disease model used here, comprise factors contributing to successful DEspR-targeted CEU-positive imaging of carotid artery vasa vasorum in the Tg25 rat model of carotid artery disease, in contrast to the negative molecular imaging results targeting VEGFR2 reported for vasa vasorum neovascularization in a carotid artery injury-induced mouse model [9]. Furthermore, differences between CEU-positive transgenic rats from CEU-negative transgenic rats reveal a putative threshold for CIS-differences (FIG. 19E) and pre-disruption CIS-peak levels (FIG. 22A). This observed threshold for CEU-positive imaging provides evidence that DEspR-targeted CEU-positive imaging can be a non-invasive biomarker for pathological angiogenesis, and have predictive value for disease progression.

Surpassing the molecular and technical threshold for successful detection of target-specific molecular imaging is concordant with the principle that reflectivity is directly proportional to the concentration of the microbubbles themselves [26]. More specifically, greater DEspR-expression and greater density of DEspR-positive endothelial cells, be it at the lumen or in vasa vasorum, can translate to greater concentration of bound microbubbles in the methods described herein. This in turn, without wishing to be bound or limited by theory, is expected to translate to greater reflectivity and detection levels since microbubble-cell binding does not dampen microbubble reflectivity in contrast to leukocyte engulfment of microbubble [27]. After clearance of most circulating microbubbles and prior to acoustic disruption, stable binding of target-specific microbubbles exhibits a relatively stable contrast-intensity level that is significantly greater than negative or background contrast-intensity (FIG. 20d, ANOVA P<0.0001) . Since high-frequency imaging can induce microbubble fragmentation or gas diffusion per se, a slight decline could also be observed prior to acoustic disruption, without wishing to be bound or limited by theory. However, upon acoustic disruption a drop in contrast-intensity due to fragmentation is observed to confirm microbubble binding (FIGS. 19A-19E). Acoustic fragmentation may not be complete due, without wishing to be bound or limited by theory, to microbubble interaction in high-density ROIs which could dampen microbubble resonance [28], or from inability of microbubbles within microvessels to reach 10-fold diameter-fluctuation that underlies acoustic fragmentation [29]. Furthermore, incomplete fragmentation with gas release and relatively low flow, as would be expected in vasa vasorum compared to carotid artery lumen, without wishing to be bound or limited by theory, could account for the secondary peak observed in rat-R3 followed by slow decline back to baseline levels. The secondary peak is likely not due to refill because at this experimental time point there is minimal, if any, circulating microbubbles (FIGS. 19A-19E, 20A-20H). The fact that rat-R3 reached higher contrast-intensity levels than rat-R1 suggests greater microbubble concentration, which can also dampen acoustic destruction due to inter-microbubble interactions [28]. Notably, while acoustic fragmentation corroborates microbubble binding, the pattern of acoustic fragmentation or diffusion can also provide further insight into microbubble concentration, as well as binding site vessel-caliber and flow. This provides a novel, alternative molecular imaging paradigm to that reported for mouse aortic root atherosclerosis [30]. While CEU-imaging in the current set-up is successful, in other embodiments, non-linear imaging of adherent microbubbles can be used to provide greater sensitivity and/or improved quantitation as observed for intravascular ultrasound for vasa vasorum flow imaging [31].

The detection of dose-dependent increase in % cells targeted by $MB_D$s and dose-dependent increase in number of MBs per cell (FIGS. 23A-23G), gives insight into the stable interaction, kinetics, specificity and non-toxicity of DEspR-targeted MB-cell interactions. More importantly, given that in vitro studies were performed using human endothelial cells and human-specific anti-DEspR monoclonal antibody for targeting, that MB-cell coupling withstood a high shear stress wash after 45 minutes and did not elicit cell toxicity on contact, these in vitro observations of $MB_D$-cell interactions demonstrate DEspR-targeted molecular imaging of pathological angiogenesis as a useful therapeutic and diagnostic tool.

Altogether, comparative analysis of molecular imaging contrast-intensity levels, histological confirmation of microbubble-to-endothelium binding, immunostaining confirmation that DEspR-positive molecular imaging is associated with DEspR-positive endothelial cell expression, and concordant patterns of bound microbubble behavior after acoustic destruction, demonstrate that target-specific molecular imaging of carotid endothelium and vasa vasorum neovascularization in carotid artery disease rat model is feasible using the methods and reagents described herein that target DEspR. The identification of DEspR as a successful target for in vivo molecular imaging of vasa vasorum neovascularization and carotid artery disease lesions can facilitate the longitudinal study of vasa vasorum neovascularization and endothelial changes in carotid artery disease progression in animal models. Along with the in vitro observations of $MB_D$-HUVECs stable binding, the data demonstrate the use of molecular imaging techniques described herein in the earlier detection of pathophysiological changes in cardiovascular disease for estimations of risk for disease progression and complications.

REFERNCES

1. Ruiz-Opazo, N.; Hirayama, K.; Akimoto, K.; Herrera, V. L M. Molecular characterization of a dual endothelin-1/angiotensin II receptor. Mol. Med. 4:96-108, 1998.

2. Herrera, V. L. M.; Ponce, L. R. B.; Bagamasbad, P. D.; VanPelt, B. D.; Didishvili, T.; Ruiz-Opazo, N. Embryonic lethality in Dear gene-deficient mice: new player in angiogenesis. Physiol. Genomics. 23:257-268, 2005.

3. Ferrara, N.; Carver-Moore, K.; Chen, H.; et al. Heterozygous embryonic lethality induced by targeted inactivation of the VEGF gene. Nature. 380:439-442, 1996.

4. Carmeliet, P,; Ferreira, V.; Breir, G.; et al. Abnormal blood vessel development and lethality in embryos lacking a single VEGF allele. Nature. 380:435-439, 1996.

5. Dunmore, B. J.; McCarthy, M. J.; Naylor, A. R.; Brindle, N.P. Carotid plaque instability and ischemic symptoms are linked to immaturity of microvessels within plaques. J. Vasc. Surg. 45:155-159, 2007.

6. Giannoni, M. F.; Vicenzini, E.; Citone, M.; et al. Contrast carotid ultrasound for the detection of unstable plaques with neoangiogenesis: a pilot study. Eur. J. Vasc. Endovasc. Surg. 2009;doi: 10.10.16/j.ejvs.2008.12.028.

7. Vincenzini, E.; Giannoni, M. F.; Benedetti-Valentini, F.; Lenzi, G.L. Imaging of carotid plaque angiogenesis. Cerbrovasc. Dis. 27(Supp12):48-54, 2009.

8. Kaufmann, B. A.; Lindner, J. R. Molecular imaging with targeted contrast ultrasound. Current Opinion in Biotech. 18:11-16, 2007.

9. Lindner, J. R. Molecular imaging of cardiovascular disease with contrast-enhanced ultrasonography. Nat. Rev. Cardiol. 6:475-481, 2009.

10. Ellegala, D. B.; Leong-Poi, H.; Carpenter, J. E. et al. Imaging tumor angiogenesis with contrast ultrasound and microbubbles targeted to alpha(v)beta3. Circulation. 108: 336-341, 2003.

11. Leong-Poi, H.; Christiansen, J.; Heppner, P.; et al. Assessment of endogenous and therapeutic arteriogenesis by contrast ultrasound molecular imaging of integrin expression. Circulation. 111:3248-3254, 2005.

12. Willmann, J. H.; Paulmurugan, R.; Chen, K.; et al. US imaging of tumor angiogenesis with microbubbles targeted to vascular endothelial growth factor receptor type 2 in mice. Radiology. 246:508-518, 2008.

13. Weller, G. E.; Lu, E.; Csikari, M. M.; et al. Ultrasound imaging of acute cardiac transplant rejection with microbubbles targeted to intercellular adhesion molecule-1. Circulation. 108:218-224, 2003.

14. Hauff, P.; Reinhardt, M.; Briel, A.; Debus, N.; Schirner, M. Molecular targeting of lymph nodes with L-selectin ligand-specific US contrast agent: a feasibility study in mice and dogs. Radiology. 231:667-673, 2004.

15. Kaufmann, B. A.; Sanders, J. M.; Davis, C. et al. Molecular imaging of inflammation in atherosclerosis with targeted ultrasound detection of vascular cell adhesion molecule-1. Circulation. 116:276-284, 2007.

16. Christiansen, J. P.; Leong-Poi, H.; Klibanov, A. L.; Kaul, S.; Lindner, J. R. Noninvasive imaging of myocardial reperfusion injury using leukocyte-targeted contrast echocardiography. Circulation. 105:1764-1767, 2002.

17. Villanueva, F. S.; Wagner, W. R. Ultrasound molecular imaging of cardiovascular disease. Nat. Clin. Pract. Cardiovasc. Med. 5:S26-S32, 2008.

18. Schumann, P. A.; Christiansen, J. P.; Quigley, R. M. al. Targeted-microbubble binding selectively to GPIIb/IIIa receptors of platelet thrombi. Invest. Radiol. 37:587-593, 2002.

19. Hamilton, A.; Huang, S. L.; Warninck, D. et al. Left ventricular thrombus enhancement after intravenous injection of echogenic immunoliposomes: studies in a new experimental model. Circulation. 105:2772-2778, 2002.

20. Lee, S.; Carr, C. L.; Belcik, T. A. et al. Contrast-enhanced ultrasound characterization of inflammation and vasa vasoral proliferation caused by mural hemorrhage and platelet deposition. Circulation. 118:S644, 2008 (Abstract 1074).

21. Decano, J. L.; Viereck, J. C.; McKee, A. C.; Hamilton, J. A.; Ruiz-Opazo, N.; Herrera V.L.M. Early-life sodium exposure unmasks susceptibility to stroke in hyperlipidemic, hypertensive heterozygous Tg25 rats transgenic for human cholesteryl ester transfer protein. Circulation. 119:1501-9, 2009.

22. Herrera, V. L. M.; Tsikoudakis, A.; Didishvili, T.; et al. Analysis of gender-specific atherosclerosis susceptibility in transgenic[hCET]1125$^{DS}$ rat model. Atherosclerosis. 177:9-18, 2004.

23. Loveless, M. E.; Li, X.; Huamani, J.; et al. A method for assessing the microvasculature in a murine tumor model using contrast-enhanced ultrasonography. J. Ultrasound Med. 27:1699-1709, 2008.

24. Herrera, V. L.; Viereck, J. C.; Lopez-Guerra, G. et al. 11.7 Tesla magnetic resonance microimaging of laryngeal tissue architecture. Laryngoscope. 119:2187-94, 2009.

25. Blindt, R.; Vogt, F.; Lamby, D.; et al. Characterization of differential gene expression in quiescent and invasive human arterial smooth muscle cells. J. Vasc. Res. 39:340-352, 2002.

26. Calliada, F.; Campani, R.; Bottinelli, O.; Bozzini, A.; Sommaruga, M. G. Ultrasound contrast agents: basic principles. Eur. J. Radiol. 27Suppl 2:S157-160, 1998.

27. Lankford, M.; Behm, C. Z.; Yeh, J.; Klibanov, A. L.; Robinson, P.; Lindner, J. R. Effect of microbubble ligation to cells on ultrasound signal enhancement: implications for targeted imaging. Invest. Radiol. 41:721-728, 2006.

28. Yasui, K.; Lee, J.; Tuziuti, T.; Towata, A.; Kozuka, T.; Iida, Y. Influence of the bubble-bubble interaction on destruction of encapsulated microbubbles under ultrasound. J. Acoust. Soc. Am. 126:973-982, 2009.

29. Chomas, J. E.; Dayton, P.; Allen, J.; Morgan, K.; Ferrara, K. W. Mechanisms of contrast agent destruction. IEEE Trans. Ultrason. Ferroelectr. Freq. Control. 48:232-248, 2001.

30. Kaufmann, B. A.; Carr, C. L.; Belcik, T. et al. Molecular imaging of the initial inflammatory response in atherosclerosis. Arterioscler. Thromb. Vasc. Biol. 30:54-59, 2010.

31. Goertz, D. E., Frijlink, M. E., Tempel, D., et al. Subharmonic contrast intravascular ultrasound for vasa vasorum imaging. Ultrasound Med. Biol. 33:1859-1872, 2007.

32. Kaufmann, B. A. Ultrasound molecular imaging of atherosclerosis. Cardiovasc. Research. 83:617-625, 2009.

TABLE 2

DEspR-targeted molecular imaging in transgenic rat model of carotid artery disease

| Rat groups: 4 m-old male | | Tg 25+ | Non-transgenic |
|---|---|---|---|
| MB$_D$ Contrast enhanced image | CEU(+) | CEU (−) | CEU (−) |
| # rats: both carotid arteries | 4 | 6 | 5 |
| # rats: one carotid artery Contrast intensity signal Δ | 3* | 3* | — |
| MB$_D$ (n = 18 rats) | 89.96 ± 11.0*** | 2.2 ± 0.9 | 2.0 ± 0.8 |
| MB$_C$ (n = 8 rats) | 1.9 ± 0.7 | ND | ND |
| Histopathology: | | | |
| Intimal lesions, plaque | (+) | +/− | (−) |
| Vasa vasorum expansion | (+) | +/− | (−) |
| Immunostaining: | | | |
| DEspR | (+): in vasa vasorum, initimal lesions | +/− | (−) |

Values are group means ± sem;
, number;
Δ, delta or difference;
(+), present;
(−), absent;
+/−, low to no expression;
*same 3 rats;
***ANOVA and Tukey's multiple pairwise comparison P < 0.0001.
CAD, carotid artery disease;
m, month;
MB$_D$, DEspR-targeted microbubble;
MB$_C$, isotype-targeted microbubble.

Example 3

Dual Endothelin-1/VEGFsp Receptor (DEspR) in Cancer: Target for Dual Anti-angiogenesis/anti-tumor Cell Invasiveness Therapy The development of intrinsic and extrinsic resistance to current anti-VEGF/VEGFR2 therapies have been observed. As described herein, DEspR expression is found to be increased in primary and metastatic tumor αSMA-positive and αSMA-negative vascular endothelium, and in tumor cell- and nuclear-membranes of different human cancer tissue types and cell lines. Further, DEspR-inhibition using the human-specific anti-DEspR antibody treatments described herein decreased human endothelial cell angiogenesis and tumor cell invasiveness. Further, it was found that ligand-specific DEspR signaling-profiles are distinct from VEGF/VEGFR2's. Accordingly, described herein are data demonstrating targeting of DEsPR for dual tumor-cell and endothelial deliveries, and for dual anti-angiogenesis/anti-invasiveness therapies.

Introduction

Although the critical role of the angiogenic switch in cancer pathogenesis has been recognized [1], anti-angiogenesis therapies directed at vascular endothelial growth factor and/or its receptor, VEGF/VEGFR2-centric anti-angiogenesis therapies, alone or in combination with other anti-cancer therapies, have not attained the hoped-for treatment goal of long-term efficacy such that cancer is reduced to a dormant, chronic manageable disease [2-5]. Cumulative observations have shows that all three FDA-approved VEGF pathway inhibitors (anti-VEGF bevacizumab or Avastin, AntiVEGFR2 sunitinib, and sorafanib) result in significant but transitory improvements in the form of tumor stasis or shrinkage, and only for certain cancers despite most, if not all cancer types exhibiting pathological angiogenesis [2,6]. Moreover, while anti-VEGF pathway therapies have reduced primary tumor growth and metastasis in preclinical studies [7], recent mouse tumor model studies report that sunitinib and an anti-mouseVEGFR2 antibody, DC101, increased metastasis of tumor cells despite inhibition of primary tumor growth and increased overall survival in some cases [8,9]. Cumulative observations implicate several mechanisms of intrinsic and evasive resistance, such as, without wishing to be bound or limited by theories, pre-existing multiplicity of redundant pro-angiogenic signals; upregulation of alternative pro-angiogenic pathways, recruitment of bone marrow-derived pro-angiogenic cells, increased pericyte coverage for the tumor vasculature obviating the need for VEGF signaling, and invasive and metastatic co-option of normal vessels without requisite angiogenesis [2-5]. Additionally, 10-fold increase in VEGF levels have been detected upon bevacizumab anti-VEGF therapy in humans [10] and upon anti-VEGFR2 ab-therapy in mice [11], which could, without wishing to be bound or limited by a theory, contribute to evasive resistance.

Both VEGF and VEGFsp (vascular endothelial growth factor signal peptide) originate from the same propeptide, and a 10-fold 'rebound' increase in VEGF could, without wishing to be bound or limited by a theory, also result in a concomitant 10-fold increase in VEGFsp, thus resulting in a 10-fold increase in VEGFsp's post-cleavage function of activating its receptor, the dual endothelin1/VEGFsp receptor or DEspR, formerly called Dear and deposited in GenBank as Dear [12]. DEspR knockout mouse exhibits arrested vasculogenesis and absent angiogenesis resulting in E10.5-E12.5 day embryonic lethality [13]. Concordantly, DEspR-haploinsufficiency resulted in decreased syngeneic melanoma tumor growth, and anti-DEspR antibody inhibition decreased tumor growth and tumor angiogenesis in rats with irradiation-induced mammary tumors [13]. Furthermore, DEspR's other ligand is endothelin-1 (ET1) [12], and all other known ET1 receptors, ETa and ETb, do not exhibit an embryonic lethal angiogenic phenotype in their respective knockout mouse models [14,15, 16.].

Described herein are novel anti-angiogenic strategies using anti-human DEspR ab-inhibition and characterizing the murine precursor of an anti-DEspR antibody therapeutic. It was found that DEspR is upregulated in some solid tumor cells and tumor vascular endothelium, and that human-specific anti-DEspR polyclonal and monoclonal antibodies inhibit human endothelial cell tube formation and tumor cell invasiveness in vitro, and that DEspR utilizes ligand-specific signaling pathways known to mediate angiogenesis and cancer cell invasiveness.

Materials and methods

Cell lines and antibody development MDA-MB-231 and PANC-1 cells were obtained from American Type Culture Collection (Rockville, Md.). MDA-MB-231 cells were maintained in DMEM media (Sigma Chemical, St. Louis, Mo.) supplemented with 10% FBS, L-glutamine, penicillin, and streptomycin (GPS). PANC-1 cells were maintained in DMEM (Sigma Chemical, St. Louis, Mo.) with high glucose, 10% FBS and GPS. Human umbilical vein endothelial cells, HUVECs, were obtained from Cascade Biologics, Inc., and maintained in Endothelial Growth Media-2 (EGM-2) containing 2% FBS and GPS. Monoclonal antibody development was custom performed by ProMab Biotechnologies, Inc (Richmond, Calif.) using a nine amino-acid DEspR $NH_2$-terminal peptide, $M_1TMFKGSNE_9$ (SEQ ID NO. 20) of hDEspR as antigen. Screening of hybridoma supernatants and initial characterization of candidate monoclonal antibodies were performed by ELISA using free hDEspR-antigenic peptide as antigen.

Monoclonal antibody characterization by ELISA and Western blot analysis. The $M_1TMFKGSNE_9$ (SEQ ID NO: 20) antigenic peptide was coated directly on wells of a microtiter plate. Appropriate dilutions of primary antibodies were incubated at 37° C. for 1 hr. The wells were then incubated with HRP labeled anti-IgG (SIGMA cat# A0168) at 1:9000 at 37° C. for 1 hr. The reactions were visualized by the addition of 3,3'5,5'-tetramethylbenzidine substrate (incubation at 37° C. for 10 min) and read spectrophotometrically at 450nm. Western blot analysis was done as described [17] using equal amounts of whole cell protein extract (40 μg) from Cos1 cell transfectants stably expressing hDEspR [17] and corresponding candidate monoclonal antibodies raised against hDEspR specific synthetic peptide Immunoreactive hDEspR (10 kDa polypeptide) was detected by chemiluminescence using the ECL Western Detection kit (GE Healthcare).

HUVEC tube formation assay for angiogenesis. Validated $2^{nd}$ passage human umbilical vein endothelial cells—HUVECs (Cascade Biologics, Oregon) were obtained and cultured until the 4th passage and were then harvested at 80% confluence using mild trypsinization. The cell pellet was then washed twice in serum free media (basal media) containing M-200 (Cascade Biologics, Oregon) 1 μg/ml hydrocortisone, 10 ng/ml EGF, 3 ng/ml bFGF and 10 μ/ml heparin. Cells were then resuspended in this serum free media and seeded at 20,000 cells per well (100 μL) onto a 96 well plate Angiogenesis System: Endothelial Cell Tube Formation Matrigel™ Matrix (BD Biosciences, MA). Different angiogenic and anti-angiogenic conditions were assayed in quadruplicate as indicated using basal media alone or with one or more of the following: 2% FBS, 20 nM VEGF, 20 nM VEGFsp, 20 nM ET1. Antibodies used for inhibition were all affinity purified and used in the following concentrations: 500 nM anti-hDEspR polyclonal antibody (Pab), 500nM anti-hDEspR 7C5B2 monoclonal antibody (Mab), 500 nM anti-VEGFsp Pab, and for corresponding isotype controls either 500 nM preimmune IgG (75 μg/ml) for Pab, and 500 nM IgG2b for anti-hDEspR Mab. Different experimental conditions were tested in quadruplicate as follows: basal media alone (BM), BM with 2% FBS; BM with 20 nM VEGF; BM with 20 nM VEGFsp; BM with 20 nM ET1; BM with 20 nM VEGF and 500 nM (75m/ml ) pre-immune IgG; BM with 20 nM VEGF and 500 nM anti-VEGFsp; BM with 20 nM VEGF and 500 nM anti-hDEspR; BM with 20 nM VEGFsp and 500 nM anti-hDEspR; BM with 20 nM ET1 and 500 nM anti-hDEspR; BM with 2% FBS and 500 nM anti-VEGFsp; and BM with 2% FBS plus 500 nM anti-hDEspR. In other experiments increasing concentrations of anti-hDEspR 7C5B2 mAb (0.05-500 nM) were tested. HUVECs were then incubated in different conditions as specified at 37 ° C. for 16 hours; after which, resulting angiogenic tube formations were viewed under the microscope and images of ~70% of the well (central parts) were taken for analysis. Various parameters were measured for each angiogenic condition using ImageJ (NIH—http://rsb.info.nih.gov/ij/) namely total tube length, average tube length, average tube thickness, number of branch points defined as cluster of cells possessing tube-like extensions measuring more than 2× the length of the cell aggregates, number of connections defined as 3 or more connections between tube-like structures in series or parallel and number of closed polygons bounded by the tubular structures.

Invasion assay. MDA-MB-231 and PANC-1 cell invasion assays were performed as described [18] using the BD Bio-Coat Matrigel invasion assay system (BD Biosciences, Franklin Lakes, N.J.). MDA-MB-231 and PANC-1 cells were suspended in growth media and seeded onto pre-coated transwell chambers ($3 \times 10^4$ cells/well). The transwell chambers were then placed into 24-well plates, to which basal medium only or basal medium containing various concentration of antibodies were added. Cells were incubated for 16 hr and the invading cells were fixed and stained with Diff-Quick stain. The number of invading cells per well were counted under the microscope. Each condition was assessed in four replicates.

Immunostaining of tumor tissue arrays and tumor cells. Human cancer cell line-array DEspR immunostaining was custom-performed by Pantomics, Inc. using our in-house polyclonal human-specific anti-DEspR antibody. Tumor tissue arrays were obtained from Pantomics, Inc. and immunostained for DEspR using polyclonal and monoclonal anti-hDEspR antibodies at 1:20 after demonstration of concentration-dependent immunostaining 1:10, 1:50, 1:100. Deoxyaminobenzidine immunostaining was done using the polyclonal antibody as described [13]. Double immunofluorescence staining was done on deparaffinized sections via the following steps: antigen retrieval, treatment to reduce background, blocking, incubation with primary antibody at 4° C. overnight, secondary antibody incubation overnight at 4° C. with AlexaFluor 568 goat anti-mouse IgG and AlexaFluor 488 goat anti-rabbit IgG, washing, and mounting using Prolong Gold with DAPI (Invitrogen). Negative controls were run using rabbit-isotype antibody for anti-rat DEspR antibody. A Zeiss Axioskop2plus microscope was used for fluorescence imaging and photomicroscopy.

Multiplex analysis of signaling proteins by Ab-microarray. Analysis of ligand-dependent modulation of different signaling pathways by DEspR was custom performed by Kinexus Corp. (Kinexus, Canada) utilizing the Kinex™ Antibody Microarray System spanning 506 phosphoprotein-specific antibodies in duplicates or multiple replicates, as well as 740 pan-specific antibodies of signaling molecules. The effects of ET1- and VEGFsp-DEspR activation were analyzed on multiplex signaling pathways after 30 minutes of ligand-treatment (ET1, 10 nM; VEGFsp, 10 nM), compared with the respective non-activated DEspR in non-treated controls, using Cos1-hDEspR permanent cell transfectants. All fluorescent signals were normalized to background. Data are presented as percentage change from control (% CFC), or change detected after 30 minutes of ET1 or VEGFsp-treatment compared with non-treated transfectant-matched controls respectively. The % CFC= [Treated$^{Ave}$−Control$^{Ave}$]/Control$^{Ave}$×100. Although % CFC>25% is suggested as a significant difference, only values exhibiting >50% CFC and with % error range between duplicates less than 20% for both test and control samples were presented. The % error range=[Duplicate$^n$−Average]/Average. A % error >20% was accepted if the % CFC remained >50% using the lesser of the duplicates in calculating % CFC.

Statistical analysis. One way analysis of variance (ANOVA) followed by all pairwise multiple comparison Tukey test were performed after ascertaining normality using SigmaStat 2.03 software package. A $P<0.05$ was considered statistically significant.

Results

Figure 24A:
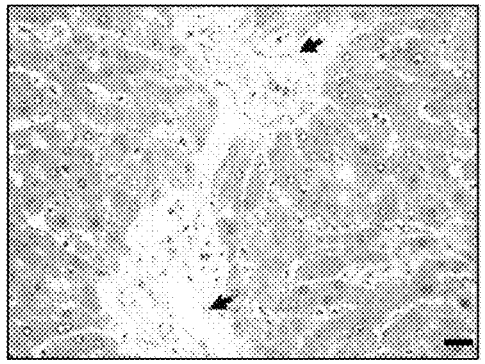
FIGS. 24A-24F show DEspR expression in liver (24A-24C) and pancreas (24D-24F) non-cancerous and cancerous tissues. (24A) Adjacent normal liver tissue; (24B, 24C) hepatic carcinoma T-2 from two patients; (24D), adjacent normal pancreatic tissue; (24E, 24F) pancreatic ductal carcinoma Grade III-IV from two patients. Black arrow, microvessels; DAB-detection of DEspR-positive immunostaining with color-intensity roughly proportional to expression; hematoxylin nuclear counterstain. Bar, 20 microns.
Figure 24D:
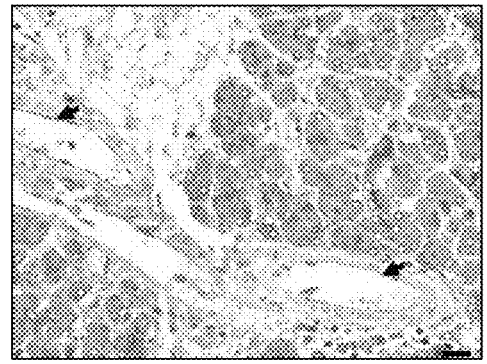
Figure 24B:
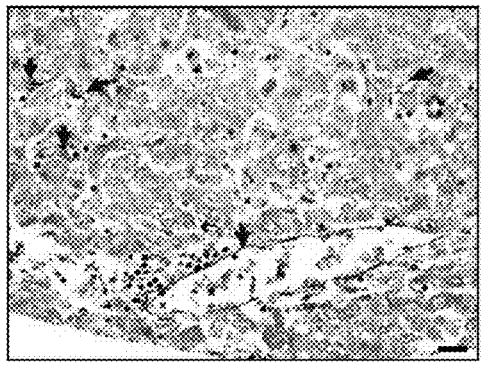
Figure 24E:
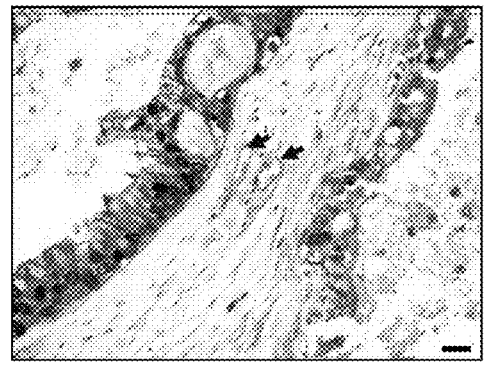
Figure 24C:
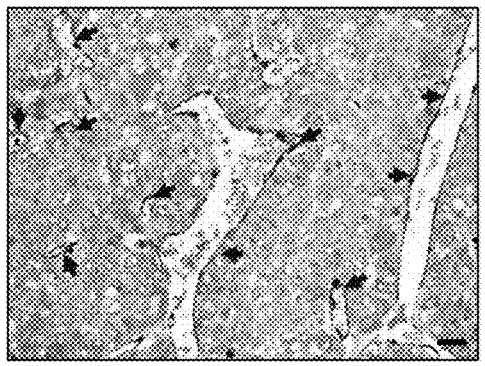
Figure 24F:
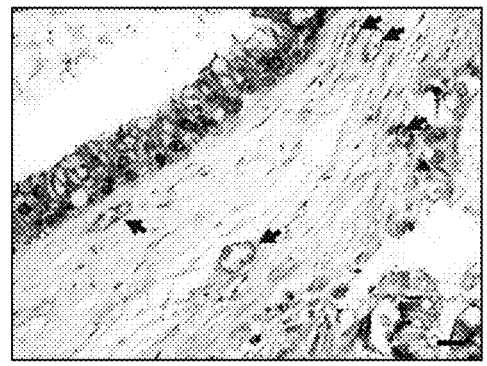
Figure 25A:
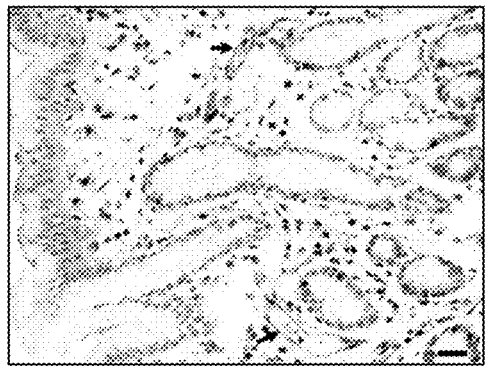
FIGS. 25A-25F show DEspR expression in a human tissue array: stomach (25A-25C) and breast (25D-25F) non-cancerous and cancerous tissues. (25A) Adjacent normal stomach tissue; (25B) stomach adenocarcinoma T-3, (25C) stomach adenocarcinoma metastasis to lung; (25D) adjacent normal breast tissue with fibrosis; (25E) breast medullary carcinoma T-2; (25F) breast tumor metastasis to lymphnode. Black arrow, vascular endothelium; DAB-detection of DEspR-positive immunostaining with color-intensity roughly proportional to expression; hematoxylin nuclear counterstain. Bar, 20 microns.
Figure 25D:
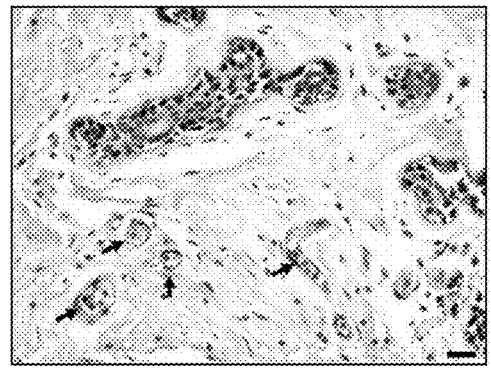
Figure 25B:
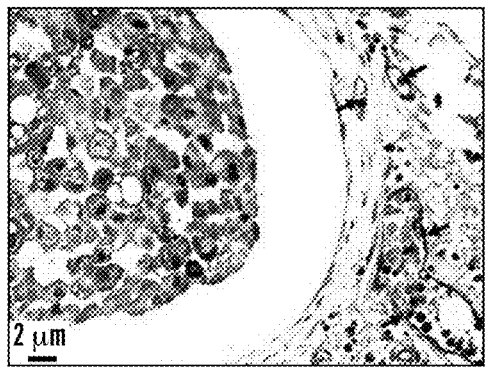
Figure 25E:
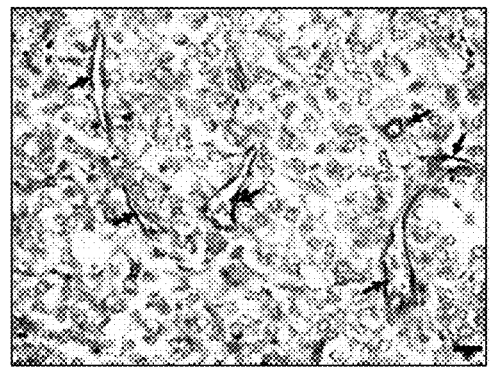
Figure 25C:
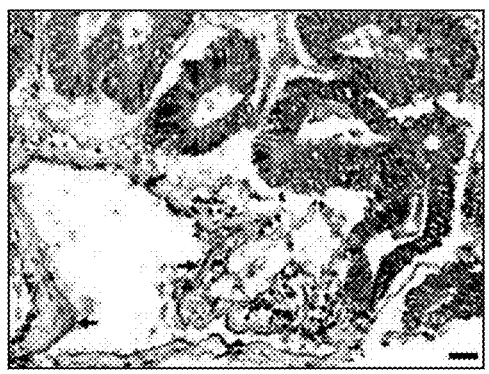
Figure 25F:
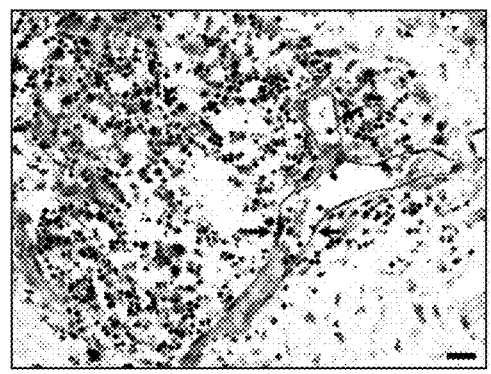
Figure 26A:
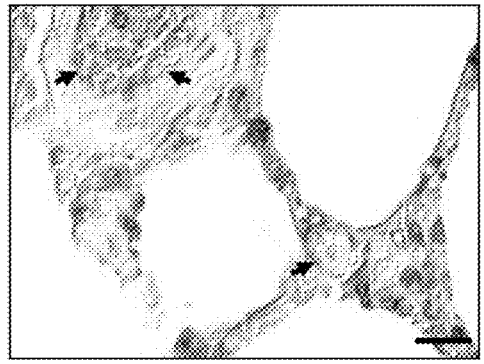
FIGS. 26A-26F show DEspR expression in lung and colon non-cancerous and cancerous tissue. (26A) adjacent normal lung; (26B) Gr-I lung adenocarcinoma; (26C), Gr.I-II,T2 lung adenocarcinoma; (26D) adjacent normal colon; (26E, 26F) colon adenocarcinoma Gr.III-IV, T2. white arrow , endothelium; black arrow →, DEspR-immunostaining of nuclear membrane in cancer cells DAB-detection of DEspR-immunostaining with color-intensity roughly proportional to expression; hematoxylin nuclear counterstain. Bar, 20 microns 26A-26C; 25 microns 26D; 10 microns 26E, 26F.
Figure 26B:
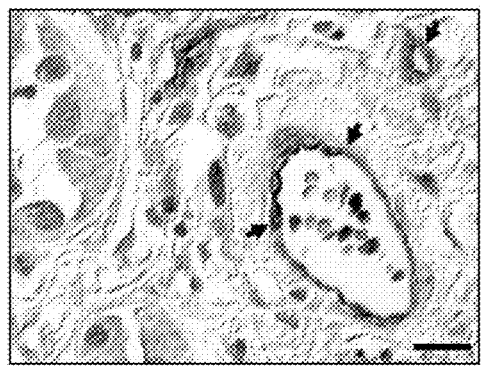
Figure 26C:
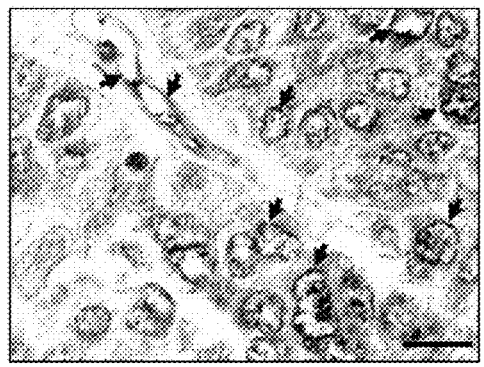
Figure 26D:
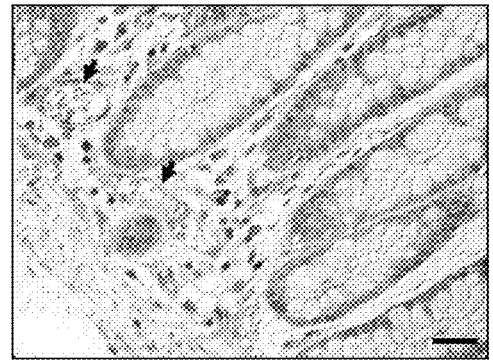
Figure 26E:
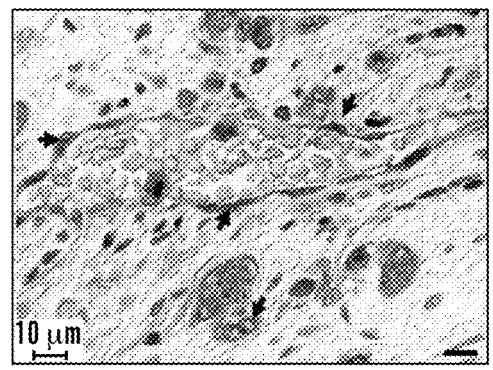
Figure 26F:
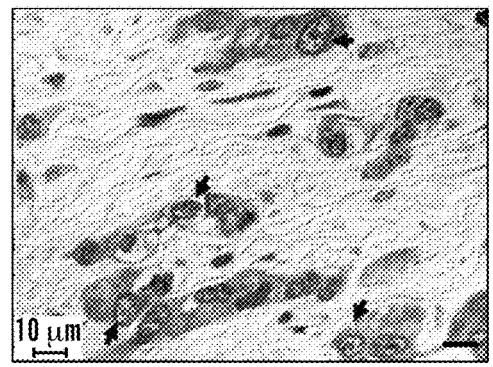
Figure 27A:
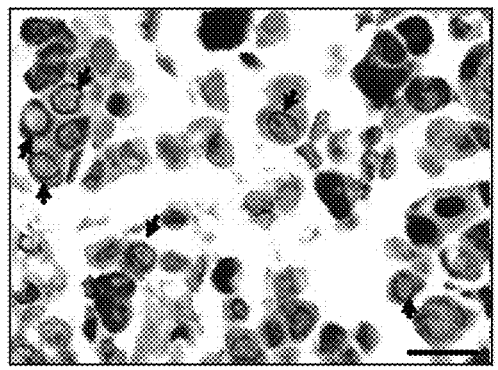
FIGS. 27A-27F show DEspR expression in different tissue-type cancer cell lines. (27A) non-small cell lung cancer cell line, #NCI-H727; (27B) colon carcinoma, SW480 Duke's type B; (27C) pancreatic carcinoma, PANC-1; (27D) breast adenocarcinoma metastasis, MDA-MB-231; (27E) bladder carcinoma 253J BV; (27F) prostate adenocarcinoma PC-3mm2. →, DEspR-immunostaining of nuclear membrane in cancer cells, DAB-detection of DEspR-immunostaining with color-intensity roughly proportional to expression; hematoxylin nuclear counterstain. Bar, 20 microns A-F.
Figure 27D:
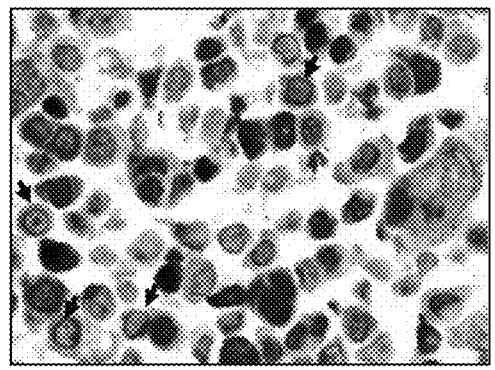
Figure 27B:
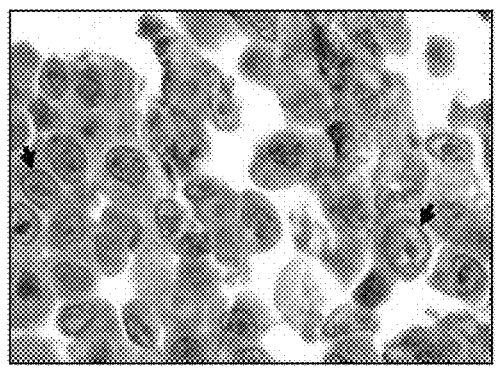
Figure 27E:
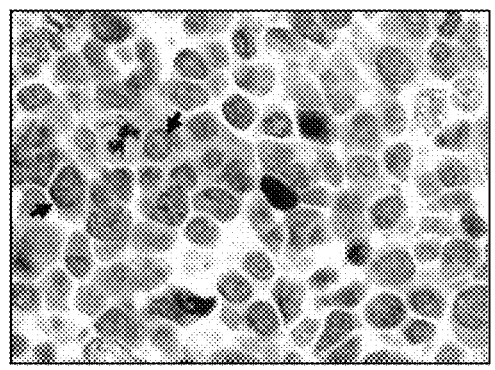
Figure 27C:
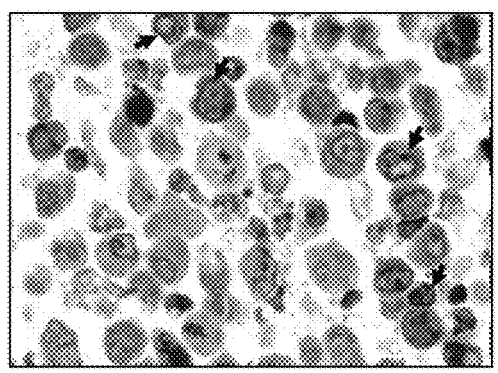
Figure 27F:
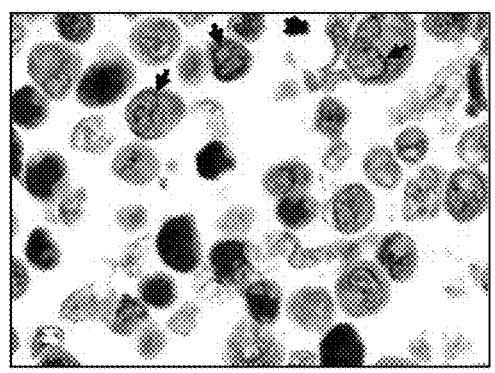

DEspR expression is increased in human tumor cells and tumor vessels. DEspR-specific expression patterns were investigated in human cancer tissues and cells. Tumor tissue array analysis was performed using a human-specific anti-DEspR polyclonal-antibody [17]. Concordant with rat irradiation-induced mammary tumor model observations of rat-specific anti-DEspR antibody [13] immunostaining, immunohistochemical analysis of DEspR expression in human tumor tissue arrays detected increased DEspR expression in thin-walled tumor vascular endothelium in hepatic, pancreatic (FIGS. 24A-24F), stomach, breast (FIGS. 25A-25F), colon and lung (FIGS. 26A-26F) cancer, compared with vascular endothelium in normal tissue biopsy cores respectively be it arterial or microvascular endothelium (FIGS. 24A-24F, 25A-25F, and 26A-26F). Notably, vascular endothelium in stomach cancer metastatic foci in the lung (FIG. 25C) and breast cancer metastatic foci in lymph node (FIG. 25F) also exhibit increased DEspR immunostaining Moreover, pancreatic (FIGS. 24E, 24F), stomach (FIGS. 25B, 25C), breast (FIG. 25E), lung (FIG. 26C) and colon (FIG. 26E, 26F) tumor cells exhibit increased DEspR expression with sub-cellular localization in the cell membrane, cytoplasm and nuclear membrane. This increased DEspR expression in tumor neovessels and tumor cells demonstrated herein indicate that that DEspR plays a role in both tumor neovascularization and in tumorigenesis.

To further confirm expression in tumor cells DEspR-immunostaining of cancer cell-array testing different types of previously characterized, established cancer cell lines was next performed (Table 3). In contrast to a few cell lines tested with minimal if any DEspR expression, several cancer cell lines exhibit DEspR expression with nuclear membrane DEspR expression associated with high-nuclear grade (Table 3, FIGS. 27A-27F). Representative photomicrographs demonstrate tumor cell expression with strongest DEspR-immunostaining in nuclear membranes of most tumor cells, but not all. The selective nuclear membrane immunostaining (FIGS. 27A-27F) confirms specificity of DEspR immunostaining, along with negative immunostaining of some cancer cell lines (Table 3). Importantly, these observations are concordant with the observations in cancer tissue sections described herein (FIGS. 24A-24F, 25A-25F, and 26A-26F). Nuclear membrane localization indicates that DEspR can play a role in crosstalk between the cell membrane and nuclear membrane, beyond receptor-mediated signal transduction.

High-affinity anti-hDEspR monoclonal antibody generated against N-terminal 9-aa extra-cellular domain. In order to investigate anti-DEspR inhibition as an anti-angiogenic strategy, a human-specific anti-DEspR monoclonal antibody was developed using a 9-aa peptide spanning the N-terminal extracellular domain of human DEspR identical to the strategy use to develop the human-specific anti-DEspR polyclonal antibody used in DEspR immunostaining (FIGS. 24A-24F, 25A-25F, 26A-26F, and 27A-27F) [17]. From 67 hybridoma clones, a preliminary screen identified top ten candidate monoclonal antibody hybridoma clones which were then analyzed for affinity to the 9-aa peptide N-terminal domain by indirect ELISA (FIG. 28A). Analysis of specificity by Western blot analysis of mab-mediated binding to hDEspR protein (10 kDa) isolated from Cos1-hDEspR transfectants in contrast to control non-transfected Cos1 cells identified hybridoma clone 7C5B2. As shown in FIG. 28B, 7C5B2 anti-hDEspR monoclonal antibody hybridoma clone exhibited specificity as both "super clone" supernatant and purified monoclonal antibody. Isotyping of 7C5B2 showed that this monoclonal antibody belongs to the murine IgG2b isotype class of antibodies.

Co-localization of DEspR and its ligand, VEGFsp in human umbilical vascular endothelial cells (HUVECs). Analysis of receptor-ligand co-localization by double immunostaining in HUVECs showed specific detection of DEspR on endothelial cell membrane cultured in pro-angiogenesis conditions using the anti-hDEspR monoclonal antibody. Double immunostaining detected co-localization of DEspR with its ligand VEGFsp using an anti-VEGFsp polyclonal antibody, thus demonstrating that anti-hDEspR monoclonal antibody specifically targets DEspR. Anti-DEspR polyclonal antibody also gave identical results.

Figure 29A:
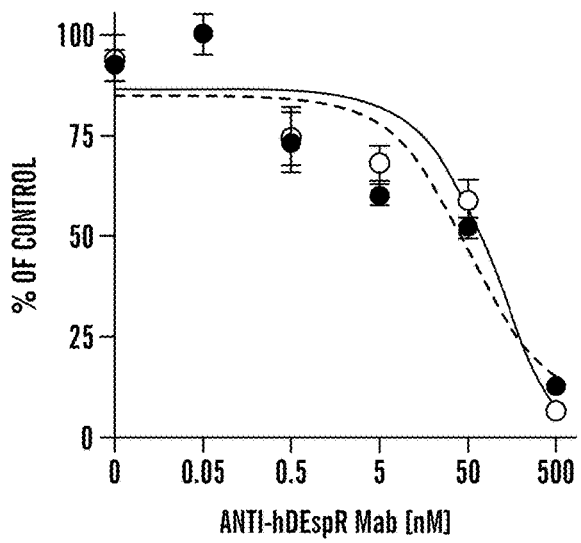
FIGS. 29A-29C demonstrate that DEspR inhibition via monoclonal antibody decreases angiogenesis in in vitro HUVECs assay. DEspR immunostaining of HUVECs using anti-DEspR Mab was performed. (29A) Dose response curve to anti-DEspR Mab inhibition of angiogenesis measuring total tube length per well (○) with $EC_{50}$=4.34 +/−0.45 nM; and number of tube branch points (●) with $EC._{50}$3.97 +/−0.51 nM. (29B) Analysis of total tube length changes upon DEspR-inhibition via anti-DEspR polyclonal (Pab) and monoclonal (Mab) antibodies compared to control untreated cells (30C), pre-immune serum (PI) and IgG2b isotype (Iso) controls for Pab and Mab, respectively. (29C) Analysis of mean number (#) of branchpoints inhibited by Pab and Mab anti-DEspR ab-inhibition compared with controls (C, PI, Iso). Data expressed as mean +/−sem; 4 replicates; *, P<0.01 (ANOVA followed by all pairwise multiple comparison Tukey test).

Anti-DEspR inhibition by anti-hDEspR polyclonal antibody and 7C5B2 monoclonal antibody decrease angiogenesis. The effects of 7C5B2 monoclonal antibody inhibition of DEspR on angiogenesis using established in vitro HUVECs-based angiogenesis assays was then assessed. It was first showed that 7C5B2 monoclonal antibody detects cell-membrane DEspR expression in tubes/"neovessels" formed by HUVECs in pro-angiogenesis conditions, thus validating the use of this angiogenesis assay system. Next, two established parameters of in vitro angiogenesis were analyzed, total tube length and branching of neovessel-tubes formed by HUVECs in pro-angiogenesis conditions. Using varying doses of 7C5B2 monoclonal antibody from 0.05 to 500 nM, concentration dependence of angiogenesis inhibition is demonstrated for both total tube length and number of branch-points, and identifies 500 nM 7C5B2 monoclonal antibody as the full-strength inhibitory dose (FIG. 29A). This dose was then applied to repeat independent inhibition experiments comparing the newly developed 7C5B2 monoclonal antibody with the previously characterized anti-hDEspR polyclonal antibody. Compared to non-treated controls, and pre-immune and IgG2b-isotype-specific negative controls for polyclonal antibody and 7C5B2 monoclonal antibody respectively, 500 nM anti-hDEspR antibody inhibited angiogenesis, measured as total tube length and mean number of branchpoints, significantly (ANOVA with all pairwise multiple comparison Tukey test, P<0.01). Other angiogenesis parameters, number of tubes and branch-interconnections were also significantly inhibited. Concordantly, a polyclonal anti-VEGFsp antibody also inhibited angiogenesis in HUVECs.

Figure 29B:
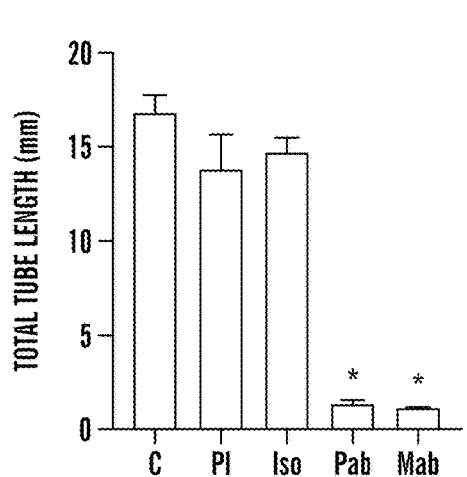
Figure 29C:
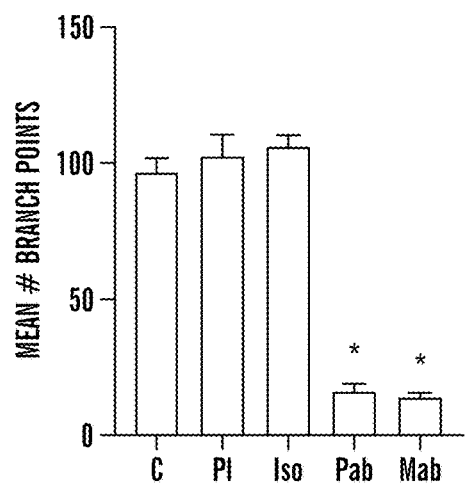
Figure 30A:
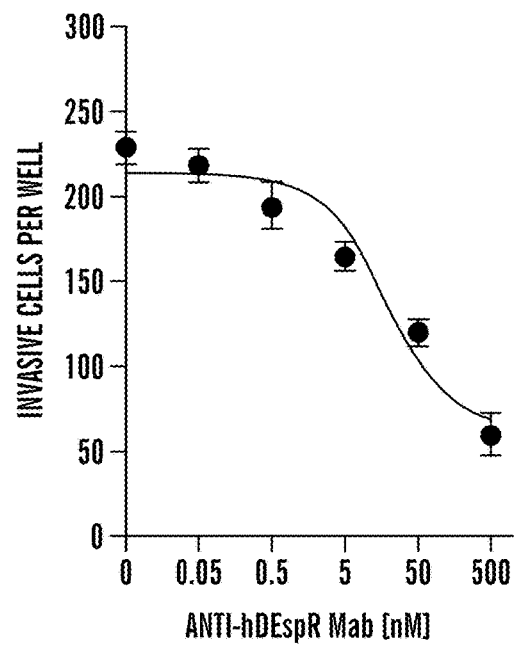
FIGS. 30A-30C demonstrate that DEspR inhibition via monoclonal antibody decreases angiogenesis in in vitro HUVECs assay. DEspR-positive immunostaining of MDA-MB-231 breast cancer cells and PANC-1 pancreatic cancer cell line via anti-DEspR Mab was performed. (30A) Dose response curve to increasing DEspR-inhibition via anti-DEspR Mab of MDA=MB-231 breast cancer cell invasiveness (black), $EC_{50}$=3.55+/−0.32 nM. (30B-30C) Analysis of cell invasiveness inhibited by anti-DEspR Mab inhibition compared to control untreated cells, and IgG2b isotype control for MDA-MB-231 breast cancer cells (31B), and PANC-1 pancreatic cell line (31C). All data shown as mean+/−sem of 4 replicates; *, P<0.01; **, P<0.001 (1-way ANOVA followed by all pairwise multiple comparison Tukey Test).
Figure 30B:
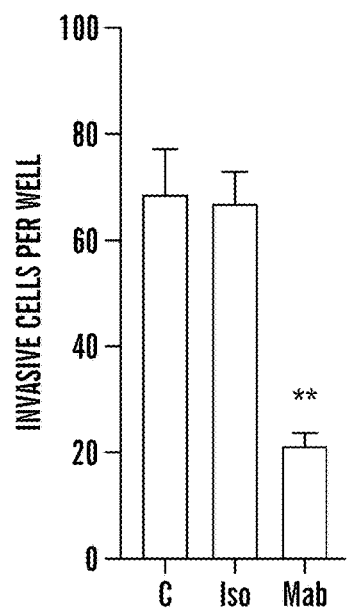
Figure 30C:
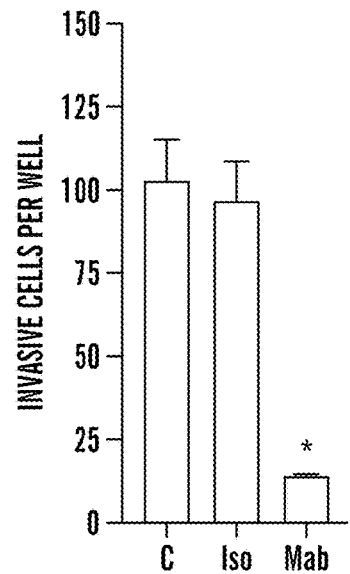

Analysis of anti-hDEspR 7C5B2 monoclonal antibody immunostaining and inhibition of tumor cell invasiveness. Having shown that DEspR inhibition reduces angiogenesis, the efficacy of 7C5B2 monoclonal antibody -mediated anti-DEspR inhibition on tumor cell invasiveness was next assessed since DEspR is detected in different tumor cell lines (FIGS. 27A-27F) and cancer tissues (FIGS. 24A-24F, 25A-25F, and 26A-26F). Two cancer cell lines representing aggressive breast cancer and pancreatic cancer, MDA-MB-231 and PANC-1 cancer cell lines respectively, were examined Immunostaining with 7C5B2 monoclonal antibody detected nuclear- and cell-membrane DEspR expression in both cell lines, as well as cytoplasmic expression. Functional analysis detected concentration dependent inhibition of tumor cell invasiveness from 0.05 to 500 nM 7C5B2 monoclonal antibody, with an EC50 of 3.55±0.32 nM. Using 500 nM 7C5B2 monoclonal antibody, DEspR inhibition was observed in both MDA-MB-231 (FIG. 30B) and PANC1 (FIG. 30C) cells, compared to control non-treated cells and IgG2b-isotype treated cells respectively (ANOVA followed by all pairwise multiple comparison test, P<0.001 and P<0.01 respectively). These observations indicate dual effects of DEspR inhibition on both angiogenesis (FIG. 29B-29C) and tumor cell invasiveness (FIG. 30B-30C).

Anti-hDEspR 7C5B2 monoclonal antibody-immunostaining of tumor vascular endothelium and tumor cells. Having shown efficacy of DEspR-inhibition on angiogenesis and tumor cell invasiveness, 7C5B2 monoclonal antibody -immunostaining in breast and pancreatic cancer tissues in contrast to normal was next evaluated to confirm increased DEspR expression in tumor vascular endothelium and tumor cells as detected using anti-hDEspR polyclonal antibody (FIGS. 24A-24F, 25A-25F, and 26A-26F), as well as to delineate DEspR-targeting profile of 7C5B2 monoclonal antibody.

Figure 31A:
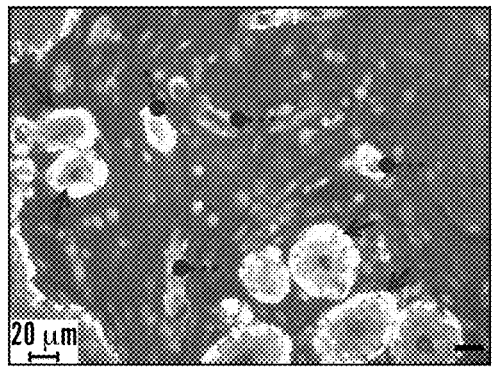
FIGS. 31A-31F show immunohistochemical analysis of DEspR expression in human breast tissue. (31A-31C) normal; (31D-31F) Grade-1, T1 invasive ductal carcinoma. 31A. Normal breast tissue: 3×-overlay of DEspR, aSMA and DAPI nuclear stain detects aSMA expression in mammary myoepithelial cells but no expression of DEspR in epithelial cells (white triangular arrowhead →) and microvessels (white rounded arrowhead). 31B, 2×-immunofluorescence overlay of DEspR and DAPI nuclear stain confirms absence of DEspR expression in normal breast tissue. 31C, 4×-overlay of DEspR, aSMA, DAPI immunofluorescence and diffusion contrast imaging (DIC) delineates tissue morphology, expression of aSMA. and non/minimal-expression of DEspR in normal mammary epithelium and endothelium. 31D, 3×-Overlay of DAPI, aSMA and DEspR immunofluorescence in Gr.I-T1 invasive ductal carcinoma detects DEspR expression in vascular endothelium, and co-localization with aSMA in mammary tissue. 31E, 2×-overlay of DAPI and DEspR of breast cancer shown in panel d highlights DEspR expression. 31F, 4×-overlay of DAPI, aSMA, DEspR, DIC elucidate DEspR spatial expression with tissue morphology. (white triangular arrowhead →), epithelial cells; (white rounded arrowhead), microvessels. DEspR-positive; aSMA-positive; DAPI nuclear stain; colocalization of aSMA and DEspR; bar=20 microns.
Figure 31D:
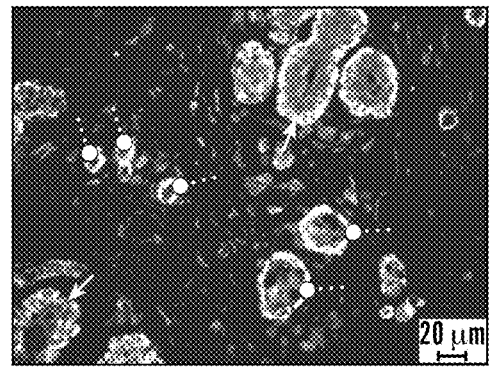
Figure 31B:
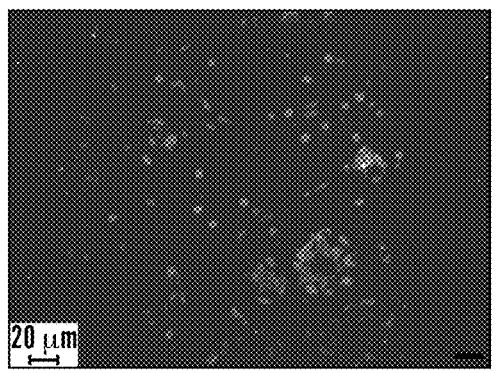
Figure 31E:
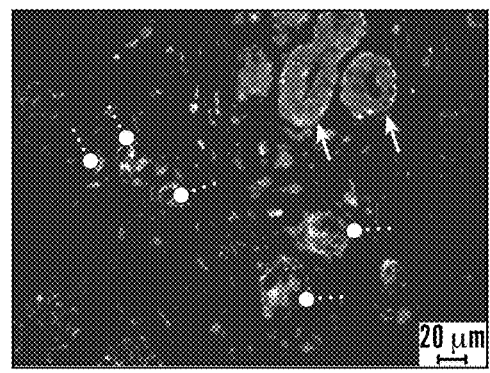
Figure 31C:
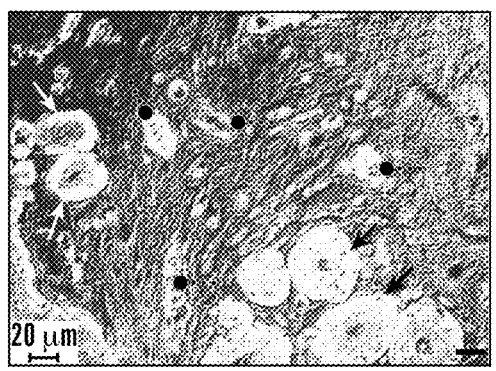
Figure 31F:
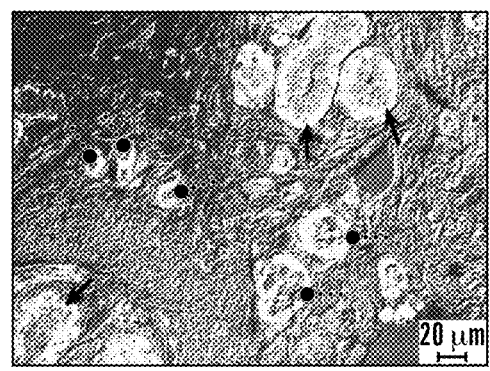

Double immunostaining of DEspR and alpha smooth muscle actin (αSMA), to track microvascular pericytes and cancer tissue stromal myofibroblasts, detected minimal DEspR expression in normal breast tissue blood vessels and mammary epithelial cells, and normal αSMA expression in mammary myoepithelial cells and arteriolar smooth muscle cells highlighting minimal to no DEspR expression (FIGS. 31A-31C). In contrast, in a representative breast cancer tissue sections of ductal invasive carcinoma, double immunostaining detected prominent DEspR expression in tumor microvascular endothelium, in microvessels and arterioles co-expressing αSMA, as well as in ductal carcinoma epithelial cells (FIGS. 31D-31F). Increased tumor vascularization is also noted compared to non-cancer 'normal' control tissue (FIGS. 31A-31C).

Figure 32A:
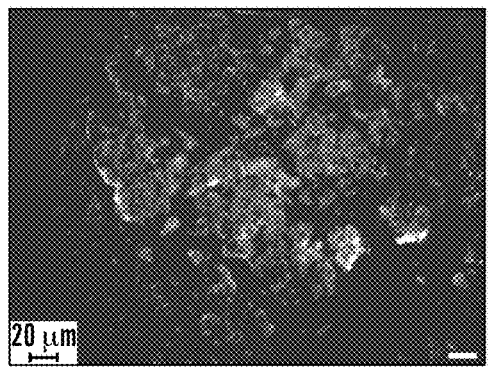
FIGS. 32A-32F demonstrate immunohistochemical analysis of DEspR expression in pancreatic tissue using anti-DEspR Mab. (32A-32C) normal; (32D-32F) Grade-3, T3 pancreatic ductal carcinoma. (32A) Normal pancreatic tissue: 3×-overlay of DEspR, aSMA and DAPI nuclear stain detects minimal DEspR expression in microvessels seen better in panel (32B) 4×-immunofluorescence overlay: DEspR, aSMA, DAPI, with DIC imaging of tissue morphology. (32C) left: 3×-overlay of DEspR, aSMA, DAPI immunofluorescence; right: 4×-overlay of DEspR, aSMA, DAPI and diffusion contrast imaging (DIC) for tissue morphology shows aSMA expression and non/minimal-expression of DEspR in normal endothelium. (32D) 3×-overlay of DAPI, aSMA and DEspR immunofluorescence in Gr.3-T3 pancreatic ductal carcinoma detects DEspR expression in vascular endothelium, and co-localization with aSMA. (32E) 2×-overlay of DAPI and DEspR of image shown in panel 32D highlights DEspR expression. (32F) 3×-overlay of DAPI, aSMA, DEspR, shows increased DEspR expression in pancreatic ductal carcinoma cells. (white →), epithelial cells; (white rounded arrowhead, microvessels. DEspR-positive; aSMA-positive; DAPI nuclear stain; colocalization of aSMA and DEspR; bar=20 microns.
Figure 32D:
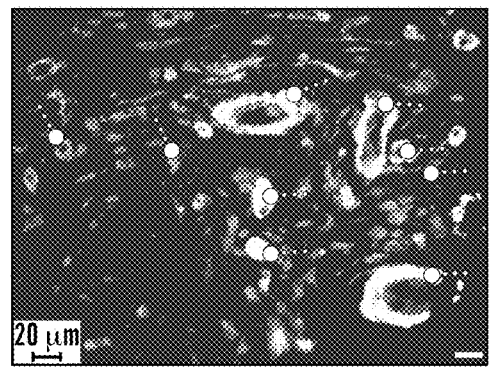
Figure 32B:
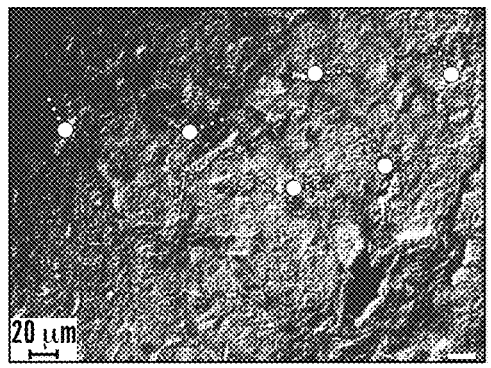
Figure 32E:
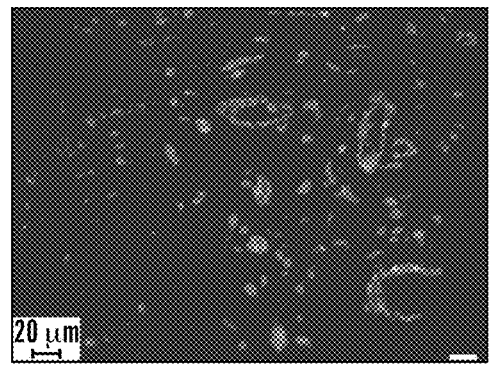
Figure 32C:
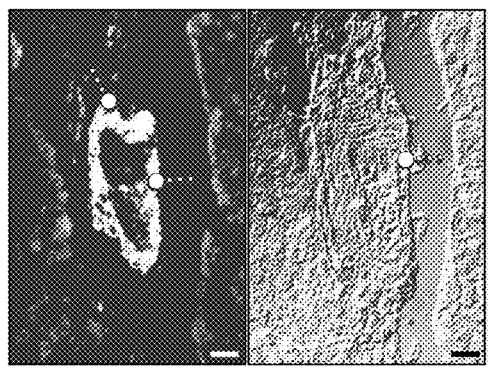
Figure 32F:
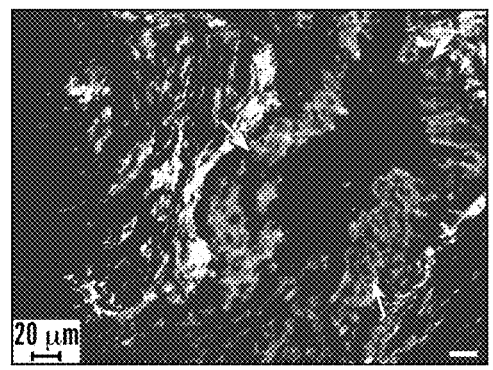

Similarly, in normal pancreas, minimal DEspR expression is detected in microvessels (FIGS. 32A-32C), and in arterial endothelium in contrast to strong αSMA expression in arterial media smooth muscle cells (FIGS. 32C). In contrast, DEspR expression is increased in pancreatic cancer αSMA-negative microvascular and αSMA-positive microvascular and arteriolar endothelium (FIGS. 32D-32E). As observed in breast cancer epithelial cells and in PANC-1 cancer cell line, pancreatic cancer ductal carcinoma epithelial cells exhibit marked DEspR-positive immunostaining (FIG. 32F).

Phosphoproteome analysis of DEspR signal transduction. Using a phosphoprotein-specific antibody-array, ligand-specific signal transduction pathways activated by DEspR upon binding to its dual ligands, ET1 and VEGFsp respectively in permanent Cos1-cell DEspR transfectants were identified (Table 4). Cos1 cells were used as these cells do not have endogenous DEspR, ET1 or VEGFR2 expression. Non-treated and treated Cos1-DEspR transfectants were compared. As shown in Table 4, regardless of ligand, DEspR's phosphoproteome (limited to signaling phosphoproteins with >50% CFC) activates signaling pathways known to be involved in mechanisms of angiogenesis, tumor cell invasiveness or metastasis. Additionally, some DEspR-phosphorylated signaling molecules for either ET1 or VEGFsp-activation of DEspR have been directly linked to either neuronal or hematopoietic stem cells, with some also implicated in cancer stem cell renewal such as ERK1/2, FAK, Met, PKC-alpha, SHP2, Smad, STAT1, and STAT3 (Table 3). It is noted herein that DEspR's phosphoproteome overlaps with VEGFR2/VEGF for some signaling molecules like FAK, ERK1/2, Raf, PKCα[19]. However, the collective signaling complexes of DEspR/ET1 and DEspR/VEGFsp (Table 3) are quite distinct from that described for VEGFR2/VEGFa [19], thus confirming non-redundant angiogenesis roles as deduced from null mutant abnormal angiogenesis phenotypes for DEspR [13] and VEGF [20,21] with identical embryonic lethality between embryonic E10.5 and E12.5 days, although VEGFR2 or Flk1 null mutants died earlier between E8.5-E9.5 days [22].

Discussion

DEspR as a novel target for anti-tumor vascularization therapy. The detection of increased DEspR expression in tumor vascular endothelium, in contrast to normal tissue-matched controls, detection of DEspR expression in both αSMA-negative capillaries/microvessels and αSMA-positive arterioles and arteries in the tumor stroma, and successful inhibition of angiogenesis through DEspR-inhibition all demonstrate that DEspR is a novel target for therapies aimed at both tumor angiogenesis and at existing or 'mature' tumor microvasculature. More specifically, targeting DEspR on αSMA-positive microvessels can address anti-VEGF therapy-resistant tumors which are thought, without wishing to be limited or bound by a theory, to have a stromal vasculature no longer dependent on VEGF due their 'maturation' as marked by αSMA-positive pericyte sheath or non-dependent on VEGF due to "cooption of existing" microvasculature [2]. Furthermore, combined targeting DEspR along with anti-VEGF therapies can address the expected concomitant 10-fold increase in VEGFsp that accompanies the observed 10-fold increase in VEGF upon anti-VEGF therapy [10], since VEGF and VEGFsp originate from a common propeptide.

Insights from the ligand-specific DEspR phosphoproteome. Given that hypoxia inducible factor-1 alpha (HIF1α) stabilization induces VEGF, and hence VEGFsp, in hypoxia, phosphorylation of BRCA1 and induction of PCNA expression by VEGFsp-DEspR activation (Table 3), indicates that DEspR can contribute to the needed DNA repair response activated in hypoxia [24], thus allowing DEspR-positive endothelial and cancer cells to proliferate despite the hypoxic microenvironment, rather than undergo hypoxia-induced cell cycle arrest and apoptosis [24,25]. The hepatocyte growth factor receptor, MET, is induced upon ET1/DEspR stimulation and Smad1/5/9 is phosphorylated upon DEspR/VEGFsp activation, thus indicating a mechanism for crosstalk and/or redundancy among VEGFsp/DEspR, MET/HGF, and TGFβ/Smad pathways pertinent to angiogenesis in endothelial cells and invasiveness in cancer cells. Importantly, DEspR phosphorylates BRCA1 and STAT3 both of which have been shown to stabilize HIF1α, and along with Raf1, lead to the induction of VEGF, and hence VEGFsp. Furthermore, the phosphorylation of BRCA1 [26] by VEGFsp/DEspR and STAT3 by both ET1/DEspR and VEGFsp/DEspR, can both lead to DEspR-mediated stabilization of HIF1-alpha without the need for hypoxia, leading to constitutive HIF1-α mediated pro-angiogenic and pro-DNA repair response which can contribute to tumor resistance to conventional therapy.

DEspR inhibition as target for dual anti-angiogenesis/anti-cancer cell invasiveness treatment paradigm. In addition to expression on tumor vascular endothelium, DEspR is expressed in solid tumor epithelial cells seen in both established cancer cell lines and histology sections of breast, pancreatic, lung, stomach, bladder and colon cancers (FIGS. 24A-24F, 25A-25F, 26A-26F, and 27A-27F). Just as anti-DEspR inhibition reduces in vitro angiogenesis (FIGS. 28A-28B), 7C5B2 monoclonal antibody-inhibition decreases tumor cell invasiveness in two aggressive cancer cell lines, breast cancer cell line MDA-MB-231 (and -468) and pancreatic cancer cell line PANC-1 (FIGS. 29A-29C).

Thus, targeting DEspR as a receptor involved in both angiogenesis and tumor cell invasiveness via anti-hDEspR monoclonal antibody -inhibition using the compositions and methods described herein provides a robust new anti-tumor therapy, and demonstrates the use of the anti-hDEspR 7C5B2 monoclonal antibody described herein aas an anti-hDEspR monoclonal antibody-therapeutic precursor.

Furthermore, dual-targeting of angiogenesis and metastasis mechanisms comprise novel methods for next-generation anti-cancer treatment strategies [2]. The data described herein demonstrate that targeting DEspR is can be used to achieve a dual-treatment paradigm. The increased expression in both pancreatic tumor neovessel and tumor cells, along with the inhibition of angiogenesis and pancreatic cancer cell line PANC-1 cell-invasiveness by anti-DEspR inhibition altogether indicate that anti-DEspR therapy can provide a new treatment approach for pancreatic cancer. The combinatorial anti-angiogenesis and anti-invasiveness caused by DEspR-inhibition, as shown herein, as well as targeting DEspR for dual tumor endothelial and tumor cell targeted-delivery, can be used, in some embodiments, as a therapeutic basis for next generation dual anti-tumor/anti-angiogenesis cancer therapies and methods thereof [2].

TABLE 3

Tumor array analysis of DEspR expression in different cancers and cancer cell lines.

| Cancer tissue-type (n) | ↑tumor vascular endothelium vs normal | Representative cancer types | Cancer cell lines ■DEspR-positive □DEspR-negative |
|---|---|---|---|
| Bladder (23) | 17/23 (74%) | Adenocarcinoma Squamous cell ca Transitional cell ca | ■*253J BV |
| Breast (36) | 34/36 (94%) | Invasive ductal ca Adenoca Medullary ca Invasive lobular ca | ■*MDA-MB-231 ■*MDA-MB-468 |
| Colon (6) | 5/6 | Adenoca | ■*SW480 |
| Liver (35) | 24/35 (68%) | Hepatocellular ca Clear cell ca Bile duct ca | ■HEP3B □HEPG2 |
| Lung (2) | 2/2 | Adenocarcinoma | ■*NCI-H627 □NCI-H292 |
| Pancreas (6) | 6/6 | Ductal carcinoma | ■*PANC-1 |
| Stomach (2) | Primary and in metastasis to lung | Adenocarcinoma | na |

*nuclear membrane immunostaining;
ca, carcinoma;
cancer cell line nomenclature based on ATCC;
na, not available on cell-line array;
n, number of biopsy cores on tissue array.

TABLE 4

Phosphoproteome of hDEspR upon ET1 and VEGFsp stimulation respectively.

| Protein Name | Symbol | P*-Site | ET1 (% CFC) | VEGFsp (% CFC) | Pro-Angiogenesis | Pro-Cancer | Pro-Stem cell |
|---|---|---|---|---|---|---|---|
| Breast cancer type 1 susceptibility protein | BRCA1 | S1497 | 32 | 82 | [26] | [27] | |
| Cyclin-dependent protein-serine kinase ½ | CDK1/2 | T14/Y15 Y15 | 53 281 | −16 −57 | | [28] | |
| Extracellular regulated protein-serine kinase ½ (p44/p42 MAP kinases) | ERK1/2 | T202 + Y204; T185 + Y187 | 135 | −25 | [29, 30] | [31-33] | NSC: [34] CSC: [35] |

TABLE 4-continued

Phosphoproteome of hDEspR upon ET1 and VEGFsp stimulation respectively.

| Protein Name | Symbol | P*-Site | ET1 (% CFC) | VEGFsp (% CFC) | Pro-Angiogenesis | Pro-Cancer | Pro-Stem cell |
|---|---|---|---|---|---|---|---|
| Focal adhesion protein-tyrosine kinase | FAK | S722 | 55 | −38 | [36, 37] | Metastasis: [37,38] | NSC: [34] CSC: [37] |
| | | S732 | 62 | −11 | | | |
| | | Panspecific | 205 | 0 | | | |
| Hepatocyte growth factor receptor-tyrosine kinase | Met | Panspecific | 384 | 0 | [39-41] | Metastasis: [42]; Resistance: [39] | [43] |
| Proliferating cell nuclear antigen | PCNA | Panspecific | −47 | 119 | | [44] | |
| Protein-serine kinase C-alpha | PKCa | T638/T641 | 137 | −17 | [45, 46] | | |
| Protein-serine kinase C-epsilon | PKCe | Panspecific | 103 | −29 | [47-50] | [50] | NSC: [34]; CSC: [50] |
| Raf1 proto-oncogene-encoded protein-serine kinase | Raf1 | S259 | 12 | 63 | [51] | [52] | |
| SH2 domain-containing transforming protein 1 | Shc1 or ShcA | Y349, Y350 | 9 | 97 | [53-55] | [53, 56, 57] | |
| Protein-tyrosine phosphatase 1D | SHP2 | S576 | 14 | 97 | [58-60] | [58, 61, 62] | [61, 63-65] |
| SMA- and mothers against decapentaplegic homologs 1/5/9 | Smad 1/5/9 | S463 + S465/ S465 + S467 | 18 | 147 | [30] | [66] | HSC: [67] |
| Src proto-oncogene-encoded protein-tyrosine kinase | Src | Y529 | −20 | 73 | [47] | [68-70] | |
| | | Y418 | −11 | 174 | | | |
| Signal transducer and activator of transcription 1 | STAT1 | S727 | 86 | 123 | | Metastasis, invasiveness: [71] | CSC: [72] |
| | | Y701 | 95 | 557 | | | |
| Signal transducer and activator of transcription 3 | STAT3 | S727 | 133 | 126 | [73-75] | [74] Invasiveness: [75] | NSC: [76] |

CSC, cancer stem cell;
ET1, endothelin 1;
hDEspR, human dual endothelin-1/vascular endothelial growth factor-signal peptide receptor;
NSC, neural stem cell;
VEGFsp, vascular endothelial growth factor-signal peptide;
% CFC, percentage change in treated vs non-treated control averages: % CFC = [Treated − Control]/Control ave] × 100.
Phospho-site, phosphorylation site detected with phosphorylated site-specific antibodies.
Data represent >50% CFC taken from mean of treated vs control non-treated duplicates (A, B) with % error range < 20%.
% error range = [Treated$_A$ − ave]/ave × 100.
Kinexus antibody array: phosphoprotein-specific ab to detect phosphorylation changes, and panspecific antibodies to detect expression changes.

[1] D. Hanahan, R. A. Weinberg, The hallmarks of cancer, Cell 100 (2000) 57-70.
[2] G. Bergers, D. Hanahan, Modes of resistance to anti-angiogenic therapy, Nature Reviews—Cancer 8 (2008) 592.
[3] A. Abdollahi, J. Folkman, Evading tumor evasion: current concepts and perspectives of anti-angiogenic cancer therapy, Drug Resist. Updat. 13 (2010) 16-28.
[4] N. Ferrara, Pathways mediating VEGF-independent tumor angiogenesis, Cytokine Growth Factor Rev. 21 (2010) 21-26.
[5] S. Loges, T. Schmidt, P. Carmeliet, Mechanisms of resistance to anti-angiogenic therapy and development of third-generation anti-angiogenic drug candidates, Genes & Cancer 1 (2010) 12-25.
[6] P. Carmeliet, Angiogenesis in life, disease and medicine, Nature 438 (2005) 932-936.
[7] Y. Crawford, N. Ferrara, Mouse models to investigate anti-cancer effects of VEGF inhibitors, Methods Enzymol. 445 (2008) 125-139.
[8] J. M. Ebos, C. R. Lee, W. Cruz-Munoz, G. A. Bjarnason, J. G. Christensen, R. S. Kerbel, Accelerated metastasis after short-term treatment with a potent inhibitor of tumor angiogenesis, Cancer Cell 15 (2009) 232-239.
[9] M. Paez-Ribes, E. Allen, J. Hudock, T. Takeda, H. Okuyama, F. Vinals, M. Inoue, G. Bergers, D. Hanahan, O. Casanovas, Antiangiogenic therapy elicits malignant progression of tumors to increased local invasion and distant metastasis, Cancer Cell 15 (2009) 220-231.
[10] C. G. Willett, Y. Boucher, D. G. Duda, E. diTomaso, L. L. Munn, R. T. Tong, S. V. Kozin, L. Petit, R. K. Jain, D. C. Chung, D. V. Sahani, S. P. Kalva, K. S. Cohen, D. T. Scadden, A. J. Fischman, J. W. Clark, D. P. Ryan, A. X. Zhu, L. S. Blaszkowsky, P. C. Shellito, M. Mino-Kenudson, G. Y. Lauwers, Surrogate markers for antiangiogenic therapy and dose-limiting toxicities for Bevacizumab with radiation and chemotherapy: continued experience of a phase I trial in rectal cancer patients, J. Clin. Oncol. 23 (2005) 8136-8139.
[11] G. Bocci, S. Man, S. K. Green, G. Francia, J. M. Ebos, J. M. du Manoir, A. Weinerman, U. Emmenegger, L. Ma, P. Thorpe, A. Davidoff, J. Huber, D.J. Hicklin, R. S. Kerbel, Increased plasma VEGF as a surrogate marker for optimal therapeutic dosing of VEGF receptor-2 monoclonal antibodies, Cancer Res. 64 (2004) 6616-6625.

[12] N. Ruiz-Opazo, K. Hirayama, K. Akimoto, V. L. M. Herrera, Molecular characterization of a dual Endothelin-1/Angiotensin II Receptor, Molecular Medicine 4 (1998) 96-108.

[13] V. L. M. Herrera, L. R. B. Ponce, P.D. Bagamasbad, B. D. VanPelt, T. Didishvili, N. Ruiz-Opazo, Embryonic lethality in Dear gene-deficient mice: new player in angiogenesis, Physiol. Genomics 23 (2005) 257-268.

[14] K. Hosoda, R. E. Hammer, J. A. Richardson, A. G. Baynash, J. C. Cheung, A. Giaid, M. Yanagisawa, Targeted and natural (piebald-lethal) mutations of endothelin-B receptor gene produce megacolon associated with spotted coat color in mice, Cell 79 (1994) 1267-1276.

[15] D. E. Clouthier, K. Hosoda, J. A. Richardson, S. C. Williams, H. Yanagisawa, T. Kuwaki, M. Kumada, R. E. Hammer, M. Yanagisawa, Cranial and cardiac neural crest defects in endothelin-A receptor-deficient mice, Development 125 (1998) 813-824.

[16] A. Bagnato, L. Rosano, The endothelin axis in cancer, Int. J. Biochem. Cell Biol. 40 (2008) 1443-1451.

[17] N. Glorioso, V. L. M. Herrera, P. Bagamasbad, F. Filigheddu, C. Troffa, G. Argiolas, E. Bulla, J. L. Decano, N. Ruiz-Opazo, Association of ATP1A1 and Dear SNP-haplotypes with essential hypertension: sex-specific and haplotype-specific effects, Circ. Res. 100 (2007) 1522-1529.

[18] Y. Matsuo, M. Raimondo, T. A. Woodward, M. B. Wallace, K. R. Gill, Z. Tong, M. D. Burdick, Z. Yang, R. M. Stricter, R. M. Hoffman, S. Guha, CXC-chemokine/CXCR2 biological axis promotes angiogenesis in vitro and in vivo in pancreatic cancer, Int. J. Cancer 125 (2009) 1027-1037.

[19] A. K. Ollson, A. Dimberg, J. Kreuger, L. Claesson-Welsh, VEGF receptor signaling—in control of vascular function. Nat Reviews: Mol. Cell Biol. 7 (2006) 359-371.

[20] P. Carmeliet, V. Ferreira, G. Breier, S. Pollefeyt, L. Lieckens, M. Gertsenstein, M. Fahrig, A. Vandenhoeck, H. Kendraprasad, C. Eberhardt, C. Declercq, J. Pawling, L. Moons, D. Collen, W. Risau, A. Nagy, Abnormal blood vessel development and lethality in embryos lacking a single VEGF allele, Nature 380 (1996) 435-439.

[21] N. Ferrara, K. Carver-Moore, H. Chen, M. Dowd, L. Lu, K.S. O'Shea, L. Powell-Braxton, K. J. Hillan, M. W. Moore, Heterozygous embryonic lethality induced by targeted inactivation of the VEGF gene, Nature 380 (1996) 439-442.

[22] F. Shalaby, J. Rossant, T. P. Yamaguchi, M. Gertsenstein, X. F. Wu, M. L. Bretman, A. C. Schuh, Nature 376 (1995) 62-66.

[23] M. Hidalgo, Pancreatic Cancer, New Engl. J. Med. 362 (2010) 1605-1617.

[24] M. L. Coleman, P. J. Ratcliffe, Angiogenesis: escape from hypoxia, Nat. Med. 15 (2009) 491-492.

[25] E. M. Hammond, A. J. Biaccia, The role of ATM and ATR in the cellular response to hypoxia and re-oxygenation, DNA Repair 3 (2004) 117-1122.

[26] H. J. Kang, H. J. Kim, J. K. Rih, T. L. Mattson, K. W. Kim, C. H. Cho, J. S. Isaacs, I. Bae, BRCA1 plays a role in the hypoxic response by regulating HIF-1 a stability and by modulating vascular endothelial growth factor expression, J. Biol. Chem. 281 (2006) 13047-13056.

[27] C. Hesling, M. D'Incan, C. D'Incan, P. Souteyrand, J. C. Monboisse, S. Pasco, J. C. Madelmont, Y. J. Bignon, Downregulation of BRCA1 in A375 melanoma cell line increases radio-sensitivity and modifies metastatic and angiogenic gene expression, J. Invest. Dermatol. 122 (2004) 369-380.

[28] N. Johnson, D. Cai, R. D. Kennedy, S. Pathania, M. Arora, Y. C. Li, A. D. D'Andrea, J. D. Parvin, G. I. Shapiro, Cdk1 participates in BRCA1-dependent S phase checkpoint control in response to DNA damage, Mol. Cell 35 (2009) 327-339.

[29] J. Xu, X. Liu, Y. Jiang, L. Chu, H. Hao, Z. Liu, C. Verfaillie, J. Zweier, K. Gupta, Z. Liu, MAPK/ERK signaling mediates VEGF-induced bone marrow stem cell differentiation into endothelial cell, J. Cell. Mol. Med. 12 (2008) 2395-2406.

[30] E. M. Langenfeld, Y. Kong, J. Langenfeld, Bone morphogenetic protein-2-induced transformation involves the activation of mammalian target of rapamycin, Mol. Cancer Res. 3 (2005) 679-684.

[31] J. A. Gollob, S. Wilhelm, C. Carter, S. L. Kelley, Role of Raf kinase in cancer: therapeutic potential of targeting the Raf/MEK/ERK signal transduction pathway, Semin. Oncol. 33 (2006) 392-406.

[32] K. Balmano, S. J. Cook, Tumor cell survival signaling by the ERK1/2 pathway, Cell Death Differ. 16 (2009) 368-377.

[33] C. Fremin, S. Meloche, From basic research to clinical development of MEK1/2 inhibitors for cancer therapy, J. Hematol. Oncology 3 (2010) 8-18.

[34] R. Morishita, H. Ueda, H. Ito, J. Takasaki, K. Nagata, T. Asano, Involvement of Gq/11 in both integrin signal-dependent and -independent pathways regulating endothelin-induced neural progenitor proliferation, Neurosci. Res. 59 (2007) 205-214.

[35] Y. Wang, Y. Zhu, F. Qiu, T. Zhang, Z. Chen, S. Zheng, J. Huang, Activation of Akt and MAPK pathways enhances the tumorigenicity of CD133+ primary colon cancer cells, Carcinogenesis 2010 Jun. 8. [Epub ahead of print]

[36] K. Vadali, X. Cai, M. D. Schaller, Focal adhesion kinase: an essential kinase in the regulation of cardiovascular functions, IUBMB Life 59 (2007) 709-716.

[37] M. Luo, J. L. Guan, Focal adhesion kinase: a prominent determinant in breast cancer initiation, progression and metastasis, Cancer Lett. 289 (2010) 127-139.

[38] P. P. Provenzano, D. R. Inman, K. W. Eliceiri, H. E. Beggs, P. J. Keely, Mammary epithelial-specific disruption of focal adhesion kinase retards tumor formation and metastasis in a transgenic mouse model of human breast cancer, Am. J. Pathol. 173 (2008) 1551-1565.

[39] S. Fan, Y. Xian, J. A. Wang, R. Q. Yuan, Q. Meng, Y. Cao, J. J. Laterra, I. D. Goldberg, E. M. Rosen, The cytokine hepatocyte growth factor/scatter factor inhibits apoptosis and enhances DNA repair by a common mechanism involving signaling through phosphatidyl inositol 3'kinase, Oncogene 19 (2000) 2212-2223.

[40] E. S. Colombo, G. Menicucci, P. G. McGuire, A. Das, Hepatocyte growth factor/scatter factor promotes retinal angiogenesis through increased urokinase expression, Invest. Ophthalmol. Vis. Sci. 48 (2007) 1793-1800.

[41] K. Matsumoto, T. Nakamura, NK4 gene therapy targeting HGF-Met and angiogenesis, Front. Biosci. 13 (2008) 1943-1951.

[42] P. C. Ma, M. S. Tretiakova, V. Nallasura, R. Jagadeeswaran, A. N. Husain, R. Salgia, Downstream signaling and specific inhibition of c-MET/HGF pathway in small cell lung cancer: implications for tumor invasion, Br. J. Cancer 97 (2007) 368-377.

[43] Z. Yang, W. Wang, D. Ma, Y. Zhang, L. Wang, Y. Zhang, S. Xu, B. Chen, D. Miao, K. Cao, W. Ma, Recruitment of stem cells by hepatocyte growth factor via intracoronary gene transfection in the postinfarction heart failure, Sci. China C. Life Sci. 50 (2007) 748-752.

[44] R. Stuart-Harris, C. Caldas, S.E. Pinder, P. Pharoah, Proliferation markers and survival in early breast cancer: a systematic review and meta-analysis of 85 studies in 32,825 patients, Breast 17 (2008) 323-334.

[45] M. Wellner, C. Maasch, C. Kupprion, C. Lindschau, F. C. Luft, H. Haller, The proliferative effect of vascular endothelial growth factor requires protein kinase C-alpha and protein kinase C-zeta, Arterioscler. Thromb. Vasc. Biol. 19 (1999) 178-185.

[46] H. Xu, P. Czerwinski, M. Hortmann, H. Y. Sohn, U. Forstermann, H. Li, Protein kinase C alpha promotes angiogenic activity of human endothelial cells via induction of vascular endothelial growth factor, Cardiovasc. Res. 78 (2008) 349-355.

[47] G. E. Davis, W. Koh, A.N. Stratman, Mechanisms controlling human endothelial lumen formation and tube assembly in three-dimensional extracellular matrices, Birth Defects Research 81 (2007) 270-285.

[48] S. Yamamura, P. R. Nelson, K. C. Kent, Role of protein kinase C in attachment, spreading, and migration of human endothelial cells, J. Surg. Res. 63 (1996) 349-354.

[49] A. M. Gardner, M. E. Olah, Distinct protein kinase C isoforms mediate regulation of vascular endothelial growth factor expression by A2A adenosine receptor activation and phorbol esters in pheochromocytoma PC12 cells, J. Biol. Chem. 278 (2003) 15421-15428.

[50] M. C. Heidkamp, A. L. Bayer, B. T. Scully, D. M. Eble, A.M. Samarel, Activation of focal adhesion kinase by protein kinase C epsilon in neonatal rat ventricular myocytes, Am. J. Physiol. Heart Circ. Physiol. 285 (2003) H1684-H1696.

[51] M. Malecki, M. Seneta, J. Miloszewska, H. Trembacz, M. Przbyszewska, P. Janik, Role of v-Raf and truncated form RAF1 in the induction of vascular endothelial growth factor and vascularization, Oncol. Rep. 11 (2004) 161-165.

[52] F. J. Hoogwater, M. W. Nijkamp, N. Smakman, E. J. Steller, B. L. Emmink, B. F. Westendorp, D. A. Raats, M. R. Sprick, U. Schaefer, W. J. Van Houdt, M. T. De Bruijn, R. C. Schackmann, P. W. Derksen, J. P. Medema, H. Walczak, I. H. Borel Rinkes, O. Kranenberg, Oncogenic K-Ras turns death receptors into metastasis-promoting receptors in human and mouse colorectal cancer cells, Gastroenterology 138 (2010) 2357-2367.

[53] J. Ursini-Siegel, W. R. Hardy, D. Zuo, S. H. L. Lam, V. Sanguin-Gendreau, R. D. Cardiff, T. Pawson, W. Muller, ShcA signaling is essential for tumor progression in mouse models of human breast cancer, EMBO J. 27 (2008) 910-920.

[54] E. Audero, I. Cascone, F. Maniero, L. Napione, M. Arese, L. Lanfrancone, F. Bussolino, Adaptor ShcA protein binds tyrosine kinase Tie2 receptor and regulates migration and sprouting but not survival of endothelial cells, J. Biol. Chem. 279 (2004) 13224-13233.

[55] C. Saucier, H. Khoury, K. M. Lai, P. Peschard, D. Dankort, M. A. Naujokas, J. Holash, G. D. Yancopoulos, W. J. Muller, T. Pawson, M. Park, The Shc adaptor protein is critical for VEGF induction by Met/HGF and Erb B2 receptors and for early onset of tumor angiogenesis, Proc. Natl. Acad. Sci. 101 (2004) 2345-2350.

[56] J. J. Northey, J. Chmielecki, E. Ngan, C. Russo, M. G. Annis, W. J. Muller, P. M. Siegel, Signaling through ShcA is required for TGF-beta and Neu/ErbB-2 induced breast cancer cell motility and invasion, Mol. Cell Biol. 28 (2008) 3162-3176.

[57] C. Saucier, V. Papavailiou, A. Palazzo, M. A. Naujokas, R. Kremer, M. Park, Use of signal specific receptor tyrosine kinase oncoproteins reveals that pathways downstream from Grb2 or Shc are sufficient for cell transformation and metastasis, Oncogene 21 (2002) 1800-1811.

[58] Y. M. Agazie, N. Movilla, I. Ischenko, M. J. Hayman, The phosphotyrosine phosphatase SHP2 is a critical mediator of transformation induced by the oncogenic fibroblast growth factor receptor 3, Oncogene 22 (2003) 6909-6918.

[59] R. D. Chernock, R. P. Cherla, R. K. Ganju, SHP2 and cbl participate in alpha-chemokine receptor CXCR4-mediated signaling pathways, Blood 97 (2001) 608-615.

[60] M. B. Marron, D. P. Hughes, M. J. McCarthy, E. R. Beaumont, N. P. Brindle, Tie-1 receptor tyrosine kinase endodomain interaction with SHP2: potential signaling mechanisms and roles in angiogenesis, Adv. Exp. Med. Biol. 476 (2000) 35-46.

[61] X. Zhou, J. Coad, B. Ducatman, Y. M. Agazie, SHP2 is up-regulated in breast cancer cells and in infiltrating ductal carcinoma of the breast, implying its involvement in breast oncogenesis, Histopathology 53 (2008) 389-402.

[62] X. Zhou, Y. M. Agazie, Molecular mechanism for SHP2 in promoting HER2-induced signaling and transformation, J. Biol. Chem. 284 (2009) 12226-12234.

[63] K. Hagihara, E. E. Zhang, Y. H. Ke, G. Liu, J. J. Liu, Y. Rao, G. S. Feng, Shp2 acts downstream of SDF-1 alpha/CXCR4 in guiding granule cell migration during cerebellar development, Dev. Biol. 334 (2009) 276-284.

[64] D. Wu, Y. Pang, Y. Ke, J. Yu, Z. He, L. Tautz, T. Mustelin, S. Ding, Z. Huang, G. S. Feng, A conserved mechanism for control of human and mouse embryonic stem cell pluripotency and differentiation by shp2 tyrosine phosphatase, PLoS One 4 (2009) e4914.

[65] Y. Ke, E. E. Zhang, K. Hagihara, D. Wu, Y. Pang, R. Klein, T. Curran, B. Ranscht, G. S. Feng, Deletion of Shp2 in the brain leads to defective proliferation and differentiation in neural stem cells and early postnatal lethality, Mol. Cell Biol. 27 (2007) 6706-6717.

[66] I. M. Liu, S. H. Schilling, K. A. Knouse, L. Choy, R. Derynck, X. F. Wang, TGFbeta-stimulated Smad1/5 phosphorylation requires the ALK5 L45 loop and mediates the pro-migratory TGFbeta switch, EMBO J. 28 (2009) 88-98.

[67] U. Blank, G. Karlsson, S. Karlsson, Signaling pathways governing stem-cell fate, Blood 111 (2008) 494-503.

[68] F. M. Johnson, G. E. Gallick, SRC family nonreceptor tyrosine kinases as molecular targets for cancer therapy, Anticancer Agents Med. Chem. 7 (2007) 651-659.

[69] E. H. Lin, A. Y. Hui, J. A. Meens, E. A. Tremblay, E. Schaefer, B. E. Elliott, Disruption of Ca2+-dependent cell-matrix adhesion enhances c-Src kinase activity, but causes dissociation of the c-Src/FAK complex and dephosphorylation of tyrosine-577 of FAK in carcinoma cells, Exp. Cell Res. 293 (2004) 1-13.

[70] B. Mezquita, J. Mezquita, M. Pau, C. Mezquita, A novel intracellular isoform of VEGFR-1 activates Src and promotes cell invasion in MDA-MB-231 breast cancer cells, J. Cell Biochem. 110 (2010) 732-742.

[71] J. Schultz, D. Koczan, U. Schmitz, S. M. Ibrahim, D. Pilch, J. Landsberg, M. Kunz, Tumor-promoting role of signal transducer and activator of transcription (Stat)1 in late-stage melanoma growth, Clin. Exp. Metastasis 27 (2010) 133-140.

[72] M. Heuser, R. K. Humphries, Biologic and experimental variation of measured cancer stem cells, Cell Cycle 9 (2010) 909-912.

[73] J. E. Jung, H. G. Lee, I. H. Cho, D. H. Chung, S. H. Yoon, Y. M. Yang, J. W. Lee, S. Choi, J. W. Park, S. K. Ye, M. H. Chung, STAT3 is a potential modulator of HIF-1-mediated VEGF expression in human renal carcinoma cells, FASEB J. 19 (2005) 1296-1298.

[74] A. Jarnicki, T. Putoczki, M. Ernst, Stat3: linking inflammation to epithelial cancer—more than a "gut" feeling? Cell Div. 5 (2010) 14.

[75] H. Yu, D. Pardoll, R. Jove, STATs in cancer inflammation and immunity—a leading role for STAT3, Nat. Rev. Cancer 9 (2009) 798-809.

[76] M. V. Covey, S. W. Levison, Leukemia inhibitory factor participates in the expansion of neural stem/progenitors after perinatal hypoxia/ischemia, Neuroscience 148 (2007) 501-509.

Example 4

7C5B2 Antibody Sequencing and hDEspR Composite Human Antibody Variant Generation Described herein are sequencing results obtained from the monoclonal antibody expressed by the murine hybridoma 7C5B2 (anti-hDEspR), in which the heavy and light chain V-region ($V_H$ and $V_L$) sequences of the 7C5B2 antibody have been determined and exemplary anti-hDEspR composite human antibody variants have been designed.

From viable frozen hybridoma cell pellets, RNA was extracted and PCR amplification of antibody specific transcripts was performed after reverse transcription of mRNA. The nucleotide and amino acid sequences of the antibody heavy and light chain V-regions were determined and the sequence data was analyzed. Fully humanized antibodies were then designed using Composite Human Antibody™ technology, as described herein.

Methods and Results

RNA Extraction, RT-PCR and Cloning

RNA was extracted from a cell pellet using an RNAqueous®-4PCR kit (Ambion cat. no. AM1914). RT-PCR was performed using degenerate primer pools for murine signal sequences with constant region primers for each of IgGVH, IgMVH, IgκVL and IgλVE Heavy chain V-region RNA was amplified using a set of six degenerate primer pools (HA to HF) and light chain V-region mRNA was amplified using a set of eight degenerate primer pools, seven for the κ cluster (KA to KG) and one for the λ cluster (LA).

Figure 33:
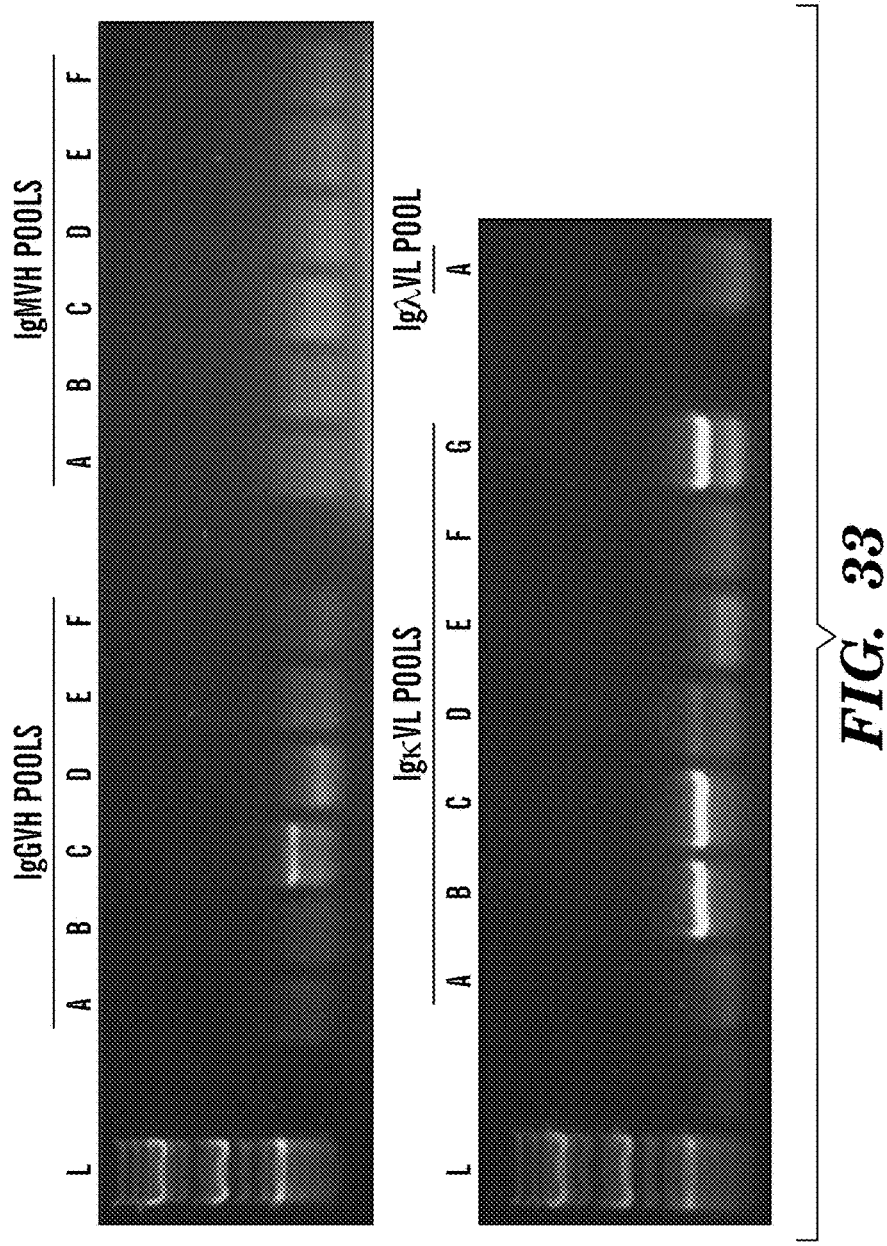
FIG. 33 demonstrates 1% agarose gel separation of RT-PCR products of antibody obtained from the 7C5B2 hybridoma. Gel was stained with SYBR® Safe DNA gel stain (Invitrogen cat. no. 533102) and photographed over ultraviolet light. Size marker (L) is GeneRuler™ 1Kb Plus (Fermentas cat. no. SM1331). RT-PCR was performed using degenerate primer pools for murine signal sequences with constant region primers for each of IgGVH, IgMVH, IgκVL and IgλVL.

For the heavy chain V-region, amplification products of the expected size were obtained from the IgGVH reverse transcription primer and primer pool HC. For the light chain V-region, amplification products were obtained from the IgκVL reverse transcription primer and light chain primer pools KB, KC, KD, and KG (FIG. 33). The PCR products from each of the above pools were purified and cloned into a 'TA' cloning vector (pGEM (R)-T Easy, Promega cat. no. A1360). Six VH and 24 Vκ clones were sequenced.

A single functional VH gene was identified in five clones from pool HC and a single functional Vκ gene sequence was identified in six clones from primer pool KG. The twelve clones from primer pools KB and KC were found to contain an aberrant transcript (GenBank accession number M35669) normally associated with the hybridoma fusion partner SP2/0 and the six clones from pool KD were found to not contain a functional Vκ transcript.

Chimeric Antibody

VH and Vκ (pool KG) genes were PCR amplified using primers that introduced flanking restriction enzyme sites for cloning into Antitope's VH and Vκ chain expression vectors. The VH region was cloned using MluI and HindIII sites, and the VκS region were cloned using BssHII and BamHI restriction sites. All constructs were confirmed by sequencing.

The chimeric antibody constructs were transiently transfected into HEK293 cells using calcium phosphate precipitation The transient transfections were incubated for three days prior to harvesting supernatants.

Sequence analysis

Analysis of sequences obtained from the hybridoma 7C5B2 is summarized in Table 1. The heavy and light chain V-regions show good homology to their closest human germline sequences (64% and 82%, respectively) and the individual framework sequences have close homologues in the human germline database.

Design of Composite Human Antibodies

Design of Composite Human Antibody™ Variable Region Sequences

Structural models of the mouse anti-hDEspR 7C5B2antibody V regions were produced using Swiss PDB and analysed in order to identify important "constraining" amino acids in the V regions that were likely to be essential for the binding properties of the antibody. Residues contained within the CDRs (using Kabat definition) together with a number of framework residues were considered to be important. Both the VH and Vκ sequences of anti-hDEspR contain typical framework residues and the CDR 1, 2 and 3 motifs are comparable to many murine antibodies.

From the above analysis, it was considered that composite human sequences of anti-hDEspR could be created with a wide latitude of alternatives outside of CDRs but with only a narrow menu of possible alternative residues within the CDR sequences. Analysis indicated that corresponding sequence segments from several human antibodies could be combined to create CDRs similar or identical to those in the murine sequences. For regions outside of and flanking the CDRs, a wide selection of human sequence segments were identified as components of the novel Composite Human Antibody™ V regions described herein (see Table 1).

Design of Variants

Based upon the above analysis, a large preliminary set of sequence segments that could be used to create anti-hDEspR Composite Human Antibody™ variants were selected and analysed using iTope™ technology for in silico analysis of peptide binding to human MHC class II alleles (Perry et al 2008), and using the TCED™ (T Cell Epitope Database) of known antibody sequence-related T cell epitopes (Bryson et al 2010). Sequence segments that were identified as significant non-human germline binders to human MHC class II or that scored significant hits against the TCED™ were discarded. This resulted in a reduced set of segments, and combinations of these were again analysed, as above, to ensure that the junctions between segments did not contain potential T cell epitopes.

Selected segments were then combined to produce heavy and light chain V region sequences for synthesis. For anti-hDEspR, five VH chains (SEQ ID NO: 13-SEQ ID NO: 17) and two Vκ chains (SEQ ID NO: 18 and SEQ ID NO: 19) were designed with sequences as detailed herein.

We claim:

1. An isolated antibody or antigen-binding fragment thereof that specifically binds DEspR (dual endothelin/VEGF signal peptide receptor) of SEQ ID NO: 1 and comprises a $V_H$ domain comprising a heavy chain CDR1 having the amino acid sequence of SEQ ID NO: 5; a heavy chain CDR2 having the amino acid sequence of SEQ ID NO: 6; and a heavy chain CDR3 having the amino acid sequence of SEQ ID NO:7 and a $V_L$ domain comprising a light chain CDR1 having the amino acid sequence of SEQ ID NO: 10; a light chain CDR2 having the amino acid sequence of SEQ ID NO: 11; and a light chain CDR3 having the amino acid sequence of SEQ ID NO: 12.

2. The isolated antibody or antigen-binding fragment of claim 1, wherein the antibody or antigen-binding fragment is a DEspR antagonist.

3. The isolated antibody or antigen-binding fragment thereof of claim 1, that specifically binds to an epitope of DEspR of comprising amino acids 1-9 of SEQ ID NO: 1.

4. An isolated antibody or antigen-binding fragment thereof that specifically binds DEspR (dual endothelin/VEGF signal peptide receptor) of SEQ ID NO: 1 comprising a $V_H$ domain comprising the amino acid sequence selected from SEQ ID NO: 4 and any one of SEQ ID NOs: 13-17.

5. An isolated antibody or antigen-binding fragment thereof that specifically binds DEspR (dual endothelin/VEGF signal peptide receptor) of SEQ ID NO: 1 comprising a $V_H$ domain comprising a heavy chain CDR1 of SEQ ID NO: 5; a heavy chain CDR2 of SEQ ID NO: 6; and a heavy chain CDR3 of SEQ ID NO: 7 and a $V_L$ domain comprising an amino acid sequence selected from SEQ ID NO:9, SEQ ID NO: 18, and SEQ ID NO: 19.

6. The antibody or antigen-binding fragment thereof according to claim 1, comprising two copies of said $V_H$ domain.

7. The antibody or antigen-binding fragment thereof according to claim 1, further comprising an agent conjugated to the antibody or fragment thereof to form an immunoconjugate specific for DEspR.

8. The antibody or antigen-binding fragment thereof according to claim 7, wherein the agent conjugated to the antibody or antibody fragment thereof is a chemotherapeutic agent, a toxin, a radioactive isotope, a small molecule, an siRNA, a nanoparticle, or a microbubble.

9. The antibody or antigen-binding fragment thereof according to claim 4, comprising two copies of said $V_H$ domain.

10. A composition comprising the antibody or antigen-binding fragment of claim 1, and a pharmaceutically acceptable excipient, diluent, or carrier.

11. The antibody or antigen-binding fragment thereof according to claim 4, wherein the antibody is a humanized antibody or antigen-binding fragment thereof, or a composite antibody or antigen-binding fragment thereof.

12. The antibody or antigen-binding fragment thereof according to claim 5, wherein the antibody is a humanized antibody or antigen-binding fragment thereof, or a composite antibody or antigen-binding fragment thereof.

13. The antibody or antigen-binding fragment thereof according to claim 4, comprising two copies of said $V_H$ domain.

14. The antibody or antigen-binding fragment thereof according to claim 4, further comprising an agent conjugated to the antibody or fragment thereof to form an immunoconjugate specific for DEspR.

15. The antibody or antigen-binding fragment thereof according to claim 14, wherein the agent conjugated to the antibody or antibody fragment thereof is a chemotherapeutic agent, a toxin, a radioactive isotope, a small molecule, an siRNA, a nanoparticle, or a microbubble.

16. A composition comprising the antibody or antigen-binding fragment of claim 4, and a pharmaceutically acceptable excipient, diluent, or carrier.

17. The antibody or antigen-binding fragment thereof according to claim 5, further comprising an agent conjugated to the antibody or fragment thereof to form an immunoconjugate specific for DEspR.

18. The antibody or antigen-binding fragment thereof according to claim 17, wherein the agent conjugated to the antibody or antibody fragment thereof is a chemotherapeutic agent, a toxin, a radioactive isotope, a small molecule, an siRNA, a nanoparticle, or a microbubble.

19. The antibody or antigen-binding fragment thereof according to claim 5, comprising two copies of said $V_H$ domain and said $V_L$ domain.

20. A composition comprising the antibody or antigen-binding fragment of claim 5, and a pharmaceutically acceptable excipient, diluent, or carrier.

* * * * *